(12) United States Patent
Yamazaki et al.

(10) Patent No.: US 11,858,987 B2
(45) Date of Patent: Jan. 2, 2024

(54) CANCER STEM CELL-SPECIFIC MOLECULE

(71) Applicant: CHUGAI SEIYAKU KABUSHIKI KAISHA, Tokyo (JP)

(72) Inventors: Tatsumi Yamazaki, Tokyo (JP); Hisafumi Okabe, Shizuoka (JP); Shinta Kobayashi, Helios (SG); Takeshi Watanabe, Shizuoka (JP); Koichi Matsubara, Helios (SG); Osamu Natori, Helios (SG); Atsuhiko Kato, Shizuoka (JP); Masami Suzuki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 512 days.

(21) Appl. No.: 16/913,341

(22) Filed: Jun. 26, 2020

(65) Prior Publication Data

US 2020/0325222 A1    Oct. 15, 2020

Related U.S. Application Data

(63) Continuation of application No. 15/042,548, filed on Feb. 12, 2016, now Pat. No. 10,934,351, which is a continuation of application No. 14/354,517, filed as application No. PCT/JP2012/077714 on Oct. 26, 2012, now abandoned.

(30) Foreign Application Priority Data

Oct. 28, 2011 (JP) .................. 2011-237438
Apr. 12, 2012 (JP) .................. 2012-091142

(51) Int. Cl.
| | | |
|---|---|---|
| C07K 16/28 | (2006.01) |
| C07K 16/30 | (2006.01) |
| C07K 14/51 | (2006.01) |
| G01N 33/574 | (2006.01) |
| C12Q 1/6886 | (2018.01) |
| A61K 39/00 | (2006.01) |
| C07K 16/18 | (2006.01) |
| C12Q 1/686 | (2018.01) |
| A61K 31/4745 | (2006.01) |
| A61K 39/395 | (2006.01) |

(52) U.S. Cl.
CPC .......... *C07K 16/28* (2013.01); *A61K 31/4745* (2013.01); *A61K 39/001102* (2018.08); *A61K 39/39558* (2013.01); *C07K 14/51* (2013.01); *C07K 16/18* (2013.01); *C07K 16/3046* (2013.01); *C12Q 1/686* (2013.01); *C12Q 1/6886* (2013.01); *G01N 33/574* (2013.01); *G01N 33/57419* (2013.01); *G01N 33/57492* (2013.01); *A61K 2039/55566* (2013.01); *C07K 2317/41* (2013.01); *C07K 2317/732* (2013.01); *C07K 2317/734* (2013.01); *C07K 2317/76* (2013.01); *C12Q 2600/106* (2013.01); *C12Q 2600/158* (2013.01); *G01N 2333/726* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,573,924 A | 11/1996 | Beckmann et al. |
| 6,852,318 B1 | 2/2005 | Varner |
| 7,145,055 B2 | 12/2006 | Ito et al. |
| 2002/0119565 A1 | 8/2002 | Clarke et al. |
| 2003/0105000 A1 | 6/2003 | Pero et al. |
| 2003/0115614 A1 | 6/2003 | Kanda et al. |
| 2004/0197328 A1 | 10/2004 | Young et al. |
| 2007/0220621 A1 | 9/2007 | Clarke et al. |
| 2008/0064049 A1 | 3/2008 | Clarke et al. |

(Continued)

FOREIGN PATENT DOCUMENTS

| | | |
|---|---|---|
| CA | 2 447 400 | 3/2005 |
| CN | 101014608 A | 8/2007 |

(Continued)

OTHER PUBLICATIONS

HPAC-CRL-2119 (ATCC, https://www.atcc.org/products/crl-2119, downloaded Jan. 31, 2023) (Year: 2023).*

(Continued)

*Primary Examiner* — Peter J Reddig
(74) *Attorney, Agent, or Firm* — Klarquist Sparkman, LLP

(57) ABSTRACT

An objective of the present invention is to obtain two types of substantively homogeneous cancer stem cell populations which can be characterized using the cell surface marker Lgr5, and to provide cancer therapeutics using an antibody against a cell membrane molecule specifically expressed in these cancer stem cells by identifying said cell membrane molecule. A further objective is to provide, using an antibody against a cell membrane molecule specifically expressed in cancer stem cells, a reagent for detecting cancer stem cells, and a method for diagnosing and sorting cancer patients. The present inventors discovered that highly pure large intestine cancer stem cells (CSC) can be obtained in a large quantity, and identified the two types of conditions of large intestine CSCs distinguishable through Lgr5 expression. Moreover, the present inventors discovered that an antibody against a cell membrane molecule specifically expressed in said cancer stem cells can damage said cells.

17 Claims, 74 Drawing Sheets

Specification includes a Sequence Listing.

(56) References Cited

U.S. PATENT DOCUMENTS

| | | | |
|---|---|---|---|
| 2008/0178305 A1 | 7/2008 | Clark et al. | |
| 2008/0268476 A1 | 10/2008 | Lopez | |
| 2009/0081221 A1 | 3/2009 | Tokoro et al. | |
| 2009/0148942 A1 | 6/2009 | McDonagh et al. | |
| 2009/0214517 A1 | 8/2009 | Wong et al. | |
| 2009/0226396 A1 | 9/2009 | Haley et al. | |
| 2009/0324491 A1 | 12/2009 | Aburatani et al. | |
| 2010/0003265 A1 | 1/2010 | Scheffler et al. | |
| 2010/0024049 A1 | 1/2010 | Marchiano | |
| 2010/0275280 A1 | 10/2010 | Clevers et al. | |
| 2010/0287638 A1 | 11/2010 | Dirks et al. | |
| 2011/0182904 A1 | 7/2011 | Zimmerman et al. | |
| 2011/0244502 A1 | 10/2011 | Ince et al. | |
| 2013/0019327 A1 | 1/2013 | Suzuki et al. | |
| 2013/0288248 A1 | 10/2013 | Yamazaki et al. | |
| 2014/0039033 A1* | 2/2014 | Song | G01N 33/6893 435/7.1 |
| 2014/0199294 A1 | 7/2014 | Mimoto et al. | |
| 2014/0302511 A1 | 10/2014 | Yamazaki et al. | |
| 2014/0314675 A1 | 10/2014 | Yamazaki et al. | |
| 2015/0110793 A1 | 4/2015 | Shiraiwa et al. | |
| 2015/0034457 A1 | 12/2015 | Igawa et al. | |
| 2015/0344570 A1 | 12/2015 | Igawa et al. | |
| 2016/0017028 A1 | 1/2016 | Yoshida et al. | |
| 2016/0159904 A1 | 6/2016 | Yamazaki et al. | |
| 2017/0129950 A1 | 5/2017 | Shiraiwa et al. | |
| 2020/0385686 A1 | 12/2020 | Kaisha | |

FOREIGN PATENT DOCUMENTS

| | | | |
|---|---|---|---|
| CN | 101506352 | 8/2009 | |
| EP | 1 338 198 A1 | 8/2003 | |
| EP | 1 637 589 A1 | 3/2006 | |
| EP | 1 686 173 A1 | 8/2006 | |
| EP | 1 792 979 | 6/2007 | |
| EP | 1815864 | 8/2007 | |
| EP | 2070548 | 6/2009 | |
| EP | 2517555 | 10/2012 | |
| EP | 2626414 A1 | 8/2013 | |
| JP | 2005-206508 | 8/2005 | |
| JP | 3753321 | 12/2005 | |
| JP | 2007-530588 | 11/2007 | |
| JP | 2008-500838 | 1/2008 | |
| JP | 2008-102012 | 5/2008 | |
| JP | 2008-514205 | 5/2008 | |
| JP | 2008-182912 | 8/2008 | |
| JP | 2009-502156 | 1/2009 | |
| JP | 2009-509510 | 3/2009 | |
| JP | 2009-519242 | 5/2009 | |
| JP | 2009-539374 | 11/2009 | |
| JP | 2010-516259 | 5/2010 | |
| JP | 2011-519567 | 7/2011 | |
| WO | WO 02/12447 | 2/2002 | |
| WO | WO 02/079255 | 10/2002 | |
| WO | WO 03/104401 | 12/2003 | |
| WO | WO 2004/101775 | 11/2004 | |
| WO | WO 2005/035740 | 4/2005 | |
| WO | WO 2005/092927 | 10/2005 | |
| WO | WO 2005/118824 | 12/2005 | |
| WO | WO 2006/039671 | 4/2006 | |
| WO | WO 2006/039678 | 4/2006 | |
| WO | WO 2006/051405 | 5/2006 | |
| WO | WO 2006/051984 | 5/2006 | |
| WO | WO 2006/138275 | 12/2006 | |
| WO | WO 2007/012811 | 2/2007 | |
| WO | WO 2007/038637 | 4/2007 | |
| WO | WO 2007/064945 | 6/2007 | |
| WO | WO 2007/132883 | 11/2007 | |
| WO | WO-2007124125 A2 * | 11/2007 | G01N 33/56966 |
| WO | WO 2007/145901 | 12/2007 | |
| WO | WO 2008/017171 | 2/2008 | |
| WO | WO 2008/033393 A2 | 3/2008 | |
| WO | WO 2008/034645 A1 | 3/2008 | |
| WO | WO 2008/047723 | 4/2008 | |
| WO | WO 2008/091908 | 7/2008 | |
| WO | WO 2008/143954 | 11/2008 | |
| WO | WO 2008/149803 | 12/2008 | |
| WO | WO 2009/005809 | 1/2009 | |
| WO | WO-2009045201 A1 * | 4/2009 | C12N 5/068 |
| WO | WO 2009/064301 | 5/2009 | |
| WO | WO 2009/135181 | 11/2009 | |
| WO | WO 2010/009121 | 1/2010 | |
| WO | WO 2010/016766 | 2/2010 | |
| WO | WO 2010/067487 | 6/2010 | |
| WO | WO 2010/102244 | 9/2010 | |
| WO | WO 2010/113117 | 10/2010 | |
| WO | WO 2010/123891 | 10/2010 | |
| WO | WO 2010/126074 | 11/2010 | |
| WO | WO 2011/027308 | 3/2011 | |
| WO | WO 2011/078301 | 6/2011 | |
| WO | WO 2011/083088 | 7/2011 | |
| WO | WO 2012/046797 | 4/2012 | |
| WO | WO-2012096545 A2 * | 7/2012 | C12N 15/113 |
| WO | WO 2013/002362 | 1/2013 | |
| WO | WO 2013/035824 | 3/2013 | |
| WO | WO 2013/100120 | 7/2013 | |

OTHER PUBLICATIONS

U.S. Appl. No. 17/992,032, filed Nov. 22, 2022, Chugai Seiyaku Kabushiki Kaisha.

Corbett et al., "Tumor Induction Relationships in Development of Transplantable Cancers of the Colon in Mice for Chemotherapy Assays, with a Note on Carcinogen Structure," *Cancer Res* 35: 2434-2439, 1975.

U.S. Appl. No. 16/994,388, US 2020-0385686-A1.

Sanz et al., "Differential transplantability of human endothelial cells in colorectal cancer and renal cell carcinoma primary xenografts," *Laboratory Investigation*, 89: 91-97, 2009.

Gullo et al., "Inhibition of Proliferation and Induction of Apoptosis in Multiple Myeloma Cell Lines by CD137 Ligand Signaling," *PLoS One*, 5(5):e10845 (11 pages), 2010.

Amendment and Response to Office Action for U.S. Appl. No. 13/519,059, submitted to the U.S. PTO dated Jun. 9, 2014 (7 pages).

Amendment and Response to Restriction Requirement for U.S. Appl. No. 13/878,181, (12 pages) (submitted to PTO dated May 23, 2014).

Amendment and Response to Restriction Requirement, U.S. Appl. No. 13/519,059, 4 pages (filed Sep. 19, 2013).

Al-Hajj, et al. "Prospective identification of tumorigenic breast cancer cells." Proceedings of the National Academy of Sciences 100:3983-3988, 2003 (epub Mar. 10, 2003).

Almagro et al., "Humanization of Antibodies," Frontiers in Bioscience, vol. 13:1619-1633, 2008.

Barker, et al. "Crypt stem cells as the cells-of-origin of intestinal cancer." Nature 457: 608-611, 2009 (epub Dec. 17, 2008).

Barker, et al. "Identification of stem cells in small intestine and colon by marker gene Lgr5." Nature 449: 1003-1007, 2007 (epub Oct. 14, 2007).

Beidler et al., "Generation and Activity of a Humanized Monoclonal Antibody That Selectively Neutralizes the Epidermal Growth Factor Receptor Ligands Transforming Growth Factor-α and Epiregulin," *J Pharmacol Exp Ther* 349:330-343, 2014.

Boiko, et al. "Human melanoma-initiating cells express neural crest nerve growth factor receptor CD271." Nature 466(7302): 133-137, 2010.

Brabletz et al., "Migrating cancer stem cells—an integrated concept of malignant tumour progression," *Nature Reviews Cancer*, 5:744-749 (2005).

Bonnet et al. "Human acute myeloid leukemia is organized as a hierarchy that originates from a primitive hematopoietic cell." *Nature Medicine* 3: 730-737, 1997.

Botchkina et al., "Phenotypic Subpopulations of Metastatic Colon Cancer Stem Cells: Genomic Analysis," *Cancer Genomics Proteomics* 6(1):19-29, 2009.

Carlone and Breault, "Slowly cycling versus rapidly cycling intestinal stem cells," *Cell Cycle* 10(5):723-724, 2011.

(56) References Cited

OTHER PUBLICATIONS

Chen et al., "Intestinal Adenomagenesis Involves Core Molecular Signatures of the Epithelial-Mesenchymal Transition," *J Mol Histol* 39(3):283-294, 2008.
Chu, et al. "Characterization of a subpopulation of colon cancer cells with stem cell-like properties." *International Journal of Cancer* 124: 1312-1321, 2009.
Clevers. "The cancer stem cell: premises, promises and challenges." *Nature Medicine* 17:313-319, 2011.
Cobleigh, "Other Options in the Treatment of Advanced Breast Cancer," *Semin. Oncol.*, vol. 38 (Suppl. 2):S11-216, 2011.
Colman, "Effects of amino acid sequence changes on antibody-antigen interactions," *Res Immunol* 145(1):33-36, 1994.
Collins, et al. "Prospective identification of tumorigenic prostate cancer stem cells." *Cancer Research* 65: 10946-10951, 2005.
Dalerba et al., "Cancer Stem Cells: Models and Concepts," *The Annual Review of Medicine*, 58:267-284 (2007) (published online Sep. 26, 2006).
Dalerba, et al. "Phenotypic characterization of human colorectal cancer stem cells." *Proceedings of the National Academy of Sciences* 104: 10158-10163, 2007 (epub Jun. 4, 2007).
DeRycke et al., "Nectin 4 Overexpression in Ovarian Cancer Tissues and Serum," *Am J Clin Pathol* 134: 835-845, 2010.
Enfortumab Vedotin (ASG-22ME, formerly AGS-22M6E) Clinical Trials, ADC Review, InPress Media Group, 2015, https://adcreview.com/enfortumab-vedotin-asg-22me-formerly-ags-22m6e-clinical -trials, downloaded Jan. 18, 2019.
English translation of the International Search Report for PCT/JP2012/072852, dated Nov. 27, 2012.
Eramo, et al. "Identification and expansion of the tumorigenic lung cancer stem cell population." *Cell Death & Differentiation* 15: 504-514, 2007 (epub Nov. 30, 2007).
European Search Report for EPC Patent Application No. 10839531.0 (5 pages) (dated Aug. 27, 2014).
Fabre-Lafay et al., "Nectin-4, a New Serological Breast Cancer Marker, Is a Substrate for Tumor Necrosis Factor-a-converting Enzyme (TACE)/ADAM-17," *J Biol Chem* 280(20): 19543-19550, 2005.
Fang et al., "A Tumorigenic Subpopulation with Stem Cell Properties in Melanomas," *Cancer Res.*, vol. 65:9328-9337, 2005.
Fang et al., "Expansion of CD133+ colon cancer cultures retaining stem cell properties to enable cancer stem cell target discovery," *British Journal of Cancer*, 102:1265-1275 (2010).
Final Office Action issued for U.S. Appl. No. 14/873,861 dated Mar. 22, 2017 (10 pages).
Fuchs et al., Irinotecan in the Treatment of Colorectal Cancer, *Cancer Treatment Rev.*, vol. 32:491-503, 2006.
Fujii et al., "Establishment and characterization of in vivo human tumor models in the NOD/SCID/$\gamma_c^{null}$ mouse," *Pathology International*, 58:559-567 (2008).
Fujii et al., "The potential of the NOD/SCID$\gamma_c^{null}$ (NOG) mouse as an in vivo human tissue model," *Toxicol Pathol* 191-P53 (Jan. 2007).
Fujii et al., Poster Presentations: *The 25th Annual Meeting of the Society of Toxicologic Pathology*, Lawrence, KS, US, Canada (Jun. 18-22, 2006).
Gou et al., "Establishment of Clonal Colony-Forming Assay for Propagation of Pancreatic Cancer Cells with Stem Cell Properties," *Pancreas* 34(4): 429-435 (2007).
Hamada et al., "Liver metastasis models of colon cancer for evaluation of drug efficacy using NOD/Shi-scid IL2R$\gamma^{null}$ (NOG) mice," *Int J Oncol* 32(1):153-159, 2008.
Haraguchi, et al. "CD133+ CD44+ population efficiently enriches colon cancer initiating cells." *Annals of Surgical Oncology* 15:2927-2933, 2008 (epub Jul. 29, 2008).
Hermann, et al. "Distinct populations of cancer stem cells determine tumor growth and metastatic activity in human pancreatic cancer." *Cell Stem Cell* 1:313-323, 2007.
Hirsch et al., "LGR5 positivity defines stem-like cells in colorectal cancer," *Carcinogenesis* 35(4):849-858, 2014.

Hsu, et al. "Characterization of Two LGR Genes Homologous to Gonadotropin and Thyrotropin Receptors with Extracellular Leucine-Rich Repeats and a G Protein-Coupled, Seven-Transmembrane Region." *Molecular Endocrinology* 12: 1830-1845, 1998.
Hu and Smyth, "ELDA; Extreme Limiting Dilution analysis for comparing depleted and enriched populations in stem cell and other assays," *J. Immunol. Meth.* 347: 70-78, 2009.
Huang, et al. "ALDH1 is a marker for normal and malignant human colonic stem cells and tracks stem cell overpopulation during colon tumorigenesis." *Cancer Res* 69: 3382-3389, 2009 (epub Mar. 31, 2009).
Imada et al., "Serial Transplantation of Adult T Cell Leukemia Cells into Severe Combined Immunodeficient Mice," *Jpn. J. Cancer Res.* 87:887-892 (Sep. 1996).
Imanshi et al., "Inhibition of Growth of Human Lung Adenocarcinoma Cell Lines by Anti-Transforming Growth Factor-α Monoclonal Antibody," *J Natl Cancer Inst* 81:220-223, 1989.
IMGT Scientific Chart (Correspondence between the IMGT unique numbering for C-DOMAIN, the IMGT exon numbering, the Wu and Kabat numberings: Human IGHG), downloaded Jan. 22, 2018.
Inagaki et al., "Long-term maintenance of brain tumor stem cell properties under at non-adherent and adherent culture conditions," *Biochem. Biophys. Res. Commun.*, 361(3):586-592 (2007).
International Search Report for PCT/JP2012/077714, mailed by the ISA (Japanese Patent Office) dated Jan. 29, 2013 (5 pages).
International Preliminary Report on Patentability (English language translation) for PCT Application No. PCT/JP2012/077714, 13 pages (dated Apr. 29, 2014).
International Preliminary Report on Patentability from PCT Application No. PCT/JP2012/072852 (in English) (11 pages) (dated Mar. 12, 2014).
International Search Report on Patentability from PCT/JP2010/073266 (2 pages) (dated Mar. 28, 2011).
InvivoGen, Immunoglobin G-Review 2011, www.invivogen.com/review-antibody-generation, downloaded May 25, 2018.
Ishizawa, et al. "Tumor-initiating cells are rare in many human tumors." *Cell Stem Cell* 7: 279-282, 2010.
Ito et al., "NOD/SCID/$\gamma_c^{null}$ mouse: an excellent recipient mouse model for engraftment of human cells," *Blood* 100(9):3175-3182, 2002.
Jonker et al., "Cetuximab for the Treatment of Colorectal Cancer," *N Engl J Med* 357:2040-2048, 2007.
Kim et al., "Role of lymphocyte-specific protein tyrosine kinase (LCK) in the expansion of glioma-initiating cells by fractionated radiation," *Biochem Biophys Res Commun* 402:631-636, 2010.
Kirchner and Brabletz "Patterning a Nuclear β-Catenin Expression in the Colonic Adenoma-Carcinoma Sequence," *American Journal of Pathology*, 157(4):1113-1121 (2000).
Kobayashi et al., "LGR5-positive colon cancer stem cells interconvert with drug-resistant LGR5-negative cells and are capable of tumor reconstitution," *Stem Cells* 30:2631-2644 (2012).
Kowalczyk, et al. "Molecular and therapeutic characterization of anti-ectodysplasin A receptor (EDAR) agonist monoclonal antibodies." *Journal of Biological Chemistry* 286: 30769-30779, 2011.
Ku et al., "Establishment and characterization of 13 human colorectal carcinoma cell lines: mutations of genes and expressions of drug-sensitivity genes and cancer stem cell markers," *Carcinogenesis* 31(6):1003-1009 (2010).
Lapidot, et al. "A cell initiating human acute myeloid leukaemia after transplantation into SCID mice." *Nature* 367: 645-648, 1994.
Li, et al. "Identification of pancreatic cancer stem cells." *Cancer Res* 67: 1030-1037, 2007.
Machine translation of JP 2008-102012, Hirao et al., published May 1, 2008.
Machida et al., "Higher susceptibility of NOG mice to xenotransplanted tumors," *J. Toxicol. Sci.* vol. 34, No. 1, pp. 123-127, 2009.
Mani et al., "The epithelial-mesenchymal transition generates cells with properties of stem cells," *Cell* 133(4):704-715, 2008.
Martin et al., "Expression of the Transcription Factors Snail, Slug, and Twist and Their Clinical Significance in Human Breast Cancer," *Ann Surg Oncol* 12:1-9, 2005.

(56) References Cited

OTHER PUBLICATIONS

McDonald, et al. "Identification and cloning of an orphan G protein-coupled receptor of the glycoprotein hormone receptor subfamily." *Biochemical and Biophysical Research Communications* 247: 266-270, 1998.
Morisot et al., "Leukemia Stem Cells (LSCs) Are Frequent in Childhood Precursor B Acute Lymphoblastic Leukemia (ALL)," *50th ASH Annual Meeting and Exposition* (2 pages) (Dec. 6, 2008).
Munoz et al., "The Lgr5 Intestinal Stem Cell Signature: Robust Expression of Proposed Quiescent'+4' Cell Markers," *EMBO J.*, vol. 31:3079-3091, 2012.
Non-Final Office Action dated Jan. 13, 2014, U.S. Appl. No. 13/519,059, 19 pages.
O'Brien, et al. "A human colon cancer cell capable of initiating tumour growth in immunodeficient mice." *Nature* 445: 106-110, 2007 (epub Dec. 9, 2008).
Office Action (Restriction Requirement) dated Feb. 25, 2014 for U.S. Appl. No. 13/878,181 (10 pages).
Office Action dated Jul. 22, 2014 for U.S. Appl. No. 13/878,181 (27 pages).
Office Action issued for U.S. Appl. No. 14/873,861 dated Aug. 5, 2016 (14 pages).
Office Action issued for U.S. Appl. No. 14/900,928 dated Aug. 16, 2017 (43 pages).
Oka et al., "Immunohistochemical evaluation of E-cadherin adhesion molecule expression in human gastric cancer," *Virchows Archiv A Pathol Anat* 421:149-159, 1992.
Pang, et al. "A Subpopulation of CD26+ Cancer Stem Cells with Metastatic Capacity in Human Colorectal Cancer." *Cell Stem Cell* 6: 603-615, 2010.
Park, et al. "Cancer stem cell-directed therapies: recent data from the laboratory and clinic." *Mol Ther* 17: 219-230, 2009.
Patrawala, et al. "Highly purified CD44+ prostate cancer cells from xenograft human tumors are enriched in tumorigenic and metastatic progenitor cells." *Oncogene* 25: 1696-1708, 2006.
Peggs et al., "Cancer immunotherapy: co-stimulatory agonists and co-inhibitory antagonists," *Clin Exp Immunol* 157:9-19, 2009.
Perego et al., "Heterogeneous Phenotype of Human Melanoma Cells with In Vitro and In Vivo Features of Tumor-Initiating Cells," *J. Invest. Dermatol.*, vol. 130:1877-1886, 2010.
Petrova et al., "Transcription Factor PROX1 Induces Colon Cancer Progression by Promoting the Transition from Benign to Highly Dysplastic Phenotype," *Cancer Cell* 13(5):407-419, 2008.
Pollard et al., "Glioma Stem Cell Lines Expanded in Adherent Culture Have Tumor-Specific Phenotypes and Are Suitable for Chemical and Genetic Screens," *Cell Stem Cell*, 4(6):568-580, 2009.
Prince, et al. "Identification of a subpopulation of cells with cancer stem cell properties in head and neck squamous cell carcinoma." *Proceedings of the National Academy of Sciences* 104:973-978, 2007.
Quintana et al., "Efficient tumour formation by single human melanoma cells," *Nature* 456:593-598 (2008).
Restriction Requirement dated Mar. 20, 2013, U.S. Appl. No. 13/519,059, 11 pages.
Restriction Requirement issued for U.S. Appl. No. 14/900,928 dated May 18, 2017 (7 pages).
Reya, et al. "Stem cells, cancer, and cancer stem cells." *Nature* 414: 105-111, 2001.

Ricci-Vitiani, et al. "Identification and expansion of human colon-cancer-initiating cells." *Nature* 445: 111-115, 2007 (epub Nov. 19, 2006).
Rudikoff et al., "Single amino acid substitution altering antigen-binding specificity," *Proc Natl Acad Sci USA* 79:1979-1983, 1982.
Sato, et al. "Single Lgr5 stem cells build crypt villus structures in vitro without a mesenchymal niche." *Nature* 459: 262-265, 2009 (epub Mar. 29, 2009).
Satpayev et al., "Abstract 2832: Development of AGS-22M6E, a novel antibody drug conjugate (ADC) targeting Nectin-4 for the treatment of solid tumors," *Cancer Res* 71(8 Supplement), Apr. 2011.
Schatton, et al. "Identification of cells initiating human melanomas." *Nature* 451: 345-349, 2008.
Singh, et al. "Identification of human brain tumour initiating cells." *Nature* 432: 396-401, 2004.
Spano et al., "Epidermal growth factor receptor signaling in colorectal cancer: preclinical data and therapeutic perspectives," *Ann Oncol* 16:189-194, 2005.
Suemizu et al., "Identification of a key molecular regulator of liver metastasis in human pancreatic carcinoma using a novel quantitative model of metastasis in NOD/SCID/$\gamma_c^{null}$ (NOG) mice," *Int J Oncol* 31:741-751, 2007.
Sun et al., "An ultra-metastatic model of human colon cancer in nude mice," *Clin Exp Metastasis*, 17(1): 41-48, 1999.
Takano et al., "Identification of Nectin-4 Oncoprotein as a Diagnostic and Therapeutic Target for Lung Cancer," *Cancer Res* 69(16): 6694-6703, 2009.
Thenappan et al., "New Therapeutics Targeting Colon Cancer Stem Cells," *Curr. Colorectal Cancer Rep.*, vol. 5:209-216, 2009.
Translation of the International Preliminary Report on Patentability, International Application No. PCT/JP2011/073067, dated May 16, 2013.
Vermeulen et al., "Single-cell cloning of colon cancer stem cells reveals a multi-lineage differentiation capacity," *Proc. Natl. Acad. Sci. USA*, 105(36):13427-13432 (Sep. 2008).
Vermeulen, et al. "Wnt activity defines colon cancer stem cells and is regulated by the microenvironment." *Nat Cell Biol* 12: 468-476, 2010 (epub Apr. 25, 2010).
Walker et al., "LGR5 is a Negative Regulator of Tumourigenicity, Antagonizes Wnt Signalling and Regulates Cell Adhesion in Colorectal Cancer Cell Lines," *PLoS ONE*, vol. 6:e22733, 2011.
Wu, et al. "Side population cells isolated from mesenchymal neoplasms have tumor initiating potential." *Cancer Res* 67: 8216-8222, 2007.
Yeung et al., "Cancer stem cells from colorectal cancer-derived cell lines," *Proc. Natl. Acad. Sci. USA*, 107(8):3722-3727 (2010).
Zahidunnabi et al., "Potential role of NK cells in tumor growth and metastasis of breast cancer cells in NOD/SCID/γcnull (NOG) mice: Implication of immune therapy," *Proc. Amer. Assoc. Cancer Res.*, 46, Abstract #4683 (2005) (2 pages).
Zhang et al., "Intratumoral Epiregulin Is a Marker of Advanced Disease in Non-Small Cell Lung Cancer Patients and Confers Invasive Properties on EGFR-Mutant Cells," *Cancer Prev Res* 1(3):201-207, 2008.
Zhou et al., "Internalizing Cancer Antibodies from Phage Libraries Selected on Tumor Cells and Yeast-Displayed Tumor Antigens," *J. Mol. Biol.*, vol. 404:88-99, 2010.
Friedrich et al., "Spheroid-based drug screen: considerations and practical approach," *Nature Protocols*, 4(3): 309-324, 2009.

\* cited by examiner

Phase contrast

| Non-adherent | Adherent |
|---|---|
|  |  |

| Cell line | Cell count per inoculation site | | |
|---|---|---|---|
| | 1,000 | 100 | 10 |
| PLR59 | 6/6 | 6/6 | 6/6 |
| PLR123 | 6/6 | 6/6 | 6/6 |

FIG. 31

PLR123

From non-adherent to adherent

From adherent to non-adherent

Scale bar: 10 μm

| Organ | Frequency of tumor formation |
|---|---|
| Lung | 5/5 |
| Liver | 4/5 |
| Kidney | 1/5 |
| Brain, pia mater | 1/5 |
| Lymph node, Armpit | 2/5 |
| Subcutaneous tissue | 5/5 |

FIG. 34

PLR59 Lgr5⁺ CSC in spheroid culture

PLR123 Lgr5⁺ CSC in spheroid culture

FIG. 50A
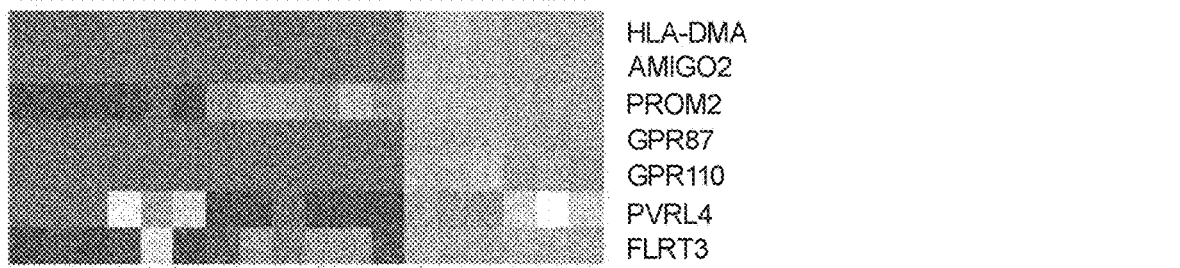
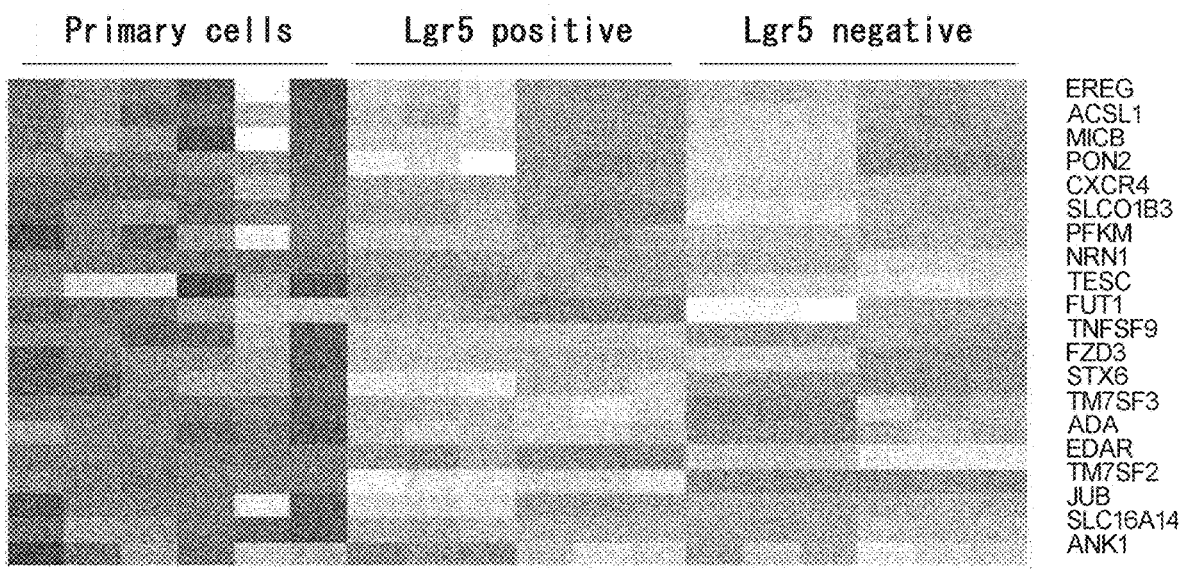
FIG. 50B

CANCER STEM CELL-SPECIFIC MOLECULE

CROSS REFERENCE TO RELATED APPLICATIONS

This is continuation of U.S. application Ser. No. 15/042,548, filed Feb. 12, 2016, which is a continuation of U.S. application Ser. No. 14/354,517, filed Apr. 25, 2014, now abandoned, which is the U.S. national stage of PCT Application No. PCT/JP2012/077714, filed Oct. 26, 2012, which claims the benefit of Japanese Patent Application No. 2011-237438, filed Oct. 28, 2011, and Japanese Patent Application No. 2012-091142, filed Apr. 12, 2012.

INCORPORATION OF ELECTRONIC SEQUENCE LISTING

The Sequence Listing is submitted as an ASCII text file, created on Jun. 1, 2020, 30.4 KB, which is incorporated by reference herein.

TECHNICAL FIELD

The present invention relates to cell surface molecules specific to Lgr5-positive cancer stem cells with a high proliferative potential or Lgr5-negative cancer stem cells with a low proliferative potential; and pharmaceutical compositions that comprise as an active ingredient an antibody against such a cell surface molecule. The present invention also relates to reagents for detecting cancer stem cells and methods for selecting cancer patients, which use an antibody described above.

BACKGROUND

Cancer stem cells (CSCs) are considered to be the origins of cancer. The reason is that these cells have the ability to self-renew and differentiate to form a tumor hierarchy (Non-patent Document 1). Furthermore, CSCs can migrate and be tolerant to anti-cancer drug therapy (Non-patent Document 1). Since CSCs are believed to be a rare subset in tumors, there have been numerous efforts to characterize them based on cell surface markers and tumor-initiating activity in xenograft transplantations. CSCs have been reported in several types of cancer, including acute myelocytic leukemia (AML) (Non-patent Documents 2 and 3), breast cancer (Non-patent Document 4), glioma (Non-patent Document 5), head and neck cancer (Non-patent Document 6), pancreatic cancer (Non-patent Documents 7 and 8), lung cancer (Non-patent Document 9), prostatic cancer (Non-patent Documents 10 and 11), mesenchymal neoplasm (Non-patent Document 12), and melanoma (Non-patent Documents 13 and 14). Earlier studies of O'Brien et al. (Non-patent Document 15) and Ricci-Vitiani et al. (Non-patent Document 16) reported that CD133 served as a CSC marker for colorectal cancer. Thereafter, different research groups have reported other markers: CD44, EpCAM, CD166 (Non-patent Document 17), and ALDH (Non-patent Documents 18 and 19). Recently, Pang et al. demonstrated that CD26 serves as a marker for a CSC subpopulation with metastatic capacity (Non-patent Document 20).

To isolate CSCs, most studies have employed a cell selection approach using in combination CSC markers such as $EpCAM^{high}/CD44^+/CD166^+$ (Non-patent Document 17), $CD133^+/CD44^+$ (Non-patent 21), $CD44^{high}/ALDH^+$ (Non-patent Document 18), and $ALDH1^+/CD133^+$ (Non-patent Document 19). In vitro spheroid (cell mass) cultures and direct cancer cell xenograft transplantation to immunodeficient mice have also been used to enrich CSCs (Non-patent Document 22). However, there was a necessity to prepare a large number of cancer stem cells with a high purity for further understanding the properties of CSCs.

One challenge in isolating CSCs arises from the phenotypic heterogeneity and/or instability of these cells (Non-patent Document 29). Three-dimensional spheroid cultures are often used as a CSC source. Spheroid cultures are applicable directly to tumor cells of clinically resected specimens and enable maintenance of heterogeneous CSC populations, and can have certain potential advantages compared to xenograft transplantations. Due to the heterogeneity, however, results of biochemical analyses often show complicated CSC characteristics. CSC selection using antibodies against cell surface marker proteins is commonly used to isolate CSCs, but the number and purity of cells obtained by this method is limited. On the other hand, phenotypes from xenografts remain stable even after frequent passages, and using xenografts as a source of CSCs is also a common approach. However, there is an argument that xenograft passages in mice only select cells viable in mice and result in elimination of cells that are hardly affected by such an environment. It goes without saying that CSCs in xenograft tumors reflect the characteristics of original CSCs, as long as they maintain the self-renewability and lineage differentiation capacity of the original tumor.

Leucine-rich repeat-containing G-protein-coupled receptor 5 (Lgr5) was originally identified as an orphan G-protein-coupled receptor of the glycoprotein hormone receptor family (Non-patent Documents 23 and 24) and was demonstrated to be a Wnt target gene whose expression is restricted to the crypt (Non-patent Document 25). The discovery that Lgr5-positive columnar cells can regenerate all epithelial lineages (Non-patent Document 25) and that a single Lgr5-positive cell can form crypt-villus organoids in vitro without a mesenchymal niche (Non-patent Document 26), conclusively proves that Lgr5-positive cells are stem cells in the normal large intestine. It has also been reported that Lgr5-positive cells form adenomas in the absence of Apc (Non-patent Document 27) and Lgr5 is expressed in colorectal cancer cell lines (Non-patent Document 25). When considered together, the findings described above suggest that Lgr5-positive cells are an origin of colorectal cancer (Non-patent Document 25). It has been proven that, as in stem cells of the normal large intestine, Wnt activity is essential for in vitro and in vivo proliferation of CSCs and that exogenous HGF enhances Wnt activity (Non-patent Document 28).

Lgr5 was identified as a marker for normal large intestine stem cells, and has been demonstrated to serve as a marker for origins of colorectal cancer (Patent Document 1 and Non-patent Document 30). Furthermore, Lgr5 was reported to be a protein that is over-expressed in colorectal cancer stem cells (Patent Document 2). The biological role of Lgr5 in the development of large intestine cancer remains poorly understood.

To date, various anti-cancer drugs and cancer therapeutic methods have been developed, but there are still issues to be solved, such as poor effectiveness, adverse effects, or being effective in only a limited number of patients. In recent years, therapeutic methods for targeting cancer stem cells have drawn attention, but their effectiveness and adverse effects remain poorly understood (Non-patent Document 31).

PRIOR ART DOCUMENTS

Patent Documents

Patent Document 1: US20100275280
Patent Document 2: WO09/005809

Non-Patent Documents

Non-patent Document 1: Reya T, Morrison S J, Clarke M F, Weissman I L (2001) Stem cells, cancer, and cancer stem cells. Nature 414:105-111.
Non-patent Document 2: Bonnet D, Dick J E (1997) Human acute myeloid leukemia is organized as a hierarchy that originates from a primitive hematopoietic cell. Nat Med 3:730-737.
Non-patent Document 3: Lapidot T, et al. (1994) A cell initiating human acute myeloid leukaemia after transplantation into SCID mice. Nature 367:645-648.
Non-patent Document 4: Al-Hajj M, Wicha M S, Benito-Hernandez A, Morrison S J, Clarke M F (2003) Prospective identification of tumorigenic breast cancer cells. Proc Natl Acad Sci USA 100:3983-3988.
Non-patent Document 5: Singh S K, et al. (2004) Identification of human brain tumour initiating cells. Nature 432:396-401.
Non-patent Document 6: Prince M E, et al. (2007) Identification of a subpopulation of cells with cancer stem cell properties in head and neck squamous cell carcinoma. Proc Natl Acad Sci USA 104:973-978.
Non-patent Document 7: Hermann P C, et al. (2007) Distinct populations of cancer stem cells determine tumor growth and metastatic activity in human pancreatic cancer. Cell Stem Cell 1: 313-323.
Non-patent Document 8: Li C, et al. (2007) Identification of pancreatic cancer stem cells. Cancer Res 67:1030-1037.
Non-patent Document 9: Eramo A, et al. (2008) Identification and expansion of the tumorigenic lung cancer stem cell population. Cell Death Differ 15:504-514.
Non-patent Document 10: Collins A T, Berry P A, Hyde C, Stower M J, Maitland N J (2005) Prospective identification of tumorigenic prostate cancer stem cells. Cancer Res 65:10946-10951.
Non-patent Document 11: Patrawala L, et al. (2006) Highly purified CD44+ prostate cancer cells from xenograft human tumors are enriched in tumorigenic and metastatic progenitor cells. Oncogene 25:1696-1708.
Non-patent Document 12: Wu C, et al. (2007) Side population cells isolated from mesenchymal neoplasms have tumor initiating potential. Cancer Res 1:8216-8222.
Non-patent Document 13: Schatton T, et al. (2008) Identification of cells initiating human melanomas. Nature 451:345-349.
Non-patent Document 14: Boiko A D, et al. (2010) Human melanoma-initiating cells express neural crest nerve growth factor receptor CD271. Nature 446:133-137.
Non-patent Document 15: O'Brien C A, Pollett A, Gallinger S, Dick J E (2007) A human colon cancer cell capable of initiating tumour growth in immunodeficient mice. Nature 445:106-110.
Non-patent Document 16: Ricci-Vitiani L, et al. (2007) Identification and expansion of human colon-cancer-initiating cells. Nature 445:111-115
Non-patent Document 17: Dalerba P, et al. (2007) Phenotypic characterization of human colorectal cancer stem cells. Proc Natl Acad Sci USA 104:10158-10163.
Non-patent Document 18: Chu P, et al. (2009) Characterization of a subpopulation of colon cancer cells with stem cell-like properties. Int J Cancer 124:1312-1321.
Non-patent Document 19: Huang E H, et al. (2009) Aldehyde dehydrogenase 1 is a marker for normal and malignant human colonic stem cells (S C) and tracks S C overpopulation during colon tumorigenesis. Cancer Res 69:3382-3389.
Non-patent Document 20: Pang R, et al. (2010) A subpopulation of CD26+ cancer stem cells with metastatic capacity in human colorectal cancer. Cell Stem Cell 6:603-615.
Non-patent Document 21: Haraguchi N, et al. (2008) CD133+CD44+ population efficiently enriches colon cancer initiating cells. Ann Surg Oncol 15:2927-2933.
Non-patent Document 22: Ishizawa K, et al. (2010) Tumor-initiating cells are rare in many human tumors. Cell Stem Cell 7:279-282.
Non-patent Document 23: McDonald T, et al. (1998) Identification and cloning of an orphan G protein-coupled receptor of the glycoprotein hormone receptor subfamily. Biochem Biophys Res Commun 247:266-270.
Non-patent Document 24: Hsu S Y, Liang S G, Hsueh A J (1998) Characterization of two LGR genes homologous to gonadotropin and thyrotropin receptors with extracellular leucine-rich repeats and a G protein-coupled, seven-transmembrane region. Mol Endcrinol 12:1830-1845.
Non-patent Document 25: Barker N, et al. (2007) Identification of stem cells in small intestine and colon by marker gene Lgr5. Nature 449:1003-1007.
Non-patent Document 26: Sato T, et al. (2009) Single Lgr5 stem cells build crypt-villus structures in vitro without a mesenchymal niche. Nature 459:262-265.
Non-patent Document 27: Barker N, et al. (2009) Crypt stem cells as the cells-of-origin of intestinal cancer. Nature 457:608-611.
Non-patent Document 28: Vermeulen L, et al. (2010) Wnt activity defines colon cancer stem cells and is regulated by the microenvironment. Nat Cell Biol 12:468-476.
Non-patent Document 29: Clevers H (2011) The cancer stem cell: premises, promises and challenges. Nat Med 17:313-319.
Non-patent Document 30: Barker N, et al. (2007) Identification of stem cells in small intestine and colon by marker gene Lgr5. Nature 449:1003-1007.
Non-patent Document 31: Park C Y, et al. (2009) Cancer stem cell-directed therapies:recent data from the laboratory and clinic. Mol Ther 17(2):219-230.

SUMMARY OF THE INVENTION

Problems to be Solved by the Invention

The present invention was achieved in view of the circumstances described above. The present invention isolates two types of cancer stem cell populations, which are substantially homogeneous and characterized with Lgr5, a cell surface marker, and identifies cell membrane molecules expressed specifically in the cancer stem cells. An objective of the present invention is to provide agents for treating cancer which use antibodies to those cell membrane molecules. Another objective of the present invention is to provide reagents for detecting cancer stem cells, methods for diagnosing and selecting cancer patients, which use antibodies to cell membrane molecules expressed specifically in cancer stem cells.

Means for Solving the Problems

In order to prove the stem cell theory that can explain the mechanism of oncogenesis, maximum efforts have been made to identify, isolate, and characterize cancer stem cells (CSCs). However, obtaining highly pure CSCs in an amount sufficient to characterize them remained difficult. It was therefore also difficult to identify cell membrane molecules specifically expressed on cancer stem cells. The present inventors conducted dedicated studies to achieve the above-described objectives.

To isolate large intestine CSCs from human colorectal cancer xenografts maintained in NOG mice, the present inventors established, for the first time, a method for preparing a large quantity of highly pure large intestine CSCs using an in vitro monolayer culture (also simply referred to as adherent culture) with serum-free stem cell media. Specifically, the present inventors demonstrated that a large number of large intestine CSCs can be obtained with high purity by performing an adherent culture of isolated cells derived from moderately-differentiated human colorectal cancer xenografts maintained in NOD/Shi-scid, IL-2Rγ null (NOG) mice. Under these conditions, only large intestine CSCs can grow, survive, and expand, and thus, the present inventors were able to obtain substantially homogeneous large intestine CSCs with high purity. When passaged by adherent culture using serum-free stem cell media, large intestine CSCs prepared by the above method were maintained stably without phenotypic alterations over a month or more. The cells expressed various previously-reported colorectal cancer stem cell markers (CD133, CD44, EpCAM, CD166, CD24, CD26, and CD29), and exhibited tumor-initiating activity at a rate of almost 100%. Furthermore, the cells formed tumors having the same histopathological features (hierarchical organization) as the original primary tumor. The cells are also characterized by being highly proliferative under adherent culture conditions and positive for Lgr5, a cell surface marker. Furthermore, the high proliferative Lgr5-positive cancer stem cells, when administered via the caudal vein to mice, formed tumor masses in organs such as lung and liver, which indicates that the cells play an essential role in cancer metastasis.

On the other hand, low proliferative Lgr5-negative cancer stem cells were isolated by treating with anti-cancer agents such as irinotecan and 5-FU cancer stem cells that are positive for cell surface marker Lgr5 and highly proliferative under adherent culture conditions. Furthermore, the isolated low proliferative Lgr5-negative cancer stem cells were revealed to be converted to high proliferative Lgr5-positive cancer stem cells by re-culturing under adherent culture conditions. This demonstrates that high proliferative Lgr5-positive cancer stem cells and low proliferative Lgr5-negative cancer stem cells are interconvertible to each other and thus have an intrinsic interchangeability. Due to this ability, actively proliferating Lgr5-positive large intestine CSCs, when cultured under an altered culture condition or in the presence of an anti-cancer drug, were converted into the Lgr5-negative quiescent state. Alternatively, Lgr5-negative CSCs, when isolated and then cultured again under an adherent culture condition, were converted to Lgr5-positive CSCs that proliferate actively. These cells also exhibited tumor-initiating activity at a rate of almost 100%. Furthermore, the high proliferative Lgr5-positive cancer stem cells, when inoculated via the caudal vein to mice, formed tumor masses in organs such as lung and liver, which indicates that the cells play an essential role in cancer metastasis.

The interconversion of CSCs between the two types of conditions due to environmental changes may be helpful in explaining drug resistance and recurrence of cancer. The involvement of Lgr5-negative CSCs in oncogenesis can be correlated with the basic nature of stem cells. A plausible hypothesis is that CSCs can use intrinsic means to convert into a different subset of a cell population under environmental changes such as by aggressive treatment with anti-cancer agents. CSCs, when exposed to stress such as anti-cancer drugs or changes in the culturing environment, convert themselves to low proliferative Lgr5-negative CSCs in order to survive avoiding the stress. Once the stress is removed, the cells can change again into high proliferative Lgr5-positive CSCs and start to proliferate. This implies that CSCs have a self-defense ability based on an intrinsic mechanism to adapt to new environments (FIG. 36).

The above-described research findings by the present inventors demonstrate that high proliferative Lgr5-positive and low proliferative Lgr5-negative cancer stem cells both play important roles in cancer development, formation, metastasis, recurrence, drug resistance, etc., and can be major target cells in the development of anti-cancer agents. In particular, high proliferative Lgr5-positive cancer stem cells are considered to be involved in oncogenesis and metastasis while low proliferative Lgr5-negative cancer stem cells are thought to be involved in cancer recurrence. Thus, if cell surface molecules that are expressed specifically on high proliferative Lgr5-positive cancer stem cells and low proliferative Lgr5-negative cancer stem cells can be identified, such molecules would enable therapies using antibodies and discovery of new anti-cancer agents and reagents for detecting cancer stem cells.

Specifically, the present invention provides:
[1] a pharmaceutical composition comprising as an active ingredient at least one antibody that binds to a protein of SEQ ID NOs: 1 to 3 and 5 to 9;
[2] the pharmaceutical composition of [1], which is an anti-cancer agent;
[3] the pharmaceutical composition of [2], which is an agent for inhibiting cancer recurrence;
[4] the pharmaceutical composition of [2], which is an agent for inhibiting cancer metastasis or an agent for postoperative adjuvant therapy;
[5] the pharmaceutical composition of [4], which is an agent for inhibiting cancer metastasis or an agent for postoperative adjuvant therapy against Lgr5-positive cancer, which comprises as an active ingredient at least one antibody that binds to a protein of SEQ ID NOs: 1 to 3 and 5 to 7;
[6] the pharmaceutical composition of [2], which is a therapeutic agent against drug-resistant cancer;
[7] the pharmaceutical composition of [6], which is a therapeutic agent against Lgr5-negative cancer, and which comprises as an active ingredient at least one antibody that binds to a protein of SEQ ID NOs: 1 to 3 and 5 to 9;
[8] the pharmaceutical composition of [7] wherein the Lgr5-negative cancer is a drug-resistant cancer;
[9] the pharmaceutical composition of any one of [2] to [8], which is an agent for inhibiting cancer stem cell proliferation or an agent for disrupting cancer stem cells;
[10] the pharmaceutical composition of any one of [2] to [9], wherein the cancer is a solid cancer;
[11] the pharmaceutical composition of any one of [2] to [10], wherein the cancer is a digestive system cancer;
[12] the pharmaceutical composition of any one of [2] to [11], wherein the cancer is a colorectal cancer;
[13] the pharmaceutical composition of any one of [1] to [12], wherein the antibody is a monoclonal antibody;

[14] the pharmaceutical composition of any one of [1] to [13], wherein the antibody is a chimeric antibody, a humanized antibody, or a human antibody;
[15] the pharmaceutical composition of any one of [1] to [14], wherein the antibody is an antibody fragment;
[16] the pharmaceutical composition of [15], wherein the antibody is linked to a cytotoxic substance or a proliferation inhibitor;
[17] the pharmaceutical composition of any one of [1] to [14], wherein the antibody has a cytotoxic activity;
[18] the pharmaceutical composition of [17], wherein the cytotoxic activity is ADCC;
[19] the pharmaceutical composition of [17] or [18], which comprises an antibody with modified sugar chains whose sugar chain composition has been altered to increase the ratio of defucosylated antibody or to increase the ratio of antibody attached with bisecting N-acetylglucosamine;
[20] the pharmaceutical composition of [17], wherein the cytotoxic activity is CDC;
[21] the pharmaceutical composition of any one of [1] to [20], wherein the antibody has a neutralizing activity;
[22] the pharmaceutical composition of any one of [2] to [21], or a pharmaceutical composition comprising the polypeptide of SEQ ID NO: 4 or a polypeptide resulting from addition, deletion, and/or substitution of one or several amino acids in the polypeptide of SEQ ID NO: 4, which is to be used in combination with a chemotherapeutic agent simultaneously or after chemotherapeutic treatment;
[23] a reagent for detecting a cancer stem cell, which comprises as an active ingredient at least one antibody that binds to a protein of SEQ ID NOs: 1 to 3 and 5 to 9;
[24] the reagent of [23], wherein it is used in detecting an Lgr5-positive cancer stem cell, and wherein the antibody is at least one antibody that binds to a protein of SEQ ID NOs: 1 to 3 and 5 to 7;
[25] the reagent of [23], wherein it is used in detecting an Lgr5-negative cancer stem cell, and wherein the antibody is at least one antibody that binds to a protein of SEQ ID NOs: 1 to 3 and 5 to 9;
[26] a method for diagnosing cancer or selecting a cancer patient (a method for testing and/or selecting cancer), wherein the method comprises, by using at least one antibody that binds to a protein of SEQ ID NOs: 1 to 3 and 5 to 9, detecting the presence of at least one of the proteins in a sample isolated from a cancer patient;
[27] the method of [26], wherein it is used in diagnosing Lgr5-positive cancer or selecting a cancer patient, and wherein the antibody is at least one antibody that binds to a protein of SEQ ID NOs: 1 to 3 and 5 to 6;
[28] the method of [26], wherein it is used in diagnosing Lgr5-negative cancer or selecting a cancer patient, and wherein the antibody is at least one antibody that binds to a protein of SEQ ID NOs: 1 to 3 and 5 to 9;
[29] a method for assessing the effectiveness of the pharmaceutical composition of any one of [1] to [22], wherein the method comprises detecting the presence of one or more of the proteins of SEQ ID NOs: 1 to 3 and 5 to 9 and/or polynucleotides encoding the proteins in a sample isolated from a subject administered with the pharmaceutical composition;
[30] the method of [29], which uses at least one antibody that binds to a protein of SEQ ID NOs: 1 to 3 and 5 to 9; and
[31] the method of [29], which uses polynucleotides encoding the proteins of SEQ ID NOs: 1 to 3 and 5 to 9 and/or complementary strands thereof.

The present invention also provides:
[A1] a method for treating cancer, comprising administering to a subject at least one antibody that binds to a protein of SEQ ID NOs: 1 to 3 and 5 to 9;
[A2] at least one antibody that binds to a protein of SEQ ID NOs: 1 to 3 and 5 to 9 for use in the treatment of cancer;
[A3] use of at least one antibody that binds to a protein of SEQ ID NOs: 1 to 3 and 5 to 9 for producing an anti-cancer agent; and
[A4] a process for manufacturing an anti-cancer agent, which comprises the step of using at least one antibody that binds to a protein of SEQ ID NOs: 1 to 3 and 5 to 9.

In a non-limiting embodiment of the present invention, treatment of cancer includes inhibition of cancer recurrence, inhibition of cancer metastasis, postoperative adjuvant therapy, treatment of drug-resistant cancer, inhibition of cancer stem cell proliferation, and disruption of cancer stem cells; and anti-cancer agents include agents for inhibiting cancer recurrence, agents for inhibiting cancer metastasis, agents for postoperative adjuvant therapy, agents for treating drug-resistant cancer, agents for inhibiting cancer stem cell proliferation, and agents for disrupting cancer stem cells.

Furthermore, the present invention provides:
[B1] a reagent for detecting the presence of one or more of the proteins of SEQ ID NOs: 1 to 3 and 5 to 9 and/or polynucleotides encoding the proteins, preferably, a reagent for detecting a cancer stem cell, a reagent for cancer diagnosis, a reagent for selecting a cancer patient, or a reagent for testing the effectiveness of the pharmaceutical compositions of [1] to [22], which contains at least one antibody that binds to a protein of SEQ ID NOs: 1 to 3 and 5 to 9, or a portion of a polynucleotide encoding the protein of SEQ ID NOs: 1 to 3 and 5 to 9 and/or the complementary strand thereof;
[B2] a method for detecting a cancer stem cell, diagnosing cancer, selecting a cancer patient, or testing the effectiveness of the pharmaceutical compositions of [1] to [22], which comprises detecting the presence of one or more of the proteins of SEQ ID NOs: 1 to 3 and 5 to 9 and/or polynucleotides encoding the proteins in a sample isolated from a cancer patient using, preferably, at least one antibody that binds to a protein of SEQ ID NOs: 1 to 3 and 5 to 9, or a portion of a polynucleotide encoding the protein of SEQ ID NOs: 1 to 3 and 5 to 9 and/or the complementary strand thereof;
[B3] a reagent for detecting the presence of one or more of the proteins of SEQ ID NOs: 1 to 3 and 5 to 9 and/or polynucleotides encoding the proteins, preferably at least one antibody that binds to a protein of SEQ ID NOs: 1 to 3 and 5 to 9, or a portion of a polynucleotide encoding the protein of SEQ ID NOs: 1 to 3 and 5 to 9 and/or the complementary strand thereof, which is for use in detecting a cancer stem cell, diagnosing cancer, selecting a cancer patient, or testing the effectiveness of pharmaceutical compositions of [1] to [22];
[B4] use of a reagent for detecting the presence of one or more of the proteins of SEQ ID NOs: 1 to 3 and 5 to 9 and/or polynucleotides encoding the proteins, preferably at least one antibody that binds to a protein of SEQ ID NOs: 1 to 3 and 5 to 9, or a portion of a polynucleotide encoding the protein of SEQ ID NOs: 1 to 3 and 5 to 9 and/or the complementary strand thereof, which is for producing a reagent for detecting a cancer stem cell, a reagent for diagnosing cancer, a reagent for selecting a cancer patient, or a reagent for testing the effectiveness of the pharmaceutical compositions of [1] to [22]; and

[B5] a process for producing a reagent for detecting a cancer stem cell, a reagent for diagnosing cancer, a reagent for selecting a cancer patient, or a reagent for testing the effectiveness of the pharmaceutical compositions of [1] to [22], which comprises using a reagent for detecting the presence of one or more of the proteins of SEQ ID NOs: 1 to 3 and 5 to 9 and/or polynucleotides encoding the proteins, preferably at least one antibody that binds to a protein of SEQ ID NOs: 1 to 3 and 5 to 9, or a portion of a polynucleotide encoding the protein of SEQ ID NOs: 1 to 3 and 5 to 9 and/or the complementary strand thereof.

BRIEF DESCRIPTION OF THE DRAWINGS

FIG. 31 After culturing for one month, adherent CSCs derived from xenografts PLR59 and PLR123 were analyzed by flow cytometry (FIG. 30), and injected to NOG mice. The indicated numbers of adherent CSCs were injected subcutaneously in the lateral abdomen of NOG mice to assess the tumor-initiating activity in NOG mice. This figure is a diagram showing the result of assessment of tumorigenesis 47 days after inoculation. Even subcutaneous injection of 10 adherent CSCs allowed tumor formation at all of the injection sites. The tumors were highly similar in histopathological morphology to the original tumors.

FIG. 34 is a diagram showing the tumor-initiating activity of adherent CSCs in various organs. $5\times10^5$ adherent CSCs from PLR123 were injected to the tail vein (n=5). The tumor formation frequency on day 40 after administration is shown for various organs.

FIGS. 41A, B, and C show stained images of the cells for 0, 48, and 72 hours, respectively. Scale bar represents 20 μm.

FIGS. 42A and 42C show images after a single division, while FIGS. 42B and 42D show images after second or third division.

FIGS. 50A-50B show diagrams depicting heat maps for (FIG. 50A) seven genes the expression of which was significantly up-regulated in Lgr5-negative cells as compared to Lgr5-positive cells and for (FIG. 50B) 20 genes the expression levels of which were elevated in Lgr5-positive and Lgr5-negative cells as compared to primary cells derived from xenograft animals. RNAs were prepared from Lgr5-positive and -negative CSCs derived from PLR59 and PLR123, and primary cells isolated from xenograft animals. RNAs were analyzed using Affymetrix U133.

In FIG. 58A, the first row shows histological staining (HE) of tumors from xenograft models prepared by intravenously injecting PLR123-derived Lgr5-positive cells to NOG mice, and the second row shows immunohistochemical staining using EREG antibody. Arrows in the panels indicate EREG-expressing cells at nodules (second row) and corresponding HE stain images (first row). FIGS. 58B and 58C show the number of tumors formed in the lungs of SCID-beige mice intravenously injected with Lgr5-positive cells derived from PLR123 xenograft models. In the EREG antibody administration group, EREG antibody was administered once a week for five times from three days after injection of Lgr5-positive cells. The number of tumor nodules per animal, found on lung thin sections, are shown in FIG. 58B. Each symbol (circle) indicates the number of tumor nodules in an animal in a group tested (FIG. 58B). The number of tumor nodules categorized by size in the antibody administration group and control group are shown in FIG. 58C. White columns indicate tumors that are smaller than 100 μm; gray columns indicate tumors of 100 to 200 μm; and black columns indicate tumors larger than 200 μm (FIG. 58C). Tissue staining (HE stain) of tumors in the EREG antibody administration and non-administration groups is shown in FIG. 58D. Scale bar represents 200 μm.

FIGS. 73A and 73B show the expression levels of CK20 in PLR59 and PLR123, respectively.

MODE FOR CARRYING OUT THE INVENTION

Figure 1:
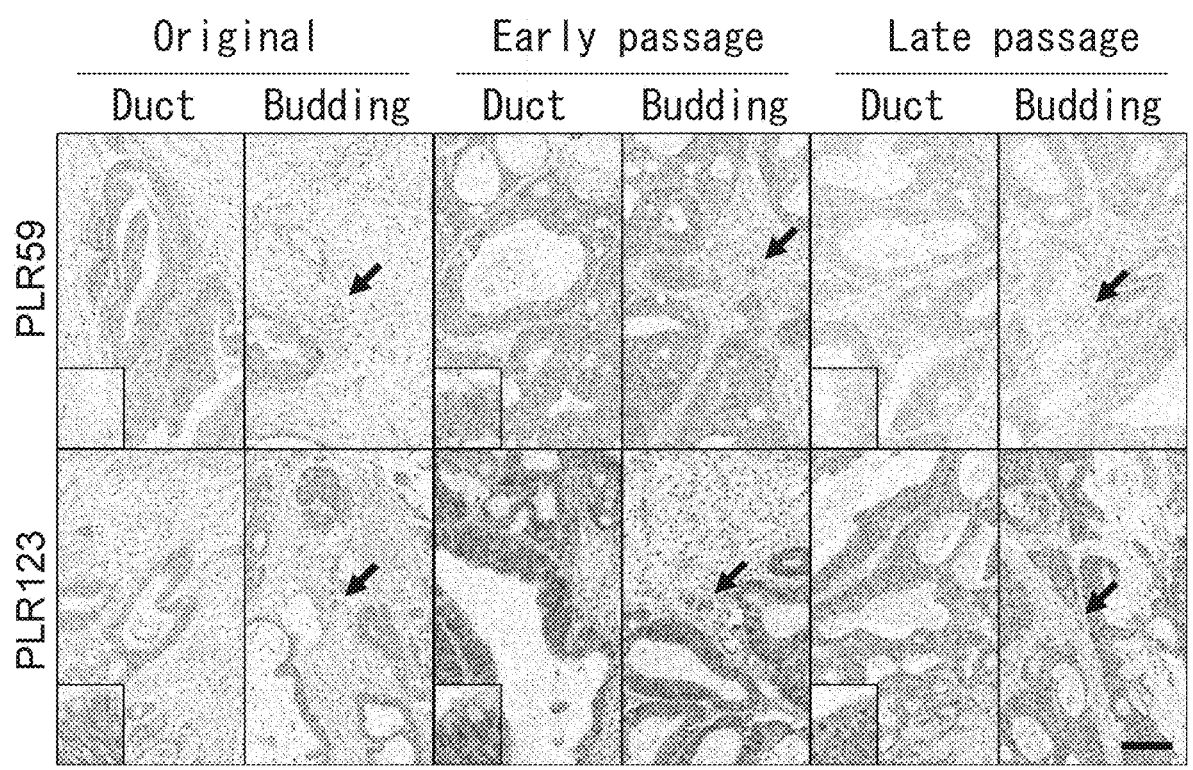
FIG. 1 shows photographs depicting histological images (HE stain) of colorectal cancer xenografts PLR59 and PLR123 derived from moderately-differentiated colorectal cancer. Even after 15 passages, cells derived from xenografts PLR59 and PLR123 formed tumors with a morphology (hierarchical organization) very similar to the original tumor, and had budding clusters (arrow) and ductal structures with goblet cells (inset). "Original" indicates tumors obtained by surgical resection; "Early passage" indicates xenografts PLR59 and PLR123 after 4 passages in NOG mice; and "Late passage" indicates xenograft PLR59 after 15 passages and PLR123 after 19 passages in MOG mice. Scale bar represents 100 µm.

The present invention relates to cell surface molecules that are specifically expressed on cancer stem cells, and pharmaceutical compositions (anti-cancer agents, etc.) and reagents for detecting cancer stem cells, which use antibodies against the cell surface molecules.

Herein, "cancer" refers to the physiological condition in mammals, which is typically characterized by unregulated cell growth, or such a physiological condition. Herein, cancer types are not particularly limited, and include those listed below. Carcinomas (epithelial cancers) include pancreatic cancer, prostatic cancer, breast cancer, skin cancer, cancers of the digestive tract, lung cancer, hepatocellular carcinoma, cervical cancer, uterine cancer, ovary cancer, fallopian tube cancer, vaginal cancer, liver cancer, bile duct cancer, bladder cancer, ureter cancer, thyroid cancer, adrenal cancer, kidney cancer, and cancers of other glandular tissues. Sarcomas (non-epithelial tumors) include liposarcoma, leiomyosarcoma, rhabdomyosarcoma, synovial sarcoma, angiosarcoma, fibrosarcoma, malignant peripheral nerve sheath tumor, gastrointestinal stromal tumor, desmoid tumor, Ewing's sarcoma, osteosarcoma, chondrosarcoma, leukemia, lymphoma, myeloma, tumors of other parenchymal organs, for example melanoma and brain tumor (Kumar V, Abbas A K, Fausio N. Robbins and Cotran Pathologic Basis of Disease. 7th Ed. Unit I: General Pathology, 7: Neoplasia, Biology of tumor growth: Benign and malignant neoplasms. 269-342, 2005).

Herein, "tumor" refers to arbitrary benign (non-cancerous) and malignant (cancerous) tissue masses, including pre-cancerous lesions, which result from overgrowth or overexpansion of cells.

Herein, cancer stem cell (CSC) refers to cells having the abilities described in (i) and/or (ii) below.
(i) The ability to self-renew. The self-renewal ability refers to the ability of either or both of the divided daughter cells to produce cells which maintain the same capacity and the degree of differentiation as the parental cell in terms of cell lineage.
(ii) The ability to differentiate into various types of cancer cells that constitute a cancer cell mass.
Like normal stem cells, various types of cancer cells differentiated from cancer stem cells generate a hierarchical organization with cancer stem cells at the top in terms of cell lineage. Various types of cancer cells are generated in a sequential manner from cancer stem cells. This results in the formation of a cancer cell mass that exhibits a variety of features.

Cancer stem cell refers to a cancer cell that has the ability to form cancers as well as, like normal stem cell, pluripotency and self-renewal ability. Cancer stem cells generate a hierarchical organization with cancer stem cells at the top. Various types of cancer cells are generated in a sequential manner from cancer stem cells. This results in the formation of a cancer cell mass that exhibits a variety of features.

Cancer cell mass refers to, not a group of individual cells, but a mass formed by the adhesion of cells etc. as in human tumor tissue, which is built with cancer cells, and other cells such as stromal cells and blood cells, extracellular matrix such as collagen and laminin, and so on.

The origin of cancer stem cells, which are the target in therapy using pharmaceutical compositions of the present invention, is not particularly limited; it is possible to use cancer stem cells derived from mammals such as humans, monkeys, chimpanzees, dogs, bovines, pigs, rabbits, rats, and mice. However, cancer stem cells derived from humans are preferred, and those derived from human tumor tissues are more preferred.

Cancer stem cells to be detected using the present invention are preferably those which reconstitute the hierarchical structure of cancer tissues. For example, cancer cell lines are prepared by grafting cancer tissues from which the detected cancer stem cells have been collected, into, preferably, nonhuman animals, and passaging them in such animals, and one can test whether the established cancer cell lines reconstitute the hierarchical structure of the cancer tissues. One can test whether the hierarchical structure of cancer tissues is reproduced by NOG-established cancer cell lines prepared by grafting and passaging cancer tissues in nonhuman animals, more preferably immunodeficient animals, and still more preferably NOG mice which lack functional T cells, B cells, and natural killer cells.

Alternatively, cancer stem cells to be detected using the present invention can be a spheroid (cell mass) formed by spheroid culture. "Spheroid culture" means that cancer stem cells are inoculated in a culture vessel such as non-adherent or low-adherent cell culture flasks, plates, or dishes using a medium capable of culturing cancer stem cells, and then the cells are cultured under a three-dimensionally floating condition. A cell mass formed by this method is called "spheroid".

NOG-established cancer cell lines can be generated by a method known to those skilled in the art, for example, the method described in Fujii E. et al., Pathol Int. 2008; 58: 559-567. Human colorectal cancer, stomach cancer, lung cancer, breast cancer, pancreatic cancer, or the like is resected surgically. After mechanically mincing it with scissors, the cancer is grafted subcutaneously in NOG mice and passaged to establish cell lines. Even after passages, NOG-established cancer cell lines maintain the properties of the original human cancer tissues.

In the present invention, cancer stem cells can be selected by using cell markers. Cell markers used in the present invention include, for example, leucine-rich repeat-containing G-protein-coupled receptor 5 (Lgr5), CD133, CD44, EpCAM, CD166, CD24, CD26, and CD29.

The present invention relates to molecules expressed in cancer stem cells that are positive for the expression of the cell marker Lgr5, and are adherent and highly proliferative under serum-free culture conditions. Hereinafter, such cancer stem cells are also referred to as "high proliferative Lgr5-positive cancer stem cells".

The present invention also relates to molecules expressed in cancer stem cells that are negative for the expression of the cell marker Lgr5, and non-adherent and poorly proliferative under serum-free culture conditions. Hereinafter, such cancer stem cells are also referred to as "low proliferative Lgr5-negative cancer stem cells".

Any culture media or liquids can be used to culture cancer stem cells of the present invention as long as they are serum-free media and capable of culturing cancer stem cells. There is no particular limitation on the culture media or liquids. For example, it is possible to use conventional basal media or mixtures thereof that are supplemented with EGF, bFGF, hLIF, HGF, NGF, NSF-1, TGF β, TNFα, heparin, BSA, insulin, transferrin, putrescine, selenite, progesterone, hydrocortisone, D-(+)-glucose, sodium bicarbonate, HEPES, L-glutamine, or N-acetylcysteine. The concentration of EGF is not particularly limited; however, it ranges from 0.1 to 100 ng/ml, preferably from 0.5 to 50 ng/ml, and more preferably from 1 to 20 ng/ml. The concentration of bFGF is not particularly limited; however, it ranges from 0.1 to 100 ng/ml, preferably from 0.5 to 50 ng/ml, and more preferably from 1 to 20 ng/ml. The concentration of hLIF is not particularly limited; however, it ranges from 0.1 to 100 ng/ml, preferably from 0.5 to 50 ng/ml, and more preferably from 1 to 20 ng/ml. The concentration of HGF is not particularly limited; however, it ranges from 0.1 to 100 ng/ml, preferably from 1 to 50 ng/ml. The concentration of NGF is not particularly limited; however, it ranges from 0.1 to 100 ng/ml, preferably from 1 to 50 ng/ml. The concentration of NSF-1 is not particularly limited; however, it ranges from 0.1 to 100 ng/ml, preferably from 1 to 50 ng/ml. The concentration of TGFβ is not particularly limited; however, it ranges from 0.1 to 100 ng/ml, preferably from 1 to 50 ng/ml. The concentration of TNFα is not particularly limited; however, it ranges from 0.1 to 100 ng/ml, preferably from 1 to 50 ng/ml. The concentration of heparin is not particularly limited; however, it ranges from 10 ng/ml to 10 µg/ml, preferably from 2 to 5 µg/ml. The concentration of BSA is not particularly limited; however, it ranges from 0.1 to 10 mg/ml, preferably from 1 to 8 mg/ml. The concentration of insulin is not particularly limited; however, it ranges from 1 to 100 µg/ml, preferably from 10 to 50 µg/ml. The concentration of transferrin is not particularly limited; however, it ranges from 10 to 500 µg/ml, preferably from 50 to 200 µg/ml. The concentration of putrescine is not particularly limited; however, it ranges from 1 to 50 µg/ml, preferably from 10 to 20 µg/ml. The concentration of selenite is not particularly limited; however, it ranges from 1 to 50 nM, preferably from 20 to 40 nM. The concentration of progesterone is not particularly limited; however, it ranges from 1 to 50 nM, preferably from 10 to 30 nM. The concentration of hydrocortisone is not particularly limited; however, it ranges from 10 ng/ml to 10 µg/ml, preferably from 100 ng/ml to 1 µg/ml. The concentration of D-(+)-glucose is not particularly limited; however, it ranges from 1 to 20 mg/ml, preferably from 5 to 10 mg/ml. The concentration of sodium bicarbonate is not particularly limited; however, it ranges from 0.1 to 5 mg/ml, preferably from 0.5 to 2 mg/ml. The concentration of HEPES is not particularly limited; however, it ranges from 0.1 to 50 mM, preferably from 1 to 20 mM. The concentration of L-glutamine is not particularly limited; however, it ranges from 0.1 to 10 mM, preferably from 1 to 5 mM. The concentration of N-acetylcysteine is not particularly limited; however, it ranges from 1 to 200 µg/ml, preferably from 10 to 100 µg/ml. Known basal culture liquids, which are not particularly limited as long as they are suitable for culturing cancer cells from which cancer stem cells are derived, include, for example, DMEM/F12, DMEM, F10, F12, IMDM, EMEM, RPMI-1640, MEM, BME, Mocoy's 5A, and MCDB131. Of them, DMEM/F12 is preferred.

The most preferred stem cell media include DMEM/F12 medium supplemented with 20 ng/ml human EGF, 10 ng/ml human bFGF, 4 µg/ml heparin, 4 mg/ml BSA, 25 µg/ml human insulin, and 2.9 mg/ml glucose where each concentration a final concentration.

As described herein, high proliferative Lgr5-positive cancer stem cells have the properties of mesenchymal cells. Meanwhile, as described herein, low proliferative Lgr5-negative cancer stem cells have the properties of epithelial cells. Herein, "epithelial cells" refers to cells that constitute epithelial tissues in the living body.

In the present invention, the origin of cancer stem cells is not particularly limited; however, they are preferably derived from a solid cancer, more preferably a gastrointestinal cancer. Gastrointestinal cancers include, for example, esophageal cancer, stomach cancer, duodenal cancer, pancreatic cancer, bile duct cancer, gallbladder cancer, biliary tract cancer, colorectal cancer, colon cancer, and rectal cancer. A preferred gastrointestinal cancer is colorectal cancer.

Furthermore, in the present invention, cancer stem cells are preferably positive for one or more of the cell markers CD133, CD44, EpCAM, CD166, CD24, CD26, and CD29, more preferably positive for CD133, CD44, EpCAM, CD166, CD24, CD26, and CD29.

In addition, in the present invention, acetaldehyde dehydrogenase (ALDH) activity can be used as a cell marker. In the present invention, Lgr5-positive adherent cancer stem cells are positive for the ALDH activity cell marker, whereas Lgr5-negative cancer stem cells are negative for ALDH activity.

In the present invention, one or more of HLA-DMA, TMEM173, ZMAT3, and GPR110 can also be used as cell markers. Lgr5-positive adherent cancer stem cells are negative for any of the cell markers HLA-DMA, TMEM173, ZMAT3, and GPR110, while Lgr5-negative cancer stem cells are positive for any of the cell markers HLA-DMA, TMEM173, ZMAT3, and GPR110.

In the present invention, cancer stem cells preferably have the feature of reconstituting the hierarchical structure of cancer tissues.

Herein, "hierarchical structure" means that some of the unique and characteristic structures observed in a normal tissue are detected histopathologically in the structure of a tumor originated from the tissue. In general, highly-differentiated cancers reconstitute the hierarchical structure to a high degree. For example, lumen formation and mucous cells are observed in the case of tumors of glandular lumen-forming organs (stomach cancer, colorectal cancer, pancreatic cancer, liver cancer, bile duct cancer, breast cancer, lung adenocarcinoma, prostatic cancer, etc.). In the case of tumors that form squamous epithelial structures (squamous cell carcinoma of lung, skin, vaginal mucosa, etc.), layer structure formation, the tendency to keratosis, and such are observed in the epithelium. On the other hand, poorly-differentiated cancers insufficiently reconstitute the hierarchical structure, and they are said to be highly atypical (Kumar V, Abbas A K, Fausio N. Robbins and Cotran Pathologic Basis of Disease. 7th Ed. Unit I: General Pathology, 7: Neoplasia, Biology of tumor growth: Benign and malignant neoplasms. 272-281, 2005). Since the hierarchical structure is considered to be reconstituted as a result of various biological reactions, cancer stem cells that reconstitute it are thought to be highly useful.

"Reconstitution of the hierarchical structure" means that the unique and characteristic structure possessed by the original cancer stem cells is also observed even after isolation or induction of cancer stem cells.

Furthermore, in the present invention, cancer stem cells preferably have the ability of epithelial-mesenchymal transition (EMT). Herein, the ability of epithelial-mesenchymal transition means both that epithelial cells transition into mesenchymal cells by obtaining their characteristics, and that mesenchymal cells transition into epithelial cells by obtaining their characteristics. EMT does not occur in normal cells except during the process of embryogenesis. Epithelial cells, which are bound together tightly and exhibit polarity, change into mesenchymal cells that are bound together more loosely, exhibit a loss of polarity, and have the ability to move. These mesenchymal cells can spread into tissues around the primary tumor, and also separate from the tumor, invade blood and lymph vessels, and move to new locations where they divide and form additional tumors. Drug resistance, metastasis, or recurrence of cancer can be explained by such additional tumor formation.

Furthermore, the present invention provides pharmaceutical compositions comprising as an active ingredient an antibody that binds to a molecule expressed in a substantially homogeneous cancer stem cell population comprising the above cancer stem cells of the present invention. "Substantially homogeneous" means that, when immunodeficient animals are grafted with 1000 cells, 100 cells, or 10 cells and analyzed for the frequency of formation of cancer cell populations using Extreme Limiting Dilution Analysis (Hu Y & Smyth G K., J Immunol Methods. 2009 Aug. 15; 347(1-2): 70-8) utilizing, for example, the method described in Hu Y & Smyth G K., J Immunol Methods. 2009 Aug. 15; 347 (1-2):70-8 or Ishizawa K & Rasheed Z A. et al., Cell Stem Cell. 2010 Sep. 3; 7(3):279-82, the frequency of cancer stem cells is 1/20 or more, preferably 1/10 or more, more preferably 1/5 or more, even more preferably 1/3 or more, still more preferably 1/2 or more, and yet more preferably 1/1.

In the present invention, cancer stem cell populations can be prepared, for example, by culturing cells or a group of cells containing the cancer stem cells described herein.

Herein, "adherent culture" means that, after seeding cells into culture vessels for adherent culture, the adhered cells are cultured and passaged while non-adherent cells are removed. The cells grown to confluency are detached with Accutase and passaged into fresh adherent culture flasks, adherent culture plates, or adherent culture dishes for further culture. Culture vessels for adherent culture are not particularly limited as long as they are used for adherent culture. It is possible to appropriately select and use flasks for adherent culture or highly adherent flasks, plates for adherent culture or highly adherent plates, flat-bottomed plates for adherent culture or highly adherent flat-bottomed plates, dishes for adherent culture or highly adherent dishes, etc.

Media used for adherent culture are not particularly limited; however, it is preferable to use serum-free stem cell culture media.

Herein, "adherent" refers to the property of cells to adhere to culture vessels for adherent culture when they are cultured in the vessels.

Herein, "suspension culture" means that, after seeding cells into culture vessels for suspension culture, the floating cells are cultured and passaged while adherent cells are removed. The cells grown to confluency are passaged into fresh low adherent cell culture flasks, ultra-low adherent cell culture flasks, low adherent plates, ultra-low adherent plates, low adherent dishes, or ultra-low adherent dishes for further culture. Culture vessels for suspension culture are not particularly limited as long as they are used for suspension culture. It is possible to appropriately select and use low adherent cell culture flasks, ultra-low adherent cell culture flasks, low adherent plates, ultra-low adherent plates, low adherent dishes, ultra-low adherent dishes, etc.

Media used for suspension culture are not particularly limited; however, it is preferable to use serum-free stem cell culture media. A cell group containing cancer stem cells are preferably expanded before performing adherent or suspension culture.

Herein, "non-adherent" refers to the property of cells to be cultured in a floating state without adherence to culture vessels for suspension culture when the cells are cultured in the vessels.

"Expansion of a cell group" means, for example, proliferation by spheroid culture or grafting and passaging in nonhuman animals, but is not particularly limited thereto.

As described herein, for nonhuman animals, immunodeficient animals can be used for grafting since they are unlikely to have rejection reactions. Immunodeficient animals preferably used include nonhuman animals that lack functional T cells, for example, nude mice and nude rats, and nonhuman animals that lack both functional T and B cells, for example, SCID mice and NOD-SCID mice. It is more preferably to use mice that lack T, B, and NK cells and have excellent transplantability, including, for example, NOG mice.

Regarding the weekly age of nonhuman animals, for example, 4 to 100-week-old athymic nude mice, SCID mice, NOD-SCID mice, or NOG mice are preferably used. NOG mice can be prepared, for example, by the method described in WO 2002/043477, and are available from the Central Institute for Experimental Animals or the Jackson Laboratory (NSG mice).

Cells to be grafted may be any cells, including cell masses, tissue fragments, individually dispersed cells, cells cultured after isolation, and cells isolated from a different animal into which the cells have been grafted; however, dispersed cells are preferred. The number of grafted cells may be $10^6$ or less; however, it is acceptable to graft more cells.

With respect to the grafting site, subcutaneous grafting is preferred because the graft technique is simple. The grafting site is not particularly limited, and it is preferable to select an appropriate grafting site depending on the animal used. There is no particular limitation on the grafting operation of NOG-established cancer cell lines, and the cells can be grafted by conventional grafting operations.

Cancer stem cells or a cancer stem cell population can be prepared, for example, by collecting cancer tissues from patients and culturing the tissues in a serum-free stem cell culture medium under adherent or floating culture conditions. Alternatively, cancer tissues collected from patients can be spheroid-cultured, and then cultured in a serum-free stem cell culture medium under adherent or floating culture conditions to prepare cancer stem cells or a cancer stem cell population Alternatively, cancer tissues collected from patients can be grafted and passaged in nonhuman animals, and then cultured in a serum-free stem cell culture medium under adherent or floating culture conditions to prepare cancer stem cells or a cancer stem cell population. Alternatively, it is possible to use a method in which cancer tissues collected from patients are grafted and passaged in NOG mice to prepare NOG-established cancer cell lines, and they are cultured in a serum-free stem cell culture medium under adherent or suspension culture conditions.

Cancer stem cells and cancer stem cell populations of the present invention can be used in methods of screening for pharmaceutical agents, anti-cancer agents, or the like.

In an embodiment of methods of screening for pharmaceutical agents, the present invention provides methods comprising the steps of:

(a) preparing a substantially homogeneous cancer stem cell population comprising an Lgr5-positive adherent cancer stem cell;

(b) contacting a test substance with the cancer stem cell population or a cancer stem cell comprised in the cancer stem cell population; and (c) detecting a change in a biological property of the cancer stem cell population or cancer stem cell contacted with the test substance.

In these methods, first, a substantially homogeneous cancer stem cell population containing Lgr5-positive adherent cancer stem cells or Lgr5-negative cancer stem cells is prepared. Then, a test substance is contacted with the prepared cancer stem cell population or cancer stem cells contained in the cancer stem cell population. In these methods, there is no particular limitation on the method for contacting a test substance with a cancer stem cell population or cancer stem cells contained in the cancer stem cell population. For example, a test substance may be contacted with cultured cells of a cancer stem cell population or cancer stem cells contained in the cancer stem cell population. This treatment can be carried out by adding a test substance to a cell culture medium or cell extract. When a test substance is a protein, this treatment can be performed, for example, as follows: a vector comprising a DNA encoding the protein is introduced into a cancer stem cell population or cancer stem cells contained in the cancer stem cell population; or the vector is added to a cell extract of a cancer stem cell population or cancer stem cells contained in the cancer stem cell population. Alternatively, it is possible, for example, to use the two-hybrid method utilizing yeast, animal cells, or the like.

In these methods, then, a change in a biological property of the cancer stem cell population or cancer stem cells treated with the test substance is detected. Such a change in a biological property includes, for example, a change in the proliferation ability, a change in the viable cell count, a change in a tissue structure characteristic of the process of cancer progression of the cancer stem cell population or cancer stem cells, and a change in the expression of a DNA, RNA, protein, or metabolite in the cancer stem cell population or cancer stem cells. A change in a biological property can be detected, for example, by the methods described below.

There is no particular limitation on the assessment of the expression of DNAs, RNAs, proteins, peptides, and metabolites; the expression can be assessed by conventional expression assessment methods. RNAs include microRNAs, siRNAs, tRNAs, snRNAs, mRNAs, and non-coding RNAs. For example, mRNAs of a gene are extracted according to a conventional method. Using the mRNAs as a template, the transcriptional level of the gene can be determined using the Northern hybridization or RT-PCR method. DNA array techniques can also be used to determine the expression level of the gene. Alternatively, fractions containing a protein encoded by a gene are collected according to a conventional method. The translational level of the gene can be determined by detecting the protein expression by an electrophoresis method such as SDS-PAGE. The translational level of a gene can also be determined by performing the Western blotting method using an antibody against a protein and detecting the protein expression. These methods can be used to screen for pharmaceutical agents (pharmaceutical compositions).

The DNAs, RNAs, and proteins that are contained in a cancer stem cell population or cancer stem cells and which are characteristic of the process of cancer progression of the cancer stem cell population or cancer stem cells, preferably include the proteins or polypeptides of any one of SEQ ID NOs: 1 to 3 and 5 to 7, and polynucleotides encoding the proteins or polypeptides.

For example, when there is no change in a biological property of a cancer stem cell population or cancer stem cells, or the degree of the change is reduced after treatment with a test substance compared to before the treatment, the test substance is expected to be useful as a pharmaceutical agent (pharmaceutical composition) that has the activity of suppressing cancer recurrence or metastasis (for example, an agent for suppressing cancer recurrence, an agent for post-chemotherapy adjuvant therapy, an agent for postoperative adjuvant therapy, an anti-cancer agent, or an agent for suppressing cancer metastasis). Such test substances can be selected as effective substances that have the therapeutic or preventive effect against cancerous diseases. Such pharmaceutical agents (pharmaceutical compositions) having the activity of suppressing cancer progression are used as an agent for suppressing cancer recurrence, an agent for post-chemotherapy adjuvant therapy, an agent for postoperative adjuvant therapy, an anti-cancer agent, or an agent for suppressing cancer metastasis. Anti-cancer agents of the present invention may be used against, for example, cancers resistant to pharmaceutical agents or chemotherapeutic agents. Specifically, pharmaceutical agents (pharmaceutical compositions) of the present invention also include therapeutic agents against drug-resistant or chemotherapeutic agent-resistant cancers.

In the present invention, the above pharmaceutical agents (pharmaceutical compositions) are not particularly limited to anti-cancer agents or agents for suppressing metastasis or recurrence, and they can also be used as an agent for inhibiting angiogenesis or cell growth. Furthermore, the pharmaceutical agents (pharmaceutical compositions) of the present invention may be used simultaneously with chemotherapeutic agents or after treatment with chemotherapeutic agents. The pharmaceutical agents are not particularly limited, and they include proteinaceous agents, nucleic acid agents, low-molecular-weight agents, and cellular agents.

In another embodiment of the screening methods, the present invention provides methods of screening for pharmaceutical agents (pharmaceutical compositions), which comprise the steps of:
(a) preparing a substantially homogeneous cancer stem cell population comprising an Lgr5-negative non-adherent cancer stem cell;
(b) contacting a test substance with the cancer stem cell population or a cancer stem cell comprised in the cancer stem cell population; and
(c) detecting a change in a biological property of the cancer stem cell population or cancer stem cell contacted with the test substance.

In these methods, first, a substantially homogeneous cancer stem cell population containing Lgr5-negative non-adherent cancer stem cells is prepared. Then, the prepared cancer stem cell population or cancer stem cells contained in the cancer stem cell population are treated with a test substance. Next, a change in a biological property of the cancer stem cell population or cancer stem cells treated with the test substance is detected.

The DNAs, RNAs, and proteins that are contained in such a cancer stem cell population or cancer stem cells, and which are characteristic of the process of cancer progression of the cancer stem cell population or cancer stem cells, preferably include the proteins or polypeptides of any one of SEQ ID NOs: 1 to 3 and 5 to 9, and polynucleotides encoding the proteins or polypeptides. In a non-limiting embodiment of the present invention, the proteins or polypeptides of SEQ ID NOs: 1 to 3 and 5 to 7, and polynucleotides encoding the proteins or polypeptides may be used. In another non-limiting embodiment of the present invention, the protein or polypeptide of SEQ ID NO: 7 or 8, and polynucleotides encoding the protein or polypeptide may be used.

Pharmaceutical agents (pharmaceutical compositions) that are obtained by the screening methods are not particularly limited, and they can be used as anti-cancer agents. Specifically, when there is no change in a biological property of a cancer stem cell population or cancer stem cells, or the degree of the change is reduced after treatment with a test substance compared to before the treatment, the test substance is expected to be useful as a pharmaceutical agent that has the activity of suppressing cancer recurrence or metastasis (for example, an agent for suppressing cancer recurrence, an agent for post-chemotherapy adjuvant therapy, an agent for postoperative adjuvant therapy, an anti-cancer agent, or an agent for suppressing cancer metastasis). Such test substances may be selected as effective substances that have the therapeutic or preventive effect against cancerous diseases. Such pharmaceutical agents (pharmaceutical compositions) having the activity of suppressing cancer progression are used as an agent for suppressing cancer recurrence, an agent for post-chemotherapy adjuvant therapy, an agent for postoperative adjuvant therapy, an anti-cancer agent, or an agent for suppressing cancer metastasis.

Furthermore, pharmaceutical agents (pharmaceutical compositions) of the present invention include cancer therapeutic agents against Lgr5-negative cancers, which contain as an active ingredient at least an antibody that binds to a protein of SEQ ID NOs: 1 to 3 and 5 to 9. The Lgr5-negative cancers include those resistant to drugs or chemotherapeutic agents.

Still another embodiment of the screening methods of the present invention includes methods that use nonhuman animals administered with a test substance, and a cancer stem cell population of the present invention or cancer stem cells contained in the cancer stem cell population. Specifically, the present invention provides methods of screening for pharmaceutical agents (pharmaceutical compositions), which comprise the steps of:
(a) preparing a substantially homogeneous cancer stem cell population comprising an Lgr5-positive adherent cancer stem cell;
(b) administering a nonhuman animal with a test substance and the cell population or a cancer stem cell comprised in the cancer stem cell population; and
(c) detecting tumor formation in the nonhuman animal.

In these methods, first, a substantially homogeneous cancer stem cell population containing Lgr5-positive adherent cancer stem cells is prepared. Then, nonhuman animals are administered with a test substance, and the cancer stem cell population prepared or cancer stem cells contained in the cancer stem cell population.

In these methods, the method for administering a test substance to nonhuman animals is not particularly limited. Oral administration, or parenteral administration such as subcutaneous, intravenous, local, transdermal, or transintestinal (transrectal) administration can be appropriately selected depending on the type of a test substance to be administered.

Furthermore, in these methods, there is no particular limitation on the method for administering a cancer stem cell population or cancer stem cells to nonhuman animals, and an appropriate method can be selected depending on the cell population to be administered. The preferred method is subcutaneous or intravenous administration.

In these methods, then, tumor formation is detected in the nonhuman animals.

The assessment of a test substance can be performed as follows: tissues administered with a test substance and a cancer stem cell population or cancer stem cells are excised from nonhuman animals, and then histological features of the tissues are observed to determine the presence or absence of tumor formation. When tumor formation is not detected, the test substance is expected to be useful as a pharmaceutical agent having the activity of suppressing cancer progression or metastasis (for example, an anti-cancer agent or an agent for suppressing cancer metastasis or recurrence), and the test substance can be selected as an effective substance that has the therapeutic or preventive effect against cancerous diseases. That is, pharmaceutical agents (pharmaceutical compositions) obtained by the screening methods are not particularly limited, and can be used as an anti-cancer agent, or an agent for suppressing cancer metastasis or recurrence.

"Test substances" used in the methods of the present invention are not particularly limited, and include, for example, single compounds such as natural compounds, organic compounds, inorganic compounds, proteins, antibodies, peptides, and amino acids, as well as compound libraries, expression products of gene libraries, cell extracts, cell culture supernatants, products of fermenting microorganisms, extracts of marine organisms, plant extracts, prokaryotic cell extracts, unicellular eukaryote extracts, and animal cell extracts. These may be purified products or crude purified products such as extracts of plants, animals, and microorganisms. Also, methods for producing test substances are not particularly limited; test substances may be isolated from natural materials, synthesized chemically or biochemically, or prepared by genetic engineering. It is also possible to appropriately use antisense and RNAi molecules that are designed by known methods based on partial sequences of polynucleotides encoding the protein of any one of SEQ ID NOs: 1 to 3 and 5 to 9. If needed, the above test substances can be appropriately labeled and used. Labels include, for example, radiolabels and fluorescent labels. Mixtures of an above-mentioned test substance and multiple kinds of such labels are included in the test substances of the present invention.

Furthermore, the present invention provides pharmaceutical agents such as vaccines comprising a partial peptide of the protein of any one of SEQ ID NOs: 1 to 3 and 5 to 9, and methods of screening for vaccines. Such screening methods preferably include methods for determining the cytotoxic activity targeted to cancer stem cells disclosed in the present application using cytotoxic T cells (CTL) or the like induced with a cancer vaccine of the present invention in vitro. Specifically, adherent and non-adherent cells are separated from peripheral blood mononuclear cells (PBMCs) collected by centrifugation of human peripheral blood in Ficoll-Conray density gradient. The adherent cells are incubated with 100 ng/ml GM-CSF (Novartis) and 10 IU/ml IL-4 (GIBCO-BRL) in AIM-V (GIBCO), and then the cells are used as antigen-presenting cells (APC). Meanwhile, the non-adherent cells are incubated with 30 to 100 IU/ml recombinant IL-4 (Ajinomoto) in AIM-V. On day 7 to 10, a partial peptide of the protein of any one of SEQ ID NOs: 1 to 3 and 5 to 9 provided by the present invention is added (at a final concentration of 30 µg/ml) to APC. On the following day, recombinant TNF-α and IFN-α (Sumitomo Pharma Co.) are added for APC maturation. Then, CD8-positive cells isolated from autologous non-adherent cells are mixed with irradiated APC in IL-2-free AIM-V. After two days of incubation, IL-2 (Takeda Pharmaceutical Company) is added at a final concentration 100 IU/ml to the culture. The CD8-positive cells are stimulated every seven days using, as APC, autologous PHA blasts (PHA-stimulated T cells) that have been stimulated with the T cell mitogen PHA. A fresh medium containing 100 IU/ml IL-2 is added to the culture at every time point of stimulation. CTL on day 28 is used for the activity assay. High proliferative Lgr5-positive cancer stem cells and low proliferative Lgr5-negative cancer stem cells that are provided by the present invention can be used as target cells of CTL. The cytotoxic activity can be assessed by determining sCr-sodium chromate uptake activity by a measurement method similar to that of ADCC activity.

Furthermore, pharmaceutical agents selected by the screening methods of the present invention may be further screened as necessary for more effective and practical preventive or therapeutic active substances by conducting additional drug effectiveness tests and safety tests, and further conducting clinical tests in human cancer patients. Based on results of structural analysis of pharmaceutical agents thus selected, they can be industrially manufactured by chemical synthesis, biochemical synthesis (fermentation), or genetic engineering.

"High proliferative ability" means that the doubling time is 6 days or less, preferably 4 days or less, and more preferably 3 days or less when cells are cultured in a serum-free medium supplemented with EGF and FGF using the method described herein.

"Low proliferative ability" means that the doubling time is 7 days or more, preferably 14 days or more, and more preferably there is no significant proliferation when cells are cultured in a serum-free medium supplemented with EGF and FGF using the method described herein.

When preparing such high proliferative Lgr5-positive cancer stem cells and low proliferative Lgr5-negative cancer stem cells, the cells can be separated using the cell marker Lgr5.

The separation methods include the following:
methods in which a cell population containing cancer stem cells is isolated by using an anti-Lgr5 antibody;
methods in which a substantially homogeneous cancer stem cell population is first prepared by culturing a population containing cancer stem cells under adherent or suspension culture conditions, and then the population is isolated by using an anti-Lgr5 antibody; and
methods in which a substantially homogeneous cancer stem cell population is first prepared by culturing a population containing cancer stem cells in a medium with or without a growth inhibitor under adherent culture conditions, and then the population is isolated by using an anti-Lgr5 antibody. Any of the above methods may be used in the present invention. Preferably, cells are isolated from cancer tissues after three or more passages in NOG mice, and cultured in a serum-free stem cell culture media under adherent culture conditions to prepare high proliferative Lgr5-positive cancer stem cells. Then, low proliferative Lgr5-negative cancer stem cells can be prepared as follows. The resulting Lgr5-positive cancer stem cells are maintained under various stresses such as a contact with a growth inhibitor, for example, treatment with irinotecan (culture for three days in a serum-free stem cell medium supplemented with 10 µg/ml irinotecan).

Furthermore, the present invention provides methods of screening for pharmaceutical agents, which comprise contacting a test substance with cancer stem cells that differ in the proliferation ability, which are induced by the methods provided by the present invention. Specifically, the present invention provides methods of screening for pharmaceutical agents, which comprises detecting a change in a biological property of cancer stem cells by contacting a test substance with high or low proliferative cancer stem cells induced by a method for converting low proliferative cancer stem cells to high proliferative cancer stem cells, or converting high proliferative cancer stem cells to low proliferative cancer stem cells.

Specifically, as described herein, low proliferative cancer stem cells can be prepared by maintaining high proliferative cancer stem cells under various stresses such as a suspension culture or in contact with a growth inhibitor. For example, high proliferative cancer stem cells can be converted to low proliferative cancer stem cells by culturing high proliferative cancer stem cells under suspension culture conditions. Alternatively, high proliferative cancer stem cells can be converted to low proliferative cancer stem cells by culturing high proliferative cancer stem cells in low adherent or ultra-low adherent cell culture vessels such as low adherent plates, ultra-low adherent plates, low adherent dishes, ultra-low adherent dishes, low adherent flasks, or ultra-low adherent cell culture flasks. In other words, low proliferative cancer stem cells can be prepared by culturing high proliferative cancer stem cells in low adherent or ultra-low adherent cell culture vessels such as low adherent plates, ultra-low adherent plates, low adherent dishes, ultra-low adherent dishes, low adherent flasks, or ultra-low adherent cell culture flasks.

In a non-limiting embodiment, high proliferative cancer stem cells can be converted to low proliferative cancer stem cells by using a growth inhibitor such as 5-FU or irinotecan. Specifically, low proliferative cancer stem cells can be produced by exposing high proliferative cancer stem cells to a growth inhibitor such as 5-FU or irinotecan. Exposure to a growth inhibitor can be achieved under any condition such as in vitro culture or inside the body of grafted nonhuman animals. In this case, those skilled in the art can select an appropriate exposure dose of a cell growth inhibitor for cancer stem cells. Alternatively, high proliferative cancer stem cells can be prepared by re-seeding low proliferative cancer stem cells into a medium without a growth inhibitor such as 5-FU or irinotecan. In another non-limiting embodiment, high proliferative cancer stem cells can be produced by discontinuing administration of a growth inhibitor to nonhuman animals having low proliferative cancer stem cells.

Furthermore, low proliferative cancer stem cells can be cultured under adherent culture conditions to convert them to high proliferative cancer stem cells. Alternatively, low proliferative cancer stem cells can be converted to high proliferative cancer stem cells by culturing low proliferative cancer stem cells in a non-low-adherent but highly adherent cell culture vessel such as a flat-bottomed plate, plate, adherent culture plate, adherent culture flask, dish, or adherent culture dish. That is, high proliferative cancer stem cells can be produced by culturing low proliferative cancer stem cells in a non-low-adherent but highly adherent cell culture vessel such as a flat-bottomed plate, plate, adherent culture plate, adherent culture flask, dish, or adherent culture dish.

The present invention also relates to cancer cell detection reagents. Cancer cell detection reagents of the present invention preferably contain as an active ingredient at least one antibody that binds to a protein of SEQ ID NOs: 1 to 3 and 5 to 9 (protein composed of the amino acid sequence of any one of SEQ ID NOs: 1 to 3 and 5 to 9). In another embodiment, the reagents of the present invention include reagents for detecting Lgr5-positive cancer cells, which preferably contain at least one antibody that binds to a protein of SEQ ID NOs: 1 to 3 and 5 to 7 (protein composed of the amino acid sequence of any one of SEQ ID NOs: 1 to 3 and 5 to 7). In still another embodiment, the reagents of the present invention include reagents for detecting Lgr5-negative cancer cells, which preferably contain at least one antibody that binds to the protein of any one of SEQ ID NOs: 1 to 3 and 5 to 9 (protein composed of the amino acid sequence of any one of SEQ ID NOs: 1 to 3 and 5 to 9).

Growth Inhibitors

In a non-limiting embodiment, preferred growth inhibitors include DNA-damaging agents, antimitotic agents, and/or anti-metabolites. Such a DNA-damaging agent may be an alkylating reagent, a topoisomerase inhibitor, and/or a DNA intercalator. Examples of preferred growth inhibitors include, but are not limited to, carboplatin (DNA alkylating reagent), etoposide (topoisomerase II inhibitor), doxorubicin (DNA intercalator), docetaxel (antimitotic agent), and Gemzar (gemcitabine; anti-metabolite).

Alkylating reagents can be at least one reagent selected from the following. Specifically, it is possible to use at least one alkylating reagent selected from:
chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119 (becatecarin), dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylene melamine, procarbazine, etc.

Topoisomerase inhibitors can be at least one inhibitor selected from the following. Specifically, it is possible to use at least one topoisomerase inhibitor selected from:
doxorubicin (Doxil), daunorubicin, epirubicin, idarubicin, anthracenedione (Novantrone), mitoxantrone, mitomycin C, bleomycin, dactinomycin, plicatomycin, irinotecan (Camptosar), camptothecin, rubitecan, belotecan, etoposide, teniposide, topotecan (Hycamptin), etc.

At least one topoisomerase inhibitor selected from the following can be used as a DNA intercalator:
proflavin, doxorubicin (adriamycin), daunorubicin, dactinomycin, thalidomide, etc.

Antimitotic agents can be at least one agent selected from the following. Specifically, it is possible to use at least one topoisomerase inhibitor selected from:
paclitaxel (Abraxane)/Taxol, docetaxel (Taxotere), BMS-275183, Xyotax, Tocosal, vinorlebine, vincristine, vinblastine, vindesine, vinzolidine, etoposide (VP-16), teniposide (VM-26), ixavepilone, larotaxel, ortataxel, tesetaxel, ispinesib, etc.

Anti-metabolites can be at least one inhibitor selected from the following. Specifically, it is possible to use at least one topoisomerase inhibitor selected from:
fluorouracil (5-FU), floxuridine (5-FUdR), methotrexate, Xeloda, Arranon, leucovorin, hydroxyurea, thioguanine (6-TG), mercaptopurine (6-MP), cytarabine, pentostatin, fludarabine phosphate, cladribine (2-CDA), asparaginase, gemcitabine, pemetrexed, bortezomib, aminopterin, raltitrexed, clofarabine, enocitabine, sapacitabine, azacytidine, etc.

Furthermore, the present invention relates to methods of screening for anti-cancer drugs, which use cancer stem cells isolated or induced by the above methods of the present invention.

The present invention also relates to methods for assessing compounds, which use cancer stem cells isolated or induced by the above methods of the present invention.

Method for Detecting Cancer Stem Cells

Furthermore, the present invention provides methods for detecting, identifying, or quantifying the presence of cancer stem cells of the present invention. Specifically, the present invention provides methods for detecting, identifying, or quantifying the presence of cancer stem cells or substantially homogeneous cancer stem cell populations of the present invention, which comprise the steps of:

(a) preparing a sample obtained from a cancer patient; and
(b) contacting a sample with an anti-Lgr5 antibody.

In these methods, first, samples obtained from cancer patients are prepared. In the present invention, a "sample" is not particularly limited as long as it is preferably an organ or tissue derived from a cancer patient. It is possible to use a frozen or unfrozen organ or tissue. Such samples include, for example, cancer (tumor) tissues isolated from cancer patients. In these methods, a sample is then contacted with an anti-Lgr5 antibody.

Methods for detecting, identifying, or quantifying the presence of above-described cancer stem cells or substantially homogeneous cancer stem cell populations of the present invention can be used in, for example, cancer diagnosis, selection of cancer patients, prediction or assessment of the effectiveness of an agent (pharmaceutical composition), treatment monitoring, and cancer imaging.

Specifically, for example, organs or tissues are isolated from cancer patients, and specimens are prepared. The specimens can be used to detect, identify, or quantify the presence of cancer stem cells. Specimens can be appropriately prepared by using known methods, for example, the PFA-AMeX-Paraffin method (WO 09/078386). The samples include, for example, frozen or unfrozen organs or tissues. First, samples from cancer patients are fixed in a PFA solution. "PFA solution" refers to a cell fixation solution which is an aqueous solution of 1 to 6% paraformaldehyde combined with a buffer such as phosphate buffer. It is preferable to use 4% PFA fixation solution (4% paraformaldehyde/0.01 M PBS (pH7.4)). For fixation with a PFA fixation solution, organs or tissues of interest are immersed in a PFA solution containing 1 to 6%, preferably 4% paraformaldehyde, at 0 to 8° C., preferably at about 4° C., for 2 to 40 hours, preferably for 6 to 30 hours. Then, fixed organs or tissues are washed with phosphate buffered saline or such. Washing may be carried out after excising portions from the observed organs or tissues.

Organs or tissues thus prepared are then embedded in paraffin by the AMeX method. The AMeX method is a paraffin embedding method with a series of the following steps: cold acetone fixation, dehydration with acetone, clearing in methylbenzoate and xylene, and paraffin embedding. Specifically, tissues are immersed in acetone at −25 to 8° C., preferably at −20 to 6° C., for 2 to 24 hours, preferably for 4 to 16 hours. Then, the tissues in acetone are warmed to room temperature. Alternatively, organs or tissues are transferred into acetone at room temperature. Then, dehydration is performed for 0.5 to 5 hours, preferably 1 to 4 hours at room temperature. Subsequently, the organs or tissues are cleared by immersion in methylbenzoate at room temperature for 0.5 to 3 hours, preferably for 0.5 to 2 hours, followed by immersion in xylene at room temperature for 0.5 to 3 hours, preferably 0.5 to 2 hours. Next, the organs or tissues are embedded in paraffin by penetration at 55 to 65° C., preferably at 58 to 62° C. for 1 to 4 hours, preferably for 1 to 3 hours. The paraffin blocks of organs or tissues prepared by the PFA-AMeX method are stored at low temperature before use.

At the time of use, the paraffin blocks thus prepared are sliced into thin sections using a microtome or the like. Then, the thin sections are deparaffinized and rehydrated. Deparaffinization and rehydration can be performed by known methods. For example, deparaffinization can be performed using xylene and toluene, while rehydration can be carried out using alcohol and acetone.

The resulting thin sections are stained, for example, by histochemistry, immunohistochemistry, or enzyme histochemistry for detection, identification, or quantitation.

When the prepared samples are stained by histochemistry (special staining), it is possible to use any staining method commonly available for paraffin-embedded sections (for example, PAS staining, giemsa staining, and toluidine blue staining). For staining by enzyme histochemistry, the sections may be stained by any staining method available for sections (for example, various staining such as with ALP, ACP, TRAP, or esterase). In addition, histopathological tissues can be stained by the following: hematoxylin-eosin staining for general staining; van Gieson staining, azan staining, and Masson Trichrome staining for collagen fiber staining; Weigert staining and *Elastica* van Gieson staining for elastic fiber staining; Watanabe's silver impregnation staining and PAM staining (periodic acid methenamine silver stain) for reticular fibers/basal membrane staining, etc.

Staining with immunohistochemistry and enzyme histochemistry can be performed by direct methods using primary antibodies labeled with an enzyme or labeling substance, or indirect methods using non-labeled primary antibodies and labeled secondary antibodies. However, such methods are not limited thereto. Antibodies can be labeled by conventional methods. Labeling substances include, for example, radioisotopes, enzymes, fluorescent substances, and biotin/avidin. The labeling substances may be those commercially available. Radioisotopes include, for example, $^{32}P$, $^{33}P$, $^{131}I$, $^{125}I$, $^{3}H$, $^{14}C$, and $^{35}S$. Enzymes include, for example, alkaline phosphatase, horse radish peroxidase, β-galactosidase, and β-glucosidase. Fluorescent substances include, for example, fluorescein isothiocyanate (FITC) and rhodamine. These may be commercially available. Labeling can be carried out by known methods.

Thin sections are stained, for example, by histochemistry, immunohistochemistry, or enzyme histochemistry for detection, identification, or quantitation.

Alternatively, detection, identification, or quantitation can be carried out by quantifying DNA or RNA in cells in organ/tissue samples. Assessment of the expression is not particularly limited, and conventional expression assessment methods can be used. RNAs include microRNAs, siRNAs, tRNAs, snRNAs, mRNAs, and non-coding RNAs. For example, Lgr5 mRNA is extracted according to conventional methods. Using the mRNA as a template, the transcriptional level of each gene can be determined by the Northern hybridization or RT-PCR method. DNA array techniques can also be used to determine the expression level of Lgr5.

Desired tissues, cells, or such can be collected from samples by the microdissection method, in particular, laser microdissection (LMD) method. The LMD method can collect a group of target cells from living tissues, and thus accurately determine which cells express a specific gene among various cells that constitute a tissue, and at what level the cells express the gene. Devices used for microdissection include, for example, the AS-LMD system (Leica Microsystems).

Furthermore, the present invention provides methods for diagnosing cancer, detecting cancer stem cells, or selecting cancer patients, which comprise using at least one antibody that binds to a protein of SEQ ID NOs: 1 to 3 and 5 to 9 to detect the presence of at least one of the proteins in a sample isolated from a cancer patient. In order to detect the presence of cancer stem cells, it is possible to use, instead of the anti-Lgr5 antibody described above, at least one antibody that binds to a protein of SEQ ID NOs: 1 to 3 and 5 to 9.

In a non-limiting embodiment, the present invention provides methods for diagnosing cancer, detecting cancer stem cells, or selecting cancer patients, which comprise using at least one antibody that binds to a protein of SEQ ID NOs: 1 to 3 and 5 to 7 to detect the presence of at least one of the proteins in a sample isolated from a cancer patient. In order to detect the presence of Lgr5-positive cancer stem cells, it is possible to use, instead of the anti-Lgr5 antibody described above, at least one antibody that binds to a protein of SEQ ID NOs: 1 to 3 and 5 to 7. The presence of Lgr5-positive cancer stem cells can be detected by detecting the presence of the protein. However, the present invention does not exclude detection of Lgr5 in addition to the protein.

In a non-limiting embodiment, the present invention provides methods for diagnosing cancer, detecting cancer stem cells, or selecting cancer patients, which comprise using at least one antibody that binds to a protein of SEQ ID NOs: 1 to 3 and 5 to 9 to detect the presence of at least one of the proteins in a sample isolated from a cancer patient. In order to detect the presence of Lgr5-negative cancer stem cells, it is possible to use, instead of the anti-Lgr5 antibody described above, at least one antibody that binds to a protein of SEQ ID NOs: 1 to 3 and 5 to 9. The presence of Lgr5-negative cancer stem cells can be detected by detecting the presence of the protein. However, the present invention does not exclude detection of Lgr5 in addition to the protein.

Furthermore, the present invention provides methods for assessing the effectiveness of a pharmaceutical composition comprising at least one antibody that binds to a protein of SEQ ID NOs: 1 to 3 and 5 to 9, which comprise detecting one or more of the proteins of SEQ ID NOs: 1 to 3 and 5 to 9 and/or polynucleotides encoding the proteins in a sample isolated from a subject administered with the pharmaceutical composition. In these methods, detection may be carried out using at least one antibody that binds to a protein of SEQ ID NOs: 1 to 3 and 5 to 9, or a portion of a polynucleotide encoding the protein of any one of SEQ ID NOs: 1 to 3 and 5 to 9 and/or a complementary strand thereof. In another non-limiting embodiment, the present invention provides methods for assessing the effectiveness of a cancer treatment in a test subject, which comprise comparing the expression of at least one of the proteins of SEQ ID NOs: 1 to 3 and 5 to 9 and/or polynucleotides encoding the proteins in a first sample obtained from a test subject before providing the subject with at least part of the treatment, to the expression of at least one of the proteins of SEQ ID NOs: 1 to 3 and 5 to 9 and/or polynucleotides encoding the proteins in a second sample obtained from the subject after providing the part of the treatment, wherein a significantly lower level of the protein and/or polynucleotide in the second sample than in the first sample is an indicator showing that the treatment is effective for inhibiting cancer in the test subject.

In a non-limiting embodiment, the present invention provides methods of monitoring in a test subject the effectiveness of a treatment with an antibody provided by the present invention, which comprise the steps of:
  (i) collecting a pre-administration sample from the subject before administration of the antibody;
  (ii) determining the expression level of at least one marker protein selected from the proteins of SEQ ID NOs: 1 to 3 and 5 to 9, or an mRNA or genomic DNA thereof in the pre-administration sample;
  (iii) collecting one or more post-administration sample(s) from the subject;
  (iv) determining the expression or activity level of at least one marker protein selected from the proteins of SEQ ID NOs: 1 to 3 and 5 to 9, or an mRNA or genomic DNA thereof in the post-administration sample(s);
  (v) comparing the expression or activity level of the marker protein, mRNA, or genomic DNA in the pre-administration sample to that of the marker protein, mRNA, or genomic DNA in the post-administration sample(s); and
  (vi) modifying the antibody administration to the test subject according to the comparison.

For example, an increased dosage of an antibody of the present invention can be used to reduce the expression or activity of a marker towards a level higher than the detected level (the expression or activity level of the marker protein, mRNA, or genomic DNA in the sample before administration), i.e., to increase the effectiveness of the antibody.

In a different non-limiting embodiment, the present invention provides methods of monitoring in a test subject the effectiveness of a treatment with an antibody provided by the present invention, which comprise the steps of:
  (i) detecting an Lgr5-positive cancer stem cell in a pre-administration sample collected from the subject before administration of the antibody;
  (ii) determining the expression level of at least one marker protein selected from the proteins of SEQ ID NOs: 1 to 3 and 5 to 7, or mRNA or genomic DNA thereof in the pre-administration sample;
  (iii) collecting one or more post-administration sample(s) from the subject;
  (iv) determining the expression or activity level of at least one marker protein selected from the proteins of SEQ ID NOs: 1 to 3 and 5 to 7, or mRNA or genomic DNA thereof in the post-administration sample(s);
  (v) comparing the expression or activity level of the marker protein, mRNA, or genomic DNA in the pre-administration sample to that of the marker protein, mRNA, or genomic DNA in the post-administration sample(s); and
  (vi) modifying the antibody administration to the test subject according to the comparison.

For example, an increased dosage of an antibody of the present invention can be used to reduce the expression or activity of a marker towards a level higher than the detected level (the expression or activity level of the marker protein, mRNA, or genomic DNA in the sample before administration), i.e., to increase the effectiveness of the antibody.

In another non-limiting embodiment, the present invention provides methods of monitoring in a test subject the effectiveness of a treatment with an antibody provided by the present invention, which comprise the steps of:
  (i) detecting an Lgr5-negative cancer stem cell in a pre-administration sample collected from the subject before administration of the antibody;

(ii) determining the expression level of at least one marker protein selected from the proteins of SEQ ID NOs: 1 to 3 and 5 to 9, or mRNA or genomic DNA thereof in the pre-administration sample;

(iii) collecting one or more post-administration sample(s) from the subject;

(iv) determining the expression or activity level of at least one marker protein selected from the proteins of SEQ ID NOs: 1 to 3 and 5 to 9, or mRNA or genomic DNA thereof in the post-administration sample(s);

(v) comparing the expression or activity level of the marker protein, mRNA, or genomic DNA in the pre-administration sample to that of the marker protein, mRNA, or genomic DNA in the post-administration sample(s); and (vi) modifying the antibody administration to the test subject according to the comparison.

For example, an increased dosage of an antibody of the present invention can be used to reduce the expression or activity of a marker towards a level higher than the detected level (the expression or activity level of the marker protein, mRNA, or genomic DNA in the sample before administration), i.e., to increase the effectiveness of the antibody.

Cancer Stem Cell Inhibitors

"Cancer stem cell inhibitor" refers to, for example, an agent having the effect of suppressing the proliferation of cancer stem cells, suppressing the metastasis or recurrence of cancer stem cells, killing cancer stem cells, etc. It may have the effect of suppressing the proliferation of cancer cells, suppressing the metastasis or recurrence of cancer cells, killing cancer cells, etc.

When used in connection with a biological activity, whose non-limiting examples include the proliferation or metastasis of cancer stem cells, the terms "suppress" and "suppressing", and synonymous expressions refer to the down-regulation of the biological activity. This can reduce or eliminate a target function such as protein production and phosphorylation of a molecule, etc. In a specific embodiment, the suppression means a decrease in a target activity by about 20%, 30%, 40%, 50%, 60%, 70%, 80%, 90%, or 95%. When used in connection with a disorder or disease, the terms refer to the prevention of development of a symptom, relief of a symptom, or successful alleviation of a disease, condition, or disorder.

"Metastasis" refers to a process where cancer spreads or moves from the primary site to another site in the body, resulting in the development of similar cancer lesions at the new site. "Metastatic cell" or "metastasizing cell" refers to a cell that loses the adhesive contact with adjacent cells, and leaves the primary site of the disease and invades a nearby body structure via blood or lymphatic circulation. "Recurrence" means that the same malignant tumor reappears in a remaining organ after partial resection of an organ for removing a malignant tumor from a cancer patient, or after postoperative chemotherapy following the resection.

Proteins

Proteins for use in the present invention can be easily prepared by any method known to those skilled in the art as follows. An expression vector containing a gene comprising a DNA encoding a protein is constructed. The protein is produced and accumulated by culturing transformants transformed with the expression vector. The transformants are harvested to prepare the protein.

Such an expression vector can be constructed according to methods known in the art, for example, by the following:

(1) excising a DNA fragment that comprises a gene comprising a DNA encoding a protein; and (2) ligating the DNA fragment downstream of a promoter in an appropriate expression vector.

Such vectors used include *E. coli*-derived plasmids (for example, pBR322, pBR325, pUC18, and pUC118), *Bacillus subtilis*-derived plasmids (for example, pUB110, pTP5, and pC194), yeast-derived plasmids (for example, pSH19 and pSH15), bacteriophages such as λ phage, and animal viruses such as retroviruses, vaccinia viruses, and Baculoviruses.

Promoters for use in the present invention may be any promoters as long as they are appropriate and compatible with a host to be used for gene expression. For example, when the host is *E. coli*, preferred promoters include the trp promoter, lac promoter, recA promoter, kPL promoter, and lpp promoter. When the host is *Bacillus subtilis*, preferred promoters include the SPO1 promoter, SPO2 promoter, and penP promoter. When the host is yeast, preferred promoters include the PHO5 promoter, PGK promoter, GAP promoter, and ADH promoter. When the host is an animal cell, promoters include the SRa promoter, SV40 promoter, LTR promoter, CMV promoter, and HSV-TK promoter.

In addition to those described above, if desired, enhancers, splicing signals, poly-A addition signals, selection markers, SV40 replication origins, or such known in the art can be added to expression vectors. As necessary, a protein for use in the present invention can be expressed as a fusion protein with another protein (for example, glutathione-S-transferase or Protein A). Such a fusion protein can be cleaved into individual proteins by using an appropriate protease.

Host cells include, for example, bacteria of the genus *Escherichia*, bacteria of the genus *Bacillus*, yeasts, insect cells, insects, and animal cells.

Specific examples of bacteria of the genus *Escherichia* include *Escherichia coli* K12 DH1 (Proc. Natl. Acad. Sci, USA, 60, 160 (1968)), JM103 (Nucleic Acids Research, 9, 309 (1981)), JA221 (Journal of Molecular Biology, 120, 517 (1978)), and HB101 (Journal of Molecular Biology, 41, 459 (1969)).

Bacteria of the genus *Bacillus* include, for example, *Bacillus subtilis* MI114 (Gene, 24, 255 (1983)) and 207-21 (Journal of Biochemistry, 95, 87 (1984)).

Yeasts include, for example, *Saccharomyces cerevisiae* AH22, AH22R-, NA87-11A, DKD-5D, and 20B-12; *Schizosaccaromyces pombe* NCYC1913 and NCYC2036; and *Pichia pastoris*.

Animal cells include, for example, monkey COS-7 cells, Vero cells, Chinese hamster CHO cells (hereinafter abbreviated as CHO cells), dhfr gene-deficient CHO cells, mouse L cells, mouse AtT-20 cells, mouse myeloma cells, rat GH3 cells, and human FL cells.

These host cells can be transformed according to methods known in the art. See, for example, the following references. Proc. Natl. Acad. Sci. USA, Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. USA), Vol. 75, 1929 (1978); and Virology, Vol. 52, 456 (1973).

Transformants thus prepared can be cultured according to methods known in the art.

For example, when hosts were bacteria of the genus *Escherichia*, in general, they are cultured at about 15 to 43° C. for about 3 to 24 hours. Aeration or stirring is performed as necessary. When hosts are bacteria of the genus *Bacillus*, in general, they are cultured at about 30 to 40° C. for about 6 to 24 hours. Aeration or stirring is performed as necessary When hosts are yeasts, in general, transformants are cultured at about 20° C. to 35° C. for about 24 to 72 hours in a medium adjusted to about pH 5 to 8. Aeration or stirring is performed as necessary.

When hosts are animal cells, in general, transformants are cultured at about 30° C. to 40° C. for about 15 to 60 hours in a medium adjusted to about pH 6 to 8. Aeration or stirring is performed as necessary.

To isolate and purify a protein for use in the present invention from the above culture, for example, cells or bacteria are harvested after culture by a known method, and this is suspended in an appropriate buffer. After disrupting the cells or bacteria by sonication, lysozyme, and/or freeze-thawing, a crude protein extract is prepared by centrifugation or filtration. The buffer may contain protein denaturants such as urea and guanidine hydrochloride, and detergents such as Triton X-100™. When the protein is secreted to the culture medium, the supernatant is separated from the cells or bacteria after culture by a known method, and the supernatant is collected. A protein contained in the resulting culture supernatant or extract can be purified by appropriately combining known isolation/purification methods.

According to known or equivalent methods, a protein prepared as described above can be arbitrarily modified or a polypeptide can be partially removed from the protein by treating the protein produced by recombinants with an appropriate protein modification enzyme such as trypsin and chymotrypsin before or after purification.

The presence of a protein for use in the present invention can be assessed by various binding assays, enzyme immunoassays using specific antibodies, etc.

Antibodies

Antibodies for use in the present invention are not particularly limited as long as they bind to proteins for use in the present invention. The antibodies may be obtained as polyclonal or monoclonal antibodies using known methods. Particularly preferred antibodies for use in the present invention include monoclonal antibodies derived from mammals. Monoclonal antibodies derived from mammals include those produced by hybridomas and those produced by hosts transformed with expression vectors carrying antibody genes using gene engineering technologies. It is preferable that antibodies for use in the present invention specifically bind to proteins for use in the present invention.

Basically, hybridomas producing monoclonal antibodies can be prepared using known techniques by the following procedure. Specifically, immunization is carried out using as a sensitizing antigen a protein for use in the present invention according to conventional immunization methods. The resulting immune cells are fused with known parental cells by conventional cell fusion methods. Monoclonal antibody-producing cells are screened using conventional screening methods. More specifically, monoclonal antibodies can be prepared by the following procedure.

A gene sequence encoding the protein is inserted into a known expression vector system, and this is transformed into appropriate host cells. Then, the protein is purified from the host cells or culture supernatant by known methods.

Next, the protein is used as a sensitizing antigen. Alternatively, a partial peptide of the protein is used as a sensitizing antigen. In this case, the partial peptide can be prepared by chemical synthesis based on the amino acid sequence of the protein according to common methods known to those skilled in the art.

Such a partial polypeptide of the protein has, for example, at least 10 or more amino acids, preferably 50 or more amino acids, more preferably 70 or more amino acids, still more preferably 100 or more amino acids, and yet more preferably 200 or more amino acids of the amino acid sequence constituting the protein, and has, for example, a biological activity substantially equivalent to the function of the protein. The C terminus of the partial peptide is generally a carboxyl group (—COH) or carboxylate (—COO—); however, the C terminus may also be amide (—CONH$_2$) or ester (—COOR). In addition, the partial peptides include those in which the amino group of the N-terminal methionine residue is protected with a protecting group, those in which a glutamyl residue resulting from in vivo N-terminal cleavage is pyroglutamine-oxidized, those in which a substituent group in the side chain of an amino acid in the molecule is protected with an appropriate protecting group, and conjugated peptides such as so-called glycopeptides linked with sugar chains.

Mammals that are immunized with a sensitizing antigen are not particularly limited, though it is preferable to take into consideration compatibility with the parent cell used for cell fusion. Thus, rodents such as mice, rats, or hamsters are generally selected.

Immunization of animals with a sensitizing antigen is performed according to known methods. For example, standard methods of delivering sensitizing antigen to mammals involve intraperitoneal or subcutaneous injection. More specifically, a sensitizing antigen is diluted to be an appropriate volume with PBS (phosphate-buffered saline), physiological saline, or the like. If desired, this may be mixed with an appropriate amount of a typical adjuvant, for example, Freund's complete adjuvant, made into an emulsion, and then administered to mammals several times every 4 to 21 days. An appropriate carrier may also be used for immunization with sensitizing antigens.

After the mammals are immunized as described above, an increase in the level of desired antibody in the serum is confirmed, immunocytes are collected from the mammals for cell fusion. Immunocytes that are preferably subjected to cell fusion are splenocytes in particular.

Regarding the other parent cell to be fused with the above-mentioned immunocytes, mammalian myeloma cells are used. For myeloma cells, it is preferable to use various known cell lines, for example, P3 (P3×63Ag8.653) (J. Immnol. (1979) 123, 1548-1550), P3×63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

In general, the above-described immunocytes and myeloma cells can be fused according to known methods, examples of which are described by Kohler and Milstein et al. (Kohler, G. and Milstein, C., Methods Enzymol. (1981) 73, 3-46).

More specifically, the above-described cell fusion is carried out, for example, in a typical nutrient culture medium in the presence of a cell fusion promoting agent. For example, polyethylene glycol (PEG), Sendai virus (HVJ), or such can be used as the fusion promoting agent. If desired, adjuvants such as dimethylsulfoxide can additionally be used to increase fusion efficiency.

It is possible to arbitrarily determine the proportion of immunocytes and myeloma cells used. The preferred ratio of myeloma cells to immunocytes is, for example, from 1:1 to 1:10. The culture medium used for the above-described cell fusion may be, for example, RPMI1640 medium, MEM medium, which are suitable for proliferation of the above-described myeloma cell lines, or other kinds of culture medium commonly used for culturing such cells. Furthermore, serum supplements such as fetal calf serum (FCS) may be used in combination.

The cell fusion is carried out by thoroughly mixing prescribed amounts of the above-described immunocytes and myeloma cells in the aforementioned culture medium, adding to the medium a PEG solution preheated to about 37° C. generally at a concentration of 30% to 60% (w/v), wherein the PEG has an average molecular weight of about 1,000 to 6,000, for example, and mixing them to form the desired fusion cells (hybridomas). An appropriate culture medium is then successively added. Cell fusing agents and such that are undesirable for the proliferation of hybridomas are removed by repeatedly removing the supernatant by centrifugation.

The hybridomas obtained in this manner are selected by culturing them in a common selection culture medium, for example, the HAT medium (a culture medium containing hypoxanthine, aminopterin, and thymidine). Culture in the HAT medium described above is continued for a sufficient time, usually from a few days to a few weeks, to allow death of all cells but the target hybridomas (the non-fused cells). The usual limiting dilution method is then performed to screen and clone hybridomas producing antibodies used the present invention.

In addition to methods obtaining the above-described hybridomas by immunizing non-human animals with an antigen, desired human antibodies having an activity of binding to the protein can also be obtained by in vitro sensitizing human lymphocytes with the protein and fusing the sensitized lymphocytes with human-derived myeloma cells having permanent cell division ability (see Japanese Patent Application Kokoku Publication No. (JP-B) HO1-59878 (examined, approved Japanese patent application published for opposition)). Furthermore, human antibodies against a protein may be obtained from immortalized antibody-producing cells that are prepared by administering the protein as an antigen to a transgenic animal having a full repertoire of human antibody genes (see, International Patent Applications WO 94/25585, WO 93/12227, WO 92/03918, and WO 94/02602).

There are known techniques for obtaining human antibodies by panning using a human antibody library. For example, the V regions of human antibodies can be expressed as single-chain antibodies (scFvs) on the surface of phages using a phage display methods, from which phages presenting scFv that binds to an antigen can be selected. The DNA sequences encoding the V regions of human antibodies that bind to the antigen can be determined by analyzing the genes of selected phages. After identifying the DNA sequences of scFvs that bind to the antigen, the V region sequences are fused in frame with the C region sequences of a desired human antibody. Then, the resulting DNA is inserted into an appropriate expression vector to construct an expression vector. The expression vector is introduced into suitable cells for expression, such as those described above. The human antibody can be obtained by expressing the gene encoding the human antibody. These methods are already known (see WO 1992/001047, WO 1992/020791, WO 1993/006213, WO 1993/011236, WO 1993/019172, WO 1995/001438, and WO 1995/015388).

The hybridomas prepared in this manner that produce monoclonal antibodies can be passaged in a common culture medium and stored for a long time in liquid nitrogen.

Monoclonal antibodies may be obtained from the hybridomas using common techniques; for example, the hybridomas are cultured according to standard methods and the antibodies may be obtained from the culture supernatants. Alternatively, the hybridomas are administered to a compatible mammal for proliferation and then the antibodies may be obtained from the ascites fluid. The former method is suitable for obtaining highly pure antibodies, while the latter method is suitable for mass production of antibodies.

Monoclonal antibodies used in the present invention may be recombinant antibodies produced by genetic engineering techniques. They can be produced, for example, by cloning an antibody gene from a hybridoma, incorporating the antibody gene into an appropriate vector, and introducing the resulting vector into a host (see, for example, Vandamme, A. M. et al., Eur. J. Biochem., (1990) 192, p. 767-775, 1990).

Specifically, mRNAs encoding antibody variable (V) regions are isolated from hybridomas producing the antibodies. mRNAs can be isolated by preparing total RNAs using known methods, for example, guanidine-ultracentrifugation method (Chirgwin, J. M. et al., Biochemistry (1979) 18, 5294-5299), AGPC method (Chomczynski, P. et al., Anal. Biochem. (1987) 162, 156-159), or such. mRNAs of interest are prepared using the mRNA Purification Kit (Pharmacia) or such. The mRNAs can be prepared directly by using the QuickPrep mRNA Purification Kit (Pharmacia).

The obtained mRNAs are used to synthesize cDNAs of the antibody V regions using reverse transcriptase. cDNAs are synthesized using the AMV Reverse Transcriptase First-strand cDNA Synthesis Kit (Seikagaku Co.) or such. Alternatively, cDNA may be synthesized and amplified following the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using the 5'-Ampli FINDER RACE Kit (Clontech) and PCR, and such.

DNA fragments of interest are purified from the resulting PCR products, and ligated to vector DNAs. From this, a recombinant vector is produced. The recombinant vector is then introduced into *E. coli* or such, and the desired recombinant vector is prepared from a selected colony. The nucleotide sequences of DNAs of interest are then determined by known methods, for example, the dideoxynucleotide chain termination method.

A DNA encoding the antibody V region of interest is obtained, and then incorporated into an expression vector carrying a DNA that encodes a desired antibody constant region (C region).

To produce an antibody used in the present invention, the antibody gene is incorporated into an expression vector so that the gene will be expressed under the control of an expression regulatory region, for example, an enhancer and a promoter. Then, host cells are transformed with the resulting expression vector to express the antibody.

When expressing antibody genes, a DNA encoding an antibody heavy chain (H chain) or light chain (L chain) can be each separately incorporated into an expression vector to simultaneously transform the host cell, or alternatively DNAs encoding H and L chains can be incorporated into a single expression vector to transform the host cells (see, WO 94/11523).

Besides the above-described host cells, transgenic animals can also be used to produce recombinant antibodies. For example, an antibody gene is prepared as a fusion gene by inserting the antibody gene into a gene encoding a protein that is specifically produced in milk, such as goat casein. DNA fragments containing the fusion gene to which the antibody gene has been inserted is injected into goat embryos, which are then introduced into female goats. The desired antibody is then obtained from the milk produced by the transgenic goats, which are born from the goats that received the embryos, or from their offspring. Hormones may be suitably given to the transgenic goat to increase the production of milk containing the antibody of interests (Ebert, K. M. et al., Bio/Technology (1994) 12, 699-702).

In the present invention, in addition to the antibodies described above, artificially modified genetically-recombinant antibodies such as chimeric, humanized, and human antibodies can be used to reduce heterologous antigenicity against humans and such. Such modified antibodies can be produced using known methods. Monoclonal antibodies of the present invention include not only those derived from animals described above but also artificially modified genetically-recombinant antibodies such as chimeric antibodies, humanized antibodies, and bispecific antibodies.

A chimeric antibody can be obtained by linking a DNA encoding the antibody V region obtained as described above to a DNA encoding the human antibody C region, incorporating this into an expression vector, and then introducing it into a host for production. Useful chimeric antibodies can be obtained using this known method.

Humanized antibodies are also referred to as "reshaped human antibodies", which are antibodies obtained by grafting the complementarity determining regions (CDRs) of an antibody from a non-human mammal (e.g., mouse antibody) to the complementarity determining regions of a human antibody. General gene recombination procedures are also known (see, European Patent Application Publication No. EP 125023; International Patent Application Publication No. WO 96/02576).

Specifically, a DNA sequence designed to link a mouse antibody CDR to the framework region (FR) of a human antibody is synthesized by PCR, using as primers several oligonucleotides prepared to contain overlapping portions in both CDR and FR terminal regions (see methods described in WO 98/13388).

The human antibody framework region to be linked via CDR is selected such that complementarity determining region forms a favorable antigen-binding site. As necessary, amino acids of the framework region in the antibody variable region may be substituted so that the complementarity determining region of the reshaped human antibody forms a suitable antigen-binding site (Sato, K. et al., 1993, Cancer Res. 53, 851-856).

Human antibody C-regions are used as the C-regions of chimeric antibodies or humanized antibodies. For example, CH1, CH2, CH3, and CH4 can be used for the H chain, while CK and Ck can be used for the L chain. The human antibody C-region may be modified in order to improve stability of the antibody or its production.

A chimeric antibody is composed of the variable region of an antibody derived from a non-human mammal and the constant region derived from a human antibody. On the other hand, a humanized antibody is composed of the complementarity determining region of an antibody derived from a non-human mammal, and the framework region and C region derived from a human antibody. Since the antigenicity of humanized antibodies is low in the human body, and humanized antibodies are useful as an active ingredient in therapeutic agents of the present invention.

Antibodies used in the present invention are not limited to whole antibody molecules, and as long as they bind to proteins used in the present invention, antibody fragments and modification products thereof as well as divalent and monovalent antibodies are also included. Antibody fragments include, for example, Fab, F(ab')2, Fv, Fab/c having an Fab and the whole Fc, single chain Fv (scFv) in which Fv fragments from H and L chains are ligated via an appropriate linker, and Diabody. Specifically, antibody fragments are prepared by treating antibodies with an enzyme, for example, papain or pepsin. Alternatively, after genes encoding such antibody fragments are constructed and introduced into an expression vector, the antibody fragments are expressed in appropriate host cells using the vector (see, for example, Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

scFv is obtained by ligating antibody H-chain V region with an antibody L-chain V region. In this scFv, the H-chain and L-chain V regions are ligated via a linker, preferably via a peptide linker (Huston, J. S. et al., Proc. Natl. Acad. Sci. U.S.A. (1988) 85, 5879-5883). The H-chain V region and L-chain V region of an scFv may be derived from any of the antibodies described herein. For example, any single-chain peptides consisting of 12 to 19 amino acid residues such as (GGGGS)n may be used as a peptide linker for ligating the V regions.

A DNA encoding an scFv can be obtained by using, among DNAs encoding the antibody H chain or H chain V region and the antibody L chain or L chain V region mentioned above, all or DNA portion encoding amino acid sequence of interest as a template, amplifying by PCR using a primer pair that defines its two ends; and then carrying out a subsequent amplification using a combination of a DNA encoding the peptide linker portion, and primer pairs that define both ends of the linker DNA to be ligated to the H chain and L chain, respectively.

Once DNAs encoding scFvs are constructed, expression vectors carrying the DNAs and hosts transformed with the expression vectors can be obtained according to conventional methods. Furthermore, scFvs can be obtained using these hosts according to conventional methods.

Diabodies are dimers formed by linking two fragments (for example, scFv) in which a variable region is linked to another variable region via a linker or such, and typically have two VLs and two VHs (P. Holliger et al., Proc. Natl. Acad. Sci. USA, 90, 6444-6448 (1993); EP 404097; WO 93/11161; Johnson et al., Method in Enzymology, 203, 88-98, (1991); Holliger et al., Protein Engineering, 9, 299-305 (1996); Perisic et al., Structure, 2, 1217-1226 (1994); John et al., Protein Engineering, 12(7), 597-604 (1999); Holliger et al., Proc. Natl. Acad. Sci. USA., 90, 6444-6448 (1993); Atwell et al., Mol. Immunol. 33, 1301-1312 (1996); and such).

These antibody fragments can be produced, in a similar manner as described above, by obtaining their genes and expressing them in hosts. Herein, "antibody" comprises such antibody fragments.

As modified antibodies, antibodies of the present invention linked to various molecules such as polyethylene glycol (PEG) may be used. Moreover, antibodies can also be linked to radioisotopes, chemotherapeutic agents, cytotoxic substances such as bacteria-derived toxins, or such. Herein, "antibody" includes such modified antibodies. Modified antibodies can be obtained by chemically modifying the prepared antibodies. Such antibody modification methods are already established in the art.

Furthermore, antibodies used in the present invention may be bispecific antibodies. Bispecific antibodies of the present invention may be those having antigen-binding sites that each recognizes different epitopes in the protein used in the present invention or those which recognize the protein used in the present invention and a different protein. Alternatively, bispecific antibodies of the present invention may be those in which one antigen-binding domain recognizes the protein used in the present invention and the other recognizes a chemotherapeutic agent or a cytotoxic substance such as a cell-derived toxin. In this case, proliferation of cancer stem cells can be suppressed by allowing a cytotoxic substance to act directly on cancer stem cells expressing a protein used in the present invention and specifically damaging the cancer stem cells. It is also possible to use bispecific antibodies in which one antigen-binding domain recognizes a molecule that constitutes the T cell receptor complex such as CD3, expressing on cytotoxic T cells, and the other recognizes an epitope in the protein of any one of SEQ ID NOs: 1 to 3 and 5 to 9 of the present invention. The bispecific antibodies may be prepared by linking pairs of H and L chains from two types of antibodies, or by fusing hybridomas that produce different monoclonal antibodies to yield a fusion cell producing bispecific antibodies. Furthermore, the bispecific antibodies can be prepared using genetic engineering techniques.

Antibody genes constructed as described above can be expressed and obtained according to known methods. When mammalian cells are used, antibody genes can be expressed using a DNA in which a common useful promoter, an antibody gene to be expressed, and a poly A signal positioned downstream of the antibody gene on the 3' side are operably linked. Promoter/enhancer includes, for example, human cytomegalovirus immediate early promoter/enhancer.

Furthermore, other promoter/enhancers that can be used to express the antibody used in the present invention include viral promoter/enhancers of retroviruses, polyoma viruses, adenoviruses, simian virus 40 (SV40), and such; and mammalian cell-derived promoter/enhancers such as human elongation factor 1α (HEF1α).

When SV40 promoter/enhancer and HEF1α promoter/enhancer is used, gene expression can be easily carried out by the method of Mulligan et al. (Nature (1979) 277, 108) and the method by Mizushima et al. (Nucleic Acids Res. (1990) 18, 5322), respectively.

Replication origin derived from SV40, polyoma viruses, adenoviruses, bovine papilloma viruses (BPV), and such can be used. Furthermore, to increase the gene copy number in a host cell system, the expression vector may include, as a selection marker, the aminoglycoside transferase (APH) gene, thymidine kinase (TK) gene, E. coli xanthine-guanine phosphoribosyltransferase (Ecogpt) gene, dihydrofolate reductase (dhfr) gene, and such.

In the case of E. coli, the antibody gene can be expressed by an operably linked common useful promoter, a signal sequence for antibody secretion, and the antibody gene to be expressed. Such promoters include, for example, the lacz promoter and araB promoter. When the lacz promoter or araB promoter is used, the gene can be expressed by the method of Ward et al. (Nature (1098) 341, 544-546; FASEB J. (1992) 6, 2422-2427) or the method of Better et al. (Science (1988) 240, 1041-1043), respectively.

When an antibody is produced into the periplasm of E. coli, the pel B signal sequence (Lei, S. P. et al., J. Bacteriol. (1987) 169, 4379) may be used as a signal sequence for antibody secretion. After antibodies produced into the periplasm is separated, the antibody structure is appropriately refolded and then used.

Any expression system that uses, for example, eukaryotic cells or prokaryotic cells may be used to produce antibodies used in the present invention. Eukaryotic cells include, for example, animal cells such as established mammalian cell systems, insect cell systems, cells of filamentous fungi, and yeast cells. Prokaryotic cells include, for example, bacterial cells such as E. coli cells. Antibodies used in the present invention are preferably expressed in mammalian cells, for example, CHO, COS, myeloma, BHK, Vero, and HeLa cells.

Then, transformed host cells are cultured in vitro or in vivo to produce antibodies of interest. Host cells are cultured according to known methods. For example, DMEM, MEM, RPMI1640, or IMDM may be used as a culture medium, and this may also be used with serum supplements such as fetal calf serum (FCS).

Antibodies expressed and produced as described above can be isolated from cells or host animals and purified to be homogeneous. Antibodies used in the present invention can be isolated/purified by using affinity columns. For example, Protein A columns include Hyper D, POROS, and Sepharose F. F. (Pharmacia). It is also possible to use other common protein isolation/purification methods. Such methods are not particularly limited. For example, antibodies may be isolated/purified by appropriately selecting/combining chromatography columns other than the above-described affinity columns, filters, ultrafiltration, salting-out, dialysis, and such (Antibodies A Laboratory Manual. Ed Harlow, David Lane, Cold Spring Harbor Laboratory, 1988).

The antigen-binding activity (Antibodies A Laboratory Manual. Ed Harlow, David Lane, Cold Spring Harbor Laboratory, 1988) and ligand-receptor binding-inhibitory activity (Harada, A. et al., International Immunology (1993) 5, 681-690) of an antibody used in the present invention can be determined by using known methods.

Enzyme-linked immunosorbent assays (ELISAs), enzyme immunoassays (EIAs), radioimmunoassays (RIAs), and fluorescent antibody methods can be used to determine the antigen-binding activity of the antibody of the present invention. For example, when an enzyme immunoassay is used, samples containing an antibody of the present invention such as a culture supernatant of cells producing the antibody or the purified antibody are added to plates coated with a protein used in the present invention. A secondary antibody labeled with an enzyme such as alkaline phosphatase is added, and the plates are incubated. After washing, an enzyme substrate such as p-nitrophenyl phosphate is added and the absorbance is measured to evaluate the antigen-binding activity.

An antibody used in the present invention may appropriately be linked to a cytotoxic substance described above such as a proliferation inhibitor, toxic peptide, or radioactive chemical substance. Such modified antibodies (hereinafter referred to as antibody conjugates) can be obtained by chemically modifying the obtained antibodies. Specifically, a linker molecule links a growth inhibitor to an antibody via chemical bonding so that the antibody and growth inhibitor or cytotoxic substance can chemically conjugate with each other (for example, can bind covalently). Preferred binders (linkers) are cleavable linkers. It is more preferable that the linkers are cleaved under mild conditions (specifically, intracellular conditions that do not affect the activity of inhibitors). Examples of suitable cleavable linkers include disulfide linkers, acid-labile linkers, photo-labile linkers, peptidase-labile linkers, and esterase-labile linkers. Disulfide-containing linkers can be cleaved via disulfide exchange, which can occur under physiological conditions. Acid-labile linkers can be cleaved at acid pH. For example, certain intracellular compartments such as endosomes and lysosomes have an acidic pH (pH 4 to 5), and provide conditions suitable for cleaving acid-labile linkers. Photolabile linkers are useful on the body surface and in many body cavities, which can be exposed to light. Furthermore, infrared light can penetrate tissues. Peptidase-labile linkers can be used to cleave certain peptides inside or outside cells (for example, see Trouet et al., Proc. Natl. Acad. Sci. USA (1982) 79, 626-629; Umemoto et al., Int. J. Cancer (1989) 43, 677-684).

Such modified antibodies can be prepared not only by chemical modification as described above, but also in a molecular form such as a bispecific antibody designed to recognize a growth inhibitor, toxic peptide, radioactive chemical substance, or the like using genetic recombination techniques. "Antibody" of the present invention also comprises such antibodies.

Examples of modified antibodies that are provided by the present invention also include those modified with a toxic peptide such as ricin, abrin, ribonuclease, onconase, DNase I, Staphylococcal enterotoxin-A, pokeweed antiviral protein, gelonin, diphtheria toxin, *Pseudomonas* exotoxin, *Pseudomonas* endotoxin, L-asparaginase, or PEG L-Asparaginase. In another embodiment, antibodies may be modified by the combined use of one or more growth inhibitors and toxic peptides. As described above, the linkage between the antibody of the present invention that binds to at least one protein described in SEQ ID NOs: 1 to 3 and 5 to 9 and an above-described growth inhibitor, toxic peptide, or radioactive chemical substance may be a covalent or non-covalent bond. Methods for preparing modified antibodies linked to such chemotherapeutic agents are known.

Furthermore, proteinaceous pharmaceutical agents and toxins can be linked to an antibody by using a genetic engineering procedure. Specifically, for example, a recombinant vector into which a DNA encoding a toxic peptide described above and a DNA encoding an antibody that binds to any of proteins of at least one of SEQ ID NOs: 1 to 3 and 5 to 9 of the present invention are fused in frame and incorporated into an expression vector is constructed. Transformed cells obtained by introducing the vector into appropriate host cells are cultured to express the incorporated DNA. The modified antibody linked to the toxic peptide is obtained as a fusion protein. When a fusion protein with an antibody is prepared, in general, a proteinaceous pharmaceutical agent or toxin is placed at the C terminus of the antibody. A peptide linker may be interposed between the antibody and a proteinaceous pharmaceutical agent or toxin.

Antibodies used in the present invention may have a cytotoxic activity. Herein, the cytotoxic activity includes, for example, complement-dependent cytotoxicity (CDC) and antibody-dependent cell-mediated cytotoxicity (ADCC). Herein, CDC refers to a cytotoxic activity mediated by the complement system, while ADCC refers to an activity of damaging target cells, which is caused by binding of Fcγ receptor-carrying cells (immunocytes, etc.) via Fcγ receptor to the Fc portion of specific antibody upon binding of the antibody to cell-surface antigens on target cells.

Whether an antibody used in the present invention has ADCC or CDC can be measured by known methods (see, for example, Current protocols in Immunology, Chapter 7. Immunologic studies in humans, Editor, John E, Coligan et al., John Wiley & Sons, Inc., (1993)).

Specifically, cytotoxicity can be measured, for example, by the following method.

Preparation of Effector Cells

Spleen is removed from a CBA/N mouse or the like, and spleen cells are dispersed in RPMI1640 medium (GIBCO). After washing with the same medium containing 10% fetal bovine serum (FBS, HyClone), effector cells with a cell concentration adjusted to $5 \times 10^6$ cells/ml were prepared.

Preparation of Complement Solution

Baby Rabbit Complement (CEDARLANE) is diluted 10-fold with a medium (GIBCO) containing 10% FBS to prepare a complement solution.

Preparation of Target Cells

Cells expressing a protein used in the present invention (cancer stem cells, etc.) are radiolabeled by incubating them with 0.2 mCi of $^{51}$Cr-sodium chromate (Amersham Pharmacia Biotech) in DMEM medium containing 10% FBS for one hour at 37° C. After radiolabeled, the cells are washed three times with RPMI1640 medium containing 10% FBS, and the target cells with a cell concentration adjusted to $2 \times 10^5$ cells/ml were prepared.

ADCC Measurement

50 μl the target cells and 50 μl of the antibody used in the present invention are each added to a 96-well U-bottom plate (Becton Dickinson), and reacted for 15 minutes on ice. Thereafter, 100 μl of effector cells are added and incubated in a carbon dioxide incubator for four hours. The final antibody concentration is adjusted to 0 or 10 μg/ml. After incubation, 100 μl of the supernatant is collected and the radioactivity is measured with a gamma counter (COBRAI-IAUTO-GMMA, MODEL D5005, Packard Instrument Company). The cytotoxic activity (%) can be calculated according to:

$$(A-C)/(B-C) \times 100.$$

A represents the radioactivity (cpm) of each sample, B represents the radioactivity (cpm) of a sample where 1% NP-40 (nacalai tesque) has been added, and C represents the radioactivity (cpm) of a sample containing the target cells alone.

CDC Measurement

50 μl of the target cells and 50 of the antibody used in the present invention are each added to a 96-well flat-bottom plate (Becton Dickinson), and reacted for 15 minutes on ice. Thereafter, 100 μl of the complement solution is added, and incubated in a carbon dioxide incubator for four hours. The antibody final concentration is adjusted to 0 or 3 μg/ml. After incubation, 100 μl of the supernatant is collected to measure the radioactivity with a gamma counter. The cytotoxic activity can be calculated by the similar way as in the ADCC determination.

Antibodies with modified sugar chains can appropriately be used in the antibodies provided by the present invention. It is known that cytotoxic activity of antibodies can be increased by modifying its sugar chains. Known antibodies with modified sugar chains include, for example: glycosylated antibodies (WO 1999/054342 and such); antibodies with defucosylated sugar chain (WO 2000/061739, WO 2002/031140, and such); and antibodies having a sugar chain with bisecting GlcNAc (bisecting N-acetylglucosamine) (WO 2002/079255).

Antibodies of the present invention preferably include antibodies with modified sugar chains whose sugar chain composition has been altered to increase the ratio of defucosylated antibody or to increase the ratio of antibody attached with bisecting N-acetylglucosamine.

Antibodies having a neutralizing activity can also be used appropriately in the present invention. In general, "neutralizing activity" refers to the activity of a foreign molecule such as a toxin or virus, or an internal molecule such as a hormone or cytokine to inhibit a ligand's biological activity on cells. Specifically, substance having a neutralizing activity refers to a substance that binds to a ligand or a receptor to which the ligand binds, thereby inhibiting the ligand-receptor binding. The receptor whose ligand binding is inhibited by the neutralizing activity cannot exert their receptor-mediated biological activity. When the antigen-binding molecule is an antibody, in general, such an antibody with a neutralizing activity is called a neutralizing antibody. The neutralizing activity of a test substance can be assessed by comparing biological activities in the presence of a ligand, in the condition of when the test substance is present or not present.

EREG, which is a target of EP27 antibody described later on in the Examples, is exemplified below. EGF receptor, which is believed to be a main receptor for the EREG represented by SEQ ID NO: 3, dimerizes upon ligand binding and activates its own cytoplasmic tyrosine kinase domain. The activated tyrosine kinase causes a peptide having phosphotyrosine by autophosphorylation, which allows association of various signal transduction accessory molecules. The molecules are mainly phospholipase Cγ (PLCγ), She, Grb2, and such. Of these accessory molecules, the former two are further phosphorylated by the tyrosine kinase of the EGF receptor. The main signaling pathway from the EGF receptor is the one in which phosphorylation occurs in order of She, Grb2, Sos, Ras, and Raf/MAPK kinase/MAP kinase. It is believed that there is also an alternative pathway from PLCγ to PKC. Since such intracellular signal cascades vary depending on cell type, a target molecule can appropriately be selected for each target cell type of interest and is not limited to the factors described above. It is possible to use an appropriate in vivo signal activation assay kit available on the market (for example, protein kinase C activation measurement system (GE Healthcare Bioscience, etc.)).

Alternatively, the in vivo signal activation can be detected by using as an indicator the transcriptional induction of a target gene downstream in the in vivo signal cascade. Changes in the transcriptional activity can be detected based on the principle of reporter assay. Specifically, a reporter gene such as GFP (Green Fluorescence Protein) or luciferase is placed downstream of the transcriptional factor or promoter region of the target gene. A change in the transcriptional activity can be determined as reporter activity by measuring the reporter activity.

In addition, the EGF receptor typically functions to promote cell proliferation, and thus the activation of in vivo signal transduction can be assessed by measuring the proliferative activity of the target cell. In the present invention, the neutralizing activities of neutralizing antibodies of the present invention are assessed by measuring the cell proliferative activity. However, methods are not limited thereto, and methods described above can suitably be used to assess the activity depending on the type of selected target cells.

Specifically, the neutralizing activity of an anti-EREG antibody can be assessed or determined by measuring the cell proliferative activity, for example, using the method described below. For example, the method where the incorporation of [$^3$H]-labeled thymidine, which is added to a culture medium, into viable cells is measured as an indicator for the DNA replication ability is used.

Simpler methods include the MTT method and dye exclusion tests in which the ability of cells to exclude dyes such as Trypan Blue outside is measured under a microscope. The MTT method utilizes the ability of viable cells to convert MTT (3-(4,5-dimethylthiazol-2-yl)-2,5-diphenyl tetrazolium bromide), a tetrazolium salt, into a blue formazan product. More specifically, the MTT method is performed as follows: a test antibody is added to a culture medium containing test cells; after a certain period, an MTT solution is added to the culture medium; the mixture is allowed to stand for a certain period so that MMT is incorporated into the cells. As a result, a yellow compound MTT is converted into a blue compound by succinate dehydrogenase in cytoplasmic mitochondria. After the blue product is dissolved for color development, the absorbance is measured as an indicator for the viable cell count.

In addition to MTT, other commercially available reagents such as MTS, XTT, WST-1, and WST-8 (nacalai tesque, etc.) can preferably be used. There are also known methods for assessing the cell proliferative activity using as an indicator an intracellular ATP content or impedance of cell culture. When assessing the activity, a control antibody that is of the same isotype as the anti-EREG antibody of interest but does not have the neutralizing activity is used in the same manner as for the anti-EREG antibody. The activity can be assessed whether the anti-EREG antibody exhibits the neutralizing activity greater than that of the control antibody.

Cells whose proliferation is inhibited by the anti-EREG antibody are not particularly limited, as long as they express EREG protein. Examples of preferred EREG-expressing cells include cancer cells. Specifically, cells derived from colorectal cancer, lung adenocarcinoma, pancreatic cancer, stomach cancer, or kidney cancer are preferable EREG-expressing cells in the present invention. A cell proliferation-inhibitory effect against both primary and metastatic lesions of all these cancers can be achieved by the present invention. More preferred cancer cells include those of primary colorectal cancer, metastatic colorectal cancer, lung adenocarcinoma, pancreatic cancer, stomach cancer, and kidney cancer. Thus, anti-EREG antibodies can be used to treat/prevent diseases caused by cell proliferation, for example, colorectal cancer, lung adenocarcinoma, pancreatic cancer, stomach cancer, and kidney cancer. These cancers can be targets of treatment or prevention, regardless of primary or metastatic lesions. More preferably, anti-EREG antibodies are used to treat and/or prevent primary colorectal cancer, metastatic colorectal cancer, and pancreatic cancer. Furthermore, among these cancers, those which grow in an EREG-dependent manner are preferred as a target of treatment and/or prevention in the present invention.

In the description and Tables herein, when nucleotides and amino acids are represented by abbreviations, these abbreviations are based on the abbreviations by IUPAC-IUB Commission on Biochemical Nomenclature, or the conventional abbreviations in the art. Regarding amino acids, when an optical isomer exists, it represents L form, unless otherwise specified.

Cancer Stem Cell Inhibitors of the Present Invention

The effective dosage of cancer stem cell inhibitors of the present invention is selected within the range of 0.001 to 1,000 mg/kg weight for each administration. Alternatively, the dosage may be selected within the range of 0.01 to 100,000 mg/body for each patient. However, the dosage of the inhibitors of the present invention is not limited to these doses. Meanwhile, with respect to the timing of administration, an inhibitor of the present invention may be administered before or after manifestation of clinical symptoms of diseases. The inhibitors of the present invention can be formulated according to conventional methods (Remington's Pharmaceutical Science, latest edition, Mark Publishing Company, Easton, US), and may contain both pharmaceutically acceptable carriers and additives. Such carriers and medical additives include, for example, water, pharmaceutically acceptable organic solvents, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants that are acceptable as a medical additive. In practice, additives are selected alone or in appropriate combination from those listed above depending on the dosage form of an inhibitor of the present invention; but are not limited thereto. For example, when used as a preparation for injection, it can be used in a form in which the inhibitor is dissolved in a medium such as physiological saline, buffer, or glucose solution and an adsorption inhibitor such as Tween80, Tween20, gelatin, or human serum albumin is added; alternatively, the inhibitor of the preset invention may be in a lyophilized form for dissolution and reconstitution before use. As excipients for lyophilization, for example, sugar alcohols and saccharides such as mannitol and glucose can be used. The inhibitors of the present invention are generally administered by a parenteral route, for example, via injection (subcutaneous, intravenous, intramuscular, intraperitoneal, etc.), transdermal, transmucosal, intranasal, or pulmonary administration; however, the inhibitor can be administered orally.

Herein, "combined use" of a cancer stem cell inhibitor and an anti-cancer agent means that these agents may be administered at the same time or in succession; alternatively, one is administered at an interval after administration of the other.

Herein, cancer stem cell inhibitors can be used as various embodiments such as, for example, prevention of cancer recurrence, suppression of cancer recurrence, prevention of cancer metastasis, suppression of cancer metastasis, and adjuvant therapy for preventing postoperative recurrence for application. When used in the above-described embodiments, any cancer stem cell inhibitor can be used as a cancer stem cell inhibitor of the present invention. However, non-limiting preferred examples include agents for inhibiting cancer stem cell proliferation or agents for disrupting cancer stem cell. As long as agents for inhibiting cancer stem cell proliferation that are provided by the present invention can suppress the proliferation of target cancer stem cells, mechanism of suppressing cancer stem cell proliferation is not relevant. As a non-limiting example, such agents for inhibiting cancer stem cell proliferation include those comprising as an active ingredient an antibody having neutralizing activity against cancer stem cell proliferation or growth or an antibody having cytotoxicity against cancer stem cells. Similarly, as long as agents for disrupting cancer stem cells that are provided by the present invention can destroy target cancer stem cells, mechanism of disrupting cancer stem cells is not relevant. As a non-limiting example, such agents for disrupting cancer stem cells include agents for inhibiting cancer stem cell proliferation comprising as an active ingredient an antibody having cytotoxicity or apoptotic activity against cancer stem cells. Those skilled in the art can determine whether a test agent for disrupting cancer stem cells has apoptotic activity by using known methods including terminal deoxynucleotidyl transferase biotin-dUTP nick end labeling (TUNEL) assay, caspase activity (in particular, caspase-3) assay, fas ligand assay, and Annexin V assay as apoptotic activity assay methods. Non-limiting preferred examples include cancer stem cell differentiation enhancers. Non-limiting examples of differentiation enhancers include BMP4, i.e., the polypeptide of SEQ ID NO: 4, or polypeptide equivalents having one or several amino acid addition(s), deletion(s), and/or substitution(s) among amino acids of the polypeptide. Such polypeptide equivalents preferably have a CSC differentiation-inducing activity equivalent to that of the polypeptide of SEQ ID NO: 4. The equivalency of the differentiation-inducing activity can be defined, for example, by whether the CK20-inducing activity for CSCs is 10%, preferably 20%, more preferably 30%, even more preferably 40%, and still more preferably 50% of that of the polypeptide of SEQ ID NO: 4. In another non-limiting embodiment, the equivalency of the differentiation-inducing activity can be defined, for example, by whether the CK20-inducing activity for CSCs is 60%, preferably 70%, more preferably 80%, even preferably 90%, and still preferably 95% of that of the polypeptide of SEQ ID NO: 4.

Anti-cancer agents that are used in combination with a cancer stem cell inhibitor of the present invention include alkylating agents, metabolic antagonists, natural products, platinum complexes, and other pharmaceutical agents. Alkylating agents include nitrogen mustards, ethylenimines, methylmelamines, alkyl sulfonates, nitrosoureas, and triazens. Nitrogen mustards include, for example, mechlorethamine, cyclophosphamide, ifosfamide, melphalan, and chlorambucil. Ethylenimines and methylmelamines include, for example, hexamethylmelamine and thiotepa. Alkyl Sulfonates include busulfan. Nitrosoureas include, for example, carmustine (BCNU), lomustine (CCNU), semustine (methyl-CCNU), and streptozocin. Triazens include dacarbazine (DTIC). Metabolic antagonists include folic acid analogs, pyrimidine analogs, and purine analogs. Folic acid analogs include methotrexate. Pyrimidine analogs include, for example, fluorouracil (5-FU), doxifluridine (5'-DFUR; trade name: FURTULON), capecitabine (trade name: Xeloda), floxuridine (FudR), and cytarabine. Purine analogs include, for example, mercaptopurine (6-MP), thioguanine (TG), and pentostatin. Natural products include *vinca* alkaloids, epipodophyllotoxins, and antibiotics. *Vinca* alkaloids include, for example, vinblastine (VLB) and vincristine (VCR). Epipodophyllotoxins include, for example, etoposide and teniposide. Antibiotics include, for example, dactinomycin (actinomycin D), daunorubicin, doxorubicin, bleomycin, plicamycin, and mitomycin. Platinum complex refers to platinum coordination complex, and includes, for example, cisplatin (CDDP) and carboplatin. Other pharmaceutical agents include: topoisomerase inhibitors such as irinotecan and camptothecin; taxols, for example, paclitaxel, docetaxel; anthracenediones, for example, mitoxantrone; urea-substituted derivatives, for example, hydroxyurea; methyl hydrazines, for example, procarbazine hydrochloride (trade name: Natulan), vitamin A metabolites, for example, tretinoin (trade name: VESANOID), as well as include rituximab, alemtuzumab, trastuzumab, bevacizumab, cetuximab, panitumumab, trastuzumab, and gemutuzumab.

All prior-art documents cited herein are incorporated herein by reference.

EXAMPLES

Herein below, the present invention will be specifically described with reference to examples, however, it is not to be construed as being limited thereto.

Establishment of Human Colorectal Cancer Cell Lines with Immunodeficient NOG Mice Colorectal cancer specimens were obtained from patients with their consent under approval of the ethical committees of PharmaLogicals Research (Singapore) and Parkway Laboratory Services (Singapore). Tumor blocks were cut into small pieces with a razor blade, and grafted in the lateral region of NOG mice. Human colorectal cancer xenografts were maintained by passaging them in NOG mice provided by the Central Institute for Experimental Animals (Japan). Mice used in this experiment were treated in accordance with the animal experiment guidelines of PharmaLogicals Research. For histopathological examination, small blocks of xenograft tumors and surgical human tissue samples were fixed with 4% paraformaldehyde at 4° C. for 16 to 24 hours, and embedded in paraffin by the AMeX method (Sato Y, et al., (1986) Am J Pathol, 125: 431-435; Sato Y, et al., (1992) Am J Pathol, 140: 775-779; Suzuki M, et al. (2002) J Toxicol Sci, 27: 165-172). The thin sections were stained with eosin and hematoxylin and assessed by microscopic observation.

Isolation and In Vitro Culture of Large Intestine CSCs

Tissues of xenograft were cut with a razor blade in order to prepare single cancer cell suspensions. After the suspensions were incubated at 37° C. for 3 hours in DPBS containing collagenase/dispase (Roche) and DNaseI (Roche), the suspensions were filtered through 40-μm Cell Strainers (BD Biosciences). The cells were suspended in the lysis buffer (BD Biosciences) to remove erythrocytes. The prepared xenograft-derived cells (such cells are referred to as primary cells) were cultured under 5% $CO_2$ atmosphere at 37° C. in DMEM/F12 (Invitrogen) containing N-2 Supplement (Invitrogen), 20 ng/ml human EGF (Invitrogen), 10 ng/ml human basic fibroblast growth factor (Sigma), 4 μg/ml heparin (Sigma), 4 mg/ml BSA (Invitrogen), 20 μg/ml human insulin zinc solution (Invitrogen), and 2.9 mg/ml glucose (Sigma) (Todaro M, et al. (2007) Cell Stem Cell 1: 389-402). Adherent and floating CSCs were cultured using conventional polystyrene-treated cell culture flasks (BD Biosciences) and Ultra-low attachment cell culture flasks (Corning), respectively.

In Vivo Tumor Formation Analysis

Cell suspensions were prepared by serial dilution. 100 μl of cancer cell suspensions in Hanks' balanced salt solution (Invitrogen) were subcutaneously inoculated into lateral region of mice using 50% matrigel (BD Bioscience). The tumor development was monitored over seven weeks. In order to inoculate single cell, cells were labeled using an FITC-labeled mouse anti-human CD326 (EpCAM) antibody (Miltenyi Biotec), and plated in a terasaki plate (Termo Fisher Scientific). Cell singularity was confirmed under a microscope. Single cells were inoculated into lateral region of mice using 50 μl of 50% matrigel. The tumor development was monitored over 10 weeks.

Establishment of Cells Expressing Full-Length Human Lgr4, Lgr5, and Lgr6

Full-length human Lgr4, Lgr5, and Lgr6 cDNAs were cloned by PCR based on the sequences of NM_018490 (Lgr4), NM_001017403 (Lgr6), and NM_003667 (Lgr5). The cloned genes were expressed with or without adding HA tag to their N termini. Cells of Chinese hamster ovary cell line CHO DG44 (Invitrogen) were transfected with expression plasmids using Gene Pulser (BioRad). Stable cell lines HA-Lgr4/DG, HA-Lgr5/DG, and HA-Lgr6/DG were selected using G418.

Preparation of Soluble Lgr5-Fc Protein

Soluble Lgr5 protein (amino acids 1 to 555) was expressed as a fusion protein with the Fc domain of mouse IgG2a in CHO DG44. Transfectants were screened by sandwich ELISA using a goat anti-mouse IgG2a (Bethyl laboratories) and HRP-rat anti-mouse IgG2a mAb (Serotec). A clone that produces sLgr5-Fc at the highest level was named 2D3. A culture supernatant of 2D3 was collected, and Lgr5-Fc protein was affinity-purified using a Protein A-Sepharose column (Pharmacia). Lgr5-Fc was used as an antigen in protein immunization and ELISA screening.

Generation of Anti-Lgr5 Monoclonal Antibody by Immunization with Lgr5-Fc Protein Balb/c mice (Charles River Japan) were immunized subcutaneously with 50 g of Lgr5-Fc emulsified in Freund's complete adjuvant. After two weeks, the mice were injected with the same amount of Lgr5-Fc in Freund's incomplete adjuvant once a week over two weeks. Three days before cell fusion, 25 μg of Lgr5Fc was intravenously injected to the mice. Spleen lymphocytes derived from the immunized mice were fused with cells of mouse myeloma line P3-X63Ag8U1 (ATCC) using a conventional method (Kremer L and Marquez G (2004) Methods Mol Biol., 239: 243-260). Hybridoma culture supernatants were screened for antibodies reactive to sLgr5-Fc by ELISA to establish Lgr5-specific mouse mAb 2T15E-2 and 2U2E-2.

Flow Cytometry Analysis

Large intestine CSCs were incubated with labeled antibodies and analyzed using the EPICS ALTRA (Beckman Coulter) and FACSCalibur (Becton Dickinson)). Antibodies used were: PE-labeled mouse anti-human CD133 antibody (Miltenyi Biotec), PE-labeled mouse anti-human CD44 antibody (BD Pharmingen), FITC-labeled mouse anti-human CD326 (EpCAM) antibody (Miltenyi Biotec), PE-labeled mouse anti-human CD166 antibody (R&D Systems), PE-labeled mouse anti-human CD24 antibody (BD Pharmingen), PE-labeled mouse anti-human CD26 antibody (BD Pharmingen), and PE-labeled mouse anti-human CD29 antibody (BD Pharmingen).

Large intestine CSCs were incubated with mouse anti-human Lgr5 antibody (2T15E-2) and then with PR-labeled rat anti-mouse IgG antibody (Invitrogen) to stain Lgr5. The aldehyde dehydrogenase activity was measured using the AldeFluor Kit (Stemcell Technologies). Mouse cells were discriminated from human large intestine CSCs by staining with anti-mouse MHC class I antibody (Abcam), and PE- or APC-labeled goat anti-human IgG2a antibody (BioLegend). Dead cells were also removed using the 7-AAD Viability Dye (Beckman Coulter).

Western Blot Analysis

Protein was extracted using RIPA buffer (Sigma) supplemented with the Complete Mini Protease Inhibitor Cocktail (Roche). Proteins were fractionated by the NuPAGE Gel (Invitrogen) and transferred onto PVDF membrane. After blocking with PBS containing 1% skimmed milk, the membrane was probed with rabbit anti-human β-catenin antibody (Sigma), rabbit anti-human phospho-c-JUN antibody (Sigma), rabbit anti-human TCF1 antibody (Cell Signaling), rabbit anti-human TCF3 antibody (Cell Signaling), rabbit anti-human TCF4 antibody (Cell Signaling), rabbit anti-human Lgr5 antibody (Abcam), mouse anti-human E-cadherin antibody (Abcam), rabbit anti-human Snail antibody (Abeam), and mouse anti-human GAPDH antibody (Santa Cruz). Reactive bands were detected using BCIP/NBT substrate (KPL).

Quantitative Real-Time Polymerase Chain Reaction

Total RNAs were isolated using the RNeasy Mini Kit including DNAase treatment (Qiagen). cDNAs were synthesized using the First-Strand cDNA Synthesis Kit (SABiosciences). Quantitative real-time PCR (QRT-PCR) analysis was performed with the SYBR Green/Rox qPCR (SABiosciences) using the Mx3005P Real-Time PCR System (Stratagene). The fold induction value was calculated according to the 2-ΔΔCt method. GAPDH and ACTB were used as a reference. All experiments were performed in triplicate.

Primers for Quantitative Real-Time PCR Analysis

The following primers were used to amplify reactive transcripts.

```
Lgr5:
forward primer:
                                    (SEQ ID NO: 10)
5'-AGTTTATCCTTCTGGTGGTAGTCC-3';

reverse primer:
                                    (SEQ ID NO: 11)
5'-CAAGATGTAGAGAAGGGGATTGA-3';

GAPDH:
forward primer:
                                    (SEQ ID NO: 12)
5'-CTCTGCTCCTCCTGTTCGAC-3';

reverse primer:
                                    (SEQ ID NO: 13)
5'-ACGACCAAATCCGTTGACTC-3';

ACTB:
forward primer:
                                    (SEQ ID NO: 14)
5'-AAGTCCCTTGCCATCCTAAAA-3';

reverse primer:
                                    (SEQ ID NO: 15)
5'-ATGCTATCACCTCCCCTGTG-3'
```

Cell Proliferation Assay

Floating and adherent CSCs were plated at about 100 and 1×10$^4$ cells/well in 96-well plates, respectively. On days 0 and 3, viable cell counts were determined by the Cell Counting Kit-8 Assay (Doujindo) according to the manufacturer's protocol. Average absorbance on day 0 was taken as 100%. For chemosensitivity assay, floating and adherent CSCs were plated at about 100 and 1×10$^4$ cells/well in 96-well plates, respectively. After 24 hours of incubation, 10 μg/ml 5-FU (Hospira), 10 μg/ml irinotecan (Hospira), 50 mM TCF inhibitor FH535 (Merck), or 50 mM β-catenin inhibitor Cardamonin (Merck) were added to the plates. After three days of culture in the presence of the agents, the Cell Counting Kit-8 was added to the cells. The average absorbance of cells exposed to DMSO or medium alone was taken as 100%. All experiments were performed in triplicate.

Immunofluorescent Staining of Cultured Cells and Xenograft Tissues

For immunofluorescent cytochemistry, cells were fixed with 4% paraformaldehyde and methanol, and incubated with a mouse anti-human E-cadherin antibody (Abcam), rabbit anti-human Snail antibody (Abcam), or rabbit anti-human β-catenin antibody (Sigma)). Then, the cells were visualized using the AlexaFluor 488-labeled goat anti-mouse IgG antibody or goat anti-rabbit IgG antibody. For immunofluorescent cytochemistry, thin sections derived from paraffin blocks of xenograft tumors described above were incubated with a mouse anti-human Lgr5 antibody (2U2E-2) or rabbit anti-human Snail antibody (Abcam). After incubation with a primary antibody, Lgr5 protein was detected with a goat anti-mouse antibody conjugated with the polymer-HRP (DAKO) and visualized with the AlexaFluor 488-labeled tyramide (Invitrogen), while Snail protein was detected with biotinylated goat anti-rabbit antibody (VECTOR) and visualized with the AlexaFluor 568-labeled streptavidin (Invitrogen). These cells and samples were also stained with DAPI (Invitrogen).

Example 1: Establishment of Colorectal Cancer Xenografts

As described in a previous report (Fujii E. et al., (2008) Establishment and characterization of in vivo human tumor models in the NOD/SCID/gamma(c)(null) mouse. Pathol Int 58: 559-567), the present inventors established 11 types of human colorectal cancer xenografts using NOD/Shi-scid, IL-2Rγnull (NOG) mice (Table 1; the number of human colorectal cancer cell lines established with immunodeficient NOG mice).

TABLE 1

|  | Adenocarcinoma | | | |
|---|---|---|---|---|
|  | G1 | G2 | G3 | Total |
| Number of cases | 4 | 46 | 3 | 53 |
| Established | 0 | 10 | 1 | 11 |
| Impracticable* | 0 | 6 | 0 | 6 |
| EBV lymphoma | 2 | 16 | 1 | 19 |
| Aggravated animal condition † | 1 | 12 | 1 | 14 |
| No viable cancer | 1 | 2 | 0 | 3 |

In the above Table 1, asterisk indicates cases established but unsuitable for experiment, and dagger indicates cases with infection and such.

As shown in Table 1, 17 types of colorectal cancer xenografts were established from samples of 53 human colorectal cancer patients. Except for the 17 types of xenografts, associated EBV-infected lymphoma cells occurred in 19 cases (which aggravated the condition of NOG mice); other infections were found in 14 cases; and no tumor growth was observed in three cases. Of the 17 types, 11 xenografts survived even after freeze-thawing, and had the capacity to reconstitute tumor, and showed similar histopathological features as those of the original tumors. Of the 11 types, 10 xenografts were derived from grade-2 moderately-differentiated adenocarcinomas, and the remaining one was derived from a grade-3 poorly-differentiated adenocarcinoma.

Of the 11 types, 10 xenografts were derived from moderately-differentiated colorectal cancer (MDCC), and the remaining one was derived from poorly-differentiated colorectal cancer (PDCC) (Table 2; histopathological classification of the original human colorectal cancers that were used to establish the 11 xenografts).

TABLE 2

| Histopathological classification of original human tumor | | | | | |
|---|---|---|---|---|---|
| Line No. | Type | Grade | TNM | AJCC stage | Dukes' stage |
| PLR30 | Adenocarcinoma | G2 | pT3N0MX | II | B |
| PLR59 | Adenocarcinoma | G2 | pT3N2MX | III | C2 |
| PLR123 | Adenocarcinoma | G2 | pT4N1MX | III | C1 |
| PLR168 | Adenocarcinoma | G2 | pT3N0MX | II | B |
| PLR215 | Adenocarcinoma | G2 | pT3N0MX | II | B |
| PLR241 | Adenocarcinoma | G2 | pT4N3M1 | IV | D |
| PLR254 | Adenocarcinoma | G2 | pT4N2MX | III | C2 |
| PLR261 | Adenocarcinoma | G2 | pT3N0MX | II | B |
| PLR325 | Adenocarcinoma | G3 | pT4N1M1 | III | C1 |

TABLE 2-continued

Histopathological classification of original human tumor

| Line No. | Type | Grade | TNM | AJCC stage | Dukes' stage |
|---|---|---|---|---|---|
| PLR379 | Adenocarcinoma | G2 | pT4N2MX | IIIC | C1 |
| PLR423 | Adenocarcinoma | G2 | pT3N0M1 | IV | D |

Figure 16:
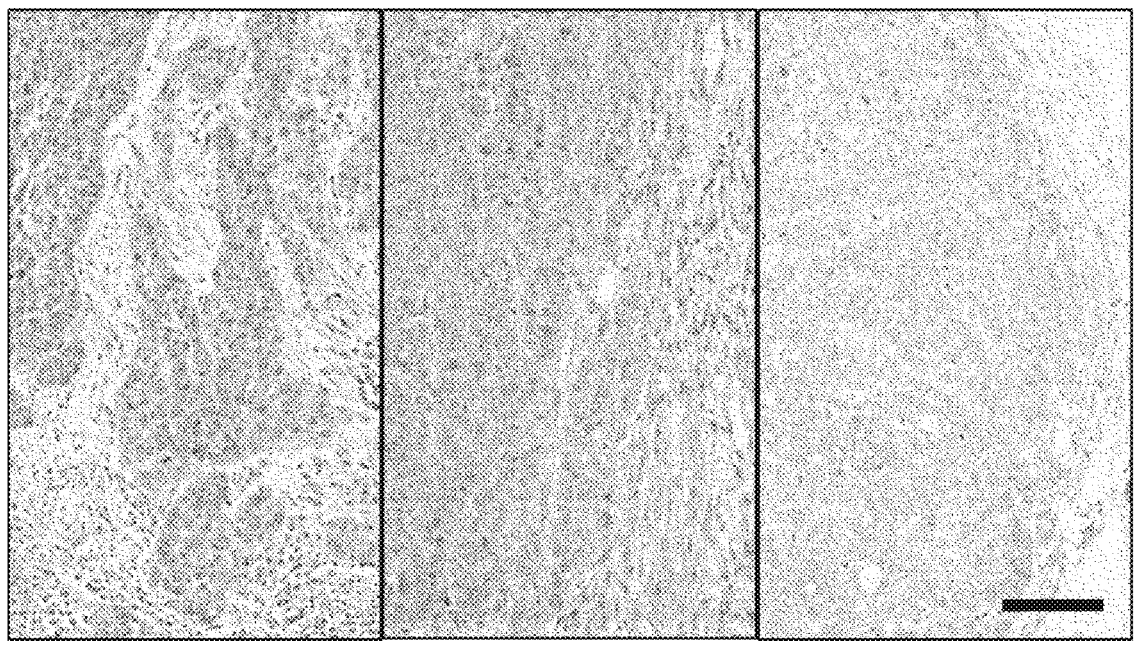
FIG. 16 shows photographs depicting histopathological features of xenograft tissues. Histopathological PDCC xenografts derived from a poorly-differentiated colorectal cancer (PDCC) xenograft reconstructed almost the same histopathological morphology as the original tumor. The PDCC xenografts did not have apparent epithelial duct structures (4 and 13 passages). Scale bar represents 100 μm.

Both MDCC and PDCC xenografts reconstituted histopathological morphologies almost equivalent to those of the original tumors. MDCC xenografts formed specific epithelial ducts which contained goblet cells, and small budding clusters (may undergo epithelial-mesenchymal transition (EMT)). In contrast, PDCC xenografts did not form such specific epithelial duct structures (FIGS. 1 and 16).

Example 2: Isolation of Large Intestine CSCs

In order to isolate large intestine CSCs, the present inventors used two types of MDCC xenografts, i.e., PLR59 and PLR123. These xenografts were chosen by the present inventors because they grew rapidly even after 10 passages in NOG mice while maintaining the capacity to reconstitute tumors with epithelial ducts and small budding clusters (FIG. 1). Thus, the present inventors predicted that stable CSCs can be obtained from the xenografts.

Figure 2:
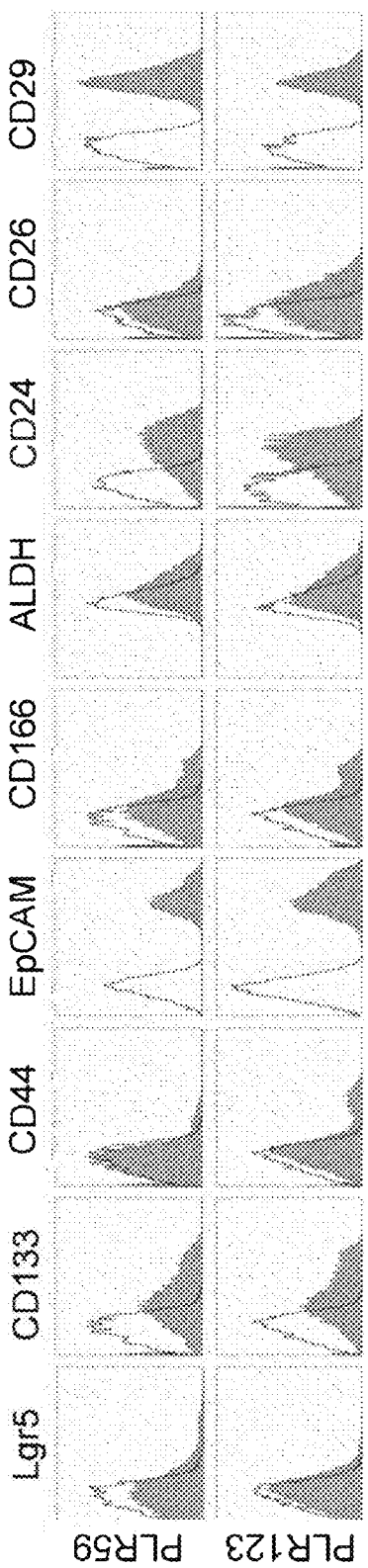
FIG. 2 is a diagram showing a result of flow cytometry analysis of cells from xenografts PLR59 and PLR123 passaged in NOG mice for known CSC markers. The cells were stained with antibodies against the markers indicated and then analyzed with flow cytometry. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 3:
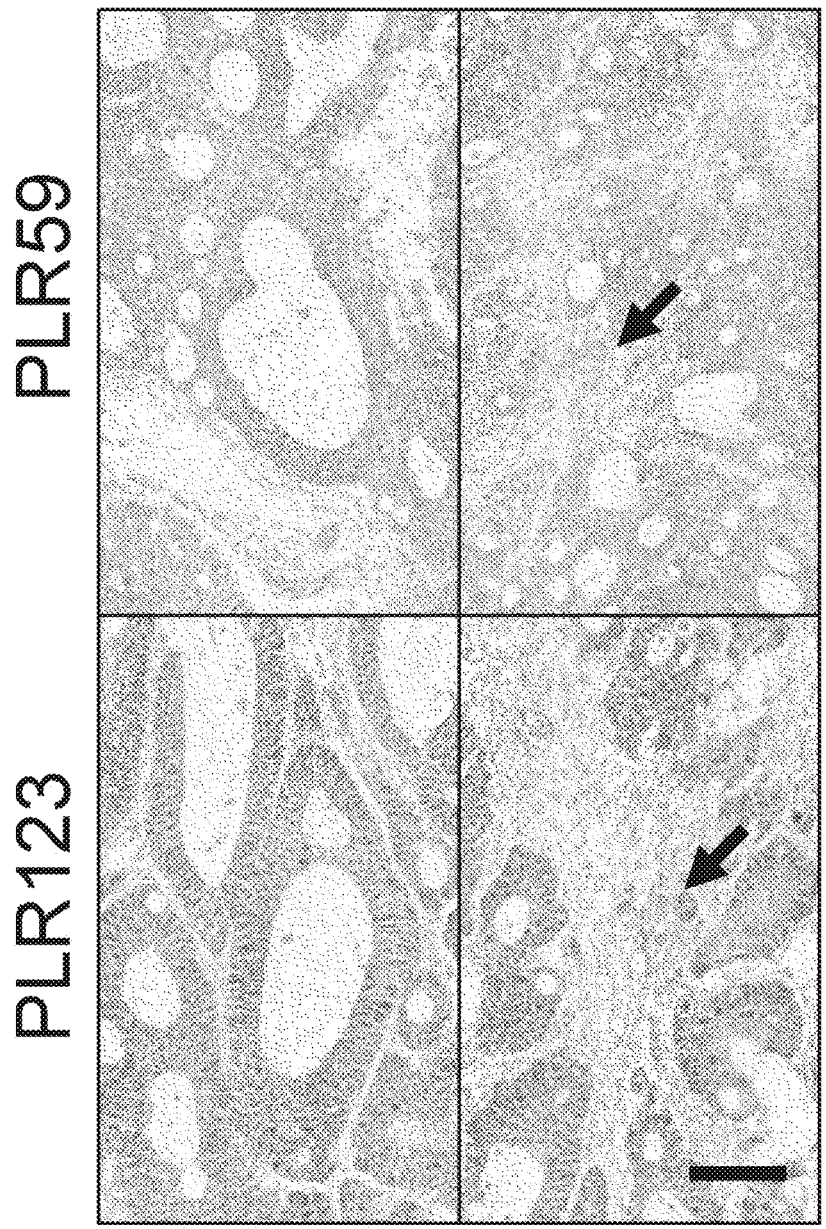
FIG. 3 shows photographs depicting histological images (HE stain) of tumors formed by injection of 100 cells each of PLR59 and PLR123 cells. The morphologies of the tumors derived from 100 cells each of PLR59 and PLR123 cells were highly similar to the original tumors. Arrows indicate budding clusters. Scale bar represents 100 µm.
Figure 4:
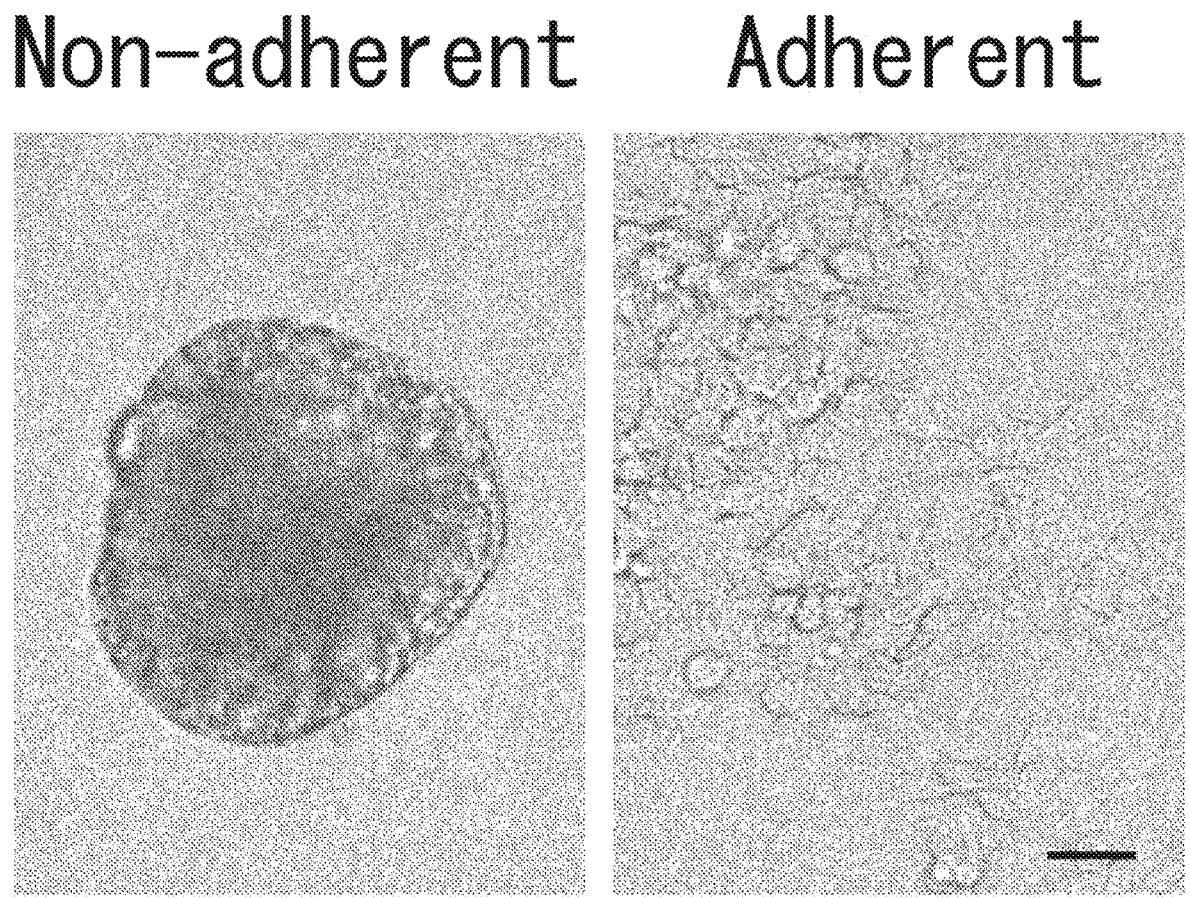
FIG. 4 shows photographs depicting a result of phase contrast microscopic observation of non-adherent and adherent cells (PLR123 cells). The cells were cultured in serum-free media supplemented with EGF and FGF. The non-adherent cells closely interacted together to form a spheroid-like structure, whereas the adherent cells proliferated without forming cell clusters. Scale bar represents 25 µm.
Figure 5:
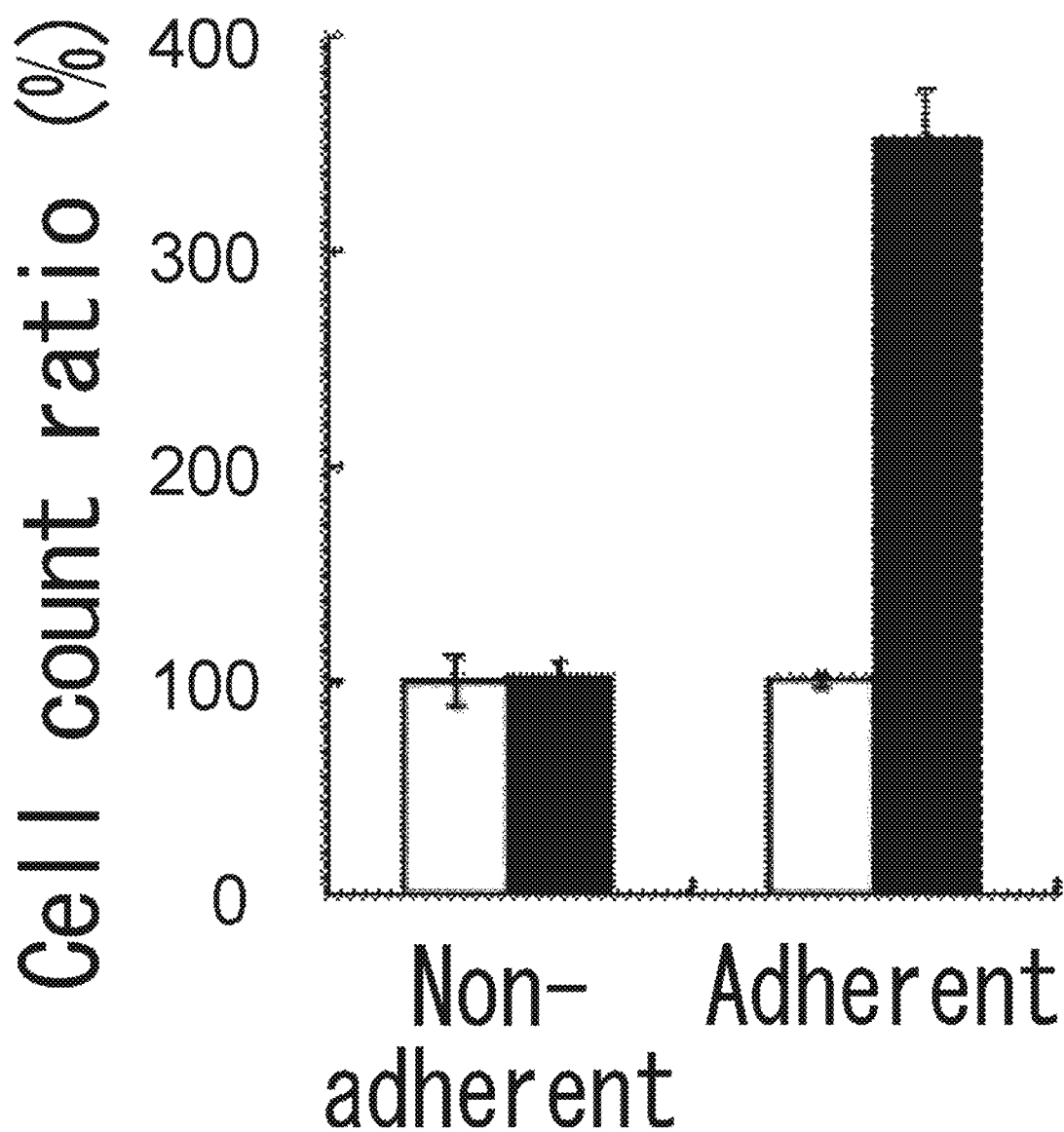
FIG. 5 is a diagram showing the proliferation of non-adherent and adherent CSCs (PLR123 cells). The viable cell count after three days of culture (black column) is shown in percentage to the count on day 0 (white column). The results were averaged from three experiments. The bar at the top of each column represents standard deviation.

Flow cytometry analysis of primary cells passaged in NOG mice derived from PLR59 and PLR123 showed that signal level of CD44, ALDH, CD26, and Lgr5 were lower than that of CD133, EpCAM, CD166, CD24, and CD29. This suggests the existence of a small population of CSCs (FIG. 2). Indeed, when primary cells derived from PLR59 and PLR123 were grafted subcutaneously to NOG mice at 100 cells/injection site, tumors were formed at half of the injection sites (five of 12 injection sites; Table 3), and the histopathological morphology of tumors is highly similar to that of original tumors in that they had hierarchical organization (FIG. 3). However, primary cells derived from PLR59 and PLR23 were injected subcutaneously at 10 cells/site, any tumor was not formed in NOG mice (Table 3). Table 3 shows the cancer formation ability 49 days after inoculation.

TABLE 3

| Cell line* | Specimen † | Number of cells/inoculation site | | |
|---|---|---|---|---|
| | | 1,000 | 100 | 10 |
| PLR59 | Primary | 12$^+$/12$^‡$ (100) | 5/12 (42) | 0/12 (0) |
| | Non-adherent (Lgr5−) | 6/6 (100) | 6/6 (100) | 1/6 (17) |
| | Adherent (Lgr5+) | 6/6 (100) | 6/6 (100) | 6/6 (100) |
| PLR123 | Primary | 12/12 (100) | 5/12 (42) | 0/12 (0) |
| | Non-adherent (Lgr5−) | 6/6 (100) | 5/6 (83) | 2/6 (33) |
| | Adherent (Lgr5+) | 6/6 (100) | 6/6 (100) | 6/6 (100) |

In Table 3 shown above, asterisk indicates tumor xenografts established with NOG mice, and dagger indicates cell preparations. Primary indicates cells (primary cells) prepared by harvesting xenograft tumor tissues grown in NOG mice and removing erythrocytes and mouse cells. Floating indicates cells prepared by in vitro culturing primary cells under a non-adherent culture condition. Adherent indicates cells prepared by in vitro culturing primary cells under adherent culture conditions. Plus symbol (single) indicates the number of formed tumors, while plus symbol (double) indicates the total number of inoculation sites. Parenthesis indicates percent tumor (cancer) formation. Lgr5$^+$ represents Lgr5 positive, and Lgr5$^-$ represents Lgr5 negative.

Figure 6:
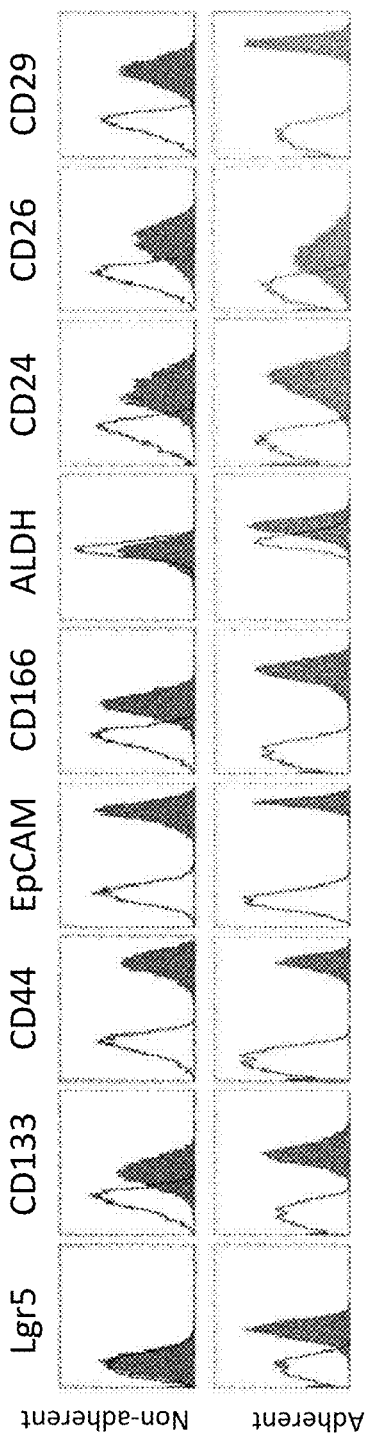
FIG. 6 is a diagram showing a result of flow cytometry analysis of non-adherent cells and adherent cells (PLR123 cells) for known CSC markers. Both types of cells were positive for known CSC markers such as CD133, CD44, EpCAM, CD166, CD24, CD26, and CD29, while the adherent cells alone were positive for Lgr5 and ALDH activity. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 20:
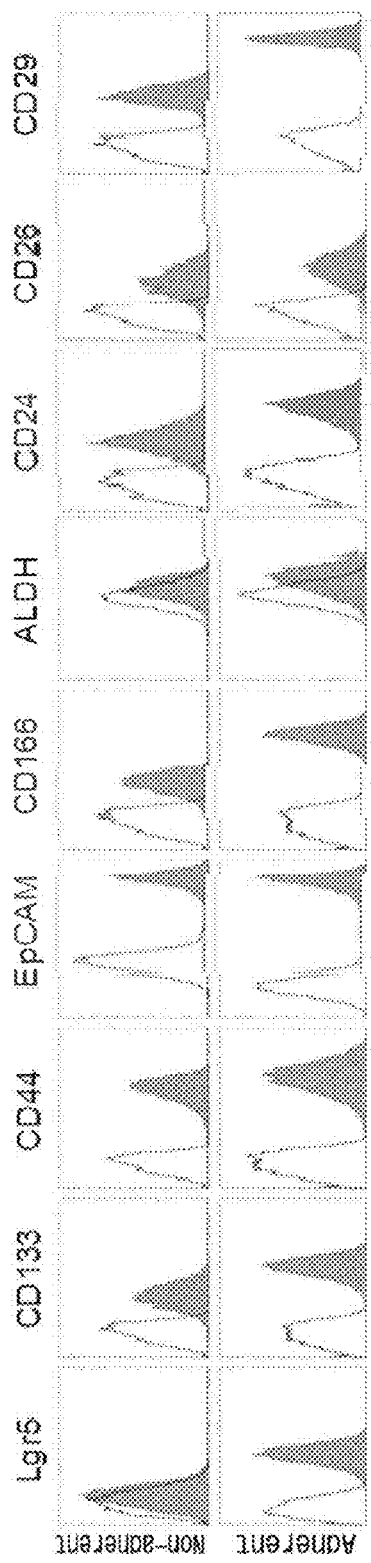
FIG. 20 is a diagram showing a result of flow cytometry analysis of non-adherent and adherent cells (PLR59 cells) for known CSC markers. Adherent cells were positive for all markers reported, whereas non-adherent cells were negative for Lgr5 and ALDH. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.

Primary cells derived from PLR59 and PLR123 were cultured in serum-free media supplemented with EGF and FGF. This yielded adherent and non-adherent cells. The present inventors harvested the adherent and non-adherent cells and cultured them separately. The adherent cells were grown with a doubling time of about 2.5 days and exhibited mesenchymal cell-like morphology. The non-adherent cells, on the other hand, formed spheroid-like cell clusters but did not proliferate significantly (FIGS. 4, 5, 18, and 19). After one-week or longer culture, the cells were assessed for large intestine CSC markers. This demonstrated that both adherent and non-adherent cells were highly homogeneous. The adherent cells were of Lgr5$^+$, ALDH$^+$, CD133$^+$, CD44$^+$, EpCAM$^+$, CD166$^+$, CD24$^+$, CD26$^+$, and CD29$^+$. Meanwhile, the non-adherent cells were of Lgr5$^-$ and ALDH$^-$, and thus were different from the adherent cells (FIGS. 6 and 20).

Figure 27:
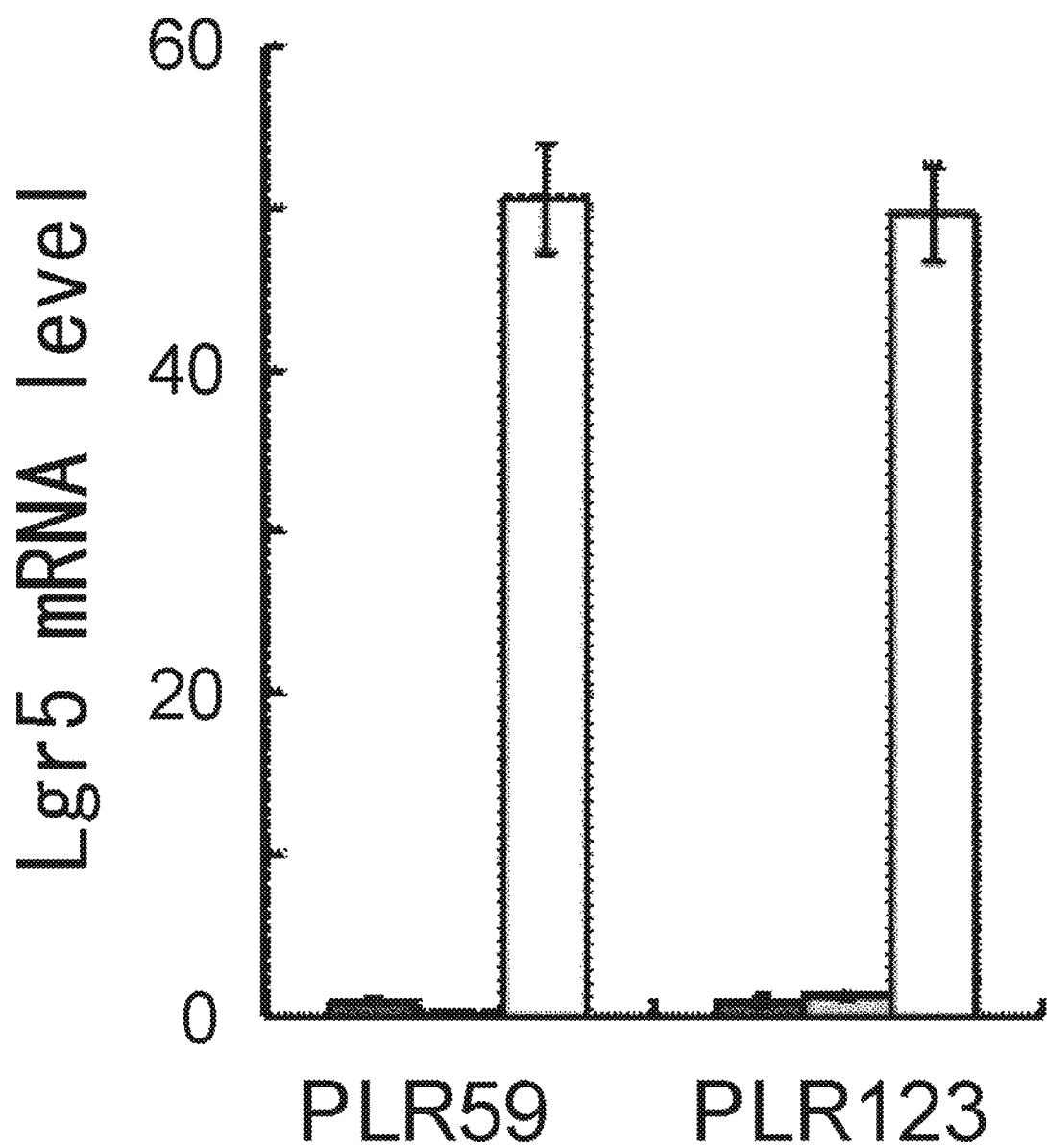
FIG. 27 is a diagram showing the expression levels of Lgr5 mRNA in Lgr5-negative non-adherent CSCs and Lgr5-positive CSCs (PLR59 cells). Levels of Lgr5 mRNA in adherent and non-adherent CSCs are shown as a ratio to the levels in primary cells from xenograft tumors PLR59 and PLR123. The level of Lgr5 mRNA in adherent CSCs (right, white column) was remarkably increased as compared to the level in the primary cells from xenografts (left, black column), while the level was not increased in non-adherent CSCs (middle, gray column). Lgr5 mRNA levels were determined by quantitative PCR and normalization with the expression of GAPDH and ACTB. All experiments were performed in triplicate. Error bars represent standard deviation.

Lgr5 mRNA was detected at a significant level in the adherent cells, while it was undetectable in non-adherent cells (FIG. 27).

Example 3: Analysis of Lgr5 Protein Expression

Figure 28:
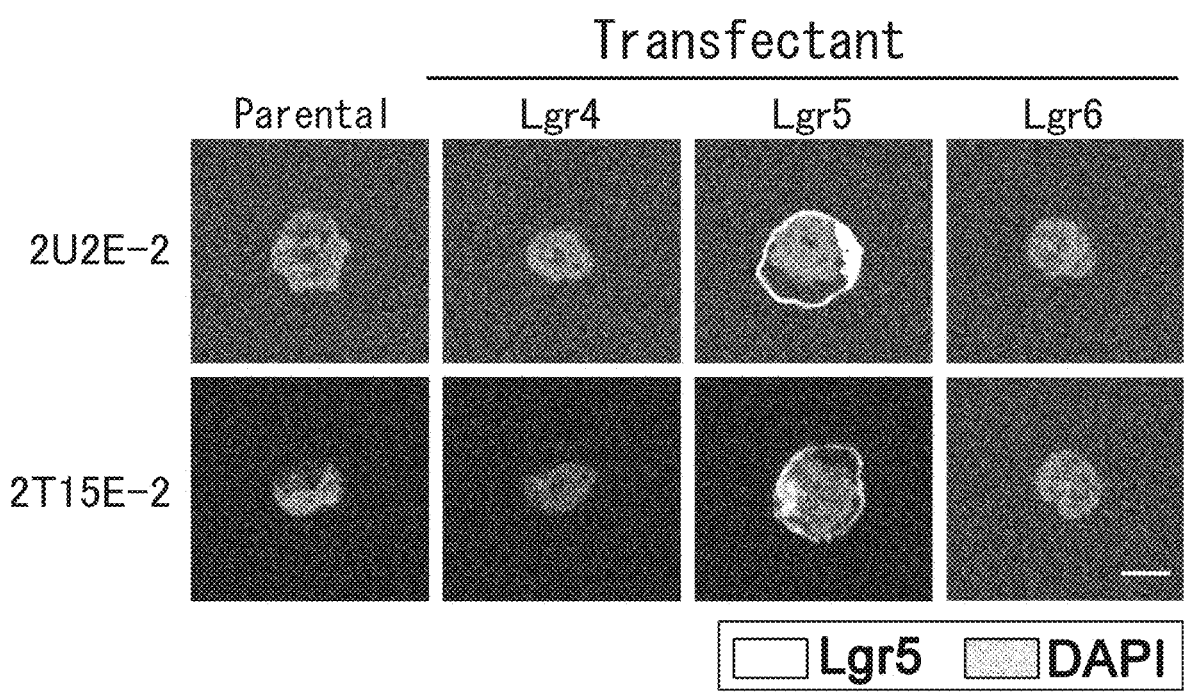
FIG. 28 shows photographs depicting a result of specificity assessment of anti-human Lgr5 monoclonal antibodies (mAbs) 2U2E-2 and 2T15E-2 by immunofluorescence microscopy observation of DG44 cells transfected with Lgr4, Lgr5, or Lgr6 cDNA. The transfectants and non-transfected parental cells were fixed and treated with 5 μg/ml antibodies. Intense fluorescence (green signals at right) was observed in cells containing Lgr5 cDNA but not in parental cells and cells containing Lgr4 or Lgr6 cDNA. Scale bar represents 5 μm.
Figure 29:
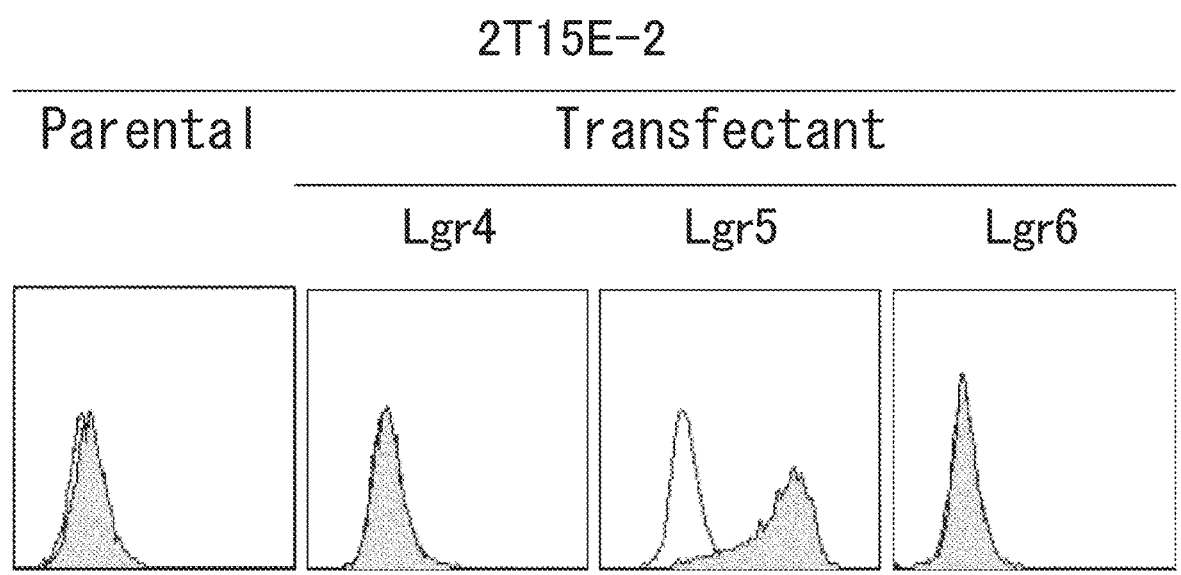
FIG. 29 is a diagram showing a result of specificity assessment of anti-human Lgr5 monoclonal antibody (mAb) 2T15E-2 by flow cytometry of DG44 cells transfected with Lgr4, Lgr5, or Lgr6 cDNA. The transfectants and non-transfected parental cells were incubated with monoclonal antibody 2T15E-2 and analyzed by FACS. Antibody 2T15E-2 reacted with cells containing Lgr5 cDNA but not with parental cell and cells containing Lgr4 or Lgr6 cDNA. The expression of Lgr4, Lgr5, and Lgr6 in the transfectants was assessed by Western blot analysis.

In order to assess the expression of Lgr5 protein, the present inventors prepared two types of Lgr5-specific monoclonal antibodies (2L36, 2T15E-2, and 2U2E-2) respectively for immunohistochemistry and flow cytometry analysis. The antibodies produced by the present inventors were highly specific to Lgr5 without any cross-reactivity to Lgr4 or Lgr6, both of which are highly homologous to Lgr5 (FIGS. 28 and 29). Using the antibodies, the present inventors demonstrated the expression of Lgr5 in the adherent CSCs.

Lgr5-positive cells were detected in tumor tissues that were the origins of PLR59 and PLR123 as well as in xenograft cancer tissues therefrom through all passages (FIG. 39). The frequency of Lgr5-positive cells was low in the original tumor tissues (0.01% and 0.04% for PLR59 and PLR123, respectively). Regarding the xenograft cancer tissues, the frequency of Lgr5-positive cells was increased as passage number increased; however, there was no further change after tenth generation (FIG. 39). On the other hand, the tumor-reconstituting capacity of primary cells from PLR123 xenograft model was also potentiated as passage number increased. The ratio of CSCs in the primary cells, which was estimated based on the capacity to reconstitute tumor, was about 0.1% after 5 passages, and was increased to about 0.4% after 14 passages.

Example 4: Tumor-Reconstituting Capacities of Lgr5-Positive and Lgr5-Negative Colorectal CSCs If a group of colorectal cancer stem cells is characterized by Wnt signaling, Lgr5-positive adherent cells alone can form tumors in vivo. To confirm whether this prediction is true, the present inventors assessed the tumor-forming capacities of Lgr5-positive adherent cells and Lgr5-negative non-adherent cells.

Figure 7:
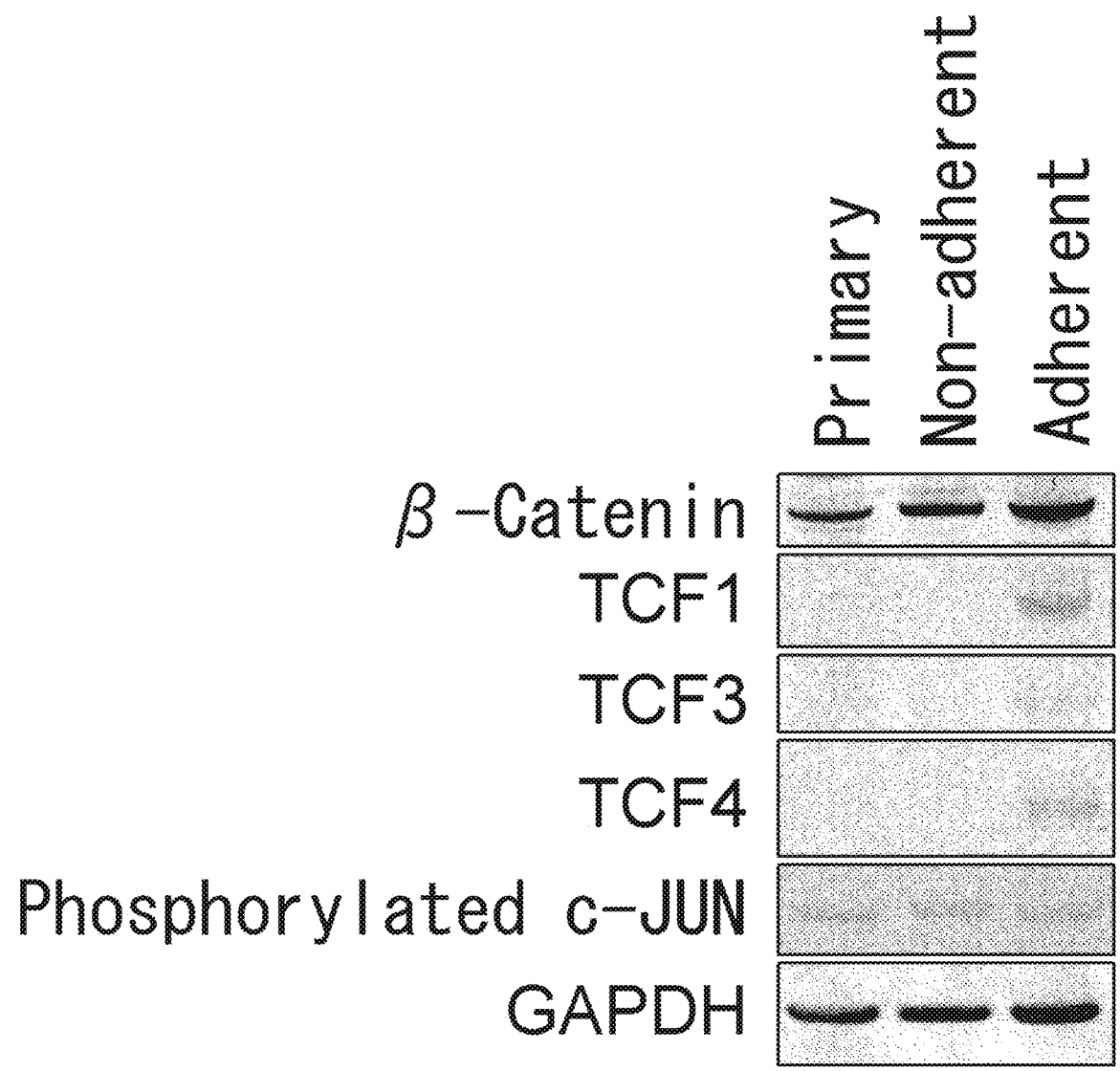
FIG. 7 is a photograph showing a result of Western blot analysis of primary cells of PLR123 cells, non-adherent CSCs, and adherent CSCs for β-catenin, TCF1, TCF3, TCF4, and phosphorylated c-JUN protein. Expression of all of the proteins was up-regulated in Lgr5-positive adherent CSCs as compared to the primary cells. GAPDH was also visualized as a reference protein for protein loading.
Figure 17:
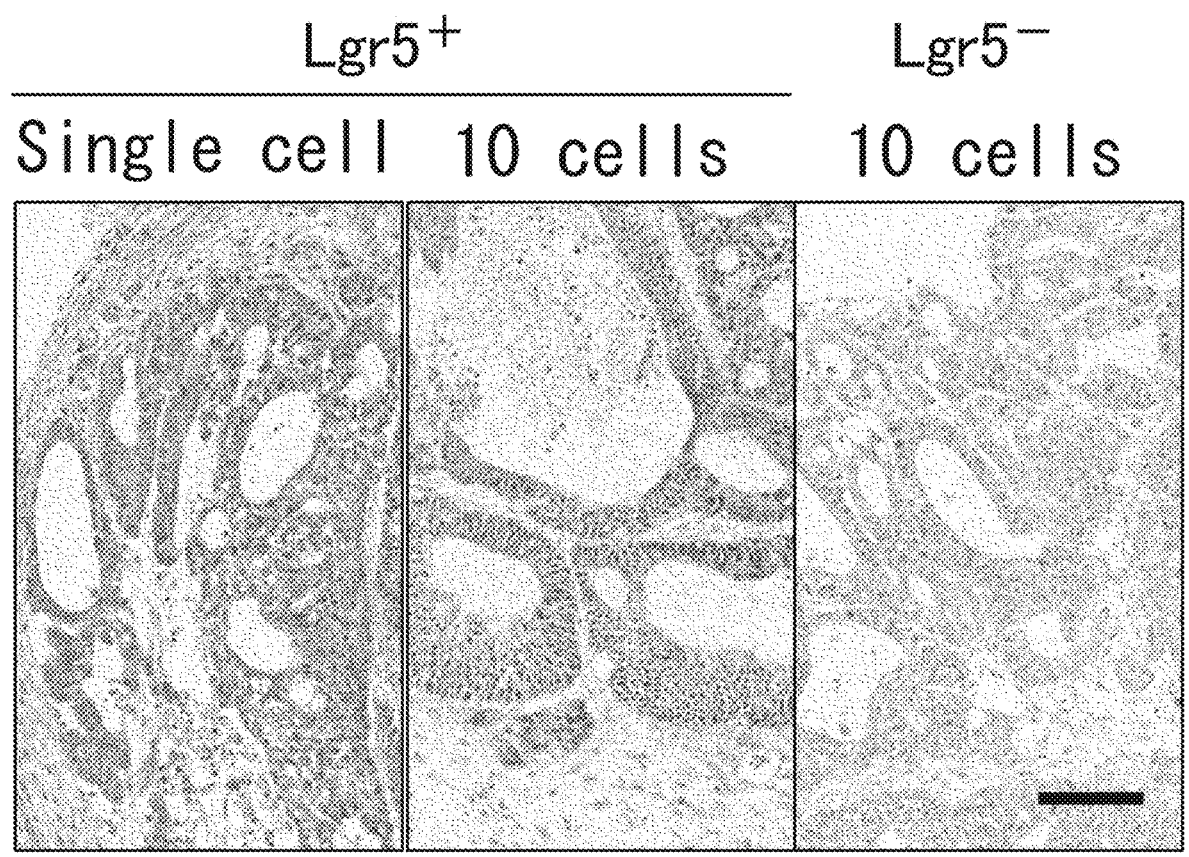
FIG. 17 shows photographs depicting a histopathological result on xenograft tumors that originated from a single or ten Lgr5-positive cells derived from PLR123, or ten Lgr5-negative cells derived from PLR123. The hierarchical organization was observed in all tumors, and their histopathological features were highly similar to the original tumor. Scale bar represents 100 μm.
Figure 18:
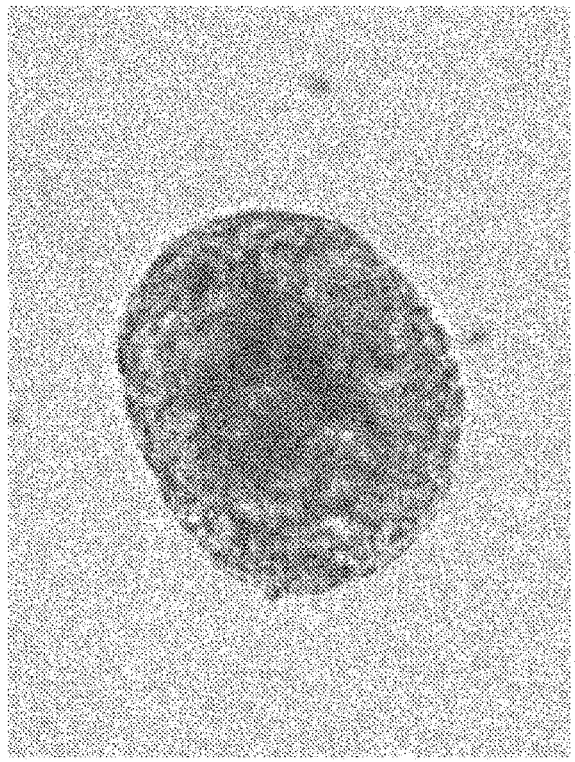
FIG. 18 shows photographs depicting a result of phase contrast microscopic observation of non-adherent and adherent large intestine CSCs (PLR59 cells). The cells were cultured in serum-free media supplemented with EGF and FGF. The non-adherent cells closely interacted together to form a spheroid-like structure, whereas the adherent cells proliferated without forming cell clusters. Scale bar represents 25 μm.
Figure 18:
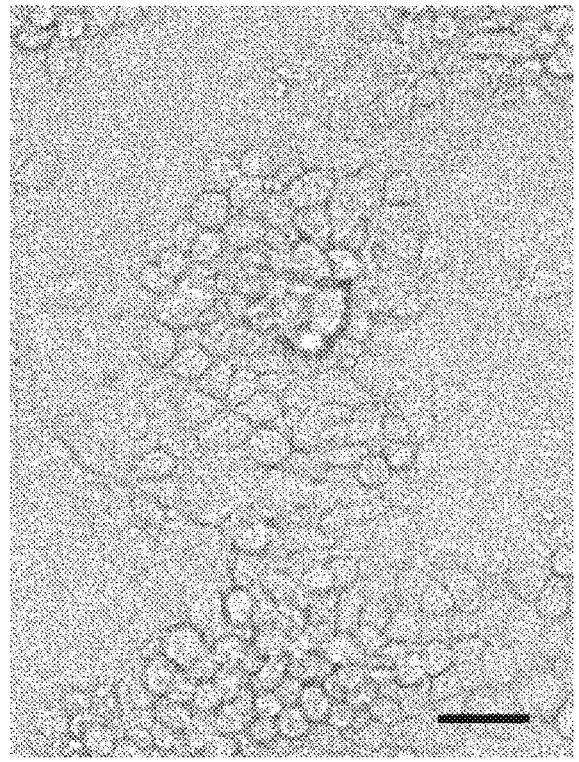
Figure 19:
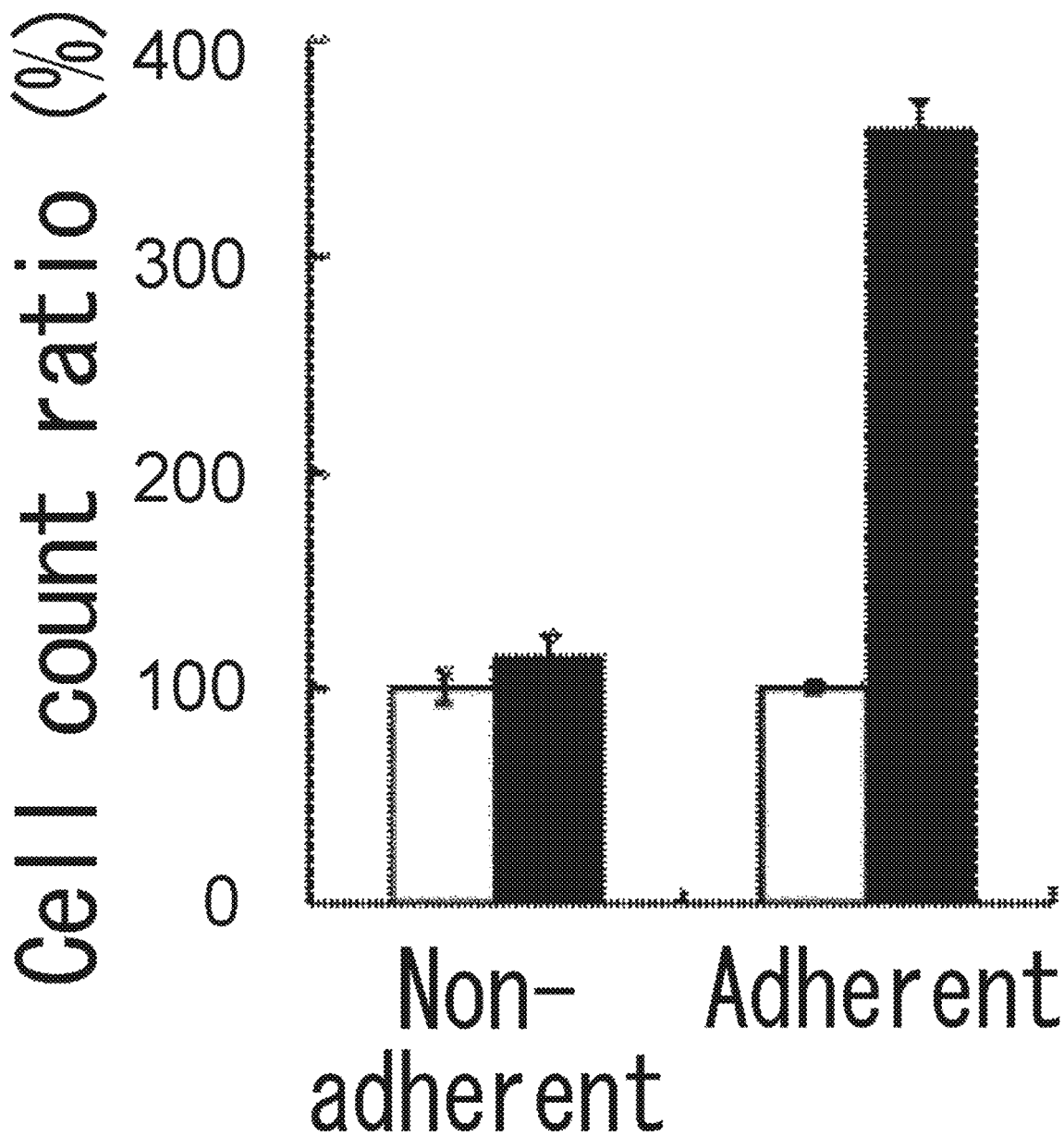
FIG. 19 is a diagram showing the proliferation of non-adherent and adherent CSCs (PLR59 cells). The viable cell count after three days of culture (black column) is shown in percentage to the count on day 0 (white column). The results were averaged from three experiments. The bar at the top of each column represents standard deviation.
Figure 30:
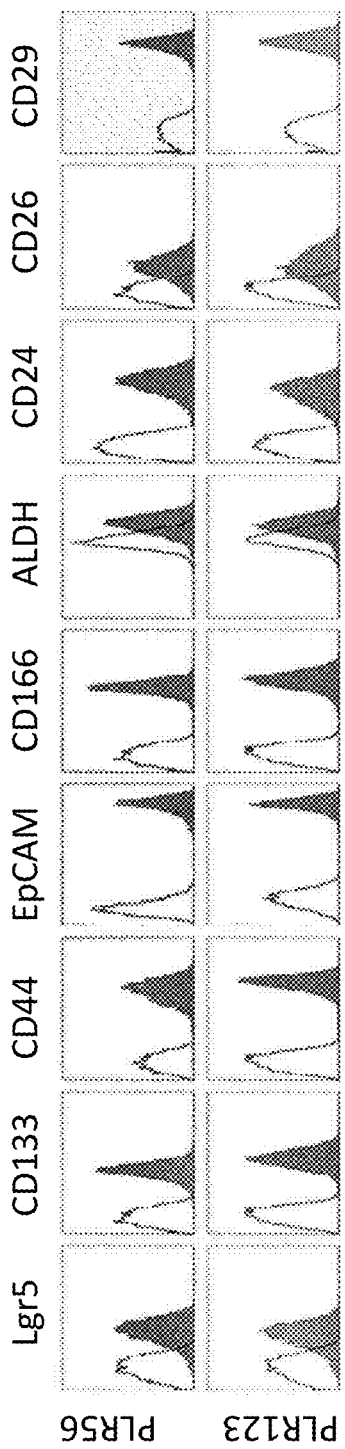
FIG. 30 is a diagram showing a result of flow cytometry analysis of adherent CSCs derived from xenografts PLR59 and PLR123. The cells were cultured for one month and analyzed for known cancer stem cell markers. Even after one month of in vitro culture, adherent CSCs derived from PLR59 and PLR123 were positive for all of known cancer stem cell markers. Gray area indicates the ALDH activity or fluorescence intensity of cells after staining with the indicated antibodies. White area indicates the treatment of cells by the ALDH activity in the presence of an ALDH inhibitor or the fluorescence intensity of cells after staining with isotype antibodies as a control.

The result showed that Lgr5-positive adherent cells were more potent than Lgr5-negative non-adherent cells in the capacity to form tumors. However, both Lgr5-positive and Lgr5-negative cells had the capacity to form tumors in NOG mice. Subcutaneous injection of ten Lgr5-positive cells caused tumor formation at every injection site (six of six sites), while Lgr5-negative cells formed tumors at two of six injection sites (PLR123-derived cells) or at a single site (PLR59-derived cells) (Table 3). Lgr5-positive cells, even when injected at only one cell per inoculation site, reconstituted tumors at two of 12 injection sites (PLR123-derived cells) or at a single site (PLR59-derived cells) (FIG. 7). The histopathological morphologies of tumors derived from the Lgr5-positive and Lgr5-negative cells were almost the same as those of the original tumors (FIGS. 17 and 40). Furthermore, there was no change in the expression of cell surface markers and tumor-initiating activity of the Lgr5-positive CSCs even after one month of passage culture (FIGS. 30 and 31).

Figure 41A:
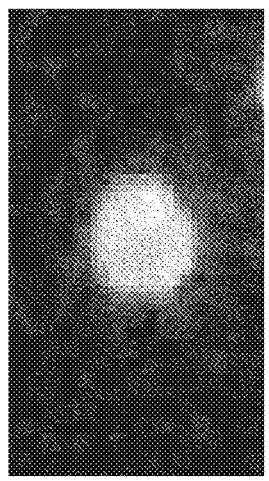
FIGS. 41A-41C show photographs depicting symmetrical cell division of Lgr5-positive cells. Lgr5-positive cells stained with PKH67 dye were cultured for 72 hours, and then observed under a fluorescent microscope.
Figure 41B:
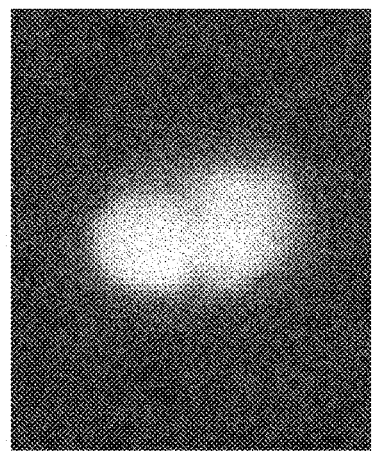
Figure 41C:
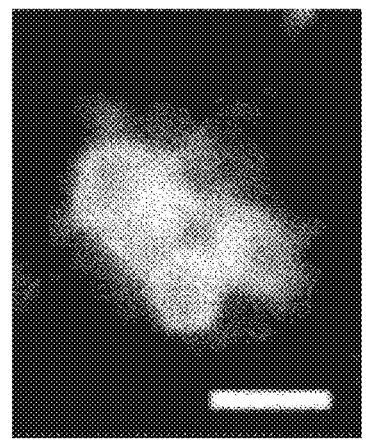
Figure 42A:
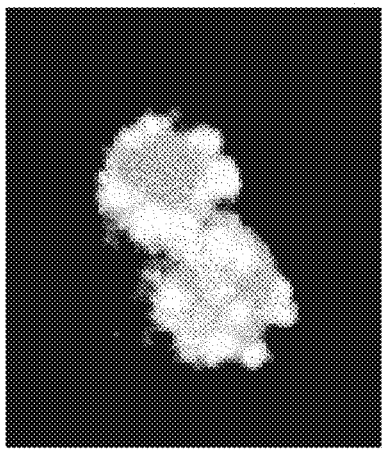
FIGS. 42A-42D shows photographs depicting symmetrical cell division of Lgr5-positive cells in the absence of matrigel and serum (FIGS. 42A and 42B), and asymmetrical cell division of Lgr5-positive cells in the presence of matrigel and serum (FIGS. 42C and 42D).
Figure 42B:
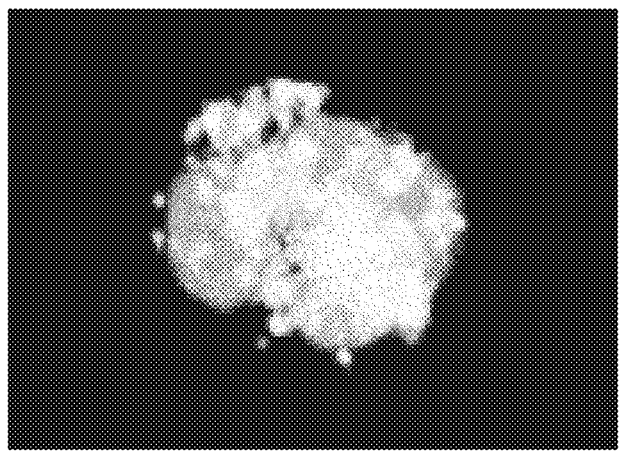
Figure 42C:
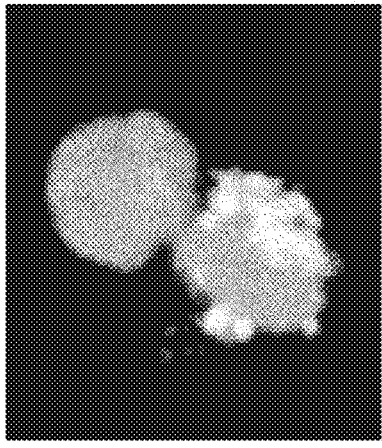
Figure 42D:
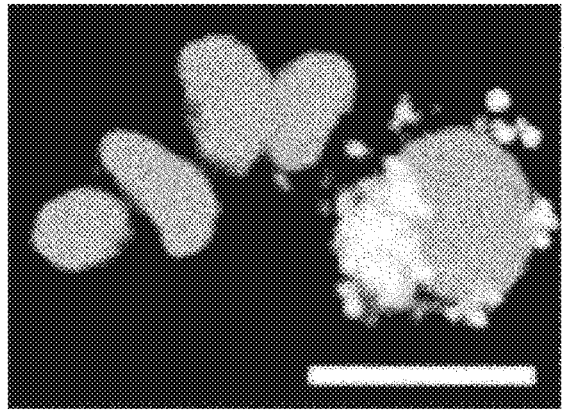
Figure 43A:
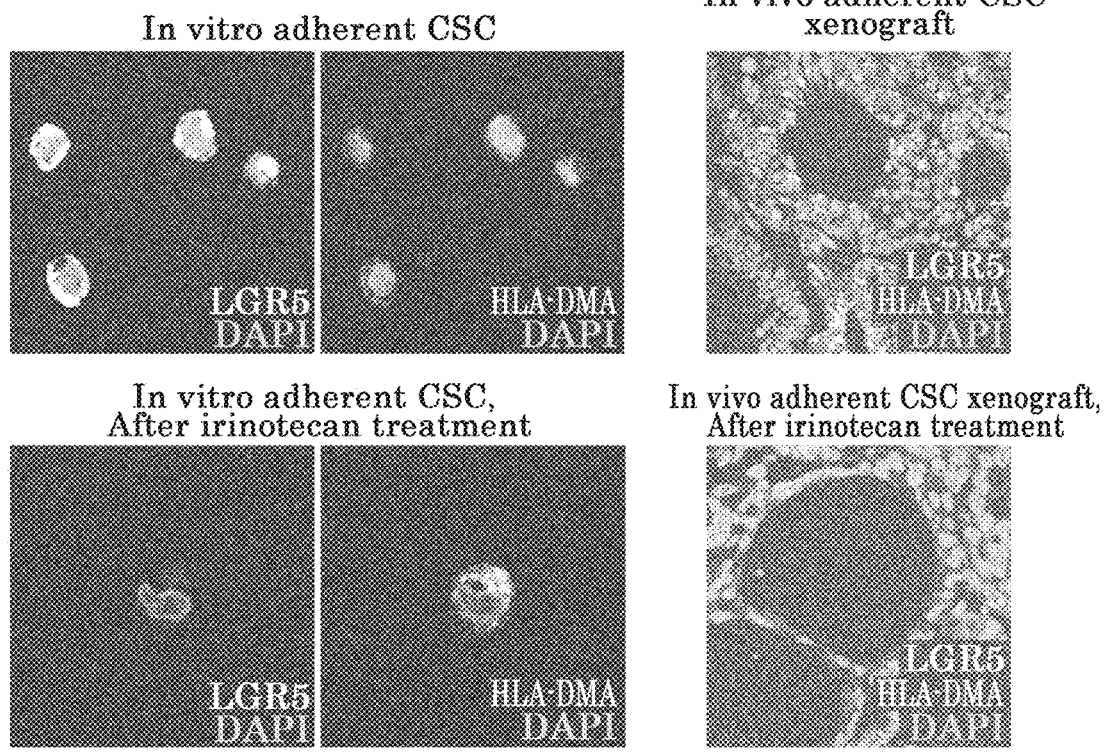
FIGS. 43A-43D show photographs depicting immunostained images of colon CSCs that varied to negative for Lgr5 after three days of exposure to irinotecan. The cells were stained with antibodies specific to HLA-DMA (FIG. 43A), TMEM173 (FIG. 43B), ZMAT3 (FIG. 43C) and GPR110 (FIG. 43D).
Figure 43B:
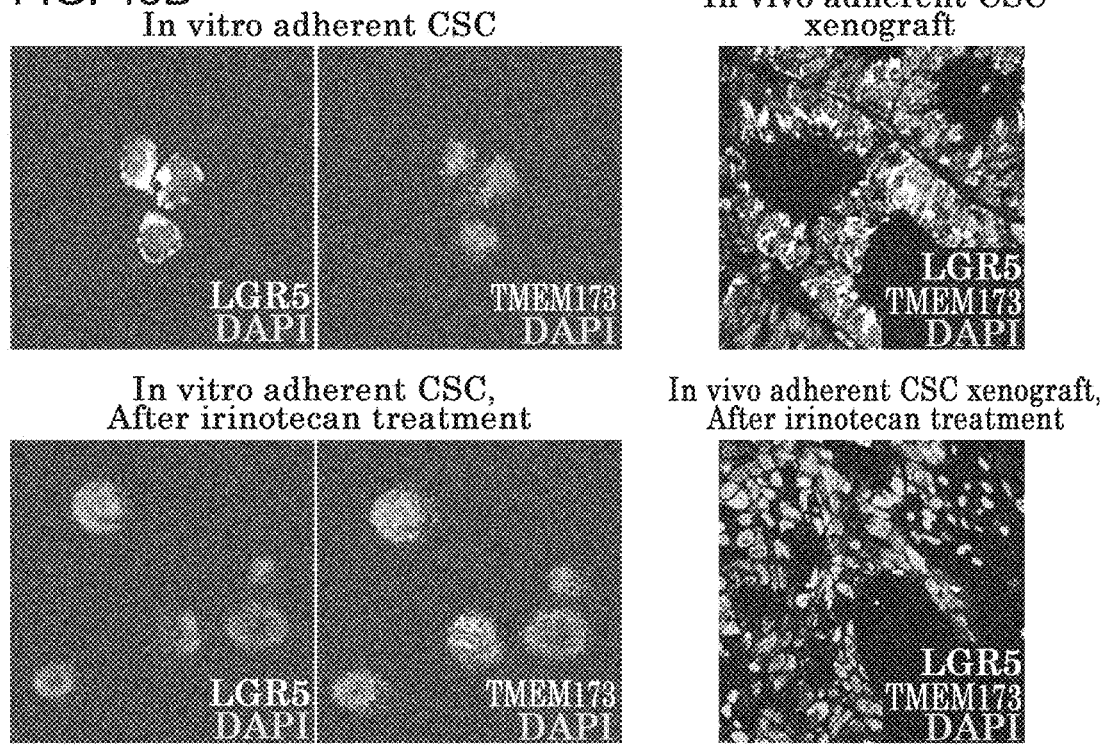
Figure 43C:
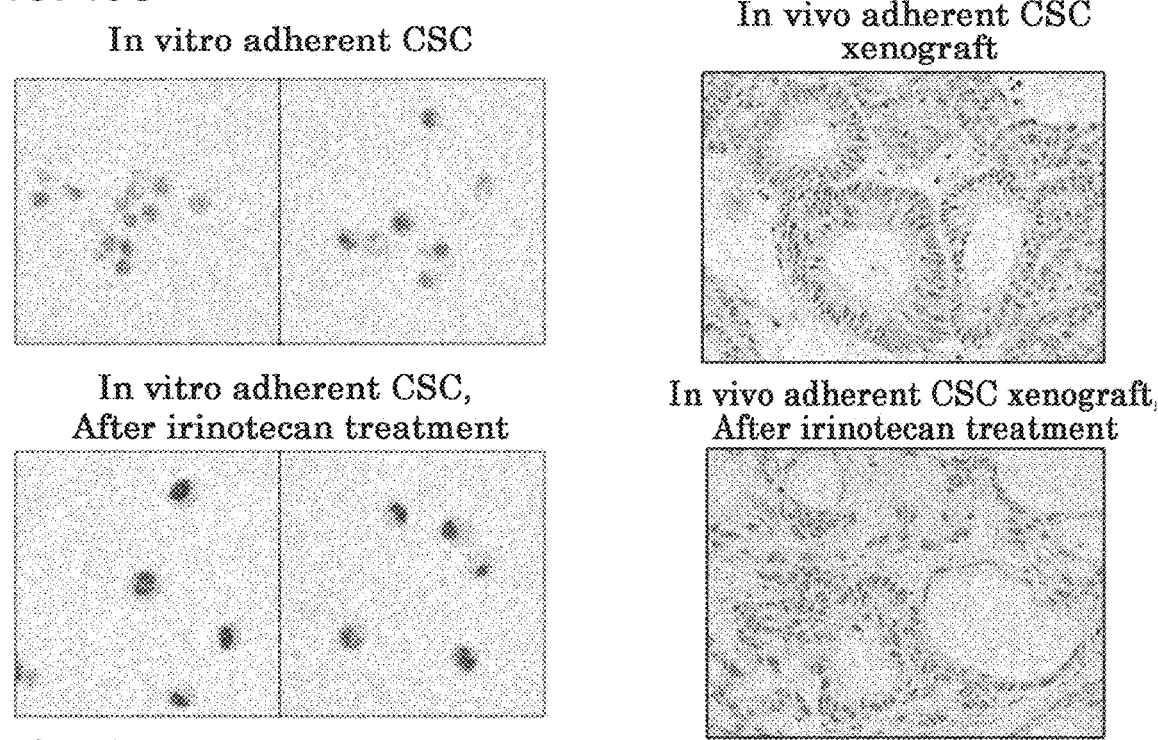
Figure 43D:
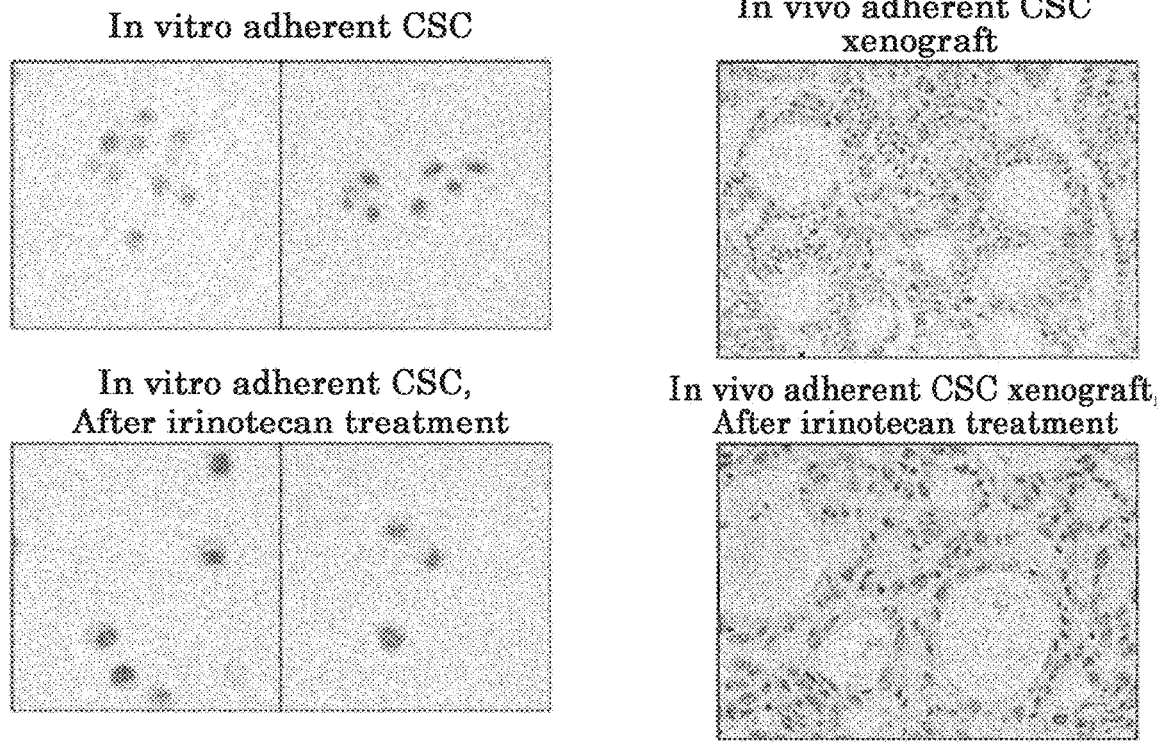

Under adherent culture conditions, the Lgr5-positive cells underwent symmetric cell division (FIG. 41). Meanwhile, in the presence of matrigel and serum, Lgr5 protein was distributed to one of two daughter cells under the same culture conditions (FIGS. 42C and 42D), demonstrating that the Lgr5-positive cells undergo asymmetrical cell division. One of CSC's properties is symmetrical cell division for self-renewal, and another characteristic property is asymmetrical cell division. The Lgr5-positive adherent cells divided symmetrically under adherent culture conditions (FIG. 41), whereas, in the presence of matrigel and FBS, as seen from the fact that Lgr5 protein was distributed to one of daughter cells (FIG. 42), the Lgr5-positive cells underwent asymmetrical cell division, which resulted in two distinct progenies.

The results described above demonstrate that Lgr5-positive and Lgr5-negative cells derived from PLR59 and PLR123 are highly pure large intestine CSCs, and that the Lgr5-positive and Lgr5-negative cells correspond to two independent CSC states in colorectal cancer.

Example 5: Effect of TCF and β-catenin

In the Lgr5-positive cells, the levels of β-catenin, TCF1, TCF3, and TCF4 proteins were upregulated in accordance with the expression of Lgr5. This was not observed in the Lgr5-negative cells (FIGS. 7 and 21).

Figure 21:
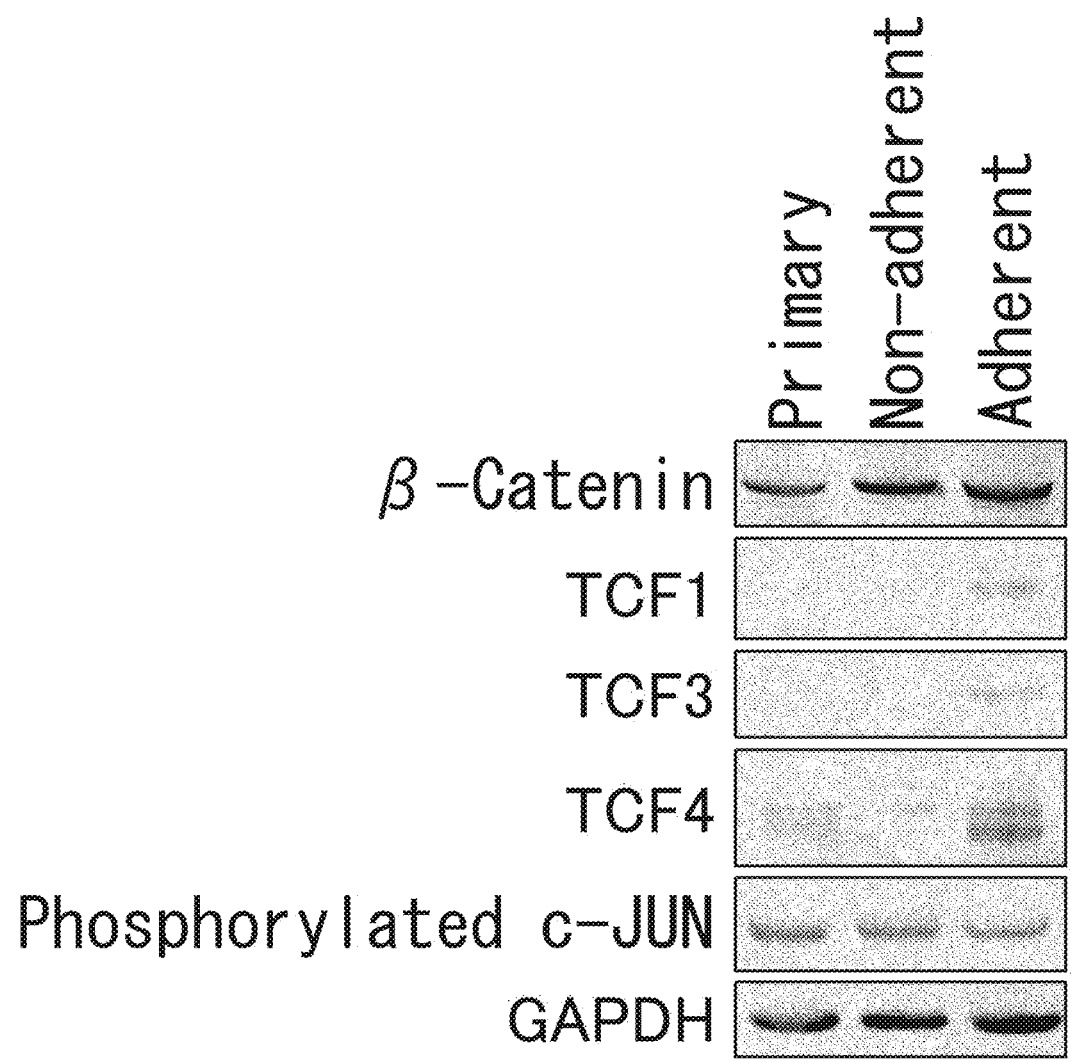
FIG. 21 shows photographs depicting a result of Western blot analysis of primary cells of PLR59 cells, non-adherent CSCs, and adherent CSCs for β-catenin, TCF1, TCF3, TCF4, and phosphorylated c-JUN protein. Expression of all of the proteins was up-regulated in Lgr5-positive adherent CSCs as compared to the primary cells. GAPDH was also visualized as a reference for protein loading.

On the other hand, the N-terminal phosphorylation of c-Jun was undetectable in the Lgr5-positive CSCs as compared to the Lgr5-negative CSCs (FIGS. 7 and 21).

To answer the question of whether Wnt signaling promotes the proliferation of large intestine CSCs, the present inventors assessed the effects of β-catenin/TCF inhibitor FH535 and Wnt/β-catenin inhibitor cardamonin (which induces β-catenin degradation) on the proliferation of large intestine CSCs.

Figure 8:
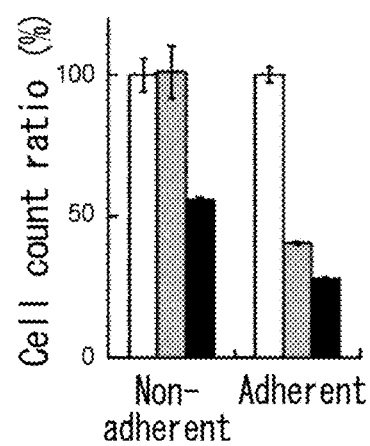
FIG. 8 is a diagram showing the inhibition of growth of Lgr5-positive adherent CSCs (PLR123 cells) by FH535 (50 µM) and Cardamonin (50 µM). The viable cell count after three days of culture in the presence of FH535 (gray column) or Cardamonin (black column) is shown in percentage to the count in the presence of DMSO alone (white column). The results were averaged from three experiments. The bar at the top of each column represents standard deviation.
Figure 22:
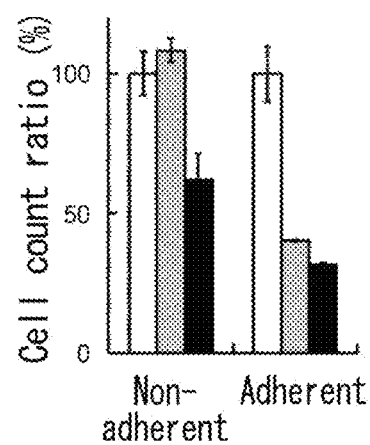
FIG. 22 is a diagram showing growth inhibition of Lgr5-positive adherent CSCs (PLR59 cells) by FH535 (50 μm) and Cardamonin (50 μm). The viable cell count after three days of culture in the presence of FH535 (gray column) or Cardamonin (black column) is shown in percentage to the count on day 0 (white column).

The result showed that 50 M FH535 significantly reduced the proliferation of Lgr5-positive large intestine CSCs but had no effect on the proliferation of Lgr5-negative large intestine CSCs (FIGS. 8 and 22). Meanwhile, 50 M cardamonin reduced the viable cell count to 70% for the Lgr5-positive large intestine CSCs and to about 50% for the Lgr5-negative large intestine CSCs (FIGS. 8 and 22).

Figure 9:
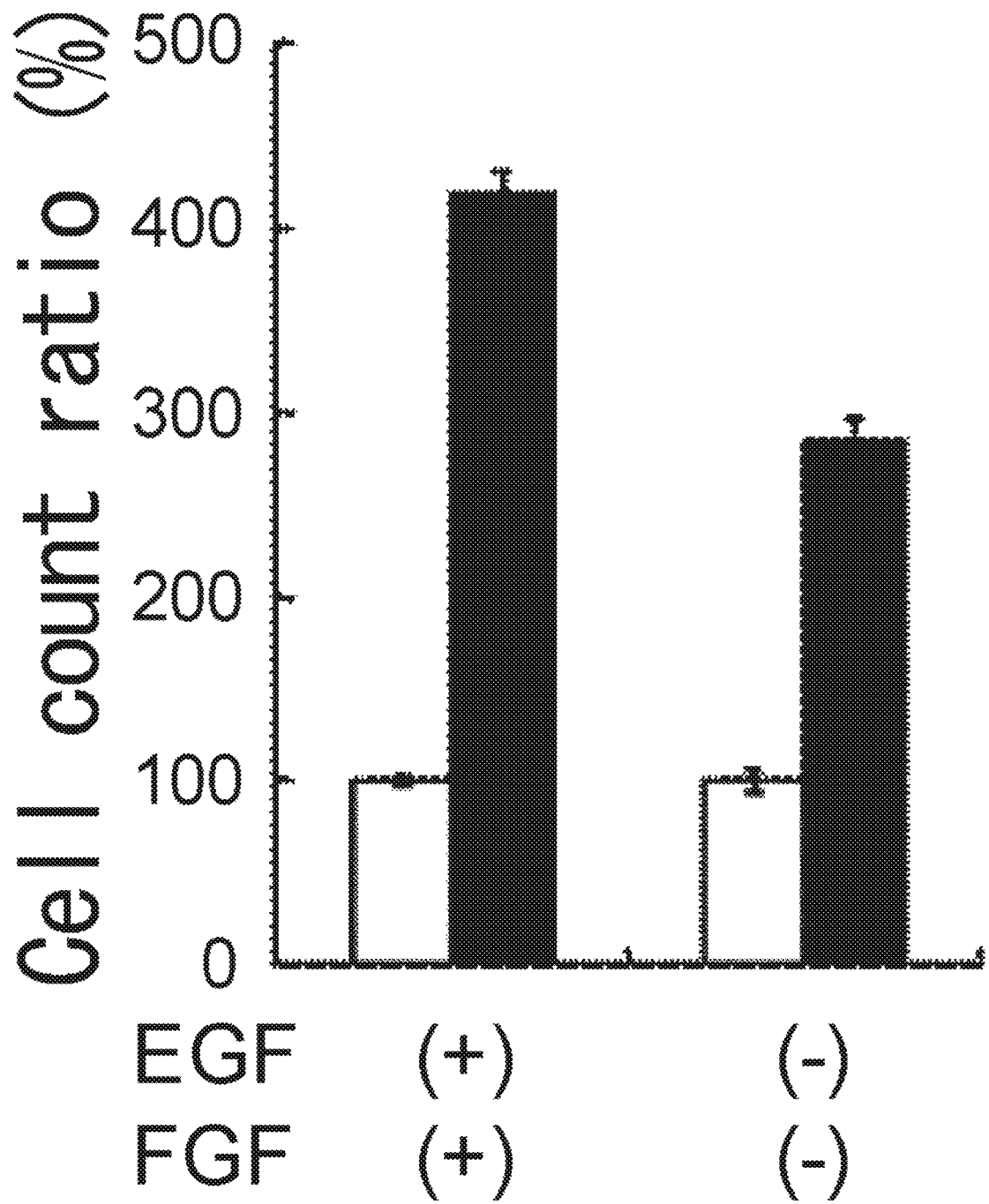
FIG. 9 is a diagram showing the proliferation of PLR123 cells in the presence or absence of EGF and FGF. Adherent CSCs were cultured for three days in the presence or absence of EGF and FGF (black column). The viable cell count is shown in percentage to the count on day 0 (white column). The results were averaged from three experiments. The bar at the top of each column represents standard deviation.
Figure 23:
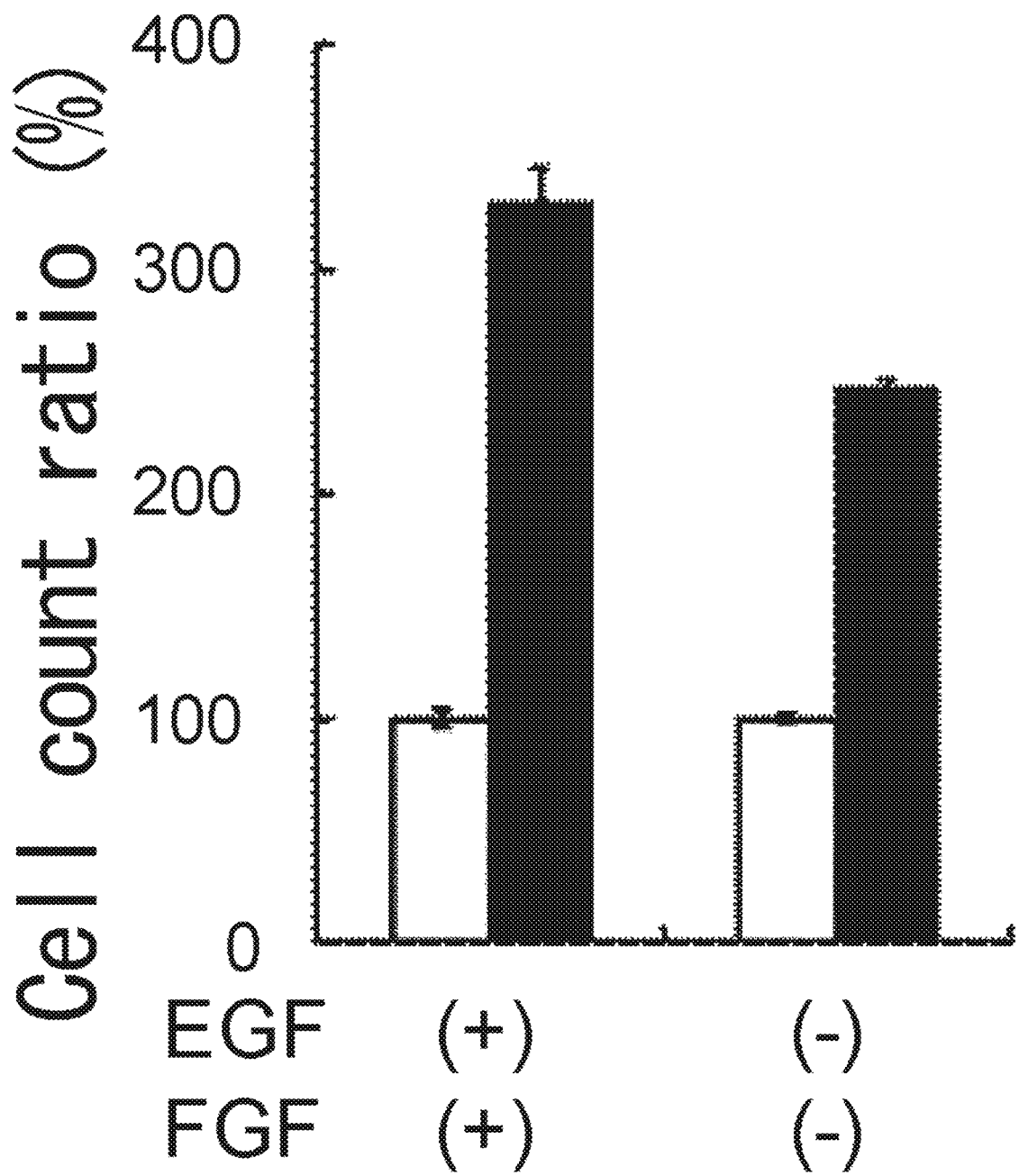
FIG. 23 is a diagram showing the proliferation of PLR59 cells in the presence or absence of EGF and FGF. Adherent CSCs were cultured for three days in the presence or absence of EGF and FGF (black column). The viable cell count is shown in percentage to the count on day 0 (white column).

This result suggests that TCF mediates the proliferation of Lgr5-positive cells and that β-catenin is involved in the survival of large intestine CSCs. Interestingly, the Lgr5-positive cells proliferated even without supplement of EGF and FGF (FIGS. 9 and 23). This finding shows that large intestine CSCs have an intrinsic/autocrine mechanism for activating the Wnt signaling for their proliferation.

Figure 10:
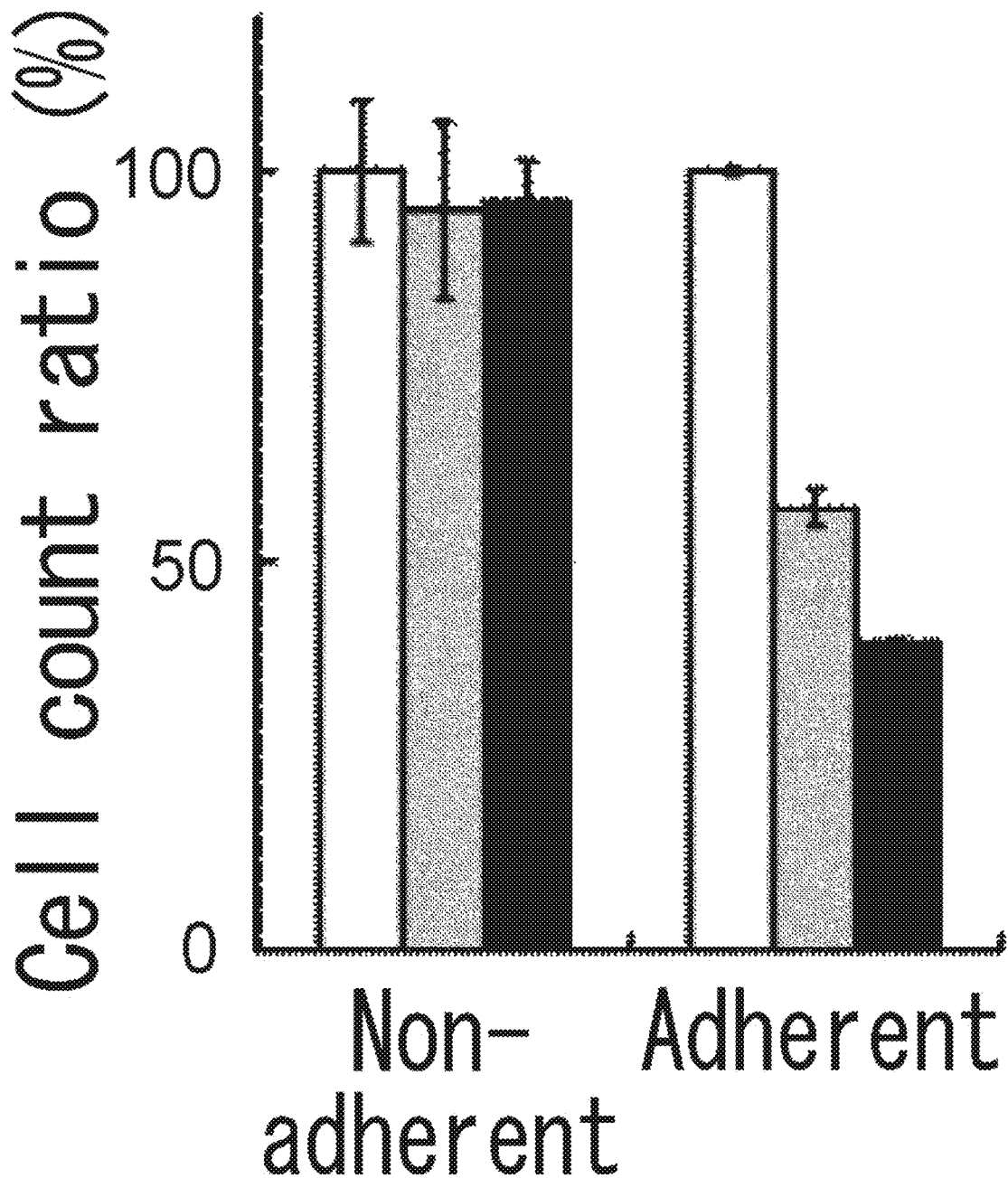
FIG. 10 is a diagram showing the effect of chemotherapeutic agents on the proliferation of Lgr5-positive adherent CSCs and Lgr5-negative non-adherent CSCs (PLR123 cells). The viable cell count after treatment with 5-FU (10 µg/ml; gray column) or irinotecan (10 µg/ml; black column) is shown in percentage to the viable cell count after culturing without the chemotherapeutic agents (white column). The results were averaged from three experiments. The bar at the top of each column represents standard deviation.
Figure 11:
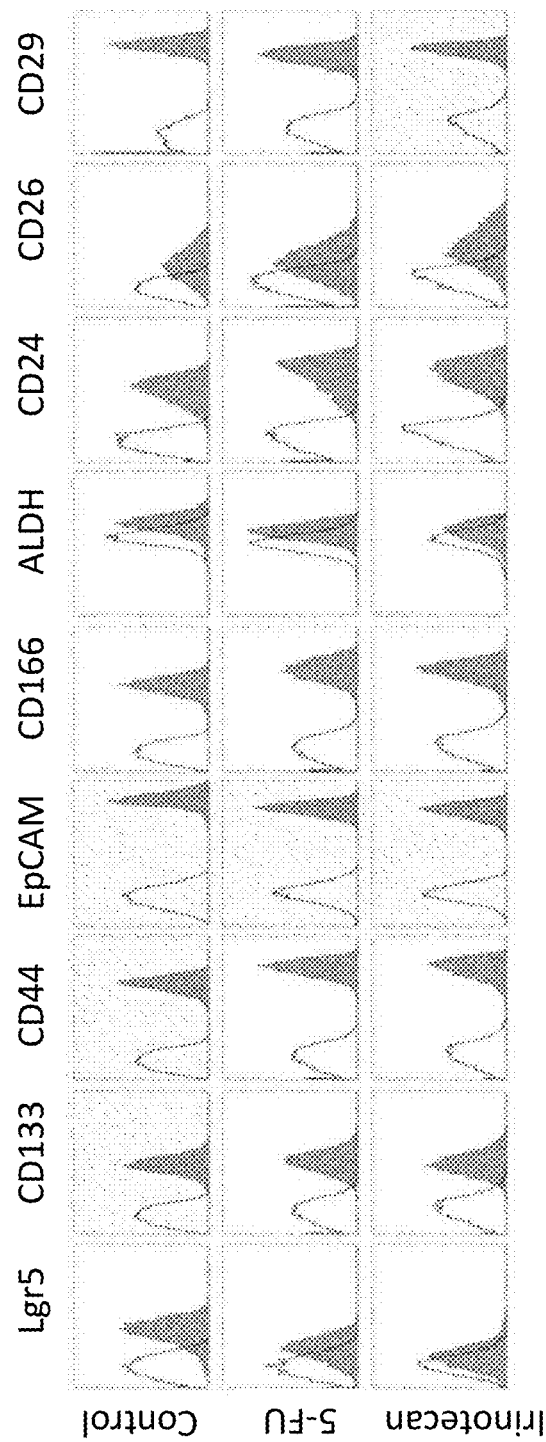
FIG. 11 is a diagram showing a change in Lgr5 expression after treatment of adherent CSCs (PLR123 cells) with a chemotherapeutic agent. This figure shows a result of flow cytometry. The upper panels show the result in the absence of chemotherapeutic agent (control); the middle panels show cells treated with 5-FU; and the bottom panels show cells treated with irinotecan. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 24:
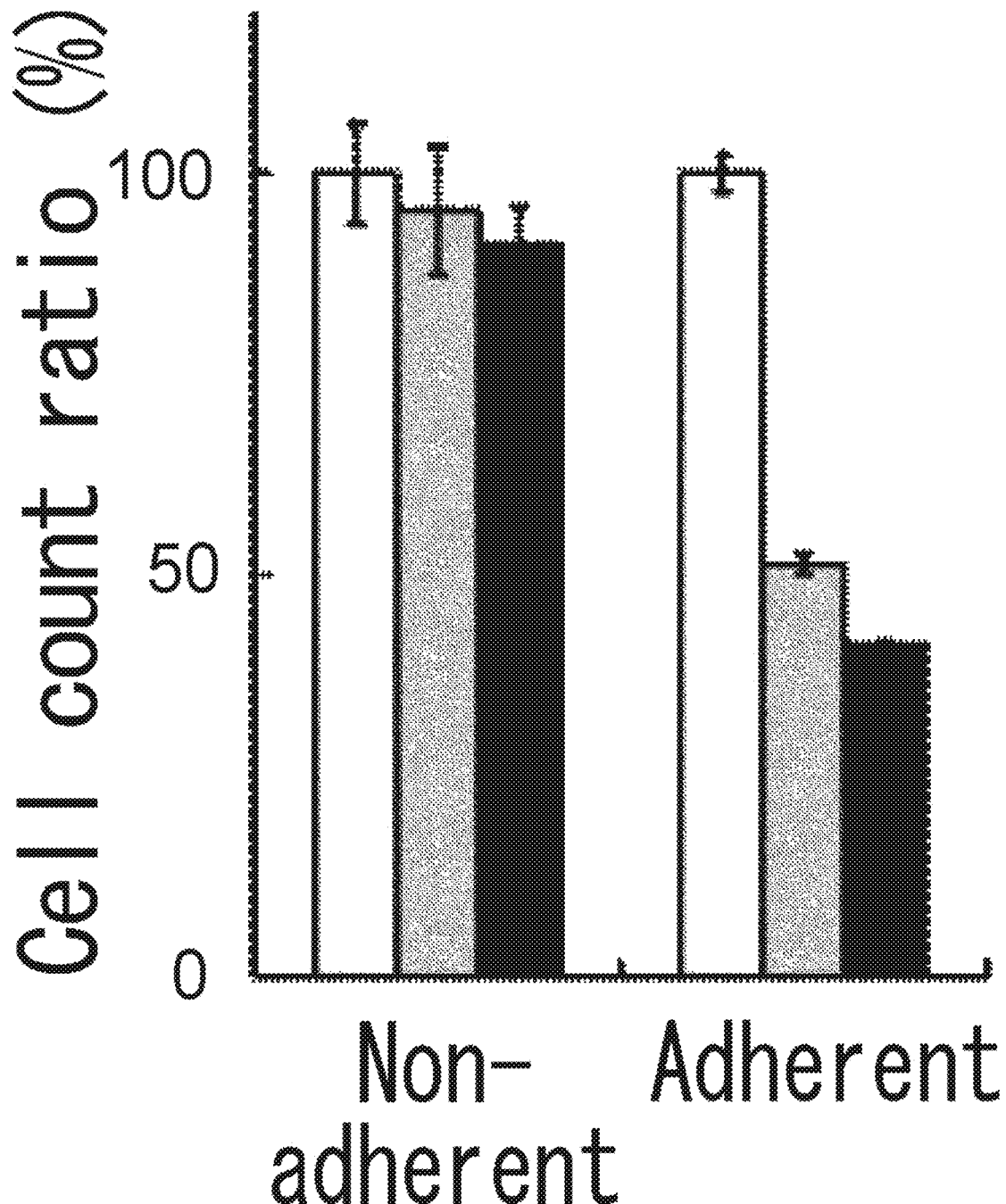
FIG. 24 is a diagram showing the effect of 5-FU (10 μg/ml) and irinotecan (10 μg/ml) on the growth of Lgr5-positive adherent CSCs and Lgr5-negative non-adherent CSCs (PLR59 cells). The viable cell count after treatment with 5-FU (gray column) or irinotecan (black column) is shown in percentage to that after culturing without the agents (white column).
Figure 25:
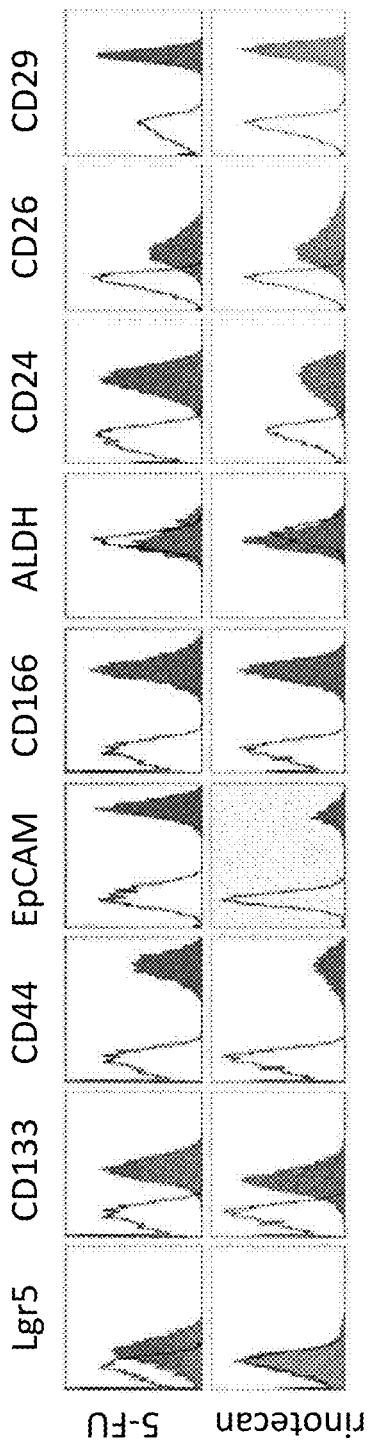
FIG. 25 is a diagram showing a result of flow cytometry analysis of adherent CSCs (PLR59 cells) for CSC markers after treatment with 5-FU or irinotecan. The upper panels show cells treated with 5-FU, and the bottom panels show cells treated with irinotecan. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 32:
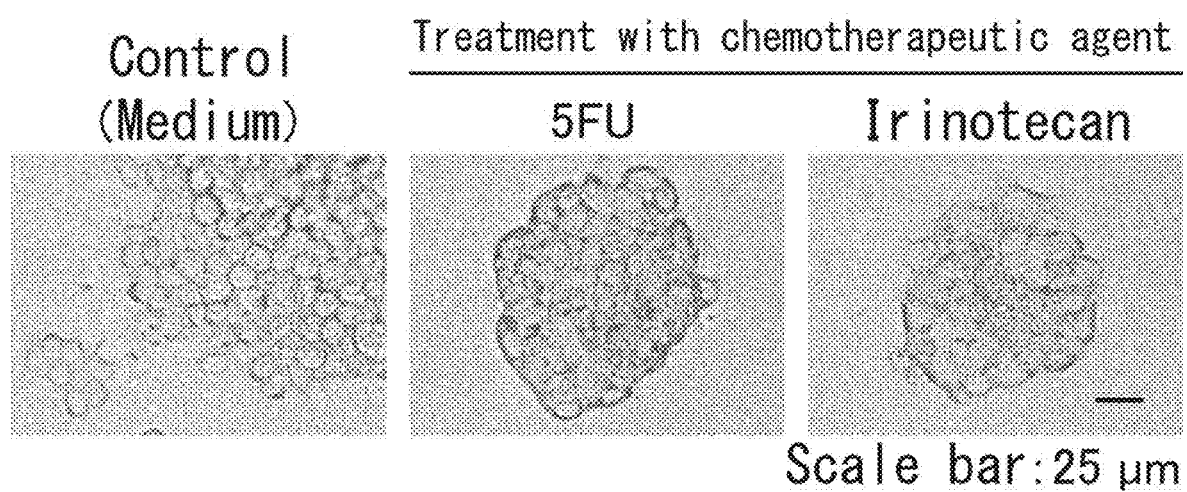
FIG. 32 shows photographs depicting the phenotypic interconversion of large intestine CSCs depending on the culture condition or chemotherapeutic treatment. Lgr5-positive CSCs were tested for the sensitivity to 5-FU and irinotecan. Both 5-FU and irinotecan significantly inhibited the proliferation of Lgr5-positive large intestine CSCs. After three days of exposure to the 5-FU or irinotecan, cells resistant to the chemotherapeutic drugs arose. The drug-resistant cells exhibited a dense, agglutinative morphology. Scale bar represents 25 μm.

Example 6: Ability of Large Intestine CSCs to Convert from Lgr5-Positive to Lgr5-Negative State One of CSC's properties is resistance to chemotherapeutic agents. Thus, the present inventors tested large intestine CSCs for the sensitivity to 5-FU and irinotecan. As described above, the Lgr5-positive cells proliferated with a doubling time of about 2.5 days. Meanwhile, the Lgr5-negative CSCs were in a quiescent state in terms of growth. Both 5-FU (10 μg/ml) and irinotecan (10 μg/ml) treatments significantly inhibited the proliferation of Lgr5-positive large intestine CSCs, while they did not affect the proliferation and survival of Lgr5-negative large intestine CSCs (FIGS. 10 and 24). Three-day exposure of the Lgr5-positive large intestine CSCs to 5-FU (10 μg/ml) or irinotecan (10 μg/ml) caused the appearance of cells resistant to the chemotherapeutic agents. Surprisingly, the drug-resistant cells were negative for Lgr5 and had changed in morphology (FIGS. 11, 32, and 25). This finding demonstrates the transition from the Lgr5-positive to Lgr5-negative state.

HLA-DMA, TMEM173, ZMAT3, and GPR110 were chosen as markers for use in specific detection of such CSCs stably negative for Lgr5. Immunostaining performed using specific antibodies against the above molecules yielded a specific staining pattern with colon CSCs that converted to negative for Lgr5 after three days of irinotecan exposure (FIG. 43). Furthermore, this immunostaining method was demonstrated to be applicable to tissue sections prepared from paraffin blocks, which are used commonly (FIG. 43). These findings suggest that HLA-DMA, TMEM173, ZMAT3, GPR110 can serve as specific markers for CSCs that converted to negative for Lgr5.

Figure 44A:
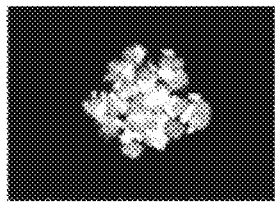
FIGS. 44A-44D show photographs depicting immunostained images of irinotecan-treated Lgr5-positive CSCs (PLR123). The cells were immunostained for Lgr5. The immunostained images include those before irinotecan treatment (FIG. 44A) and after irinotecan treatment (FIG. 44B). From Lgr5-negative cells inoculated again and cultured in the absence of irinotecan, Lgr5-positive cells appeared at the latest by four days after reinoculation (FIG. 44C), and expanded by eight days after reinoculation (FIG. 44D). Scale bar represents 50 μm.
Figure 44B:
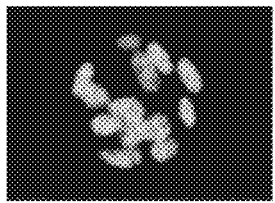
Figure 44C:
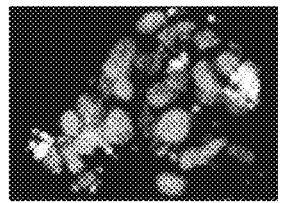
Figure 44D:
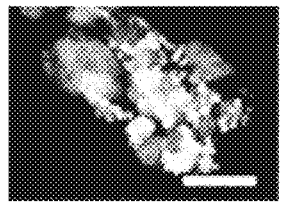
Figure 45:
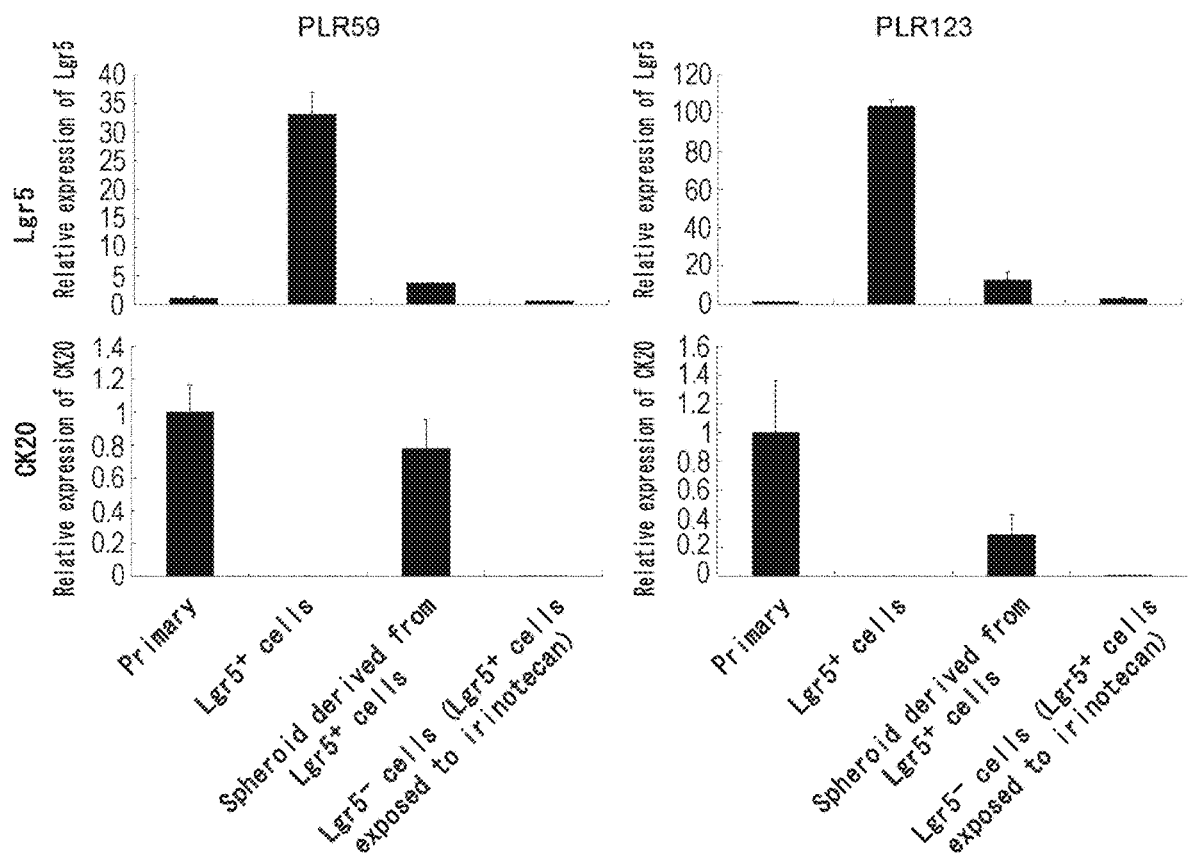
FIG. 45 shows graphs depicting transcript levels for the Lgr5 gene determined by quantitative real-time PCR. The level of Lgr5 mRNA was high in Lgr5-positive cells prepared by adherent culture. The level was decreased under the spheroid culture condition and was almost undetectable in Lgr5-negative cells after irinotecan treatment. Meanwhile, in Lgr5-positive and -negative cells prepared by adherent culture, the mRNA level for the CK20 gene was below the detection limit. The level was increased in Lgr5-positive cells of the spheroid culture condition.
Figure 46A:
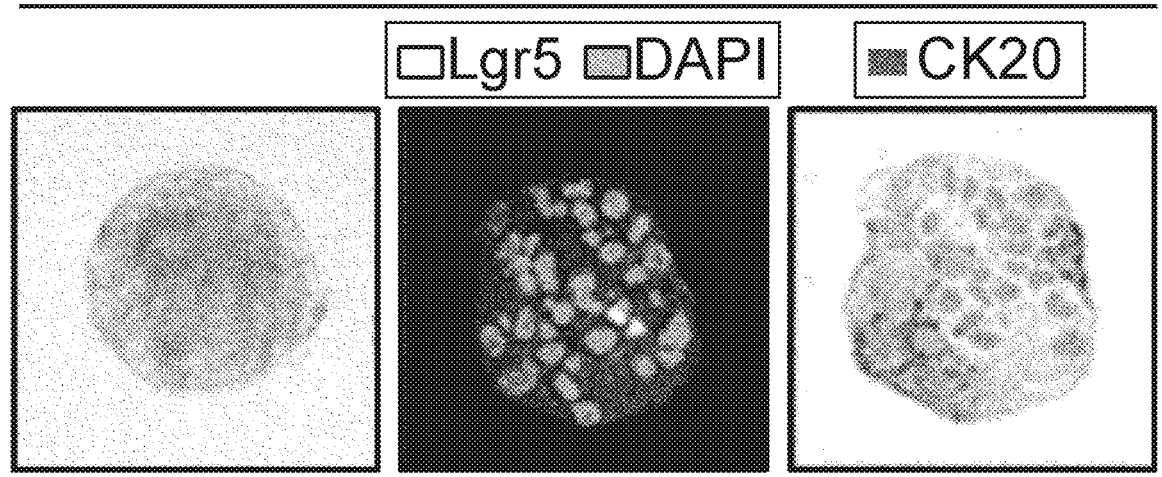
FIGS. 46A-46B show photographs depicting the expression of Lgr5 and CK20 proteins assessed by immunohistochemical staining. Spheroid cultures of Lgr5-positive CSCs (PLR59 (FIG. 46A) and PLR123 (FIG. 46B)) were fixed and sliced into thin sections and then reacted with Lgr5 antibody (2L36) and CK20 antibody (DAKO). The spheroids contained a small number of Lgr5-positive cells as well as a large number of CK20-positive cells that were negative for Lgr5.
Figure 46B:
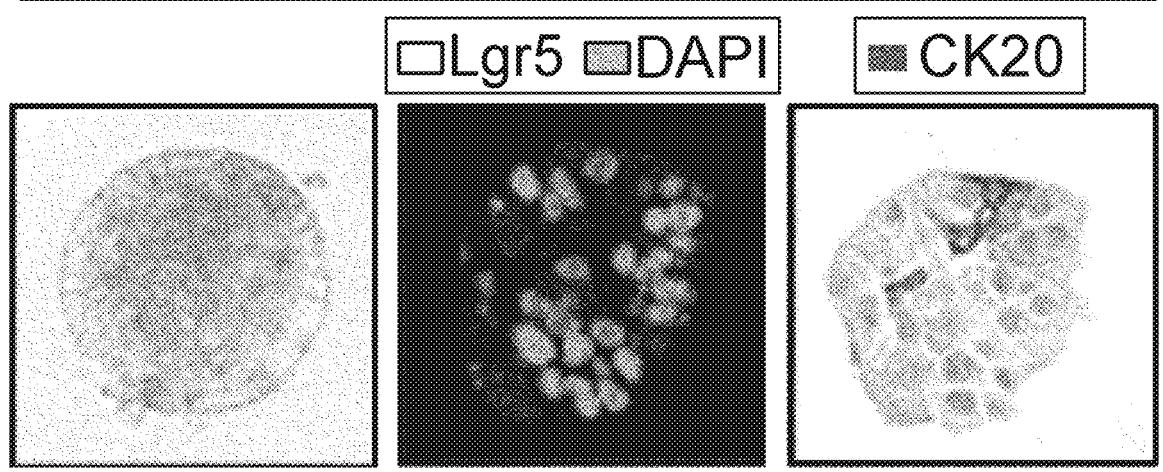
Figure 47:
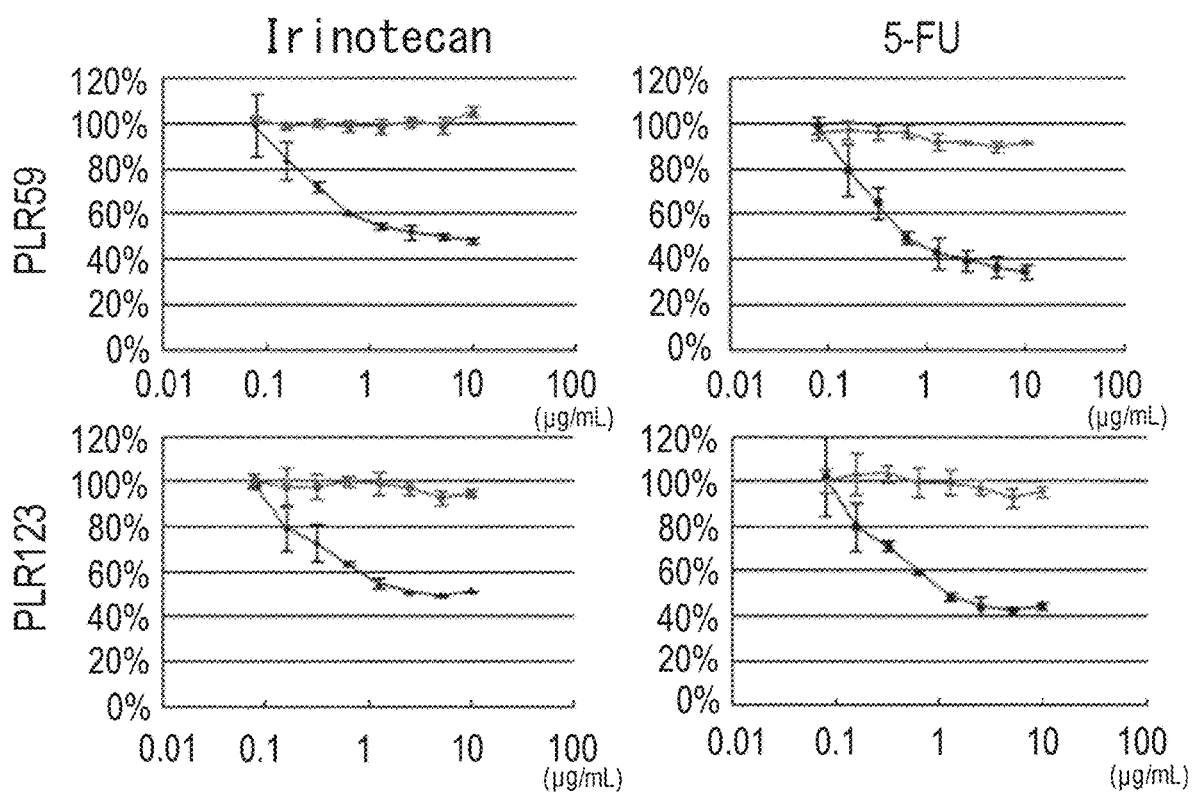
FIG. 47 shows graphs depicting the percentage of viable cells, relative to non-treated control cells, of Lgr5-positive (black line) and -negative (gray line) CSCs (PLR59 and PLR123) cultured for three days in the absence or presence of irinotecan or 5-FU at each concentration indicated on the horizontal axis. Lgr5-negative cells were fully resistant to both growth inhibitors.
Figure 48:
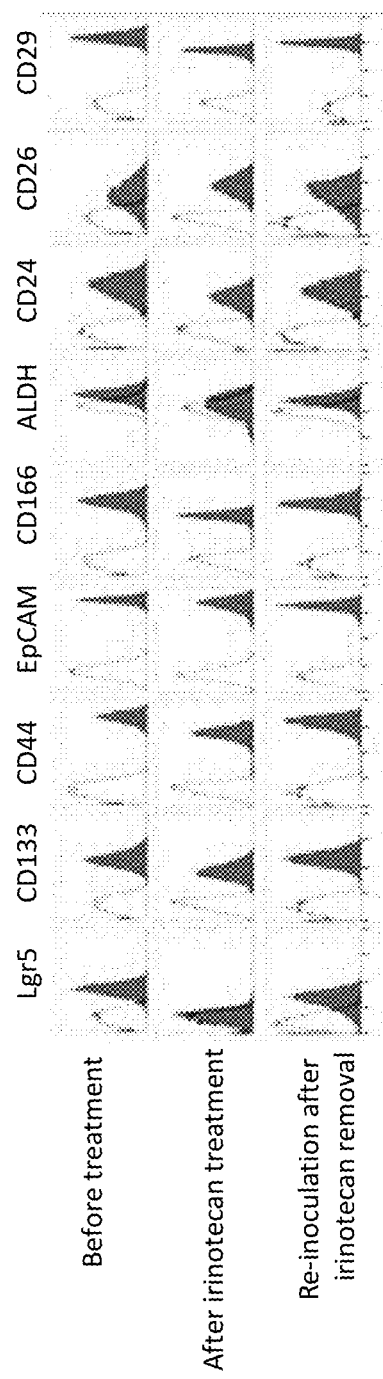
FIG. 48 is a diagram showing the expression of CSC markers. "Before treatment" indicates the expression of CSC markers in Lgr5-positive cells prepared by an adherent culture, which are derived from a PLR123 xenograft model. "After irinotecan treatment" indicates the expression of CSC markers in Lgr5-negative cells prepared via irinotecan treatment. "Re-inoculation after irinotecan removal" indicates the expression of CSC markers in Lgr5-negative cells re-inoculated to an irinotecan-free medium. Gray area indicates the ALDH activity or fluorescence intensity of cells after staining with the indicated antibodies. White area indicates the ALDH activity in the presence of an ALDH inhibitor.

The fluorescence representing Lgr5 positivity (FIG. 44A), which had been observed before irinotecan treatment, disappeared after the treatment (FIG. 44B). From Lgr5-negative cells again inoculated and cultured in the absence of irinotecan, Lgr5-positive cells appeared four days after the inoculation (FIG. 44C), and expanded by eight days after the inoculation (FIG. 44D). All the Lgr5-negative drug-resistant cells are negative for Lgr5 (FIGS. 44 and 45) and remained negative for CK20 (FIG. 46). This suggests that the transition of colon CSCs from the actively proliferating state to a quiescent state is correlated with the disappearance of Lgr5 molecule. The correlation was also verified by in vitro growth inhibitor-resistance assay (FIG. 47). In addition, the ALDH activity was reduced, while there was no alteration in other CSC markers (FIG. 48).

The Lgr5-negative cells prepared via irinotecan treatment were assessed for the tumor-forming activity. Subcutaneous injection of ten cells derived from PLR59 and PLR123 resulted in formation of tumors in two and one NOG mice (Table 4), respectively. Table 4 shows the tumor-forming activity of Lgr5-negative CSCs 49 days after inoculation. In Table 4 shown below, asterisk indicates tumor xenografts established in NOG mice; plus symbol (single) indicates the number of animals bearing tumors, and plus symbol (double) indicates the total number of animals.

TABLE 4

| Cell | Number of cells/inoculation site | | |
|---|---|---|---|
| line* | 1,000 | 100 | 10 |
| PLR59 | 6†/6‡ | 6/6 | 2/6 |
| PLR123 | 6/6 | 6/6 | 1/6 |

Figure 12:
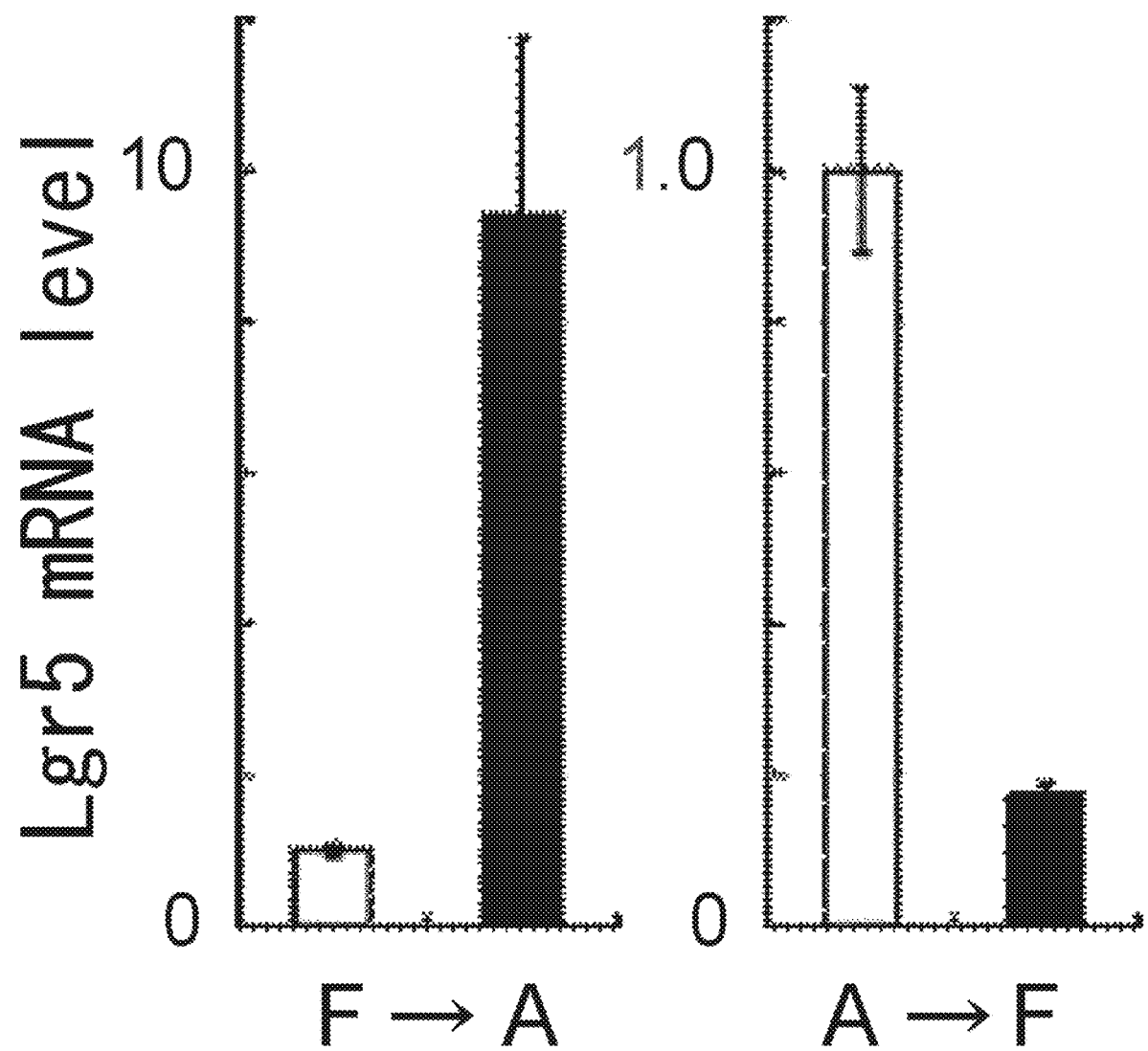
FIG. 12 is a diagram showing Lgr5 mRNA levels in PLR123 cells before and after switching to adherent culture or suspension culture (normalized to 1). F→A represents the switching from suspension culture to adherent culture, while A→F represents the switching from adherent culture to suspension culture. The results were averaged from three experiments. The bar at the top of each column represents standard deviation.
Figure 33:
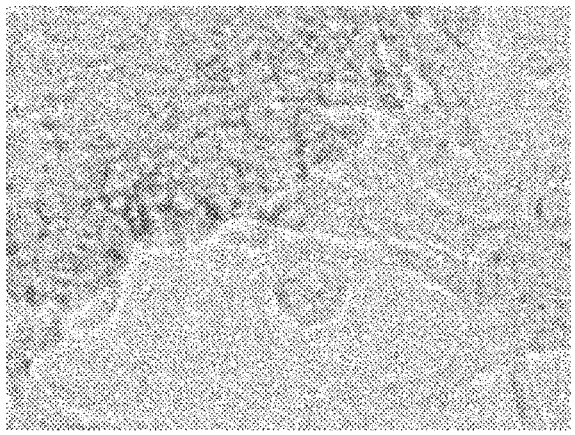
FIG. 33 shows photographs depicting the morphological interconversion of CSCs. When Lgr5-negative large intestine CSCs were dispersed and then cultured in a flat-bottomed plate, some of the cells adhered to the plate bottom, became positive for Lgr5, and showed a mesenchymal cell-like morphology (at left). On the other hand, when Lgr5-positive adherent large intestine CSCs were cultured in an ultra-low adherent plate, some of the cells halted their growth and formed a spheroid-like structure. Scale bar represents 10 μm.
Figure 33:
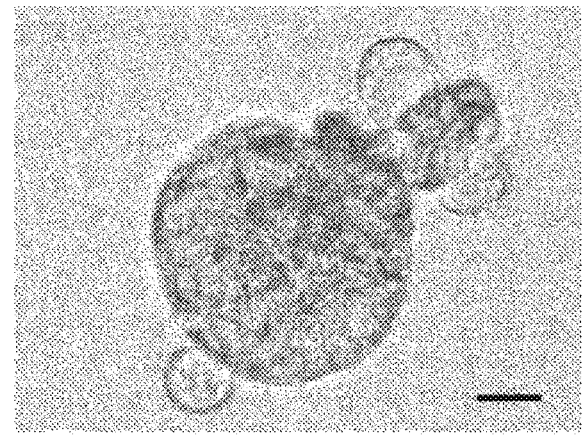
Figure 49:
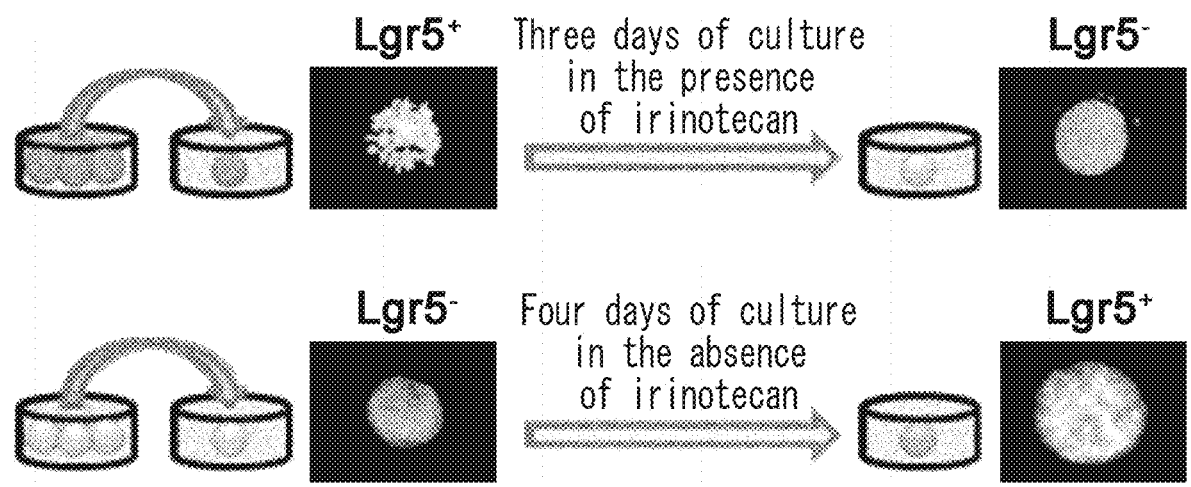
FIG. 49 is a diagram showing interconversion between Lgr5-positive and -negative cells. Lgr5-positive cells were collected by FACS. After limiting dilution, the cells were inoculated and cultured for three days in the presence of irinotecan under adherent culture conditions. On the other hand, irinotecan-treated Lgr5-negative cells were diluted by limiting dilution, and then inoculated and cultured for four days in the absence of irinotecan under adherent culture conditions. Lgr5 expression was visualized with PE-labeled anti-mouse IgG antibody (indicated in red) or AlexaFluor 488-labeled anti-mouse IgG antibody (indicated in green).

In addition, to assess whether Lgr5-negative large intestine CSCs undergo a transition into an Lgr5-positive state, the present inventors cultured adherently Lgr5-negative large intestine CSCs prepared via irinotecan treatment again in a serum-free stem cell culture medium. The cells became positive for Lgr5 and exhibited mesenchymal cell-like morphology (FIGS. 12 and 33), and started to proliferate. On the other hand, when Lgr5-positive adherent large intestine CSCs were cultured in an ultra-low adherent plate, the present inventors observed that some of the cells halted their growth and formed a spheroid-like structure and that the Lgr5 mRNA level was very low (FIGS. 12 and 33). The transition from the Lgr5-positive to Lgr5-negative state (and the reverse) was also confirmed by observations using a single cell in culture. When single Lgr5-positive cells were individually cultured in a multi-well plate, the cells underwent a transition into the Lgr5-negative state within three days after irinotecan treatment. When single Lgr5-negative cells prepared via irinotecan treatment were individually cultured in a multi-well plate in the absence of irinotecan, 19 to 43% of the cells underwent a transition into the Lgr5-positive state within four days (FIG. 49 and Table 5).

TABLE 5

| Transition of state | Cell line | Number of cells | | |
| --- | --- | --- | --- | --- |
| | | Lgr5 positive | Lgr5 negative | Total |
| Lgr5 positive to negative | PLR59 | 0 (0%) | 132 (100%) | 132 |
| | PLR123 | 1 (1%) | 173 (99%) | 174 |
| Lgr5 negative to positive | PLR59 | 18 (19%) | 78 (81%) | 96 |
| | PLR123 | 29 (43%) | 39 (57%) | 68 |

Table 5 shows cell count ratios of Lgr5-positive and -negative cells stained by 5 immunocytochemistry using an anti-Lgr5 antibody (antibody 2L36). Number in parenthesis represents the ratio of Lgr5-positive or -negative cell count.

Thus, the present inventors concluded that large intestine CSCs underwent interconversion between the Lgr5-positive and -negative states and the transition does not require any exogenous factor and/or niche environment.

Example 7: In Vitro and In Vivo EMT of Lgr5-Positive Large Intestine CSCs

Figure 13:
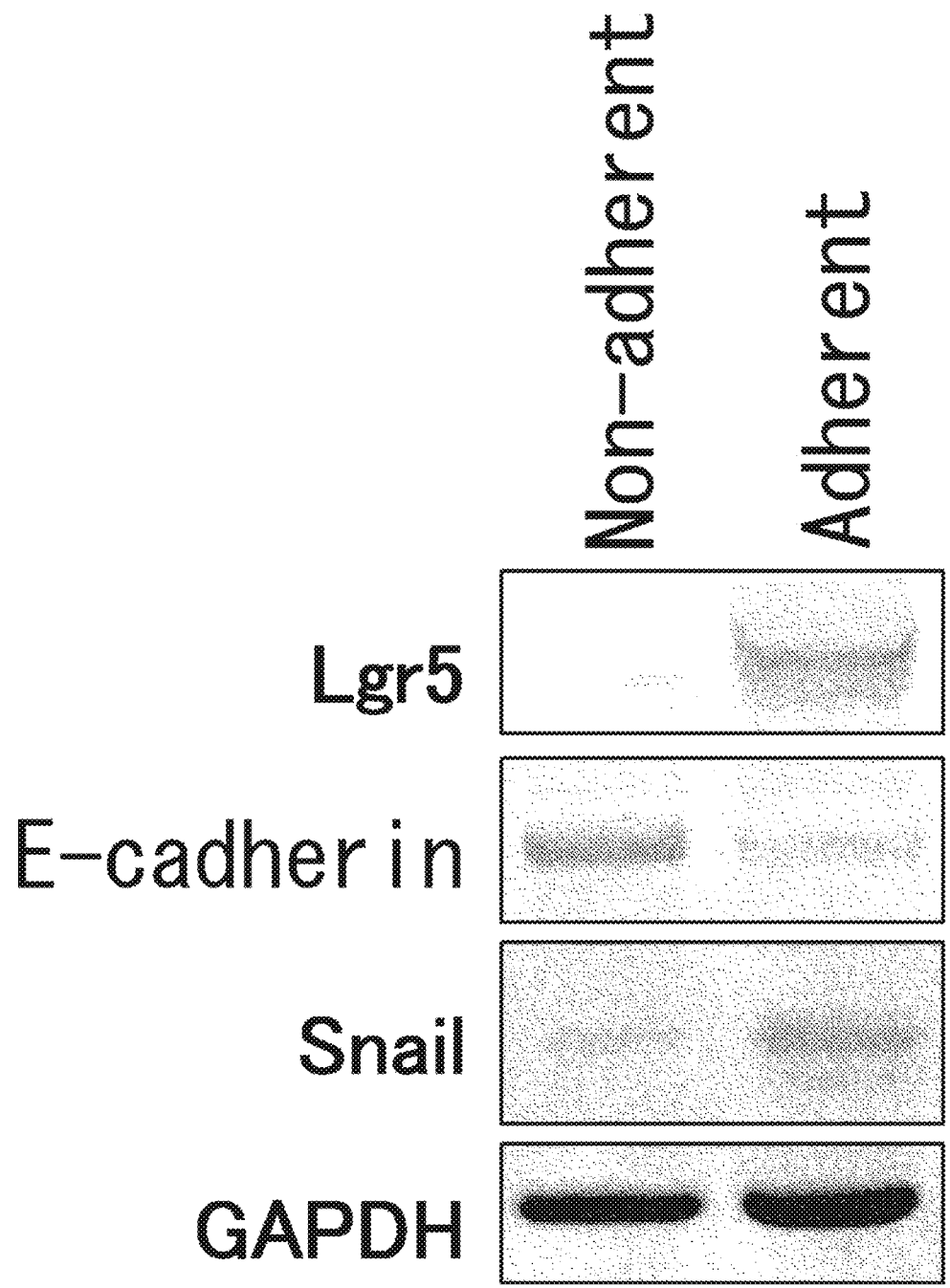
FIG. 13 shows photographs depicting a result of Western blot analysis of Lgr5-negative non-adherent CSCs and Lgr5-positive adherent CSCs (PLR123 cells) for E-cadherin and Snail. Non-adherent CSCs expressed E-cadherin at a high level, while adherent CSCs expressed Snail at a high level. GADPH was used as a loading control.
Figure 14:
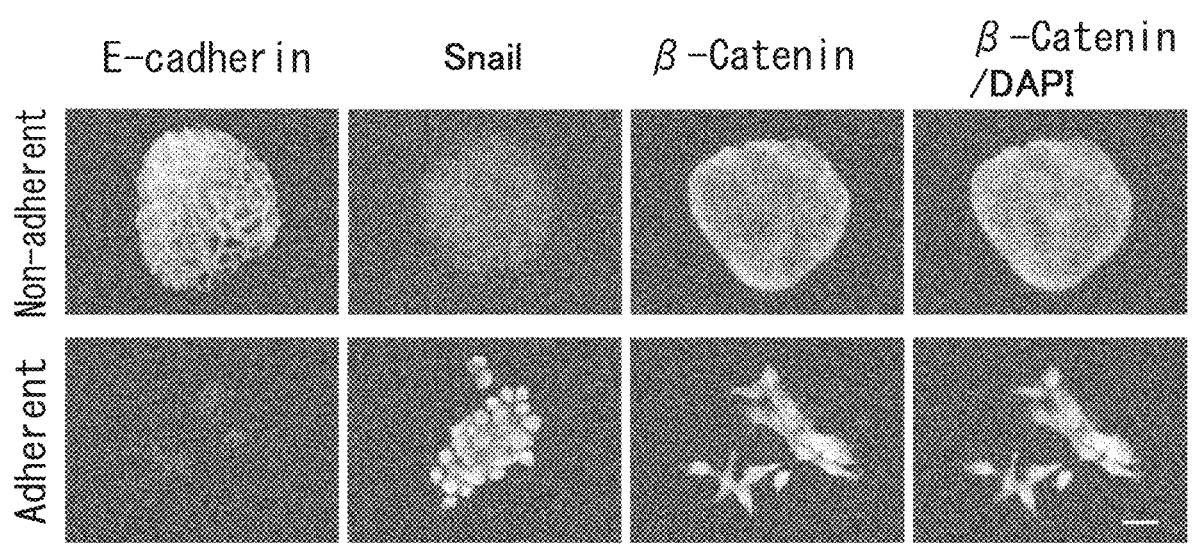
FIG. 14 shows photographs depicting a result of immunocytochemistry of Lgr5-negative non-adherent CSCs and Lgr5-positive adherent CSCs (PLR123 cells) using E-cadherin antibody, Snail antibody, and β-catenin antibody. Non-adherent CSCs were epithelium-like cells expressing cell-surface E-cadherin and β-catenin at high levels, while adherent CSCs were mesenchyme-like cells with nuclear localization of Snail and β-catenin. Scale bar represents 25 μm.
Figure 15:
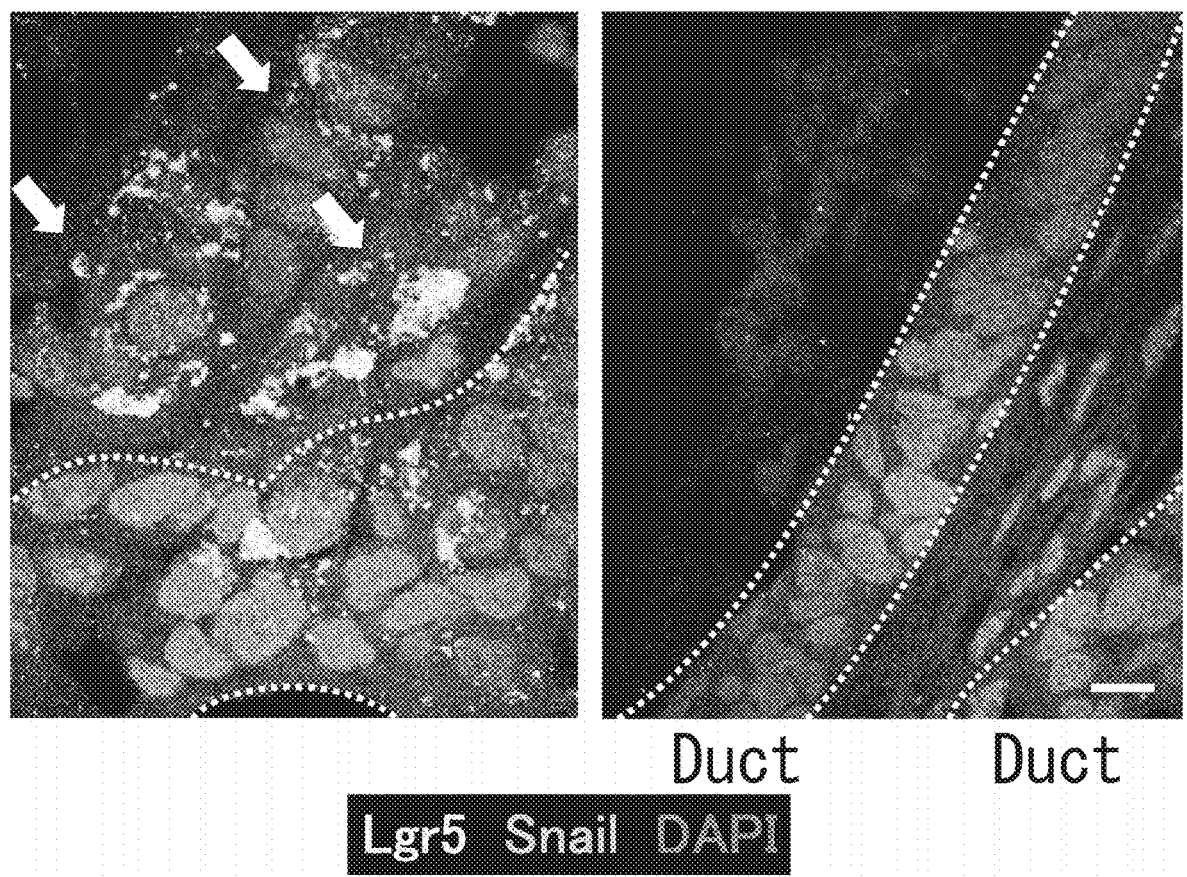
FIG. 15 shows photographs depicting a result of immunohistochemistry of PLR123-derived xenograft tissues using anti-Lgr5 antibody and anti-Snail antibody. The concomitant expression of nuclear Snail and cytoplasmic Lgr5 was detected in EMT-like cells of budding areas (left panel), while such expression was not observed in the ducts (right panel). Arrows indicate Lgr5-positive budding cells. Scale bar represents 10 μm.
Figure 26:
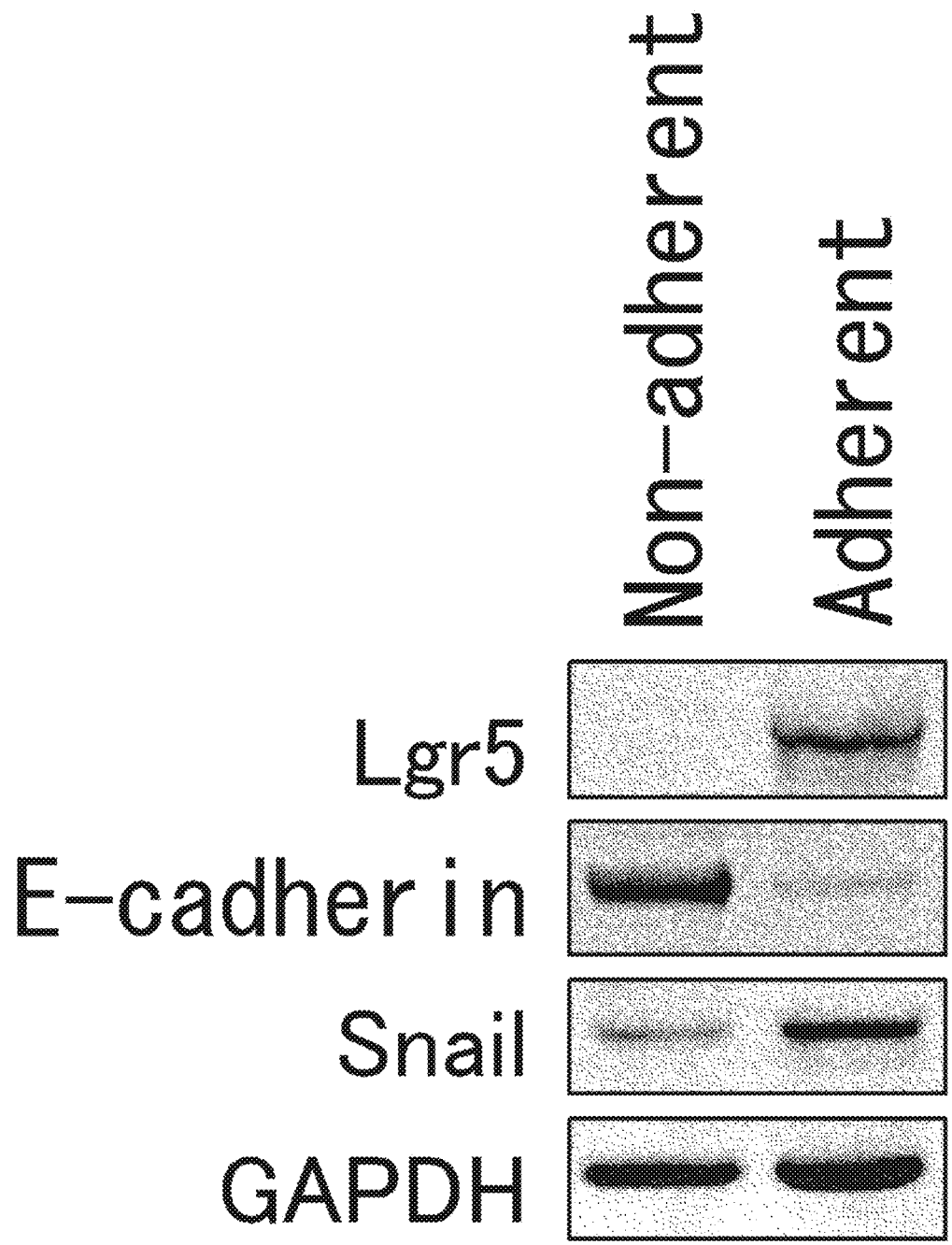
FIG. 26 shows photographs depicting a result of Western blot analysis of Lgr5-negative non-adherent CSCs and Lgr5-positive adherent CSCs (PLR59 cells) for E-cadherin and Snail. Non-adherent CSCs expressed E-cadherin at a high level and adherent CSCs expressed Snail at a high level. GADPH was used as a loading control.

Mesenchymal-like cells expressing nuclear β-catenin are considered migratory CSCs and metastatic CSCs that undergo EMT (Brabletz T, Jung A, Spaderna S, Hlubek F, Kirchner T (2005) Opinion: migrating cancer stem cells—an integrated concept of malignant tumor progression. Nat Rev Cancer 5:744-749). Since the morphology of Lgr5-positive large intestine CSCs was similar to that of mesenchymal cells, the present inventors tested whether Lgr5-positive large intestine CSCs correspond to migratory CSCs. Western blot analysis revealed low level expression of cell-surface E-cadherin, high level expression of Snail, and nuclear β-catenin (which is characteristic of EMT) in the Lgr5-positive large intestine CSCs (FIGS. 13, and 14, and 26). In contrast, the Lgr5-negative colorectal CSCs did not show any evidence of EMT. Specifically, cell-surface E-cadherin was expressed at a high level; Snail was expressed at a low level, and there was no nuclear localization of β-catenin. Furthermore, concomitant expression of Snail and Lgr5 was observed in cells that underwent EMT in budding areas of xenograft tumor tissues (FIG. 15). This finding supports the view that the Lgr5-positive large intestine CSCs correspond to migratory stem cells.

Figure 35:
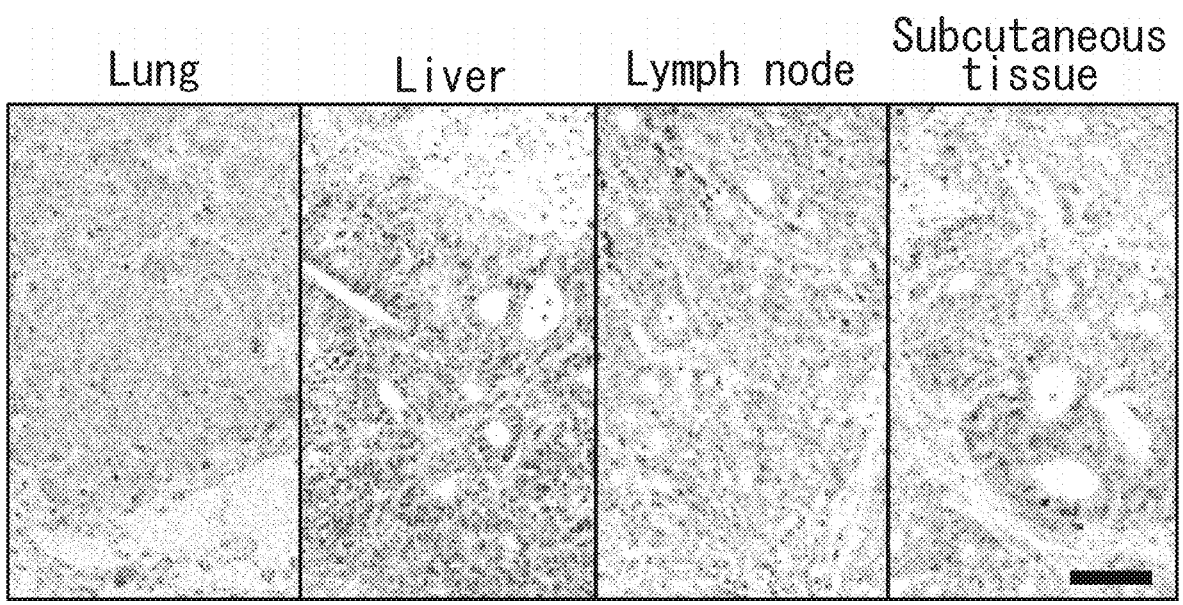
FIG. 35 shows photographs depicting a result of histopathological experiments on tumors in the lungs, liver, lymph nodes, and subcutaneous tissues. In the lungs, tumor cells formed undifferentiated tumor foci. Meanwhile, in the liver and other organs, tumor cells formed a ductal structure involving multiple differentiation stages. Scale bar represents 100 μm.
Figure 36:
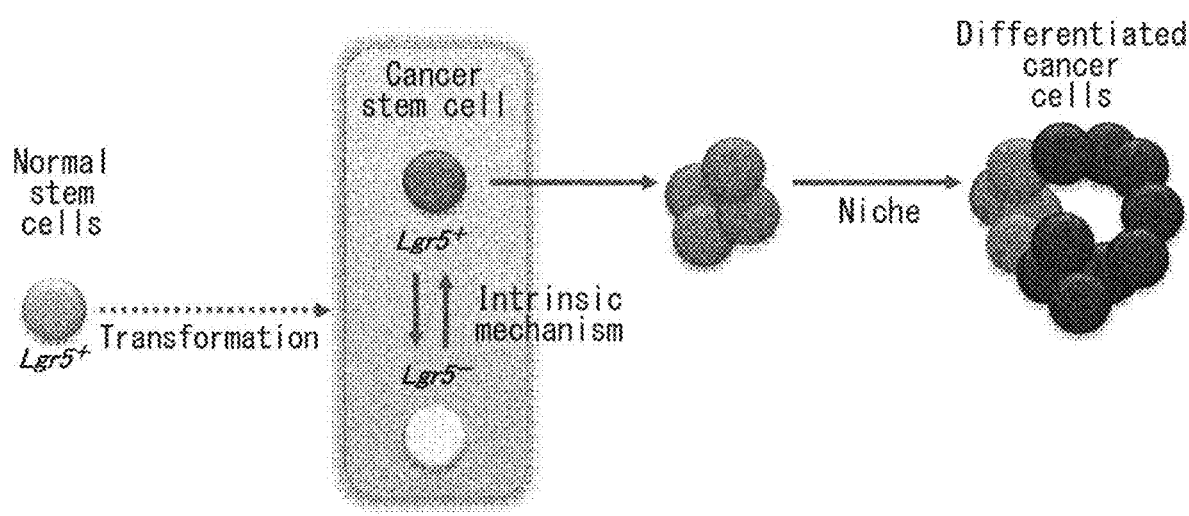
FIG. 36 is a schematic diagram for the proposed CSC model. CSCs undergo an intrinsic interconversion between two types of independent states in response to environmental changes such as the presence of anti-cancer drugs. According to previous findings, normal stem cells expressing Lgr5 are assumed to transform into CSCs via mutation in multiple genes. High proliferative CSCs express Lgr5, and undergo EMT. Under a specific stressful environment, the cells can change into the Lgr5-negative quiescent state. Niche environment is involved in stimulating the transition of CSCs to the differentiation stage.

In addition, the present inventors demonstrated that the Lgr5-positive large intestine CSCs formed tumors in multiple tissues including lung, liver, lymph node, and subcutaneous tissues. Interestingly, in the liver, lymph node, and subcutaneous tissues, tumors with epithelial ductal structures were reconstituted by at least 40 days after intravenous injection of tumor cells, whereas such structures were not reconstituted in the lung (FIGS. 34 and 35).

Figure 51:
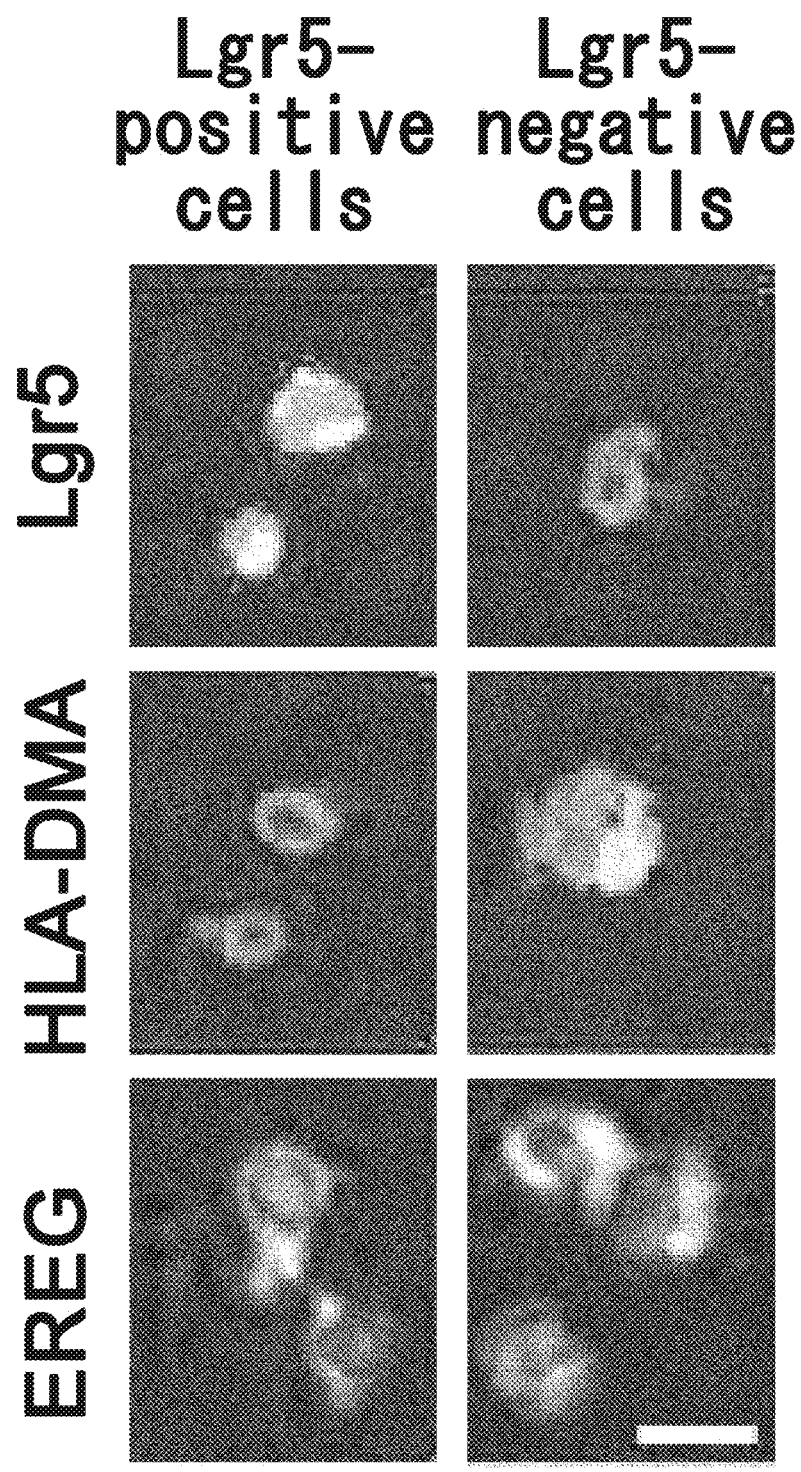
FIG. 51 shows photographs depicting the binding of anti-HLA-DMA antibody and anti-EREG antibody to Lgr5-positive and Lgr5-negative CSCs with immunohistochemical staining. CSCs (PLR123) were fixed and treated with anti-HLA-DMA antibody (Dako) and anti-EREG antibody (EP27). Intense fluorescence signals (red for both HLA-DMA and EREG) were observed on Lgr5-negative cells treated with anti-HLA-DMA antibody, whereas weak fluorescence (green) or no fluorescence was detected on Lgr5-positive cells. Fluorescence signals were detected on both Lgr5-negative and -positive cells treated with anti-EREG antibody.
Figure 52:
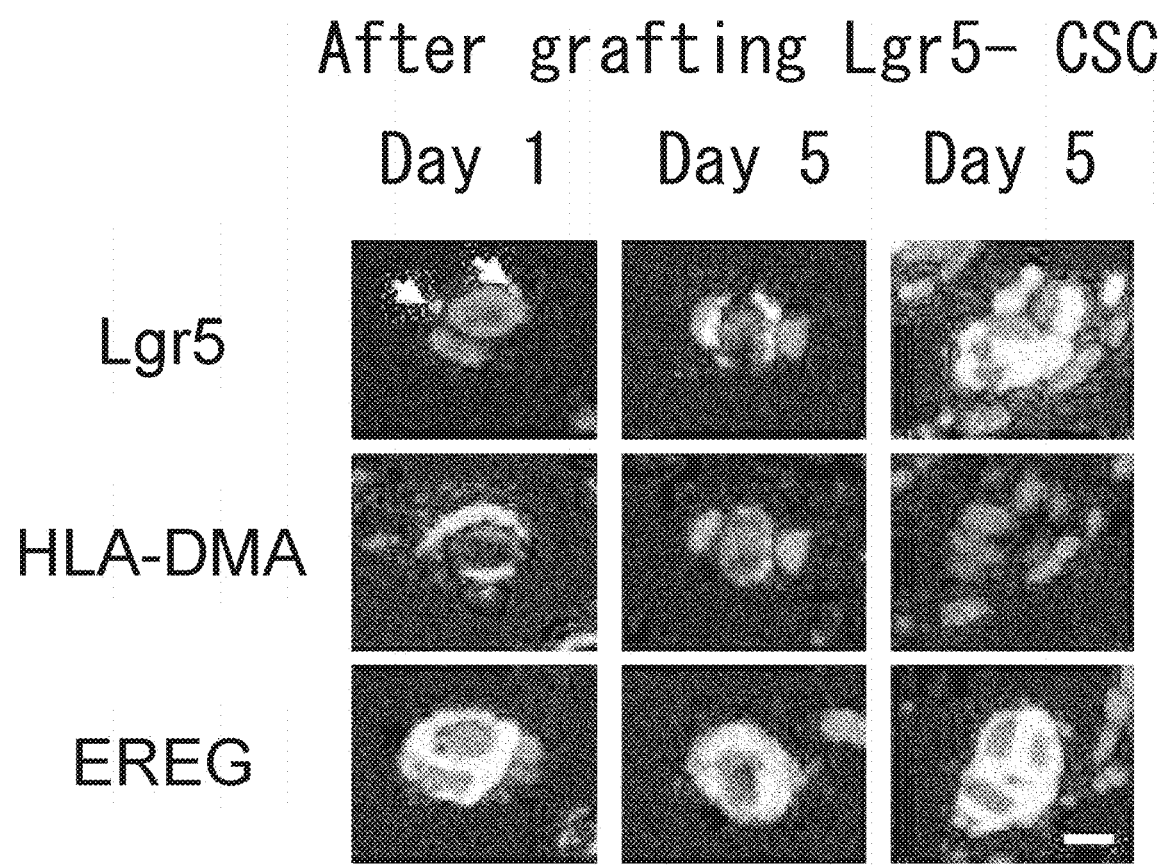
FIG. 52 shows photographs depicting the transition from Lgr5-negative CSCs to Lgr5-positive CSCs at an early stage of tumor formation. In NOG mice injected with PLR123 xenograft animal-derived Lgr5-negative CSCs, tumors derived from Lgr5-negative CSCs were stained with antibodies against Lgr5 (green), HLA-DMA (red), and EREG (green). Lgr5-weakly-expressing, HLA-DMA-positive, EREG-positive cells, and Lgr5-positive, HLA-DMA-negative, EREG-positive cells were observed to be present on day 5. Scale bar represents 10 μm.
Figure 53A:
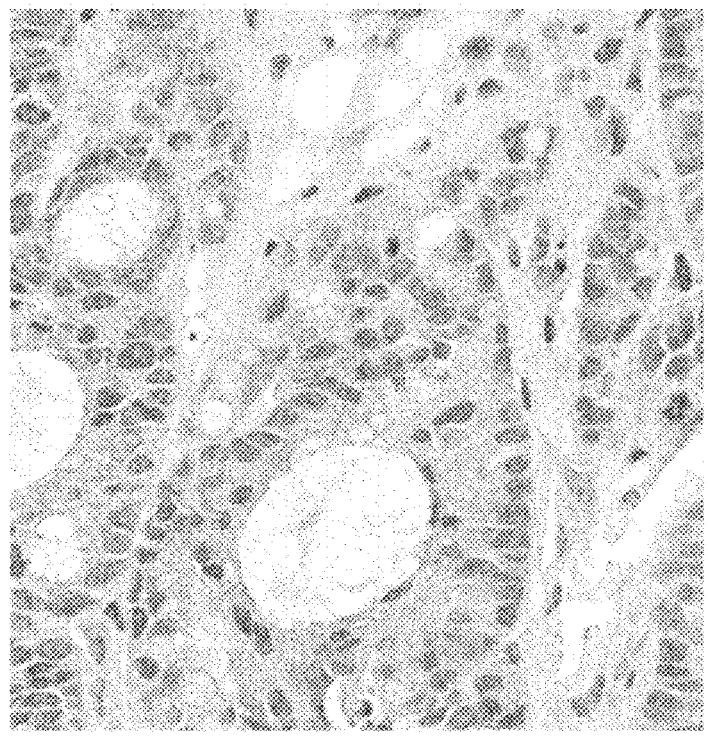
FIGS. 53A-53B show photographs depicting the reconstitution of tumor hierarchy from Lgr5-negative CSCs. The tissue structure (FIG. 53A) is shown along with an image obtained by immunofluorescence microscopic observation using anti-Lgr5 antibody and anti-E-cadherin antibody (FIG. 53B). Green and red indicate the presence of Lgr5 and E-cadherin, respectively. Scale bar represents 50 μm.
Figure 53B:
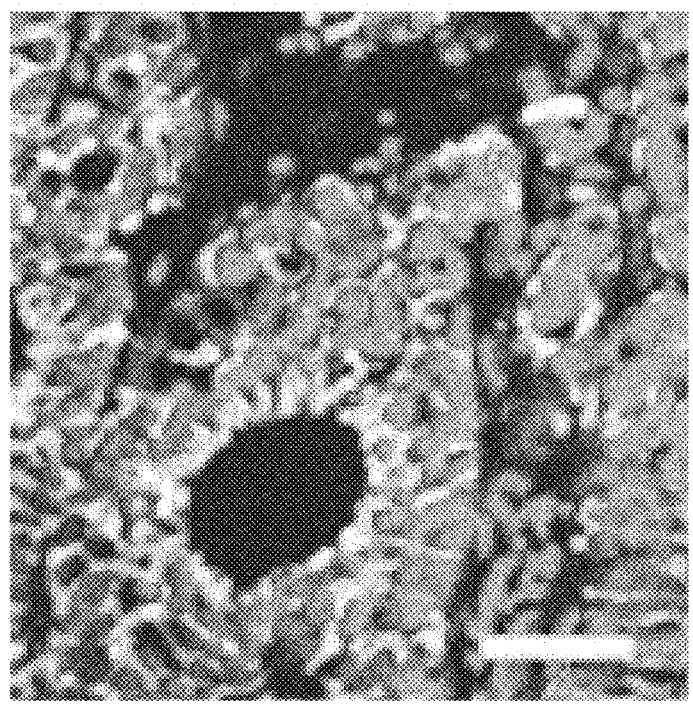

Next, the present inventors examined whether Lgr5-negative CSCs directly form the hierarchical organization of cancer or first undergo transition to Lgr5-positive cells in vivo. To find markers for detecting Lgr5-negative CSCs, gene expression profiling was carried out using Lgr5-positive cells, Lgr5-negative cells, and primary cells from xenograft tumors. As a result, HLA-DMA was selected from molecules whose expression can be detected at high level in the Lgr5-negative CSCs as compared to the Lgr5-positive CSC and primary cells (FIG. 50). By immunohistochemistry using anti-Lgr5 antibody, anti-HLA-DMA antibody, and anti-EREG antibody, HLA-DMA was demonstrated to be specifically expressed in the Lgr5-negative CSCs (FIG. 51). HLA-DMA is also expressed in macrophages. Then, to rule out the possibility that cells stained by immunohistochemistry using the anti-HLA-DMA antibody are macrophages, the present inventors tested not only HLA-DMA but also other markers expressed in CSCs. Immunohistochemistry using an antibody against EREG expressed in both Lgr5-positive and -negative CSCs (FIG. 50) confirmed that EREG was expressed in both of Lgr5-positive and Lgr5-negative CSCs (FIG. 51). It was demonstrated that Lgr5-negative CSCs could be identified as cells that are positive for both HLA-DMA and EREG by detection using both markers in combination. After injection of a homogeneous population of Lgr5-negative CSCs to NOG mice, cells expressing Lgr5 only weakly for one day after the injection, which however remained positive for HLA-DMA and EREG, appeared. Then, cells that are negative for HLA-DMA but remain positive for Lgr5 and EREG appeared by five days after the injection (FIG. 52). Tumors derived from Lgr5-negative CSCs had specific ductal structures and included Lgr5-positive cells (FIG. 53).

Figure 54:
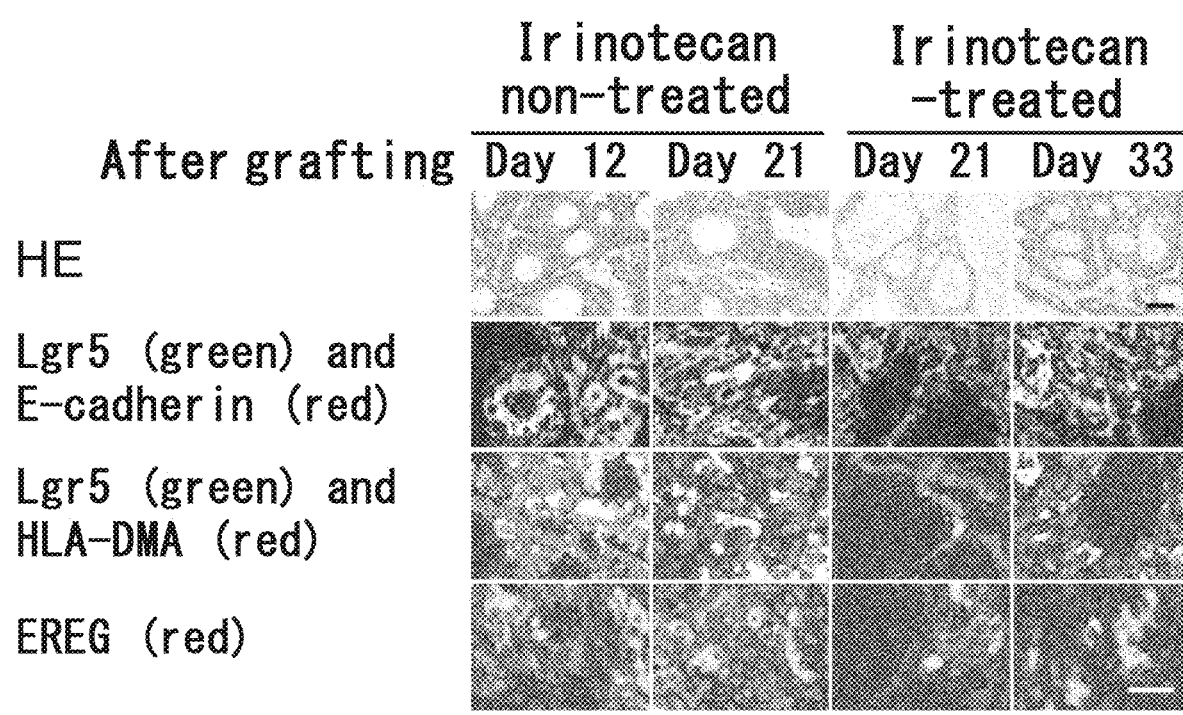
FIG. 54 shows photographs depicting histopathology (HE) (first row), immunostaining using Lgr5 antibody (green) and E-cadherin antibody (red) (second row), immunostaining using Lgr5 antibody (green) and HLA-DMA antibody (red) (third row), and immunostaining using EREG antibody (red) (fourth row), of tumors after irinotecan treatment. Mice bearing tumors derived from Lgr5-positive CSCs (PLR123) were treated with irinotecan, and their tumors were observed. Irinotecan or vehicle was administered to mice at days 12, 15, and 18 after tumor grafting. Scale bar represents 25 μm.
Figure 55:
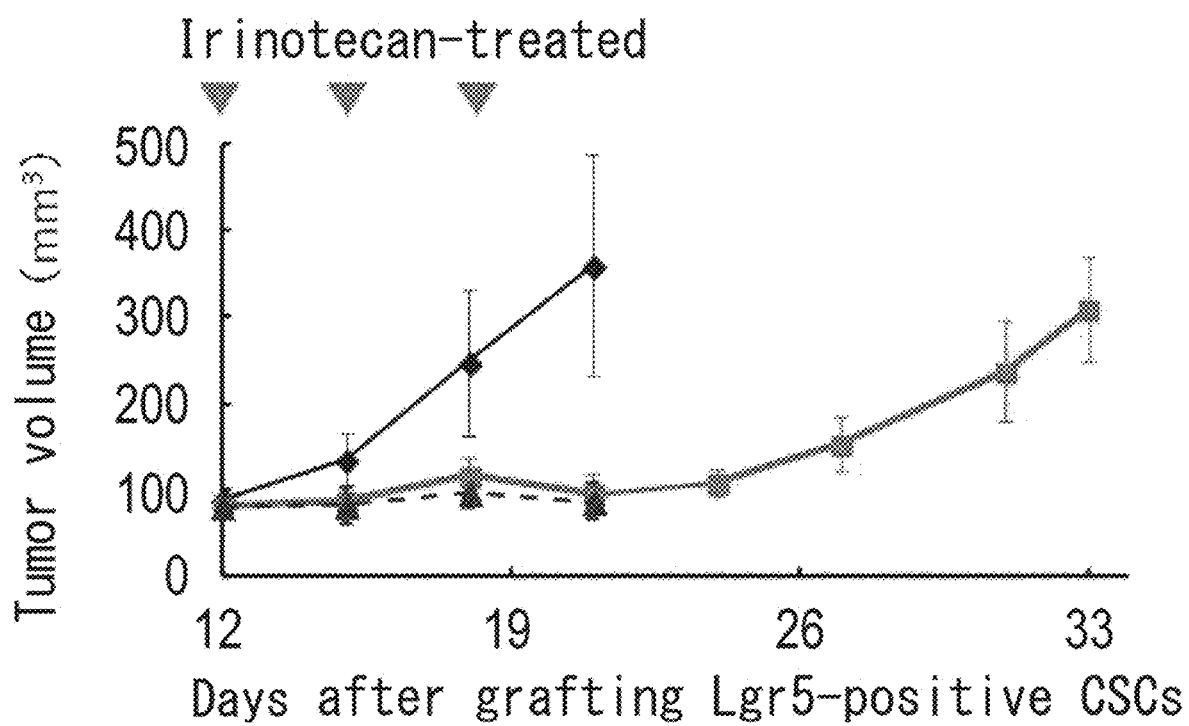
FIG. 55 Irinotecan was administered at a dose of 120 mg/kg/day to NOG mice at days 12, 15, and 18 after grafting tumors derived from Lgr5-positive CSCs (PLR123). This figure is a graph showing tumor volumes in control mice administered with vehicle (closed diamond) and mice administered with irinotecan (closed square or triangle). Each value represents mean+standard deviation.
Figure 56:
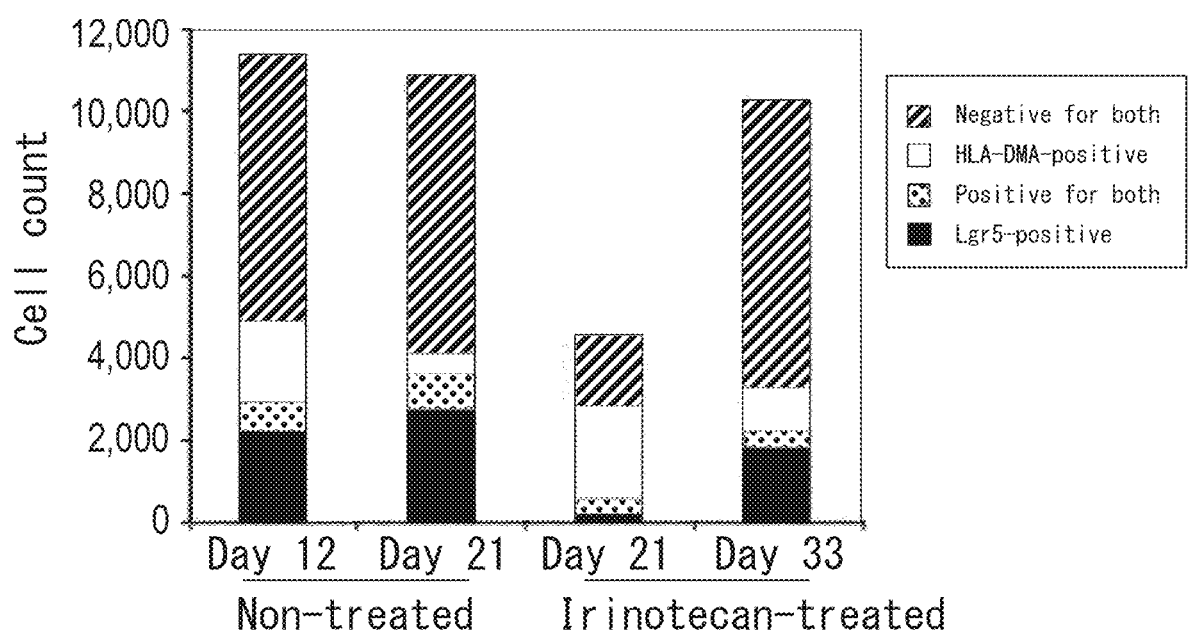
FIG. 56 is a graph showing the numbers of Lgr5-positive and HLA-DMA-positive cells in xenograft tumor tissues. Thin sections of tissues were treated with Lgr5 antibody and HLA-DMA antibody, and then the numbers of Lgr5-positive and HLA-DMA-positive cells were measured. Values represent the total numbers of cells counted for respective groups (n=3).

To probe the possibility of in vivo transition to a growth inhibitor-resistant state, irinotecan was administered at the maximum tolerated dose (MTD) (120 mg/kg) into the peritoneal cavities of NOG mice bearing tumors derived from Lgr5-positive CSCs. Tumor growth was inhibited almost completely (FIG. 55), and the ductal structures were collapsed extensively (FIG. 54). This condition resulted in a dramatic decrease of Lgr5-positive cells (FIGS. 54 and 56). The number of Lgr5-negative and HLA-DMA-positive cells increased significantly after irinotecan treatment. By contrast, in vehicle-treated control mice, about one third of cancer cells were positive for Lgr5 in both ductal and budding areas (FIG. 54). Both Lgr5-positive cells and HLA-DMA-positive and Lgr5-negative cells were positive for EREG, and were identified to be CSCs (FIG. 54). After irinotecan treatment, Lgr5-positive cells appeared again (FIG. 54). The results described above, when considered together, suggest that Lgr5-negative CSCs can be the origin of colorectal cancer after growth inhibitor treatment and reconstitute cancer hierarchy via transition to Lgr5-positive cells.

Example 8: Identification of Molecules Specifically Expressed in Cancer Stem Cells 1. Preparation of Lgr5-Negative Adherent Cells by Irinotecan Treatment Using a stem cell medium, Lgr5-positive adherent cells were seeded at $3\times10^5$ cells/well in a 6-well plate (BD, Cat. No. 353046). On the following day, irinotecan (Hospira, 61703-349-09) was added to cells at a final concentration of 10 μg/ml. After three-day culture, irinotecan-resistant cells were detected. The cells were harvested using Accutase, and suspended in FACS buffer. Then, the cells were incubated at 4° C. for 30 minutes with 7-AAD Viability Dye as dead cell staining and each of the following antibodies as cancer stem cell markers:

FITC-labeled mouse mAb to human CD326 (EpCAM), PE-labeled mouse mAb to human CD133/1 (AC133), PE-labeled mouse mAb to human CD44, PE-labeled mouse mAb to human CD166, PE-labeled mouse mAb to human CD24, PE-labeled mouse mAb to human CD26, or PE-labeled mouse mAb to human CD29. To detect Lgr5, the cells were incubated with the mouse mAb to human Lgr5 at 4° C. for 30 minutes. After washing once with FACS buffer, the cells were incubated with the PE-labeled goat Ab to mouse IgG2a at 4° C. for 30 minutes. Then, after washing once with FACS buffer, the cells were subjected to flow cytometry analysis. The ALDH activity was detected using AldeFluor Kit according to the procedure recommended by the manufacturer. Flow cytometry analysis was performed using EPICS ALTRA. Cells negative for 7-AAD Viability Dye were analyzed for cancer stem cell markers. The irinotecan-resistant cells were demonstrated to change from positive to negative for Lgr5.

2. Identification of Molecules Specifically Expressed in Cancer Stem Cells

Primary cells from PLR59 and PLR123, high proliferative Lgr5-positive cancer stem cells prepared by adherent culture of primary cells, and low proliferative Lgr5-negative cancer stem cells prepared by irinotecan treatment of the cells as described above were homogenized mechanically with QIAshredder (Qiagen, Cat. No. 79654), and RNAs were extracted from them using RNeasy Mini Kit (Qiagen, Cat. No. 74104) and RNase-Free DNase Set (Qiagen, Cat. No. 79254) according to the procedure recommended by the manufacturer. The extracted RNAs were analyzed for the purity and quality using Agilent 2100 Bioanalyzer. Following cRNA synthesis, gene expression information was obtained using GeneChip (HG-U133 plus2) of Affymetrix. Data analysis was performed with Microsoft Excel and Statistics software R. The three types of cells (primary cells, Lgr5-positive cells, and Lgr5-negative cells) were compared to each other to make a list of genes whose expression levels are significantly increased in each cell type. Specifically, raw data from GeneChip were normalized and log 2 transformed by GCRMA to calculate differences in the expression level between distinct sample types (three types: primary cells and Lgr5-positive cells, Lgr5-positive cells and Lgr5-negative cells, and Lgr5-negative cells and primary cells). The criteria used for selecting differently expressed genes were:

(1) genes showing a twofold or more change in Lgr5-positive cells as compared to primary cells and a twofold or more change in Lgr5-negative cells as compared to primary cells (expressed at high levels in both Lgr5-positive and -negative cancer stem cells) (Table 6-1 to 6-10) (partial amino acid sequences of proteins encoded by the genes are shown in SEQ ID NOs: 1 to 7);

(2) genes showing a twofold or more change in Lgr5-positive cells as compared to primary cells and a less than twofold change in Lgr5-negative cells as compared to primary cells and (expressed at a high level in Lgr5-positive cancer stem cells alone) (Table 7-1 to 7-5);

(3) genes showing a less than twofold change in Lgr5-positive cells as compared to primary cells and a twofold or more change in Lgr5-negative cells as compared to primary cells (expressed at a high level in Lgr5-negative cancer stem cells alone) (Table 8-1 and 8-2) (partial amino acid sequences of proteins encoded by the genes are shown in SEQ ID NOs: 8 and 9).

Furthermore, to identify genes encoding proteins that are presented specifically on cell membrane of cancer stem cells, genes of GO:0005886 [plasma membrane] were extracted from GeneOntology (GO). Then, the present inventors extracted genes with GO:0005576 [extracellular region], GO:0009986 [cell surface], and GO:0016020 [membrane], or genes which are predicted to have a trans-membrane region by membrane protein prediction software TMHMM and to have a signal peptide by signal peptide prediction software SignalP, and which do not have GO:0031090 [organelle membrane]. Furthermore, with the aid of GeneChip data from normal colorectal tissues, the present inventors exclude genes whose expression levels are relatively high in normal tissues or primary cells as well as gene only showing a small fold-change in Lgr5-positive or Lgr5-negative cells.

TABLE 6-1

| DB accession NO. | Abbreviation | Molecule name | PLR59 primary Lgr5+ | PLR123 primary Lgr5+ | PLR59 primary- Lgr5- | PLR123 primary- Lgr5- | SEQ ID NO. |
|---|---|---|---|---|---|---|---|
| NP_036438.2 | FAIM2 | Fas apoptotic inhibitory molecule 2 | 8.4 | 7.0 | 5.4 | 4.1 | — |
| NP_116265.1 | JUB | jub, ajuba homolog (Xenopus laevis) | 5.8 | 5.7 | 6.2 | 5.5 | — |
| NP_116281.2 | FRMD5 | FERM domain containing 5 | 4.0 | 6.7 | 2.5 | 4.8 | — |
| NP_071731.1 | EDAR | ectodysplasin A receptor | 7.0 | 7.6 | 5.3 | 4.6 | 1 |
| NP_001240622.1 | MCOLN3 | mucolipin 3 | 3.7 | 5.1 | 0.8 | 2.5 | — |
| NP_001007098.1 | NTRK2 | neurotrophic tyrosine kinase, receptor, type 2 | 3.6 | 5.2 | 1.0 | 2.6 | — |
| NP_001243.1 | CD70 | CD70 molecule | 4.0 | 4.9 | 4.1 | 4.7 | 2 |
| NP_062818.1 | SLCO1B3 | solute carrier organic anion transporter family, member 1B3 | 4.9 | 4.4 | 3.0 | 3.9 | — |
| NP_003606.3 | SLC4A7 | solute carrier family 4, sodium bicarbonate cotransporter, member 7 | 2.9 | 4.0 | 1.6 | 3.2 | — |
| NP_005836.2 | ABCC4 | ATP-binding cassette, sub-family C (CFTR/MRP), member 4 | 4.0 | 4.0 | 1.8 | 2.4 | — |
| NP_003920.1 | RAB7L1 | RAB7, member RAS oncogene family-like 1 | 5.5 | 5.3 | 5.6 | 6.0 | — |
| NP_009162.1 | SLC6A14 | solute carrier family 6 (amino acid transporter), member 14 | 1.9 | 3.7 | 4.7 | 6.3 | — |
| NP_872631.1 | EFNA4 | ephrin-A4 | 2.6 | 3.6 | 1.4 | 2.5 | — |
| NP_001423.1 | EREG | epiregulin | 2.5 | 3.3 | 2.6 | 3.1 | 3 |
| NP_001127839.1 | SLC6A6 | solute carrier family 6 (neurotransmitter transporter, taurine), member 6 | 3.3 | 3.3 | 0.8 | 1.6 | — |
| NP_003497.2 | FZD6 | frizzled homolog 6 (Drosophila) | 3.7 | 3.2 | 4.6 | 4.0 | — |

TABLE 6-1-continued

| DB accession NO. | Abbreviation | Molecule name | PLR59 primary Lgr5+ | PLR123 primary Lgr5+ | PLR59 primary Lgr5− | PLR123 primary Lgr5− | SEQ ID NO. |
|---|---|---|---|---|---|---|---|
| NP_003264.2 | TM7SF2 | transmembrane 7 superfamily member 2 | 4.0 | 4.2 | 6.8 | 6.2 | — |
| NP_001172024.1 | AIF1L | allograft inflammatory factor 1-like | 3.5 | 2.9 | 2.3 | 2.0 | — |
| NP_060033.3 | IL17RD | interleukin 17 receptor D | 3.1 | 2.8 | 2.4 | 3.0 | — |
| NP_000013.2 | ADA | adenosine deaminase | 2.1 | 2.7 | 2.8 | 2.9 | — |
| NP_004834.1 | IL27RA | interleukin 27 receptor, alpha | 3.6 | 2.6 | 2.2 | 1.8 | — |

Table 6-2 is a continuation of Table 6-1.

TABLE 6-2

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001731.2 | CALB2 | calbindin 2 | 3.8 | 2.5 | 2.4 | 0.5 | — |
| NP_065209.2 | ANK1 | ankyrin 1, erythrocytic | 5.8 | 2.5 | 4.9 | 2.4 | — |
| NP_001157412.1 | PYGL | phosphorylase, glycogen, liver | 1.2 | 2.5 | 1.7 | 2.1 | — |
| NP_001097.2 | ACVR2B | activin A receptor, type IIB | 2.4 | 2.5 | 1.5 | 1.2 | — |
| NP_001129141.1 | XPR1 | xenotropic and polytropic retrovirus receptor 1 | 3.4 | 2.5 | 3.5 | 2.4 | — |
| NP_001523.2 | SLC29A2 | solute carrier family 29 (nucleoside transporters), member 2 | 1.6 | 2.4 | 0.5 | 1.7 | — |
| NP_563615.3 | DCBLD2 | discoidin, CUB and LCCL domain containing 2 | 2.9 | 5.3 | 5.2 | 4.9 | — |
| NP_689522.2 | PIK3AP1 | phosphoinositide-3-kinase adaptor protein 1 | 3.5 | 2.4 | 1.3 | 1.0 | — |
| NP_054772.1 | FLVCR1 | feline leukemia virus subgroup C cellular receptor 1 | 3.5 | 2.4 | 1.7 | 1.2 | — |
| NP_006849.1 | TMED1 | transmembrane emp24 protein transport domain containing 1 | 2.6 | 2.3 | 2.4 | 1.9 | — |
| NP_116254.4 | TNS4 | tensin 4 | 1.9 | 2.3 | 1.9 | 1.5 | — |
| NP_001193874.1 | CSPG5 | chondroitin sulfate proteoglycan 5 (neuroglycan C) | 3.9 | 2.2 | 1.5 | 0.5 | — |
| NP_000667.1 | ADORA2B | adenosine A2b receptor | 1.5 | 2.1 | 0.7 | 1.5 | — |
| NP_064423.2 | ACCN2 | amiloride-sensitive cation channel 2, neuronal | 1.8 | 1.9 | 1.7 | 1.3 | — |
| NP_001018000.1 | KAZ | kazrin | 2.5 | 1.8 | 2.0 | 1.8 | — |
| NP_004773.1 | SNAP29 | synaptosomal-associated protein, 29 kDa | 0.3 | 1.7 | 0.8 | 1.9 | — |
| NP_066292.2 | KCNJ12 | potassium inwardly-rectifying channel, subfamily J, member 12 | 3.4 | 3.5 | 4.0 | 3.4 | — |
| NP_938205.1 | FLRT3 | fibronectin leucine rich transmembrane protein 3 | 2.8 | 1.5 | 7.1 | 5.0 | — |
| NP_115899.1 | PARD6G | par-6 partitioning defective 6 homolog gamma (C. elegans) | 1.8 | 1.0 | 2.7 | 1.9 | — |
| NP_066924.1 | CLDN1 | claudin 1 | 1.4 | 0.7 | 3.4 | 3.5 | — |
| NP_066939.1 | ADCY1 | adenylate cyclase 1 (brain) | 2.9 | 2.2 | 2.1 | 1.4 | — |

Table 6-3 is a continuation of Table 6-2.

TABLE 6-3

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001127807.1 | AIMP2 | aminoacyl tRNA synthetase complex-interacting multifunctional protein 2 | 1.0 | 0.6 | 1.2 | 0.7 | — |
| NP_619539.1 | AKAP7 | A kinase (PRKA) anchor protein 7 | 2.0 | 1.3 | 1.4 | 1.2 | — |
| NP_064715.1 | ANKMY2 | ankyrin repeat and MYND domain containing 2 | 2.7 | 2.5 | 3.2 | 3.4 | — |
| NP_112591.2 | APH1B | anterior pharynx defective 1 homolog B (C. elegans) | 0.8 | 1.6 | 1.1 | 3.1 | — |
| NP_658985.2 | APOA1BP | apolipoprotein A-I binding protein | 1.8 | 1.3 | 2.2 | 1.6 | — |
| NP_940852.3 | APOOL | apolipoprotein O-like | 1.6 | 1.6 | 2.3 | 2.3 | — |
| NP_647537.1 | ATRN | attractin | 1.5 | 2.1 | 1.1 | 1.8 | — |
| NP_001193.2 | BMP4 | bone morphogenetic protein 4 | 2.9 | 4.2 | 1.9 | 2.8 | 4 |
| NP_001720.1 | BTC | betacellulin | 1.4 | 2.5 | 1.7 | 3.2 | — |
| NP_001224.1 | CAV2 | caveolin 2 | 1.9 | 2.9 | 3.7 | 4.2 | — |
| NP_001788.2 | CDH11 | cadherin 11, type 2, OB-cadherin (osteoblast) | 6.2 | 2.4 | 3.8 | 0.6 | — |
| NP_857592.1 | CKLF | chemokine-like factor | 0.9 | 1.6 | -0.8 | 1.1 | — |
| NP_612419.1 | CMTM7 | CKLF-like MARVEL transmembrane domain containing 7 | 2.8 | 4.2 | 2.3 | 3.2 | — |
| NP_054860.1 | CNTNAP2 | contactin associated protein-like 2 | 4.6 | 4.3 | 3.8 | 3.7 | — |
| NP_004738.3 | DLG5 | discs, large homolog 5 (Drosophila) | 1.5 | 1.0 | 1.5 | 1.2 | — |
| NP_001926.2 | DPP4 | dipeptidyl-peptidase 4 | 0.1 | 1.3 | 2.0 | 3.8 | — |
| NP_690611.1 | FAS | Fas (TNF receptor superfamily, member 6) | 1.4 | 0.1 | 3.4 | 2.1 | — |
| NP_001099043.1 | FBXO45 | F-box protein 45 | 1.0 | 1.3 | 0.3 | 1.2 | — |
| NP_001138390.1 | FGFR2 | fibroblast growth factor receptor 2 | 3.9 | 1.7 | 3.0 | 1.0 | — |

TABLE 6-3-continued

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001457.1 | FZD2 | frizzled homolog 2 (Drosophila) | 5.2 | 5.4 | 2.6 | 2.9 | — |
| NP_031379.2 | GNA12 | guanine nucleotide binding protein (G protein) alpha 12 | 1.2 | 0.5 | 1.1 | 0.3 | — |

Table 6-4 is a continuation of Table 6-3.

TABLE 6-4

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001243343.1 | GNAI1 | guanine nucleotide binding protein (G protein), alpha inhibiting activity polypeptide 1 | 4.0 | 4.6 | 7.6 | 8.2 | — |
| NP_002766.1 | HTRA1 | HtrA serine peptidase 1 | 5.1 | 7.0 | 5.0 | 6.3 | — |
| NP_001543.2 | IGEBP4 | insulin-like growth factor binding protein 4 | 3.4 | 2.7 | 0.5 | 1.1 | — |
| NP_001002915.2 | IGFL2 | IGF-like family member 2 | 3.0 | 3.3 | 2.3 | 2.5 | — |
| NP_001034659.2 | KREMEN1 | kringle containing transmembrane protein 1 | 3.0 | 3.7 | 1.3 | 2.3 | — |
| NP_005597.3 | LGMN | legumain | 1.1 | 1.8 | 0.5 | 1.4 | — |
| NP_002303.2 | LIG4 | ligase IV, DNA, ATP-dependent | 3.7 | 3.7 | 5.6 | 5.4 | — |
| NP_006024.1 | LIPG | lipase, endothelial | 2.1 | 2.6 | 0.1 | 1.1 | — |
| NP_001392.2 | LPAR1 | lysophosphatidic acid receptor 1 | 2.9 | 3.4 | 1.3 | 2.4 | — |
| NP_036284.1 | LPAR3 | lysophosphatidic acid receptor 3 | 6.7 | 4.9 | 3.7 | 2.9 | — |
| NP_002327.2 | LRP6 | low density lipoprotein receptor-related protein 6 | 2.8 | 1.8 | 1.5 | 0.6 | — |
| NP_055414.2 | MAGED2 | melanoma antigen family D, 2 | 1.1 | 1.8 | 2.7 | 0.9 | — |
| NP_005922.2 | MICB | MHC class I polypeptide-reiated sequence B | 2.6 | 3.6 | 2.3 | 3.7 | — |
| NP_001182555.1 | MLLT10 | myeloid/lymphoid or mixed-lineage leukemia (trithorax homolog, Drosophila); translocated to, 10 | 2.5 | 2.0 | 1.0 | 1.3 | — |
| NP_002435,1 | MSN | moesin | 3.0 | 1.7 | 2.2 | 0.0 | — |
| NP_001018169.1 | NAE1 | NEDD8 activating enzyme EI subunit 1 | 1.8 | 1.7 | 1.2 | 1.8 | — |
| NP_056146.1 | NCSTN | nicastrin | 1.5 | 0.4 | 2.3 | 0.8 | — |
| NP_060562.3 | NETO2 | neuropilin (NRP) and tolloid (TLL)-like 2 | 7.3 | 6.1 | 8.0 | 6.9 | — |
| NP_009014.2 | NUDT6 | nudix (nucleoside diphosphate linked moiety X)-type motif 6 | 3.2 | 1.9 | 4.2 | 2.9 | — |
| NP_689501.1 | ORAI3 | ORAI calcium release-activated calcium modulator 3 | 1.5 | 1.1 | 4.3 | 2.2 | — |
| NP_002605.2 | PDZK1 | PDZ domain containing 1 | 8.1 | 8.3 | 4.9 | 3.6 | — |

Table 6-5 is a continuation of Table 6-4.

TABLE 6-5

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_055824.1 | PDZRN3 | PDZ domain containing ring finger 3 | 2.6 | 2.5 | 1.4 | 0.6 | — |
| NP_077734.1 | PLA2G4A | phospholipase A2, group IVA (cytosolic, calcium-dependent) | 7.7 | 8.2 | 5.0 | 5.9 | — |
| NP_001123508.1 | PLEKHB1 | pleckstrin homology domain containing, family B (evectins) member 1 | 4.0 | 5.3 | 5.1 | 6.3 | — |
| NP_079501.2 | PNPLA3 | patatin-like phospholipase domain containing 3 | 4.4 | 4.9 | 1.7 | 3.5 | — |
| NP_004641.1 | PNPLA4 | patatin-like phospholipase domain containing 4 | 2.3 | 1.9 | 2.8 | 2.2 | — |
| NP_006395.2 | PROCR | protein C receptor, endothelial | 1.3 | 1.5 | 4.2 | 3.6 | 5 |
| NP_001159449.1 | PROM2 | prominin 2 | 5.4 | 4.6 | 10.5 | 10.4 | 6 |
| NP_077748.3 | PSTPIP2 | proline-serine-threonine phosphatase interacting protein 2 | 2.2 | 2.7 | 5.1 | 4.9 | — |
| NP_002834.3 | PTPRJ | protein tyrosine phosphatase, receptor type, J | 2.9 | 3.0 | 1.5 | 2.2 | — |
| NP_002861.1 | RAB13 | RAB13, member RAS oncogene family | 1.3 | 0.9 | 2.0 | 1.4 | — |
| NP_066361.1 | RAP2A | RAP2A, member of RAS oncogene family | 2.0 | 1.7 | 2.4 | 1.7 | — |
| NP_001094058.1 | RC3H2 | ring finger and CCCH-type zinc finger domains 2 | 1.2 | 0.3 | 2.0 | 0.0 | — |
| NP_002897.1 | RDX | radixin | 4.7 | 5.3 | 4.5 | 4.6 | — |
| NP_006502.1 | RSC1A1 | regulatory solute carrier protein, family 1, member 1 (DNA-damage inducible 1 homolog 2) | 1.1 | 0.0 | 1.2 | 0.4 | — |
| NP_004162.2 | SLC1A2 | solute carrier family 1 (glial high affinity glutamate transporter), member 2 | 7.4 | 7.3 | 2.1 | 1.9 | — |
| NP_006349.1 | SLC25A17 | solute carrier family 25 (mitochondrial carrier; peroxisomal membrane protein, 34 kDa), member 17 | 2.4 | 1.9 | 2.4 | 1.5 | — |
| NP_075053.2 | SLC30A5 | solute carrier family 30 (zinc transporter), member 5 | 1.3 | 0.9 | 1.2 | 0.8 | — |
| NP_001070253.1 | SLC7A6 | solute carrier family 7 (cationic amino acid transporter, y+ system), member 6 | 1.0 | 0.2 | 1.5 | 0.8 | — |

TABLE 6-5-continued

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_071420.1 | SMOC1 | SPARC related modular calcium binding 1 | 2.6 | 5.4 | −0.1 | 2.4 | — |
| NP_001159884.1 | SMOC2 | SPARC related modular calcium binding 2 | 7.2 | 8.4 | −0.9 | 2.2 | — |
| NP_054730.1 | SOCS5 | suppressor of cytokine signaling 5 | 2.3 | 1.7 | 2.5 | 1.9 | — |

Table 6-6 is a continuation of Table 6-5.

TABLE 6-6

| DB accession NO. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001030127.1 | SORBS1 | sorbin and SH3 domain containing 1 | 6.4 | 4.3 | 1.1 | −0.2 | — |
| NP_003095.2 | SORD | sorbitol dehydrogenase | 1.5 | 1.8 | 1.0 | 2.1 | — |
| NP_003705.1 | STC2 | stanniocalcin 2 | 3.6 | 3.1 | 1.2 | 2.3 | — |
| NP_005810.1 | STX6 | syntaxin 6 | 3.4 | 2.5 | 4.4 | 3.2 | — |
| NP_003229.1 | TGFB2 | transforming growth factor, beta 2 | 5.3 | 5.1 | 4.2 | 3.6 | — |
| NP_001124388.1 | TGFBR1 | transforming growth factor, beta receptor 1 | 1.9 | 1.8 | 1.5 | 1.0 | — |
| NP_057635.1 | TM7SF3 | transmembrane 7 superfamily member 3 | 1.9 | 1.6 | 2.7 | 2.2 | — |
| NP_653233.3 | TMEM182 | transmembrane protein 182 | 3.3 | 3.4 | 4.6 | 4.6 | — |
| NP_003802.1 | TNFSF9 | tumor necrosis factor (ligand) superfamily, member 9 | 4.5 | 4.4 | 5.2 | 4.9 | 7 |
| NP_005714.2 | TSPAN5 | tetraspanin 5 | 1.8 | 2.9 | 0.0 | 1.5 | — |
| NP_068835.1 | UTS2 | urotensin 2 | 2.4 | 1.7 | 2.5 | 2.3 | — |

Table 6-7 is a continuation of Table 6-6.

TABLE 6-7

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_056222.2 | ABHD14A | abhydrolase domain containing 14A | 1.3 | 0.9 | 2.7 | 1.9 | — |
| NP_004449.1 | ACSL4 | acyl-CoA synthetase long-chain family member 4 | 4.5 | 4.5 | 3.6 | 4.2 | — |
| NP_665812.1 | AIFM1 | apoptosis-inducing factor, mitochondrion-associated, 1 | 1.9 | 1.6 | 2.0 | 1.9 | — |
| NP_001344.2 | AKR1C1 | aldo-keto reductase family 1, member C1 (dihydrodiol dehydrogenase 1; 20-alpha (3-alpha)-hydroxysteroid dehydrogenase) | 9.4 | 7.8 | 8.1 | 2.7 | — |
| NP_940683.1 | ANKRD46 | ankyrin repeat domain 46 | 2.6 | 1.8 | 3.5 | 2.2 | — |
| NP_077027.1 | APOO | apolipoprotein O | 1.4 | 1.5 | 1.2 | 1.0 | — |
| NP_004766.2 | B4GALT6 | UDP-Gal:betaGlcNAc beta 1,4-galactosyltransferase, polypeptide 6 | 2.0 | 1.5 | 0.3 | 1.1 | — |
| NP_004326.1 | BST2 | bone marrow stromal cell antigen 2 | −3.9 | 4.4 | −3.9 | 5.9 | — |
| NP_001185983.1 | C16orf5 | chromosome 16 open reading frame 5 | 3.1 | 2.6 | 6.9 | 5.4 | — |
| NP_115700.1 | C1orf57 | chromosome 1 open reading frame 57 | 1.5 | 1.3 | 3.0 | 3.0 | — |
| NP_653181.1 | C1orf85 | chromosome 1 open reading frame 85 | 1.1 | 0.8 | 2.9 | 2.4 | — |
| NP_001074293.1 | C2orf89 | chromosome 2 open reading frame 89 | 1.9 | 1.7 | 0.8 | 1.1 | — |
| NP_775823.1 | C3orf58 | chromosome 3 open reading frame 58 | 2.0 | 0.3 | 1.6 | −0.4 | — |
| NP_439896.1 | C6orf192 | chromosome 6 open reading frame 192 | 4.0 | 2.5 | 4.5 | 3.3 | — |
| NP_001135942.1 | C6orf203 | chromosome 6 open reading frame 203 | 1.2 | 1.0 | 2.0 | 1.8 | — |
| NP_620140.1 | C6orf72 | chromosome 6 open reading frame 72 | 1.3 | 1.8 | 1.2 | 1.7 | — |
| NP_001243894.1 | CCDC51 | coiled-coil domain containing 51 | 1.1 | 0.9 | 3.6 | 3.1 | — |
| NP_001157882.1 | CDK5 | cyclin-dependent kinase 5 | 1.9 | 2.0 | 3.5 | 3.3 | — |
| NP_055061.1 | CELSR1 | cadherin, EGF LAG seven-pass G-type receptor 1 (flamingo homolog, Drosophila) | 0.5 | 1.5 | 0.6 | 1.1 | — |
| NP_004077.1 | COCH | coagulation factor C homolog, cochlin (Limulus polyphemus) | 2.1 | 2.3 | 0.5 | 2.2 | — |
| NP_001896.2 | CTPS | CTP synthase | 2.0 | 1.0 | 1.4 | 0.7 | — |
| NP_055191.2 | CYFIP2 | cytoplasmic FMR1 interacting protein 2 | 2.6 | 3.9 | 5.0 | 5.3 | — |

TABLE 6-7-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_004393.1 | DFFB | DNA fragmentation factor, 40kDa, beta polypeptide (caspase-activated DNase) | 2.3 | 1.8 | 1.7 | 1.5 | — |
| NP_001077058.1 | E2F5 | E2F transcription factor 5, p130-binding | 2.8 | 2.2 | 2.7 | 2.2 | — |

Table 6-8 is a continuation of Table 6-7.

TABLE 6-8

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_056067.2 | EHBP1 | EH domain binding protein 1 | 2.3 | 1.9 | 1.1 | 0.4 | — |
| NP_060682.2 | ENAH | enabled homolog (Drosophila) | 4.4 | 3.5 | 1.5 | 1.2 | — |
| NP_001180289.1 | EXD2 | exonuclease 3'-5' domain containing 2 | 2.3 | 1.2 | 2.7 | 1.9 | — |
| NP_660323.3 | FAM119A | family with sequence similarity 119, member A | 5.4 | 5.1 | 3.0 | 3.7 | — |
| NP_620775.2 | FAM175A | family with sequence similarity 175, member A | 3.4 | 2.8 | 3.8 | 2.8 | — |
| NP_937995.1 | FAM189B | family with sequence similarity 189, member B | 1.7 | 1.7 | 1.3 | 1.1 | — |
| NP_055679.1 | FAM20B | family with sequence similarity 20, member B | 1.6 | 0.8 | 1.5 | 0.8 | — |
| NP_942600.1 | FIBP | fibroblast growth factor (acidic) intracellular binding protein | 1.0 | 1.2 | 2.0 | 1.7 | — |
| NP_000139.1 | FUT1 | fucosyltransferase 1 (galactoside 2-alpha-L-fucosyltransferase, H blood group) | 7.0 | 5.6 | 3.1 | 4.0 | — |
| NP_000135.2 | FXN | frataxin | 1.7 | 1.1 | 2.0 | 1.6 | — |
| NP_000393.4 | G6PD | glucose-6-phosphate dehydrogenase | 0.8 | 1.0 | 2.0 | 1.4 | — |
| NP_000143.2 | GAA | glucosidase, alpha; acid | 1.2 | 1.4 | 3.3 | 2.2 | — |
| NP_000160.1 | GLA | galactosidase, alpha | 2.0 | 1.1 | 1.5 | 0.9 | — |
| NP_002072.2 | GPC1 | glypican 1 | 1.0 | 1.2 | 2.6 | 0.5 | — |
| NP_001008398.2 | GPX8 | glutathione peroxidase 8 (putative) | 5.0 | 5.5 | 7.1 | 7.0 | — |
| NP_005329.3 | HIP1 | huntingtin interacting protein 1 | 2.6 | 2.7 | 2.6 | 2.5 | — |
| NP_254274.1 | IL33 | interleukin 33 | −0.5 | 1.2 | 3.6 | 3.4 | — |
| NP_002262.3 | IPO5 | importin 5 | 3.6 | 2.3 | 1.9 | 0.4 | — |
| NP_060573.2 | LRRC8D | leucine rich repeat containing 8 family, member D | 2.0 | 1.0 | 1.9 | 1.2 | — |
| NP_067679.6 | MFAP3L | microfibrillar-associated protein 3-like | 1.5 | 0.2 | 3.3 | 1.2 | — |
| NP_612440.1 | MFSD3 | major facilitator superfamily domain containing 3 | 0.9 | 1.3 | 2.0 | 2.4 | — |
| NP_066014.1 | MOV10 | Mov10, Moloney leukemia virus 10, homolog (mouse) | 0.5 | 1.4 | 1.3 | 2.0 | — |
| NP_036351.3 | MRAS | muscle RAS oncogene homolog | 1.1 | 0.6 | 4.3 | 1.3 | — |
| NP_057034.2 | MRPL2 | mitochondrial ribosomal protein L2 | 1.3 | 0.8 | 0.8 | 0.0 | — |
| NP_065972.3 | NIN | ninein (GSK3B interacting protein) | 2.0 | 3.1 | 2.7 | 3.0 | — |

Table 6-9 is a continuation of Table 6-8.

TABLE 6-9

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_065181.1 | NIPAL3 | NIPA-like domain containing 3 | 1.7 | 1.3 | 3.0 | 2.3 | — |
| NP_002504.2 | NME3 | non-metastatic cells 3, protein expressed in | 1.1 | 2.1 | 1.5 | 1.9 | — |
| NP_057672.1 | NRN1 | neuritin 1 | 8.5 | 5.7 | 7.7 | 6.3 | — |
| NP_689643.1 | OR51 E1 | olfactory receptor, family 51, subfamily E, member 1 | 6.9 | 9.8 | 0.3 | 3.0 | — |
| NP_071748.2 | OSGEPL1 | O-sialoglycoprotein endopeptidase-like 1 | 4.1 | 4.7 | 3.1 | 4.4 | — |
| NP_079431.1 | PAAF1 | proteasomal ATPase-associated factor 1 | 1.9 | 2.1 | 1.5 | 1.9 | — |
| NP_000523.2 | PCCB | propionyl CoA carboxylase, beta polypeptide | 1.4 | 1.6 | 1.4 | 2.0 | — |
| NP_061757.1 | PCDHB14 | protocadherin beta 14 | 1.4 | 0.5 | 1.4 | 0.1 | — |
| NP_002622.2 | PGD | phosphogluconate dehydrogenase | 1.2 | 1.4 | 1.2 | 1.2 | — |
| NP_003550.1 | PIP4K2B | phosphatidylinositol-5-phosphate 4-kinase, type II, beta | 1.8 | 1.3 | 1.8 | 1.1 | — |
| NP_056530.2 | PLA2G3 | phospholipase A2, group III | 2.6 | 4.3 | 0.1 | 3.2 | — |
| NP_005038.1 | PSMD5 | proteasome (prosome, macropain) 26S subunit, non-ATPase, 5 | 1.5 | 0.7 | 1.7 | 0.7 | — |
| NP_006255.1 | PTPN13 | protein tyrosine phosphatase, non-receptor type 13 (APO-1/CD95 (Fas)-associated phosphatase) | 0.1 | 1.1 | 0.7 | 2.2 | — |
| NP_057161.1 | PTRH2 | peptidyl-tRNA hydrolase 2 | 1.4 | 1.4 | 1.5 | 1.8 | — |
| NP_037390.2 | PYCARD | PYD and CARD domain containing | 0.2 | 1.3 | 1.1 | 2.1 | — |
| NP_055113.2 | QPRT | quinolinate phosphoribosyltransferase | 2.5 | 3.6 | 3.1 | 4.5 | — |
| NP_060233.3 | RNF43 | ring finger protein 43 | 2.7 | 2.7 | 1.2 | 1.5 | — |
| NP_060616.1 | RNMTL1 | RNA methyltransferase like 1 | 1.5 | 0.9 | 1.7 | 1.1 | — |
| NP_003698.1 | RUVBL1 | RuvB-like 1 (E. coli) | 1.9 | 2.2 | 1.3 | 2.2 | — |

TABLE 6-9-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_002949.2 | RYK | RYK receptor-like tyrosine kinase | 1.5 | 1.0 | 1.2 | 1.2 | — |
| NP_116250.3 | SERAC1 | serine active site containing 1 | 1.8 | 0.8 | 2.7 | 1.5 | — |
| NP_005016.1 | SERPINI1 | serpin peptidase inhibitor, clade I (neuroserpin), member 1 | 5.5 | 8.7 | 2.1 | 4.2 | — |
| NP_008927.1 | SLC19A2 | solute carrier family 19 (thiamine transporter), member 2 | 3.8 | 2.7 | 2.0 | 1.2 | — |
| NP_065075.1 | SLC39A10 | solute carrier family 39 (zinc transporter), member 10 | 2.9 | 3.1 | 2.6 | 2.7 | — |
| NP_060306.3 | SLC41A3 | solute carrier family 41, member 3 | 1.9 | 1.5 | 1.3 | 0.8 | — |

Table 6-10 is a continuation of Table 6-9.

TABLE 6-10

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_005692.1 | SNUPN | snurportin 1 | 2.2 | 2.4 | 2.3 | 2.5 | — |
| NP_055563.1 | SNX17 | sorting nexin 17 | 0.8 | 1.1 | 1.0 | 1.0 | — |
| NP_003156.1 | STXBP1 | syntaxin binding protein 1 | 4.3 | 5.7 | 4.9 | 5.3 | — |
| NP_003192.1 | TFAM | transcription factor A, mitochondrial | 2.1 | 1.6 | 1.1 | 1.6 | — |
| NP_444283.2 | THEM4 | thioesterase superfamily member 4 | 1.6 | −0.5 | 2.8 | 0.4 | — |
| NP_612472.1 | TLCD1 | TLC domain containing 1 | 2.7 | 2.1 | 3.9 | 4.2 | — |
| NP_057548,1 | TMEM138 | transmembrane protein 138 | 1.8 | 2.2 | 2.0 | 2.7 | — |
| NP_085054,2 | TMEM177 | transmembrane protein 177 | 3.1 | 3.2 | 3.5 | 4.1 | — |
| NP_056236.2 | TMEM186 | transmembrane protein 186 | 2.4 | 2.0 | 2.0 | 2.3 | — |
| NP_078863.2 | TMEM53 | transmembrane protein 53 | 1.2 | 1.3 | 1.2 | 1.0 | — |
| NP_001008495.2 | TMEM64 | transmembrane protein 64 | 6.7 | 5.7 | 8.3 | 8.0 | — |
| NP_669630.1 | TMEM68 | transmembrane protein 68 | 1.8 | 1.8 | 3.4 | 2.9 | — |
| NP_861448.2 | TMTC3 | transmembrane and tetratricopeptide repeat containing 3 | 2.5 | 1.8 | 3.8 | 2.3 | — |
| NP_775107.1 | TRIM59 | tripartite motif-containing 59 | 3.7 | 4.3 | 3.0 | 4.0 | — |
| NP_003293.2 | TRIP6 | thyroid hormone receptor interactor 6 | 2.7 | 1.3 | 5.1 | 3.3 | — |
| NP_009215.1 | TWF2 | twinfilin, actin-binding protein, homolog 2 (Drosophila) | 0.6 | 1.5 | 1.4 | 1.8 | — |
| NP_079094.1 | UBA5 | ubiquitin-like modifier activating enzyme 5 | 1.8 | 2.1 | 2.4 | 2.4 | — |
| NP_060769.4 | UBE2W | ubiquitin-conjugating enzyme E2W (putative) | 1.3 | 1.7 | 2.4 | 2.4 | — |
| NP_001017980.1 | VMA21 | VMA21 vacuolar H+-ATPase homolog (S. cerevisiae) | 3.0 | 2.6 | 2.9 | 2.6 | — |
| NP_660295.2 | ZG16B | zymogen granule protein 16 homolog B (rat) | 1.1 | 2.0 | 1.4 | 1.9 | — |
| NP_115549.2 | ZNRF3 | zinc and ring finger 3 | 4.7 | 4.1 | 2.2 | 2.6 | — |

(The values in Tables 6-1 to 6-10 shown above represent the expression difference (log 2 ratio).)

TABLE 7-1

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_003658.1 | LGR5 | leucine-rich repeat-containing G protein-coupled receptor 5 | 3.0 | 3.8 | −1.5 | 0.4 | — |
| NP_066301.1 | SNTB1 | syntrophin, beta 1 (dystrophin-associated protein A1, 59kDa, basic component 1) | 3.1 | 3.1 | 0.0 | 0.4 | — |
| NP_001123575.1 | COL13A1 | collagen, type XIII, alpha 1 | 2.0 | 2.9 | −0.2 | 0.3 | — |
| NP_001167538.1 | FGER1 | fibroblast growth factor receptor 1 | 1.3 | 2.3 | −0.7 | 0.6 | — |
| NP_004432.1 | EPHB1 | EPH receptor B1 | 1.0 | 2.3 | −0.3 | 0.7 | — |
| NP_002002.3 | FGFR4 | fibroblast growth factor receptor 4 | 2.0 | 2.2 | −1.9 | −0.5 | — |
| NP_004622.2 | LRP8 | low density lipoprotein receptor-related protein 8, apolipoprotein e receptor | 2.3 | 2.1 | 0.5 | 0.7 | — |
| NP_002832.3 | PTPRG | protein tyrosine phosphatase, receptor type, G | 1.8 | 2.1 | −5.0 | −5.4 | — |
| NP_004727.2 | XPR1 | xenotropic and polytropic retrovirus receptor 1 | 1.5 | 2.1 | 0.7 | 0.9 | — |
| NP_859052.3 | QSOX2 | quiescin Q6 sulfhydryl oxidase 2 | 1.8 | 2.0 | 0.7 | 0.8 | — |
| NP_003876.1 | CDK5R1 | cyclin-dependent kinase 5, regulatory subunit 1 (p35) | 3.1 | 3.3 | 0.3 | 2.0 | — |
| NP_002821.1 | PTPN4 | protein tyrosine phosphatase, non-receptor type 4 (megakaryocyte) | 1.7 | 1.9 | 0.3 | 0.7 | — |
| NP_001457.1 | FZD2 | frizzled homolog 2 (Drosophila) | 5.2 | 5.4 | 2.6 | 2.9 | — |
| NP_000674.2 | ADRA2C | adrenergic, alpha-2C-, receptor | 1.8 | 1.6 | 0.1 | −0.1 | — |
| NP_000334.1 | SLC5A1 | solute carrier tam ly 5 (sodium/glucose cotransporter), member 1 | 2.2 | 1.6 | 0.2 | 0.6 | — |
| NP_005901.2 | MAPT | microtubule-associated protein tau | 1.9 | 1.5 | 0.4 | 0.6 | — |
| NP_598328.1 | SYN2 | synapsin II | 0.3 | 1.7 | 0.2 | 0.5 | — |
| NP_005496.4 | SCARB1 | scavenger receptor class B, member 1 | 1.1 | 1.2 | −0.3 | −0.3 | — |

TABLE 7-1-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_004434,2 | EPHB3 | EPH receptor B3 | 0.7 | 1.0 | −0.5 | −0.4 | — |
| NP_000259.1 | NF2 | neurofibromin 2 (merlin) | 1.2 | 0.9 | 0.6 | 0.1 | — |
| NP_003477.4 | SLC7A5 | solute carrier family 7 (cationic amino acid transporter, y+ system), member 5 | 2.0 | 0.8 | −0.4 | −0.7 | — |
| NP_054740.3 | SSX2IP | synovial sarcoma, X breakpoint 2 interacting protein | 1.8 | 0.7 | 0.9 | −0.3 | — |
| NP_055736.2 | LPHN1 | latrophilin 1 | 1.4 | 0.6 | 0.9 | 0.3 | — |
| NP_004435.3 | EPHB4 | EPH receptor B4 | 1.3 | 0.5 | 0.7 | −0.1 | — |

Table 7-2 is a continuation of Table 7-1.

TABLE 7-2

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_116197.4 | LINGO1 | leucine rich repeat and Ig domain containing 1 | 1.2 | 0.0 | 0.6 | −1.3 | — |
| NP_004987.2 | ABCC1 | ATP-binding cassette, sub-family C (CFTR/MRP), member 1 | 1.1 | 0.9 | 0.0 | −0.2 | — |
| NP_003174.3 | ADAM17 | ADAM metallopeptidase domain 17 | 1.0 | 0.3 | −0.3 | −0.4 | — |
| NP_620686.1 | ADAMTS15 | ADAM metallopeptidase with thrombospondin type 1 motif, 15 | 6.1 | 4.6 | −3.6 | −4.2 | — |
| NP_005091.2 | AKAP12 | A kinase (PRKA) anchor protein 12 | 2.4 | 3.7 | −1.2 | 0.3 | — |
| NP_001618.2 | ALCAM | activated leukocyte cell adhesion molecule | 1.3 | 0.9 | 0.3 | 0.6 | — |
| NP_001648.1 | AREGB | amphiregulin B | 1.7 | 0.4 | 0.0 | −0.5 | — |
| NP_001164.2 | ARHGAP5 | Rho GTPase activating protein 5 | 1.2 | 0.4 | 0.8 | 0.3 | — |
| NP_542172.2 | B3GALT6 | UDP-Gal:betaGal beta 1,3-galactosyltransferase polypeptide 6 | 1.1 | 0.6 | 0.6 | 0.3 | — |
| NP_001711.2 | BMP8B | bone morphogenetic protein 8b | 0.9 | 1.3 | 0.4 | 0.3 | — |
| NP_006560.3 | CGREF1 | cell growth regulator with EF-hand domain 1 | 0.9 | 1.0 | 0.3 | 0.8 | — |
| NP_058647.1 | CKLF | chemokine-like factor | 0.9 | 1.5 | −0.5 | 0.9 | — |
| NP_849199.2 | CMTM8 | CKLF-like MARVEL transmembrane domain containing 8 | 1.3 | 1.4 | 0.6 | 0.7 | — |
| NP_001422.1 | EPB41L2 | erythrocyte membrane protein band 4.1-like 2 | 1.3 | 0.9 | −0.4 | −0.4 | — |
| NP_004433.2 | EPHB2 | EPH receptor 62 | 1.0 | 0.5 | −3.1 | −2.8 | — |
| NP_000496.2 | F12 | coagulation factor XII (Hageman factor) | 1.2 | 1.6 | 0.2 | 1.0 | — |
| NP_057133.2 | FAM158A | family with sequence similarity 158, member A | 0.8 | 1.2 | 0.1 | 0.4 | — |
| NP_001990.2 | FBN2 | fibrillin 2 | 2.6 | 2.5 | −0.4 | 0.1 | — |
| NP 068656,21 | FGG (OSMR) | fibrinogen gamma chain (oncostatin M receptor) | 1.3 | 0.6 | 0.6 | 0.5 | — |
| NP_001439.2 | GPC4 | glypican 4 | 2.0 | 2.1 | −0.9 | 0.0 | — |
| NP_065857.1 | GPHN | gephyrin | 3.2 | 2.9 | −3.4 | −2.6 | — |
| NP_057399.1 | GULP1 | GULP, engulfment adaptor PTB domain containing 1 | 1.4 | 2.0 | 0.4 | 0.9 | — |
| NP_036616.2 | HMMR | hyaluronan-mediated motility receptor (RHAMM) | 5.0 | 4.5 | −1.7 | −1.5 | — |
| NP_0008661 | IGF1R | insulin-like growth factor 1 receptor | 0.7 | 1.1 | −1.9 | −1.2 | — |

Table 7-3 is a continuation of Table 7-2.

TABLE 7-3

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_000588.2 | IGFBP2 | insulin-like growth factor binding protein 2, 36kDa | 1.4 | 0.7 | 0.3 | −0.4 | — |
| NP_0611952 | IL17RB | interleukin 17 receptor B | 1.0 | 1.2 | −2.7 | −1.9 | — |
| NP_002326.2 | LRP5 | low density lipoprotein receptor-related protein 5 | 1.2 | 1.7 | −0.8 | −0.2 | — |
| NP_006491.21 | MCAM | melanoma cell adhesion molecule | 2.1 | 1.5 | −0.2 | −0.4 | — |
| NP_055456.2 | MDC1 | mediator of DNA-damage checkpoint 1 | 2.6 | 2.2 | −1.3 | −1.7 | — |
| NP_055606.1 | MELK | maternal embryonic leucine zipper kinase | 1.5 | 1.6 | −2.0 | −1.1 | — |
| NP_000236.2 | MET | met proto-oncogene (hepatocyte growth factor receptor) | 1.2 | 1.2 | 0.6 | 0.4 | — |
| NP_065825.1 | MIB1 | mindbomb homolog 1 (Drosophila) | 1.3 | 1.3 | 0.7 | 0.5 | — |
| NP_005952.2 | MUC6 | mucin 6, oligomeric mucus/gel-forming | 1.1 | 3.0 | −0.1 | 1.0 | — |
| NP_777596.2 | PCSK9 | proprotein convertase subtilisin/kexin type 9 | 1.5 | 1.8 | −1.6 | −0.4 | — |
| NP_003619.2 | PKP4 | plakophilin 4 | 1.5 | 1.4 | 0.0 | −0.1 | — |
| NP_003042.3 | SLC16A1 | solute carrier family 16, member 1 (monocarboxylic acid transporter 1) | 1.7 | 0.6 | 0.3 | 0.3 | — |
| NP_057438.3 | SLCO4A1 | solute carrier organic anion transporter family, member 4A1 | 0.5 | 1.2 | −1.4 | −0.2 | — |
| NP_003093.2 | SOD3 | superoxide dismutase 3, extracellular | 2.2 | 1.7 | 0.6 | −1.2 | — |
| NP_006425.2 | SORBS1 | sorbin and SH3 domain containing 1 | 3.2 | 3.4 | −0.9 | 0.2 | — |

TABLE 7-3-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_003095.2 | SORD | sorbitol dehydrogenase | 1.1 | 0.7 | 0.9 | 0.8 | — |
| NP_000342.2 | STS | steroid sulfatase (microsomal), isozyme S | 1.8 | 2.2 | −0.5 | −0.7 | — |
| NP_003234.2 | TGFBR3 | transforming growth factor, beta receptor III | 1.4 | 1.8 | −0.2 | −0.2 | — |
| NP_055388.2 | TMEM97 | transmembrane protein 97 | 2.6 | 2.1 | 1.0 | −0.3 | — |
| CAA26435.1 | TRAC | T cell receptor alpha constant | 0.0 | 1.1 | 0.0 | 0.0 | — |

Table 7-4 is a continuation of Table 7-3.

TABLE 7-4

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_076417.2 | AACS | acetoacetyl-CoA synthetase | 1.1 | 1.6 | 0.2 | 0.6 | — |
| NP_653191.2 | ANKRD22 | ankyrin repeat domain 22 | 2.0 | 1.5 | −1.8 | −1.7 | — |
| NP_056020.2 | ATP11A | ATPase, class VI, type 11A | 1.3 | 1.0 | 0.7 | 0.6 | — |
| NP_001159.2 | BIRC5 | baculoviral IAP repeat-containing 5 | 2.7 | 2.4 | −4.8 | −4.4 | — |
| NP_061189.2 | CDCA7L | cell division cycle associated 7-like | 2.1 | 1.8 | −0.6 | 0.4 | — |
| NP_005183.2 | CDKN3 | cyclin-dependent kinase inhibitor 3 | 4.8 | 5.3 | −3.1 | −1.8 | — |
| NP_004077.1 | COCH | coagulation factor C homolog, cochlin (*Limulus polyphemus*) | 1.2 | 1.2 | −0.4 | 0.7 | — |
| NP_0053023 | GRB10 | growth factor receptor-bound protein 10 | 1.1 | 0.4 | −1.2 | −1.5 | — |
| NP_6717043 | HS6ST2 | heparan sulfate 6-O-sulfotransferase 2 | 1.8 | 1.6 | −1.1 | −0.2 | — |
| NP_002262.3 | IPO5 | importin 5 | 2.6 | 1.7 | 0.5 | −0.3 | — |
| NP_114428.1 | ITFG3 | integrin alpha FG-GAP repeat containing 3 | 1.0 | 0.9 | 0.0 | −1.1 | — |
| NP_002241.1 | KCNN4 | potassium intermediate/small conductance calcium-activated channel, subfamily N, member 4 | 1.2 | 0.9 | −0.7 | −0.7 | — |
| NP_061159.1 | KIAA1199 | KIAA1199 | 1.1 | 1.1 | −1.5 | −2.4 | — |
| NP_115940.2 | KISS1R | KISS1 receptor | 1.1 | 1.8 | −3.0 | 0.2 | — |
| NP_057034.2 | MRPL2 | mitochondrial ribosomal protein L2 | 1.3 | 0.8 | 0.8 | 0.0 | — |
| NP_000242.1 | MSH2 | mutS homolog 2, colon cancer, nonpolyposis type 1 (*E. coli*) | 2.5 | 2.8 | −0.8 | −0.4 | — |
| NP_055452.3 | MTFR1 | mitochondrial fission regulator 1 | 1.6 | 0.9 | 0.2 | −0.1 | — |
| NP_005947.3 | MTHFD1 | methylenetetrahydrofolate dehydrogenase (NADP+ dependent) 1, methenyltetrahydrofolate cyclohydrolase, formyltetrahydrofolate synthetase | 1.7 | 1.6 | 0.3 | 0.1 | — |
| NP_005366.2 | MYB | v-myb myeloblastosis viral oncogene homolog (avian) | 2.7 | 2.3 | −4.4 | 0.2 | — |
| NP_078938.2 | NAT10 | N-acetyltransferase 10 (GCN5-related) | 1.9 | 1.3 | 0.1 | −0.1 | — |
| NP_777549.1 | NDUFAF2 | NADH dehydrogenase (ubiquinone) 1 alpha subcomplex, assembly factor 2 | 1.0 | 1.4 | −0.9 | 0.1 | — |
| NP_004280.5 | NFE2L3 | nuclear factor (erythroid-derived 2)-like 3 | 1.2 | 1.2 | −0.9 | −0.1 | — |
| NP_006672.1 | NMU | neuromedin U | 0.2 | 1.6 | −4.7 | 0.2 | — |
| NP_055950.1 | NUP205 | nucleoporin 205kDa | 1.9 | 1.7 | −0.3 | −0.2 | — |

Table 7-5 is a continuation of Table 7-4.

TABLE 7-5

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_942590.1 | NUP43 | nucleoporin 43kDa | 1.3 | 0.9 | 0.0 | 0.0 | — |
| NP 0554843 | NUP93 | nucleoporin 93kDa | 2.1 | 2.4 | 0.1 | 0.8 | — |
| NP_006614.2 | PHGDH | phosphoglycerate dehydrogenase | 3.0 | 3.4 | −2.0 | −0.4 | — |
| NP_060904.2 | RNF130 | ring finger protein 130 | 0.9 | 1.0 | 0.4 | 0.3 | — |
| NP_060259.4 | SEMA4C | sema domain, immunoglobulin domain (Ig), transmembrane domain (TM) and short cytoplasmic domain, (semaphorin) 4C | 1.9 | 2.3 | 0.2 | 0.5 | — |
| NP_005857.1 | SIGMAR1 | sigma non-opioid intracellular receptor 1 | 1.0 | 1.1 | 0.8 | 0.9 | — |
| NP_055413.1 | SOCS7 | suppressor of cytokine signaling 7 | 1.0 | 0.6 | 0.7 | 0.1 | — |
| NP_005554.1 | STMN1 | stathmin 1 | 1.9 | 2.1 | −3.1 | −1.4 | — |
| NP_054897,4 | STXBP6 | syntaxin binding protein 6 (amisyn) | 2.1 | 2.1 | −3.4 | −0.1 | — |
| NP_001070884.1 | TMEM231 | transmembrane protein 231 | 0.5 | 1.5 | −2.2 | −0.8 | — |
| NP_002537.3 | TNFRSF11B | tumor necrosis factor receptor superfamily, member 11b | 1.7 | 6.3 | −2.9 | −0.9 | — |

TABLE 7-5-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_443195.1 | TOP1MT | topoisomerase (DNA) I, mitochondrial | 1.1 | 0.4 | 0.5 | −0.1 | — |
| NP_001058.2 | TOP2A | topoisomerase (DNA) II alpha 170kDa | 2.2 | 2.7 | −6.1 | −3.1 | — |
| NP_006364.2 | VAT1 | vesicle amine transport protein 1 homolog (T. californica) | 1.0 | 1.5 | 0.5 | 1.0 | — |
| NP_612471.1 | ZMYND19 | zinc finger, MYND-type containing 19 | 1.2 | 0.7 | 0.7 | 0.3 | — |

(The values in Tables 7-1 to 7-5 shown above represent the expression difference (log 2 ratio).)

TABLE 8-1

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_076404.3 | GPR87 | G protein-coupled receptor 87 | 0.0 | 0.0 | 7.1 | 7.4 | — |
| NP_005109.2 | TNFSF15 | tumor necrosis factor (ligand) superfamily, member 15 | −2.4 | −2.3 | 3.5 | 3.3 | — |
| NP_001926.2 | DPP4 | dipeptidyl-peptidase 4 | 0.1 | 1.3 | 2.0 | 3.8 | — |
| NP_149017.2 | BBS4 | Bardet-Biedl syndrome 4 | 0.2 | 0.6 | 1.7 | 2.6 | — |
| NP_542386.1 | C9orf30 | chromosome 9 open reading frame 30 | 0.2 | 0.2 | 1.5 | 1.7 | — |
| NP_001447.2 | FLNA | filamin A, alpha | −0.4 | 0.8 | 0.7 | 1.7 | — |
| NP_000425.1 | NEU1 | sialidase 1 (lysosomal sialidase) | 0.3 | 0.4 | 1.9 | 1.7 | — |
| NP_002125.3 | HMOX2 | heme oxygenase (decycling) 2 | 0.3 | 0.4 | 1.5 | 1.6 | — |
| NP_001078.2 | AAMP | angio-associated, migratory cell protein | 0.1 | 0.3 | 1.2 | 1.6 | — |
| NP_061985.2 | ABCA7 | ATP-binding cassette, sub-family A (ABC1), member 7 | −1.3 | 0.4 | 2.1 | 1.6 | — |
| NP_000401.1 | HFE | hemochromatosis | 2.2 | 2.0 | 1.2 | 2.8 | — |
| NP_001142.2 | SLC25A4 | solute carrier family 25 (mitochondrial carrier: adenine nucleotide translocator), member 4 | 0.6 | 0.8 | 1.3 | 1.5 | — |
| NP_006569.1 | GNB5 | guanine nucleotide binding protein (G protein), beta 5 | 0.2 | 0.8 | 0.9 | 1.4 | — |
| NP_005846.1 | RAMP1 | receptor (G protein-coupled) activity modifying protein 1 | −0.5 | −0.5 | 1.1 | 1.4 | — |
| NP_598378.3 | RHOV | ras homolog gene family, member V | 0.1 | −0.2 | 0.5 | 1.4 | — |
| NP_112178.2 | PVRL4 | poliovirus receptor-related 4 | −0.3 | −2.8 | 6.1 | 1.8 | 7 |
| NP_003686.1 | LY6D | lymphocyte antigen 6 complex, locus D | −3.8 | −1.8 | −0.5 | 2.7 | — |
| NP_775876.1 | KCNRG | potassium channel regulator | 1.0 | 0.2 | 2.6 | 1.9 | — |
| NP_005063.1 | 9LC12A4 | solute carrier family 12 (potassium/chloride transporters), member 4 | −0.2 | −0.1 | 1.2 | 1.2 | — |
| NP_005292.2 | GPR35 | G protein-coupled receptor 35 | −0.8 | −1.4 | 1.1 | −0.8 | — |
| NP_001607.1 | ACVR2A | activin A receptor, type IIA | 0.2 | −0.5 | 1.4 | 1.0 | — |
| NP_001687.1 | ATP6V1E1 | ATPase, H+ transporting, lysosomal 31kDa, V1 subunit E1 | −0.1 | 0.3 | 1.1 | 1.2 | — |
| NP_036474.1 | BAMBI | BMP and activin membrane-bound inhibitor homolog (Xenopus laevis) | −0.8 | 0.7 | 1.3 | 2.4 | — |
| NP_005177.2 | CAPN1 | calpain 1, (mu/l) large subunit | −1.3 | −1.3 | 1.3 | −0.2 | — |

Table 8-2 is a continuation of Table 8-1.

TABLE 8-2

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_001798.2 | CEL | carboxyl ester lipase (bile salt-stimulated lipase) | 0.0 | 0.0 | 7.4 | 5.4 | — |
| NP_056034.2 | EXOC7 | exocyst complex component 7 | −0.2 | −0.2 | 1.9 | 1.2 | — |
| NP_000034.1 | FAS | Fas (TNF receptor superfamily, member 6) | 0.8 | 0.4 | 2.8 | 2.3 | 9 |
| NP_005802.1 | GDF11 | growth differentiation factor 11 | 0.7 | 0.9 | 1.3 | 1.9 | — |
| NP_060456.3 | GPR172B | G protein-coupled receptor 1728 | 0.0 | 0.0 | 5.6 | 4.3 | — |
| NP_665895.1 | KLK10 | kallikrein-related peptidase 10 | −0.9 | 0.4 | 1.2 | 1.6 | — |
| NP_055414.2 | MAGED2 | melanoma antigen family D, 2 | 0.0 | 0.3 | 2.1 | 3.0 | — |
| NP_000519.2 | MAN2B1 | mannosidase, alpha, class 2B, member 1 | −0.2 | −0.2 | 2.3 | 1.5 | — |
| NP_002434.1 | MSMB | microseminoprotein, beta- | 0.0 | 0.0 | 5.6 | 4.7 | — |
| NP_009014.2 | NUDT6 | nudix (nucleoside diphosphate linked moiety X)-type motif 6 | 0.0 | 0.0 | 1.3 | 0.8 | — |
| NP_036528.1 | PHLDA3 | pleckstrin homology-like domain, family A, member 3 | −0.3 | −0.2 | 2.9 | 1.0 | — |
| NP_002629.1 | PI3 | peptidase inhibitor 3, skin-derived | −7.6 | −7.9 | 1.4 | −0.6 | — |
| NP_597998.1 | SAT2 | spermidine/spermine N1-acetyltransferase family member 2 | 0.7 | 0.9 | 1.7 | 1.2 | — |

TABLE 8-2-continued

| DB accession No. | Abbreviation | Molecule name | PLR59 primary Lgr5+ | PLR123 primary Lgr5+ | PLR59 primary Lgr5− | PLR123 primary Lgr5− | SEQ ID NO |
|---|---|---|---|---|---|---|---|
| NP_006207.1 | SERPINE2 | serpin peptidase inhibitor, clade E (nexin, plasminogen activator inhibitor type 1), member 2 | −3.2 | −2.5 | 1.3 | 0.7 | — |
| NP_036303.1 | TSPAN17 | tetraspanin 17 | 0.6 | 0.4 | 1.7 | 1.3 | — |

(The values in Tables 8-1 and 8-2 shown above represent the expression difference (log 2 ratio).)

Furthermore, genes that meet a criterion described below and have GO:0005886 [plasma membrane] from GeneOntology (GO) (Tables 9 and 10) were extracted in order to obtain genes encoding proteins that are specifically presented on cell membrane of cancer stem cells.

Markers common for both proliferating and quiescent CSCs:
genes whose expression levels are in average greater than 64 in Lgr5-negative and Lgr5-positive cells; which show a greater than four-fold change in both Lgr5-negative and Lgr5-positive cells relative to primary cells; and which show a significant difference by t-test (Table 9).

TABLE 9

| DB accession No. | Abbreviation | Molecule name | PLR59 primary Lgr5+ | PLR123 primary Lgr5+ | PLR59 primary Lgr5− | PLR123 primary Lgr5− | PLR59 Lgr5+ Lgr5− | PLR123 Lgr5+ Lgr5− | SEQ ID NO |
|---|---|---|---|---|---|---|---|---|---|
| NP_001423.1 | EREG | epiregulin | 2.2 | 3.4 | 2.5 | 3.1 | 0.3 | −0.3 | 3 |
| NP_001986.2 | ACSL1 | acyl-CoA synthetase long-chain family member 1 | 3.0 | 3.9 | 2.9 | 3.7 | −0.2 | −0.2 | — |
| NP_005922.2 | MICB | MHC class I polypeptide-related sequence B | 2.3 | 3.8 | 2.2 | 3.7 | −0.1 | −0.1 | — |
| NP_000296.2 | PON2 | paraoxonase 2 | 2.3 | 4.6 | 2.9 | 4.6 | 0.7 | 0.0 | — |
| NP_003458.1 | CXCR4 | chemokine (C-X-C motif) receptor 4 | 10.2 | 9.5 | 8.5 | 7.8 | −1.7 | −1.7 | — |
| NP_062818.1 | SLCO1B3 | solute carrier organic anion transporter family, member 1B3 | 4.4 | 5.1 | 3.0 | 4.1 | −1.4 | −1.0 | — |
| NP_000280.1 | PFKM | phosphofructokinase, muscle | 3.3 | 2.3 | 3.3 | 2.1 | 0.0 | −0.2 | — |
| NP_057672.1 | NRN1 | neuritin 1 | 8.8 | 8.5 | 7.8 | 6.5 | −1.0 | −2.0 | — |
| NP_060369.3 | TESC | tescalcin | 3.3 | 5.0 | 2.0 | 36 | −1.3 | −1.3 | — |
| NP_000139.1 | FUT1 | fucosyltransferase 1 (galactoside 2-alpha-L-fucosyltransferase, H blood group) | 6.9 | 5.9 | 3.1 | 4.3 | −3.9 | −1.6 | — |
| NP_003802.1 | TNFSF9 | tumor necrosis factor (ligand) superfamily, member 9 | 4.5 | 4.4 | 5.4 | 5.1 | 0.9 | 0.7 | 7 |
| NP_059108.1 | FZD3 | frizzled homolog 3 (Drosophila) | 2.8 | 2.6 | 2.6 | 3.2 | −0.2 | 0.6 | — |
| NP_005810.1 | STX6 | syntaxin 6 | 2.8 | 2.7 | 4.2 | 3.5 | 1.4 | 0.9 | — |
| NP_057635.1 | TM7SF3 | transmembrane 7 superfamily member 3 | 3.0 | 2.5 | 3.9 | 3.0 | 0.9 | 0.5 | — |
| NP_000013.2 | ADA | adenosine deaminase | 2.0 | 2.7 | 2.8 | 2.9 | 0.8 | 0.2 | — |
| NP_071731.1 | EDAR | ectodysplasin A receptor | 6.2 | 6.8 | 5.0 | 3.7 | −1.2 | −3.1 | 1 |
| NP_003264.2 | TM7SF2 | transmembrane 7 superfamily member 2 | 3.6 | 4.3 | 6.9 | 6.7 | 3.2 | 2.4 | — |
| NP_116265.1 | JUB | jab, ajuba homolog (*Xenopus laevis*) | 3.7 | 4.3 | 4.7 | 3.8 | 1.0 | −0.5 | — |
| NP_689740.2 | SLC16A14 | solute carrier family 16, member 14 (monocarboxylic acid transporter 14) | 5.4 | 6.6 | 5.8 | 6.1 | 0.3 | −0.4 | — |
| NP_065209.2 | ANK1 | ankyrin 1, erythrocytic | 6.6 | 3.0 | 5.3 | 2.7 | −1.3 | −0.3 | — |

Quiescent CSC-specific markers: genes whose expression levels are in average greater than 64 in Lgr5-negative cells and are in average less than 64 in both primary cells and Lgr5-positive cells; which show a greater than 20 fold change in Lgr5-negative cells relative to Lgr5-positive cells; and which show a significant difference by t-test (Table 10).

TABLE 10

| DB accession No. | Abbreviation | Molecule name | PLR59 primary Lgr5+ | PLR123 primary Lgr5+ | PLR59 primary Lgr5− | PLR123 primary Lgr5− | PLR59 Lgr5+ Lgr5− | PLR123 Lgr5+ Lgr5− | SEQ ID NO |
|---|---|---|---|---|---|---|---|---|---|
| NP_006111.2 | HLA-DMA | major histocompatibility complex, class II, DM alpha | 0.0 | 0.2 | 8.0 | 8.7 | 8.0 | 8.5 | — |
| NP_862830.1 | AMIGO2 | adhesion molecule with Ig-like domain 2 | 0.0 | 0.0 | 7.0 | 7.5 | 7.0 | 7.5 | — |
| NP_001159449.1 | PROM2 | prominin 2 | 3.3 | 2.9 | 10.1 | 10.5 | 6.9 | 7.6 | 6 |
| NP_076404.3 | GPR87 | G protein-coupled receptor 87 | 0.0 | 0.0 | 7.0 | 7.4 | 7.0 | 7.4 | — |
| NP_722582.2 | GPR110 | G protein-coupled receptor 110 | 0.0 | 0.0 | 6.0 | 7.0 | 6.0 | 7.0 | — |
| NP_112178.2 | PVRL4 | poliovirus receptor-related 4 | −0.6 | −2.7 | 5.8 | 1.7 | 6.4 | 4.4 | 8 |
| NP_938205.1 | FLRT3 | fibronectin leucine rich transmembrane protein 3 | 1.3 | 0.2 | 6.8 | 5.4 | 5.5 | 5.2 | — |

3. Expression Analysis by Flow Cytometry Analysis 3.1. Flow Cytometry Analysis of NOG-Established Cancer Cell Lines After suspending in FACS buffer, cells of NOG-established cancer lines collected from mice were incubated at 4° C. for 30 minutes with rat mAb to mouse MHC I (Abcam; ab15680) and mAb to human EREG (EP27; WO2008/047723). Then, following washing once with FACS buffer, the cells were incubated at 4° C. for 30 minutes with 7-AAD Viability Dye (Beckman Coulter; A07704) as dead cell staining and secondary antibodies: PE-labeled goat F(ab')2 fragment to mouse IgG (H+L) (Beckman Coulter; IM0855) and APC-labeled goat Ab to rat IgG (BioLegend; 405406). After washing once with FACS buffer, the cells were subjected to flow cytometry analysis. Flow cytometry analysis was performed using EPICS ALTRA. Cells negative for 7-AAD Viability Dye and mouse MHC were analyzed for EREG expression.

3.2. Flow Cytometry Analysis of In Vitro Cultured Cancer Cell Lines

Lgr5-positive adherent cells and Lgr5-negative adherent cells resulting from induction by irinotecan treatment were harvested using Accutase. The cells were suspended in FACS buffer, and then incubated at 4° C. for 30 minutes with mouse mAb to human EREG. After the cells were washed once with FACS buffer, 7-AAD Viability Dye as dead cell staining and a PE-labeled goat F(ab')2 fragment to mouse IgG (H+L) as a secondary antibody were added thereto. The cells were incubated at 4° C. for 30 minutes. Then, the cells were washed once with FACS buffer, and subjected to flow cytometry analysis. Flow cytometry analysis was performed using EPICS ALTRA. Cells negative for 7-AAD Viability Dye were analyzed for EREG expression. The result showed that the corresponding protein was expressed at a high level on cell membrane surface.

Figure 37:
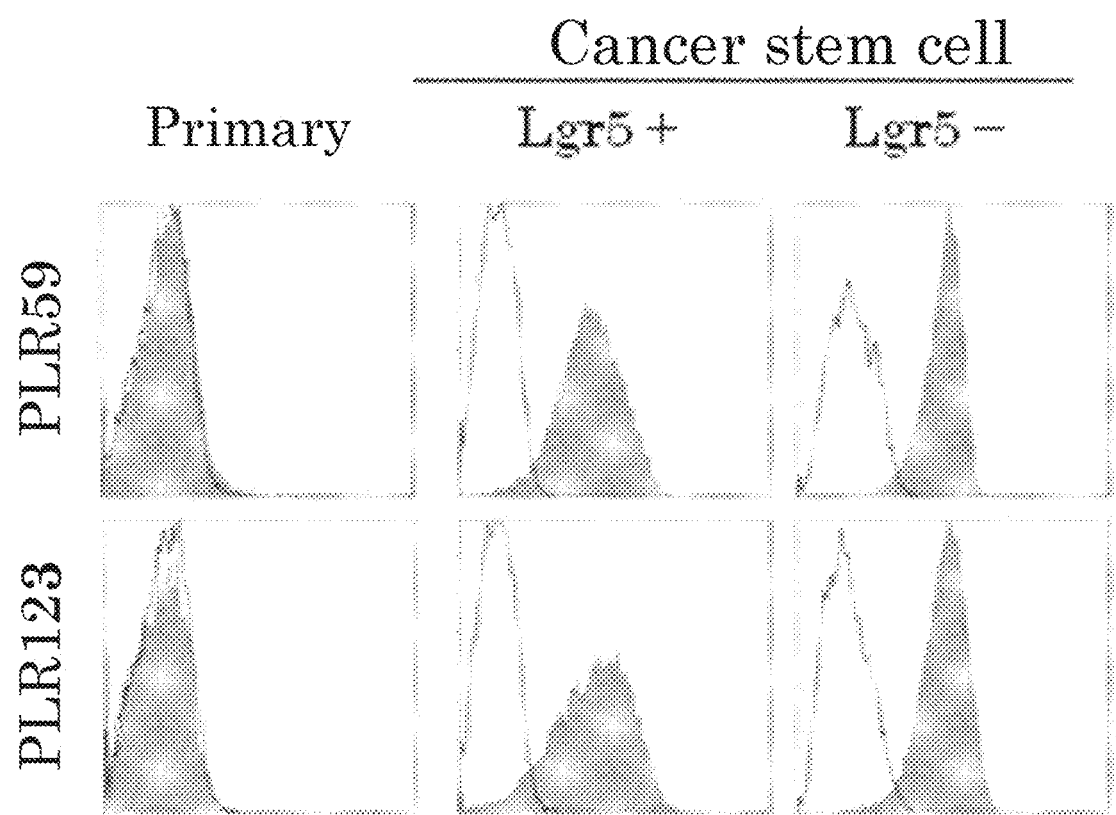
FIG. 37 is a diagram showing a result of flow cytometric analysis of primary cells from PLR59 and PLR123, Lgr5+ cancer stem cells, and Lgr5− cancer stem cells with EREG.

The result obtained by EREG flow cytometry analysis of primary cells from PLR59 and PLR123, and Lgr5$^+$ and Lgr5$^-$ cancer stem cells is shown in FIG. 37. The cells were stained using an antibody against EREG and analyzed by flow cytometry. It was demonstrated that primary cells were negative for EREG while Lgr5$^+$ and Lgr5$^-$ cancer stem cells were homogeneous EREG-positive cell populations. Gray indicates fluorescence intensity after cell staining with an indicated antibody; and white indicates fluorescence intensity after cell staining with a control isotype antibody.

4. In Vitro Assessment of Drug Efficacy by ADCC Activity Measurement 4.1. Preparation of Effector Cell Suspension A mononuclear cell fraction collected from human peripheral blood was used as human effector cells. Fifty ml of peripheral blood was collected from a healthy volunteer (adult male) of the inventors' company using a syringe loaded in advance with 200 µl of 1000 units/ml heparin solution (Novo-Heparin 5,000 units/5 ml for Injection; Novo Nordisk). The peripheral blood was diluted twofold with PBS(−), and then introduced into a Leucosep lymphocyte separation tube (Greiner bio-one) in advance loaded with Ficoll-Paque PLUS and subjected to centrifugation. After centrifugation (2150 rpm, room temperature, 10 minutes), the monocyte fraction layer was collected from the tube. The cells were washed once with 10% FBS/D-MEM, and then suspended at a cell density of $5 \times 10^6$/ml in 10% FBS/D-MEM. The suspension was used as an effector cell suspension.

4.2. Preparation of Target Cell Suspensions

Target cell suspensions were prepared at the time of use. One$\times 10^6$ cells of cancer lines were centrifuged (1200 rpm, room temperature, 5 minutes). The cell pellets were suspended in 200 µl of 0.2 mg/ml calcein-AM (Nacalai Tesque)/DMEM (10% FBS) medium. Cell suspensions in calcein-AM solution were incubated for two hours in a $CO_2$ incubator set to 37° C. and to a $CO_2$ concentration of 5%. After washing once with 10% FBS/D-MEM, the cells were adjusted to a cell density of $2 \times 10^5$/ml with 10% FBS/D-MEM to prepare target cell suspensions.

4.3. ADCC Activity Measurement

Anti-EREG antibody was prepared at a concentration of 0.5 mg/ml, which was further diluted with 10% FBS/D-MEM to give antibody solutions. The final concentration was adjusted to 0.4, 4, and 40 µg/ml. The antibody solutions of respective concentrations or 10% FBS/D-MEM were each added at 50 µl/well to a 96-well round-bottomed plate. Then, the target cell suspensions were added at 50 µl/well to every well. The plate was incubated at room temperature for 15 minutes. Next, 100 µl of the effector cell suspension was added to each well containing target cell suspension, and antibody solution or 10% FBS/D-MEM. One-hundred µl of 10% FBS/D-MEM or 2% NP-40 solution (NP-40 substitute; Wako Pure Chemical Industries) was added to each of other wells containing 10% FBS/D-MEM and target cell suspension. The plate was centrifuged (1200 rpm, room temperature, 5 minutes) and incubated for 4 hours in a $CO_2$ incubator set to 37° C. and to a $CO_2$ concentration of 5%. The plate was centrifuged (1200 rpm, room temperature, 5 minutes), and a 100-µl aliquot of supernatant was collected from each well. The fluorescence intensity ($\lambda_{ex}$=490 nm, $\lambda_{em}$=515 nm) was determined using a spectrofluorometer. The specific calcein release rate (cytotoxicity (%)) was determined according to the following formula.

$$\text{cytotoxicity}(\%) = (A-C) \times 100/(B-C) \qquad \text{Formula 1:}$$

where A represents the fluorescence intensity in each well; B represents the mean value of fluorescence intensity in a well where 50 µl of target cell suspension and 100 µl of NP-40 solution were added to 50 µl of 10% FBS/D-MEM; and C represents the mean value of fluorescence intensity in a well where 50 µl of target cell suspension and 100 µl of 10% FBS/D-MEM were added to 50 µl of 10% FBS/D-MEM. This assay was carried out in triplicate, and the cytotoxicity (%) at each antibody concentration was determined using Microsoft Office Excel 2007.

Figure 38:
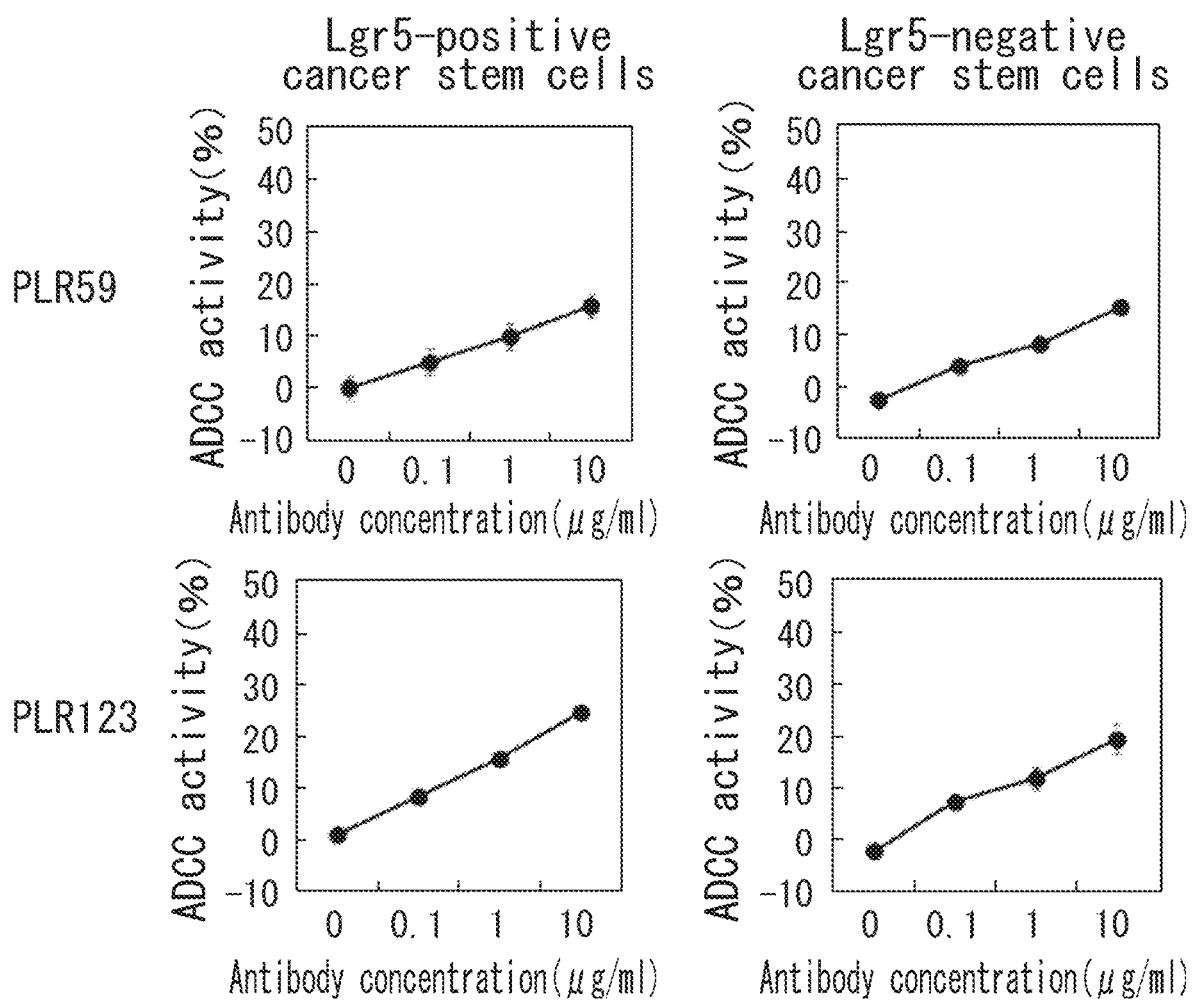
FIG. 38 shows graphs depicting the ADCC activity of anti-EREG antibody against Lgr5-positive and Lgr5-negative cells derived from PLR59 and Lgr5-positive and Lgr5-negative cells derived from PLR123 cells.
Figure 39A:
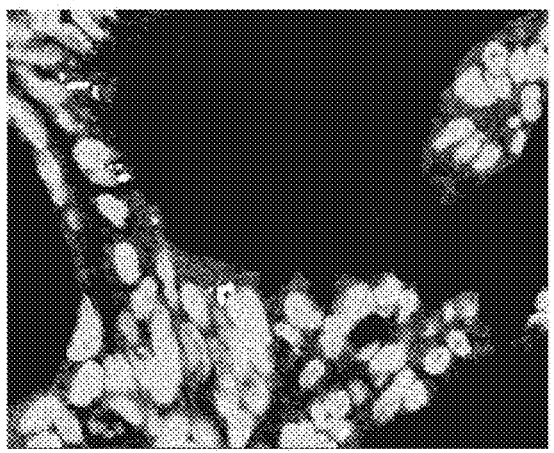
FIGS. 39A-39D show photographs depicting immunostaining of tumor (PLR123) obtained by surgical resection, and a PLR123-derived xenograft model (5 passages (FIG. 39B), 10 passages (FIG. 39C), and 15 passages (FIG. 39D)) in terms of Lgr5. Tissue sections were stained with anti-Lgr5 antibody. "Original" indicates the tumor obtained from a patient by surgical resection (FIG. 39A). Scale bar represents 25 μm.
Figure 39B:
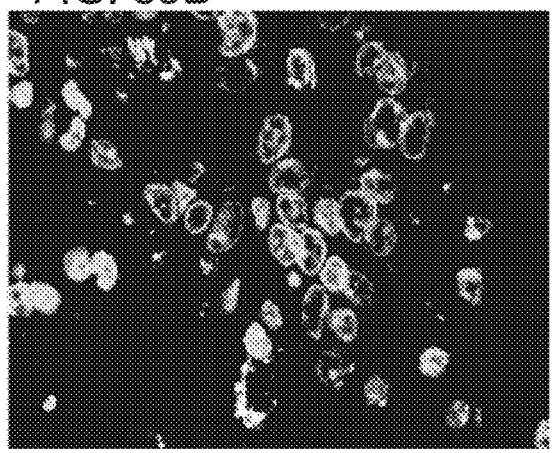
Figure 39C:
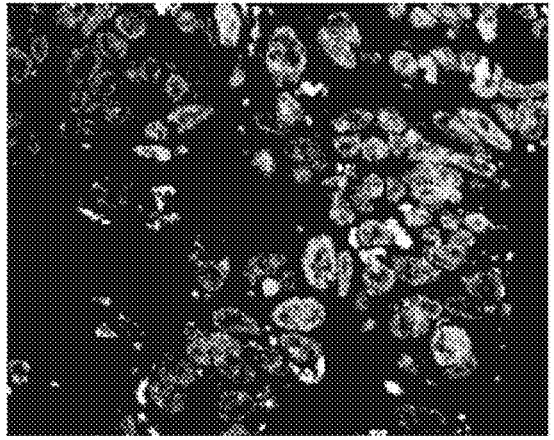
Figure 39D:
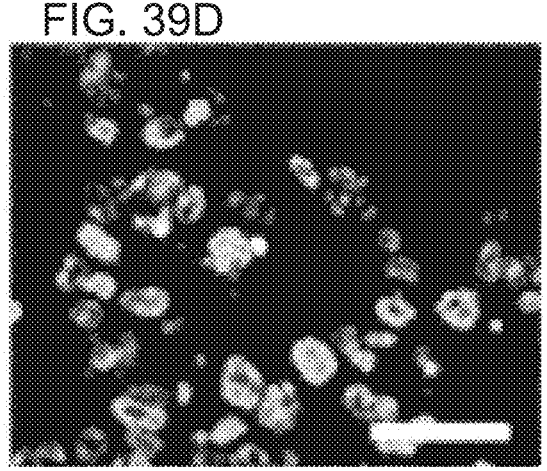
Figure 40A:
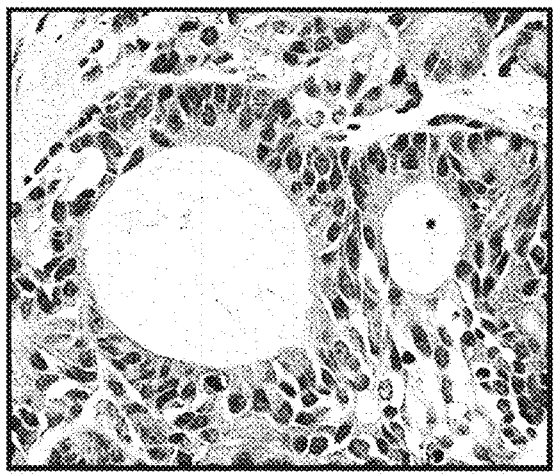
FIGS. 40A-40D show photographs depicting a histopathological result (HE stain) on xenograft tumors derived from Lgr5-positive cells of PLR59 (FIGS. 40A and 40B) and PLR123 (FIGS. 40C and 40D). NOG mice were subcutaneously injected with ten (FIGS. 40A and 40C) or a single (FIGS. 40B and 40D) Lgr5-positive cell(s) obtained from PLR59 or PLR123 by adherent culture. All tumors showed histopathological features highly similar to the original tumors. Scale bar represents 50 μm.
Figure 40B:
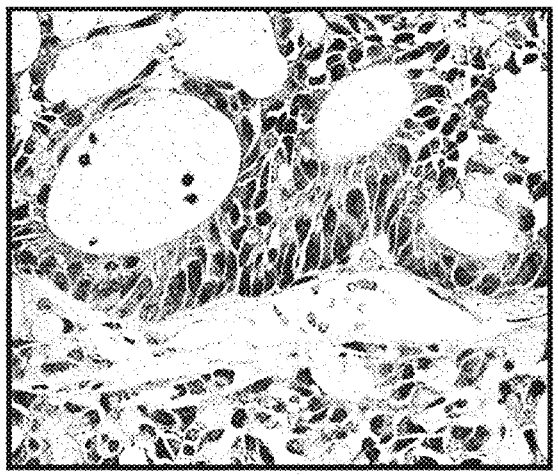
Figure 40C:
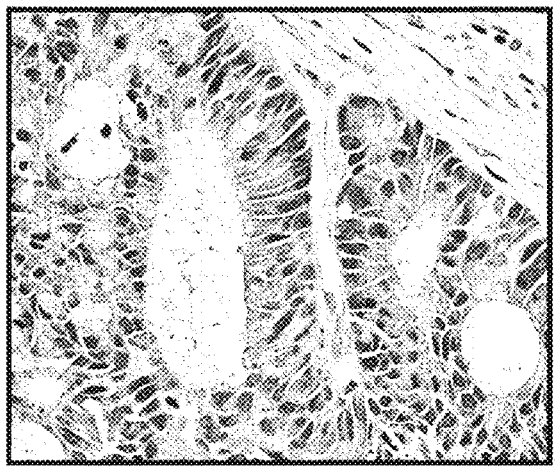
Figure 40D:
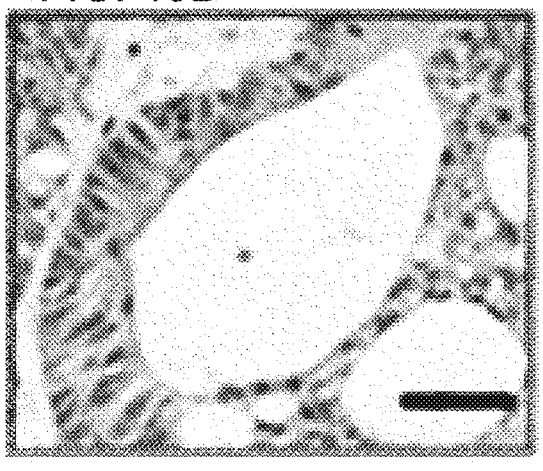

The anti-EREG antibody-mediated ADCC activities against Lgr5-positive and -negative cells derived from PLR59 cells, and those against Lgr5-positive and -negative cells derived from PLR123 cells are shown in FIG. 38. The result showed that the anti-EREG antibody exerted cytotoxic activity against both Lgr5-positive and -negative cancer stem cells from PRL59 or PLR123 in a dose dependent manner whereas the control antibody had no cytotoxic activity.

Figure 57:
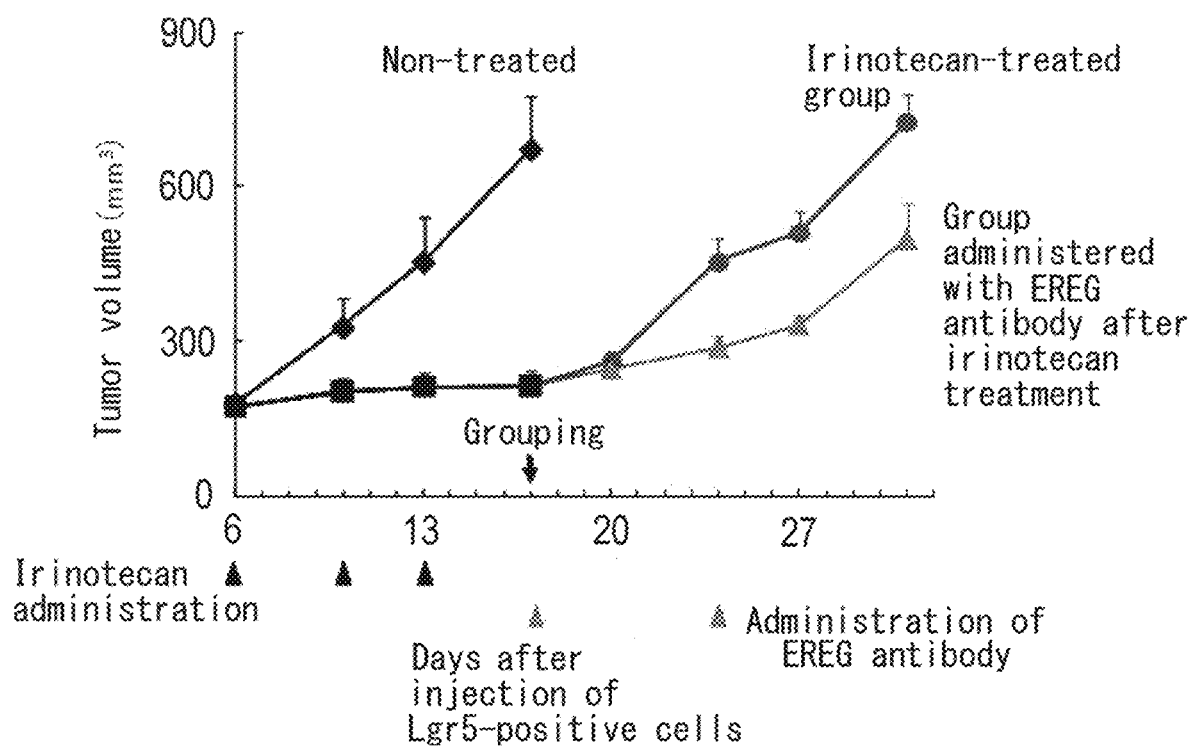
FIG. 57 is a graph showing the anti-tumor effect of EREG antibody after irinotecan treatment. PLR123-derived Lgr5-positive cells were injected to the peritoneal cavities of SCID mice, and irinotecan was administered at a dose of 100 mg/kg/day at days 6, 10, and 13 after injection of Lgr5-positive cells. Then, EREG antibody was administered at a dose of 10 mg/kg/day 17 and 24 days after injection of Lgr5-positive cells. Each value represents mean±standard deviation (n=4).

To assess in vivo EREG expression, the Lgr5-positive cells were administered into the peritoneal cavities of NOG mice. In the early stage of tumor generation, EREG was expressed at a high level. In the late stage where the tumor formed specific ductal structures, EREG expression was somewhat localized to the budding clusters rather than ductal structures. EREG-positive cells were detected even after irinotecan administration to tumor-bearing mice (FIG. 54). The anti-EREG antibody was assessed for anti-tumor activity after irinotecan treatment. Effector cells are essential for the anti-EREG antibody to mediate ADCC activity. Thus, SCID mice were used as a model to assess the pharmacological efficacy of the anti-EREG antibody. Tumor growth was suppressed when the antibody was administered at the time points of days 4 and 11 after the final irinotecan administration (FIG. 57).

Figure 58A:
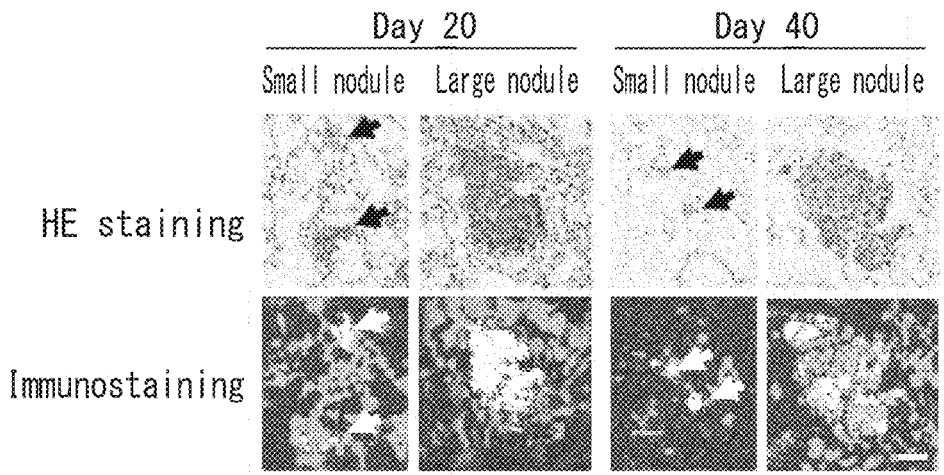
FIGS. 58A-58D show photographs and diagrams depicting the anti-tumor effect of EREG antibody.
Figure 58B:
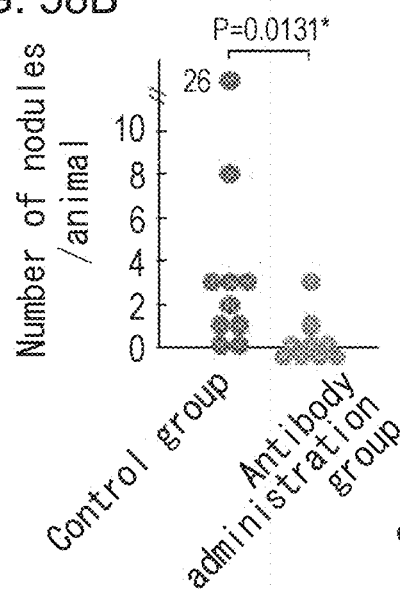
Figure 58C:
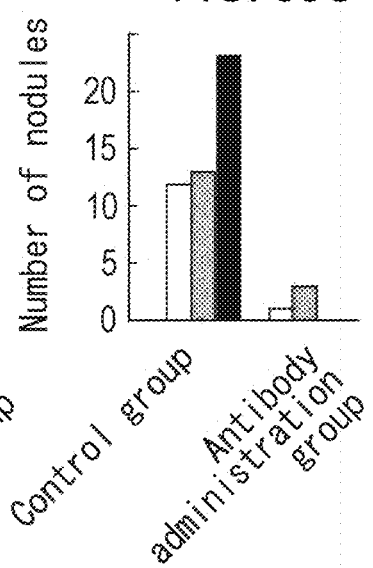
Figure 58D:
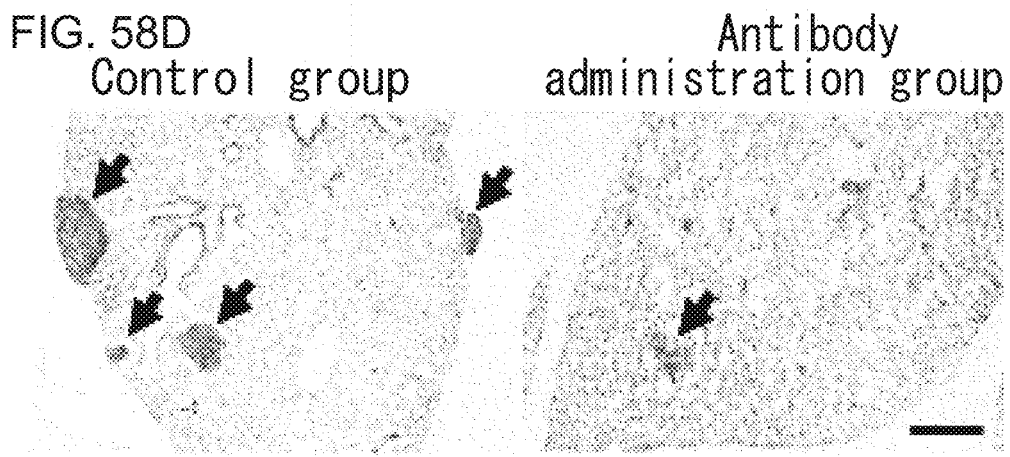

As a first step to assess the pharmacological efficacy based on the metastasis model, it was tested whether EREG is expressed in the metastasis model. When Lgr5-positive cells were intravenously injected into NOG mice, tumors were formed in multiple tissues including lung. Cells of the tumors formed in lungs are mostly positive for EREG (FIG. 58A). The pharmacological efficacy of the anti-EREG antibody was assessed using SCID-Beige mice where macrophages and mononuclear cells can serve as effector cells to mediate ADCC. The anti-EREG antibody was administered to mice once a week for a total of five times starting at three days after the injection of Lgr5-positive cells. The number of tumor cells in distal locations was demonstrated to be markedly reduced as compared to that in control mice (FIG. 58B). In addition, the size of each tumor was also shown to be remarkably reduced in mice administered with the antibody (FIGS. 58C and 58D).

Figure 59:
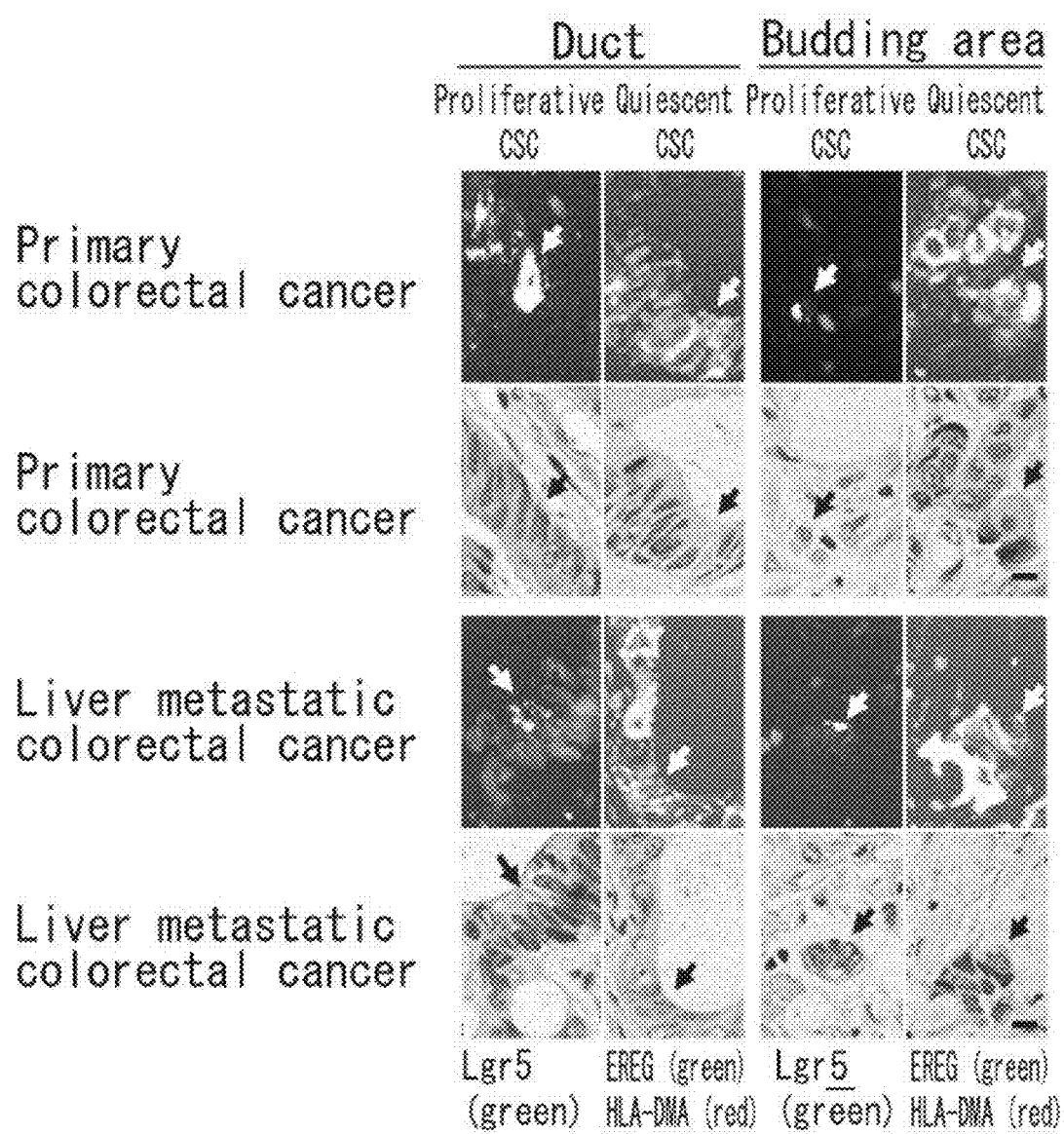
FIG. 59 shows photographs depicting the same tissue sections from primary and liver metastatic colorectal cancers isolated from patients, which were stained with HE (second and fourth rows), and antibodies against Lgr5 (green), HLA-DMA (red), and EREG (green) (first and third rows). Positivity for Lgr5 indicates proliferating CSCs, while positivity for EREG and HLA-DMA implies Lgr5-negative quiescent CSCs. Both Lgr5-negative and -positive CSCs were detected in ductal structures and budding areas of primary and liver metastatic tumors. Lgr5-positive CSCs were also found as single cells in stromal regions. The same staining patterns were also observed in multiple tumor tissues isolated from different patients. Arrows indicate CSCs. Scale bar represents 10 μm.

Example 9: Presence of Lgr5-Negative and -Positive CSCs in Clinical Tumor Specimens Proliferating and quiescent CSCs were identified by immunohistochemistry using anti-Lgr5 antibody (2U2E-2), anti-HLA-DMA antibody, and anti-EREG antibody (FIG. 59 and Table 11). Proliferative CSC represents Lgr5-positive cell, while quiescent CSC represents HLA-DMA-positive and EREG-positive cell (Table 11). Lgr5-positive cells which are positive for both HLA-DMA and EREG, and Lgr5-negative cells which are positive for both HLA-DMA and EREG were present in a very small number in primary and metastatic colorectal cancer specimens isolated from colorectal cancer patients (FIG. 59). Both Lgr5-positive and -negative cells were detected in eight of 12 specimens of human colorectal cancer tissues. Meanwhile, either Lgr5-positive or Lgr5-negative cells were observed in the remaining four specimens. Throughout all specimens, Lgr5-positive cells accounted for 0.003 to 1.864%, and Lgr5-negative cells accounted for 0.001 to 10.243% (Table 11).

protein expressed at a high level as the target in irinotecan-treated or non-treated PLR59 and PLR123. Commercially available antibodies shown in Table 12 were assessed by flow cytometry (FCM) for the binding activity to antigens expressed on the cell surface of irinotecan-treated or non-treated PLR59 or PLR123. The result is summarized in Table 13.

TABLE 12

| Antigen name | Subtype | Manufacturer |
|---|---|---|
| CD70 | mIgG3 | BD Pharmingen |
| EDAR | mIgG1 | MBL |
| FAS | mIgG1 | BD Pharmingen |
| PROM2 | mIgG2b | R & D Systems |
| PVRL4 | mIgG2b | R & D Systems |
| TNFSF9 | mIgG1 | BioLegend |
| PROCR | ratIgG1 | BD Pharmingen |
| EPCAM | mIgG2a | ABGENT |

TABLE 13

| | Irinotecan non-treated | | | | Irinotecan-treated | | | |
|---|---|---|---|---|---|---|---|---|
| CSC | PLR59 | | PLR123 | | PLR59 | | PLR123 | |
| Antibody +/− | − | + | − | + | − | + | − | + |
| CD70 | 4 | 1177 | 4 | 1843 | NT | NT | NT | NT |
| EDAR | 7 | 37 | 7 | 61 | NT | NT | NT | NT |
| FAS | 4 | 519 | 4 | 230 | 22 | 1871 | 25 | 1480 |
| PROM2 | NT | NT | NT | NT | 29 | 391 | 19 | 298 |
| PVRL4 | 4 | 8 | 4 | 19 | 22 | 109 | 25 | 129 |
| TNFSF9 | 4 | 86 | 4 | 33 | 22 | 183 | 25 | 104 |
| PROCR | 6 | 19 | 5 | 13 | 22 | 519 | 25 | 127 |
| EPCAM | 7 | 7563 | 7 | 7701 | NT | NT | NT | NT |

(NT indicates not tested.)

Using Mab-ZAP and Rat-ZAP, various antibodies that had been demonstrated to have binding activity were assessed for the activity of internalization (into cells). Mab-ZAP and Rat-ZAP are anti-mouse IgG antibody and anti-rat IgG antibody, respectively, conjugated with saporin, a toxin that

TABLE 11

| Property of | | Case number | | | | | | | | | | | |
|---|---|---|---|---|---|---|---|---|---|---|---|---|---|
| CSC | | 1 | 2 | 3 | 4 | 5 | 6 | 7 | 8 | 9 | 10 | 11 | 12 |
| Duct | Proliferative | P† | P | P | P | P | P | P | P | P | N | P | N |
| | Quiescent | N | P | N | P | P | P | P | P | P | P | N | P |
| Budding | Proliferative | P | N | N | P | P | N | N | P | P | P | N | N |
| area | Quiescent | N | P | N | P | N | P | N | P | N | N | N | P |
| Frequency | Proliferative | 1.864 | 0.786 | 0.136 | 0.121 | 0.119 | 0.095 | 0.063 | 0.054 | 0.018 | 0.010 | 0.003 | 0.000 |
| | Quiescent | 0.000 | 0.243 | 0.000 | 0.187 | 0.001 | 0.228 | 0.045 | 0.065 | 0.003 | 0.003 | 0.000 | 0.073 |

(P† indicates that proliferating or quiescent CSCs were detected; N indicates that proliferating or quiescent CSCs were undetectable)
(Frequency indicates cell percentage)

Both Lgr5-positive and -negative CSCs were detected in the ductal and budding areas (FIG. 59). Furthermore, in ducts, Lgr5-positive and -negative CSCs were not limited to particular areas but distributed at random over the entire ducts.

Example 10: Anti-Tumor Effect of Various Antibodies Used in Combination with Mab-ZAP and Rat-ZAP The present inventors tested whether an anti-tumor effect can be expected with target therapy using a membrane inhibits protein synthesis (Advanced Targeting Systems). To assess the activity of internalization into irinotecan-non-treated cells, PLR59 and PLR123 cells were seeded at a cell density of 30000 cells/80 μl/well to respective wells of a 96-well plate. Following day, each antibody solution was added at a final concentration of 0.01, 0.1, or 1 μg/ml to the respective wells. Then, Mab-ZAP or Rat-ZAP was added at a final concentration 1 μg/ml to the respective wells, and the plate was incubated at 37° C. for 72 hours in a $CO_2$ incubator. To assess the activity of internalization into irinotecan-treated cells, PLR59 and PLR123 cells were seeded in a 96-well plate, and irinotecan was added at a final concentration of 15 M to each well. The plate was incubated at 37° C. for 72 hours in a $CO_2$ incubator. Various antibodies were assessed for the activity of internalization to cells cultured as described above in the presence or absence of irinotecan. For assay, the various antibodies were each assessed for the internalization activity into cells contained in each well where the medium was replaced with the same irinotecan-free medium as used for irinotecan-non-treated cells. Seventy-two hours after addition of antibodies and Mab-ZAP or Rat-ZAP, 10 µl of 3% SDS (Nacalai Tesque) was added to each well of the plate. The cells in the plate were lysed thoroughly by stirring the plate using a plate mixer. Then, 100 µl of CellTiter-Glo™ Luminescent Cell Viability Assay (Promega) was added to each well. The mixture in each well was assayed to determine its luminescent signal. The determined anti-tumor activity is shown in Table 14 and FIGS. 60 to 72. In FIGS. 60 to 72, the percent suppression of cell proliferation indicated by the vertical axis represents a relative value for the difference in the luminescence signal value between the mixtures in wells, one of which contained a test antibody alone (without Mab-ZAP and Rat-ZAP) and the other contained a test antibody, and Mab-ZAP or Rat-ZAP, when taking as 100% the difference in the luminescence signal value between the mixtures in wells, one of which contained a test antibody alone (without Mab-ZAP and Rat-ZAP) and the other did not contain any cells. In Table 14, symbols, −, +, ++, and +++, represent relative values for the internalization activity when a test antibody was assayed at a concentration of 1 µg/µl. The relative value refers to a relative value for the difference in the luminescence signal value between the mixtures in wells, one of which contained a test antibody alone (without Mab-ZAP and Rat-ZAP) and the other contained a test antibody, and Mab-ZAP or Rat-ZAP, when taking as 100% the difference in the luminescence signal value between the mixtures in wells, one of which contained a test antibody alone (without Mab-ZAP and Rat-ZAP) and the other did not contain any cells. Symbols, −, +, ++, and +++, indicate that the relative value is less than 5%, 5% or more and less than 15%, 15% or more and less than 25%, and 25% or more, respectively.

TABLE 14

| Antigen name | PLR59 | | PLR123 | |
| --- | --- | --- | --- | --- |
| | Irinotecan non-treated | Irinotecan-treated | Irinotecan non-treated | Irinotecan-treated |
| CD70 | +++ | NT | +++ | NT |
| EDAR | ++ | NT | − | NT |
| FAS | +++ | +++ | +++ | +++ |
| PROM2 | NT | + | NT | + |
| PVRL4 | + | +++ | − | + |
| TNFSF9 | − | +++ | − | +++ |
| PROCR | + | ++ | − | + |
| EPCAM | +++ | +++ | +++ | +++ |

Figure 60:
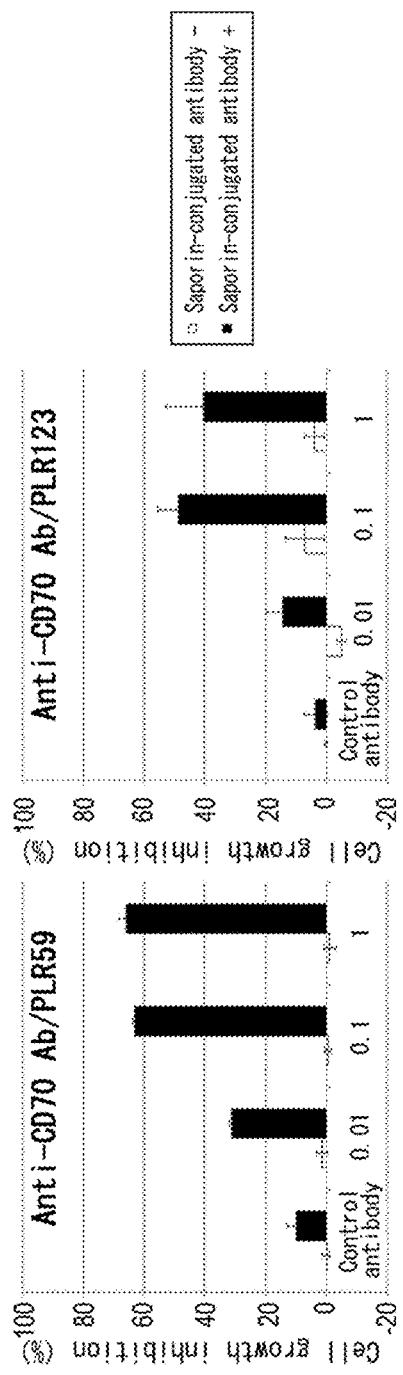
FIG. 60 is a diagram showing the anti-tumor effect of anti-CD70 antibody on irinotecan non-treated CSCs. The horizontal and vertical axes indicate the antibody concentration and % inhibition of cell growth by anti-CD70 antibody, respectively.
Figure 61:
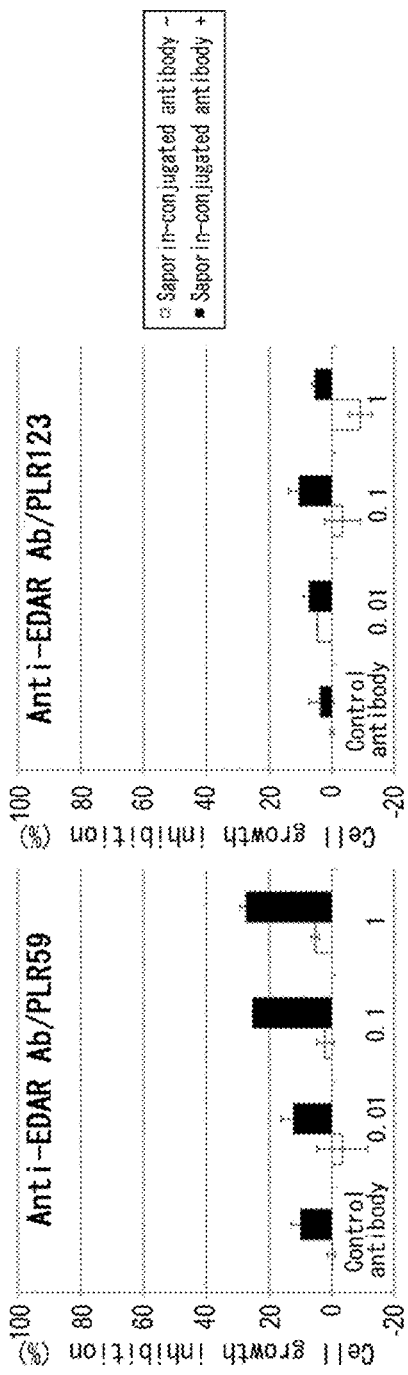
FIG. 61 is a diagram showing the anti-tumor effect of anti-EDAR antibody on irinotecan non-treated CSCs. The horizontal and vertical axes indicate the antibody concentration and % inhibition of cell growth by anti-EDAR antibody, respectively.
Figure 62:
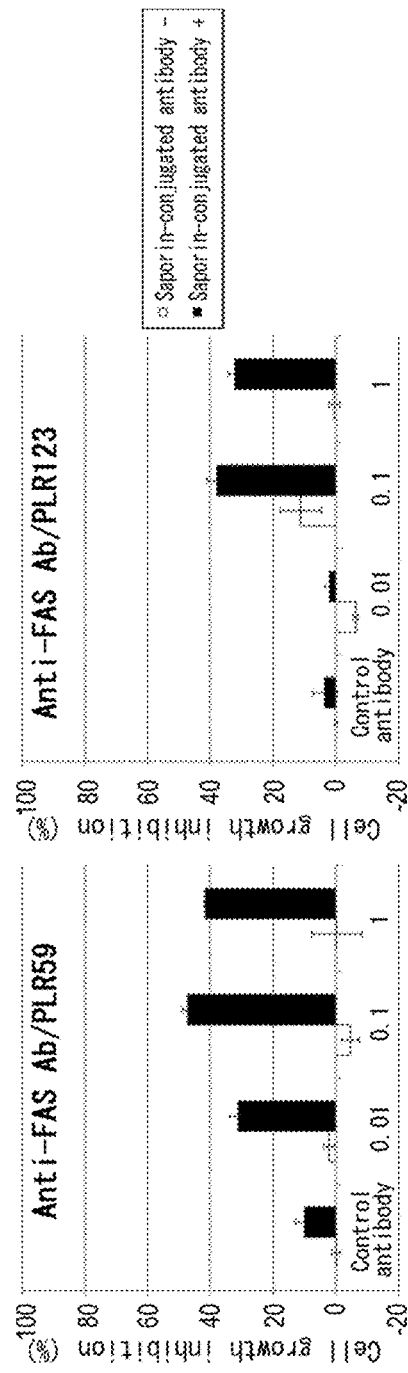
FIG. 62 is a diagram showing the anti-tumor effect of anti-FAS antibody on irinotecan non-treated CSCs. The horizontal and vertical axes indicate the antibody concentration and % inhibition of cell growth by anti-FAS antibody, respectively.
Figure 63:
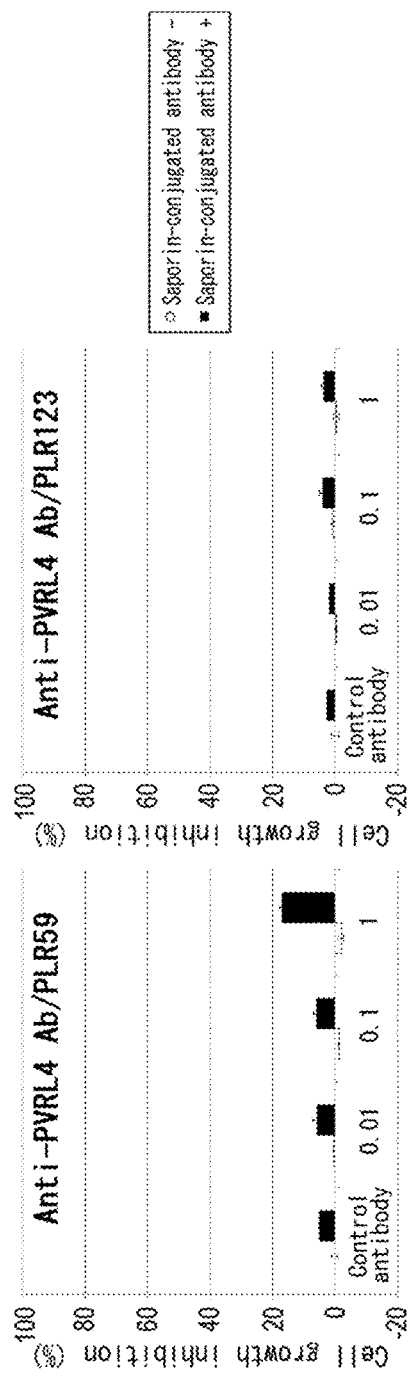
FIG. 63 is a diagram showing the anti-tumor effect of anti-PVRL4 antibody on irinotecan non-treated CSCs. The horizontal and vertical axes indicate the antibody concentration and % inhibition of cell growth by anti-PVRL4 antibody, respectively.
Figure 64:
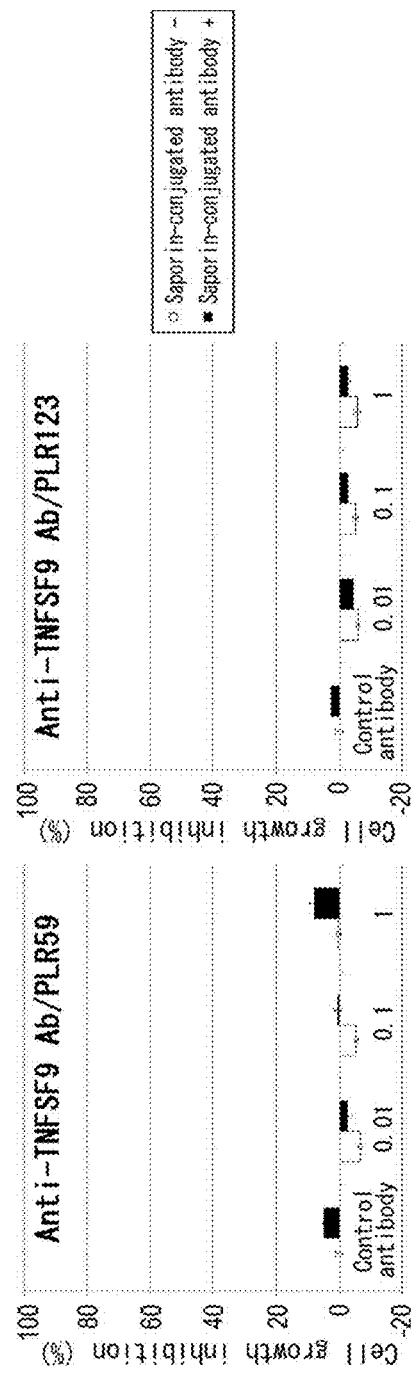
FIG. 64 is a diagram showing the anti-tumor effect of anti-TNFSF9 antibody on irinotecan non-treated CSCs. The horizontal and vertical axes indicate the antibody concentration and % inhibition of cell growth by anti-TNFSF9 antibody, respectively.
Figure 65:
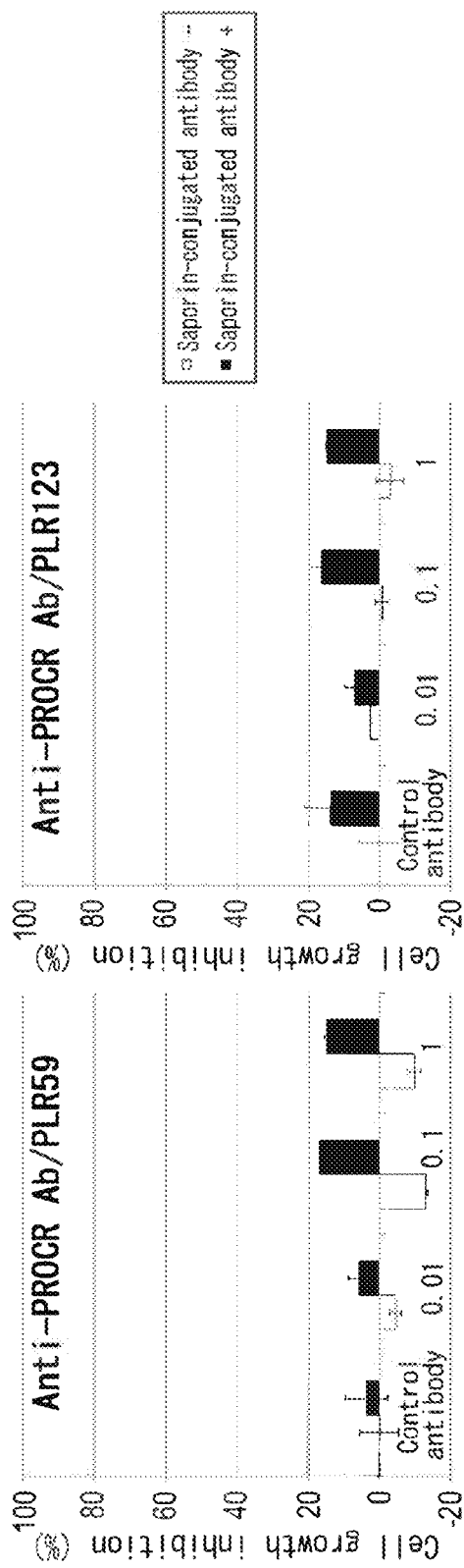
FIG. 65 is a diagram showing the anti-tumor effect of anti-PROCR antibody on irinotecan non-treated CSCs. The horizontal and vertical axes indicate the antibody concentration and % inhibition of cell growth by anti-PROCR antibody, respectively.
Figure 66:
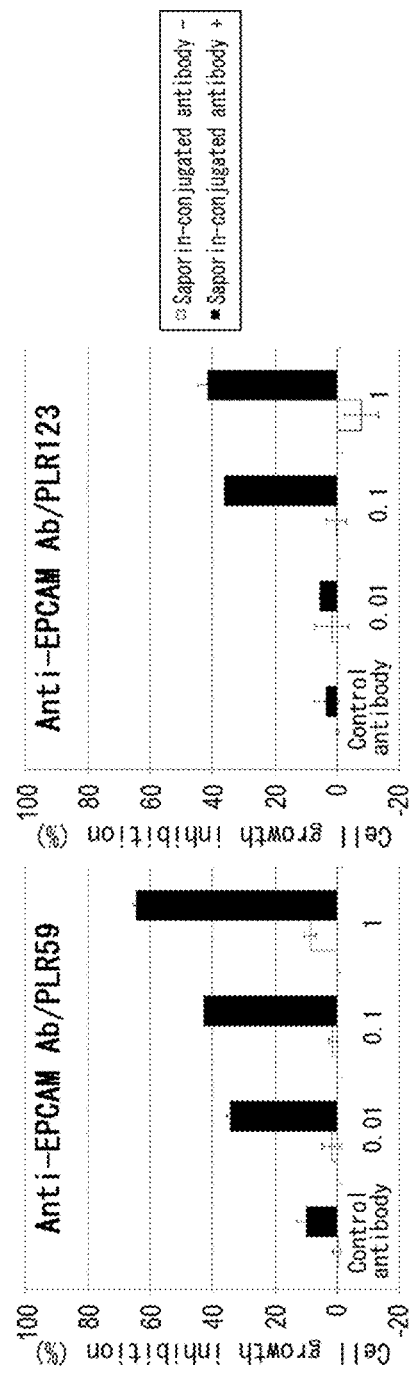
FIG. 66 is a diagram showing the anti-tumor effect of anti-EPCAM antibody on irinotecan non-treated CSCs. The horizontal and vertical axes indicate the antibody concentration and % inhibition of cell growth by anti-EPCAM antibody, respectively.
Figure 67:
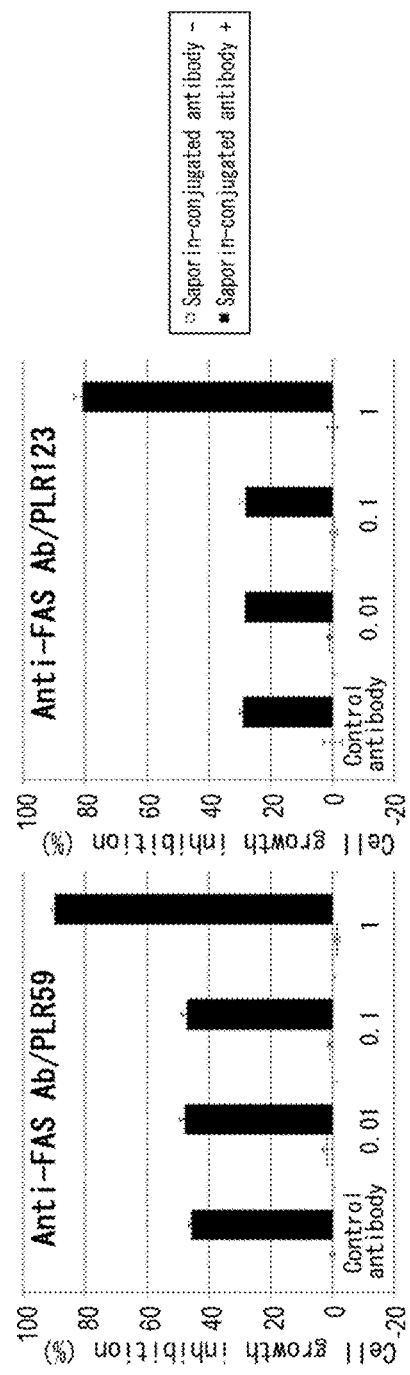
FIG. 67 is a diagram showing the anti-tumor effect of anti-FAS antibody on irinotecan treated CSCs. The horizontal and vertical axes indicate the antibody concentration and % inhibition of cell growth by anti-FAS antibody, respectively.
Figure 68:
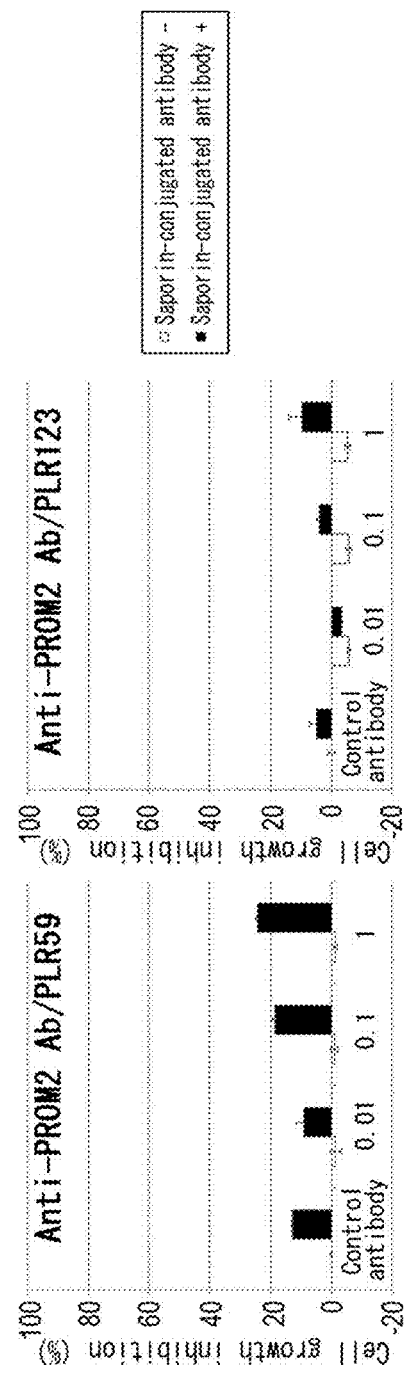
FIG. 68 is a diagram showing the anti-tumor effect of anti-PROM2 antibody on irinotecan treated CSCs. The horizontal and vertical axes indicate the antibody concentration and % inhibition of cell growth by anti-PROM2 antibody, respectively.
Figure 69:
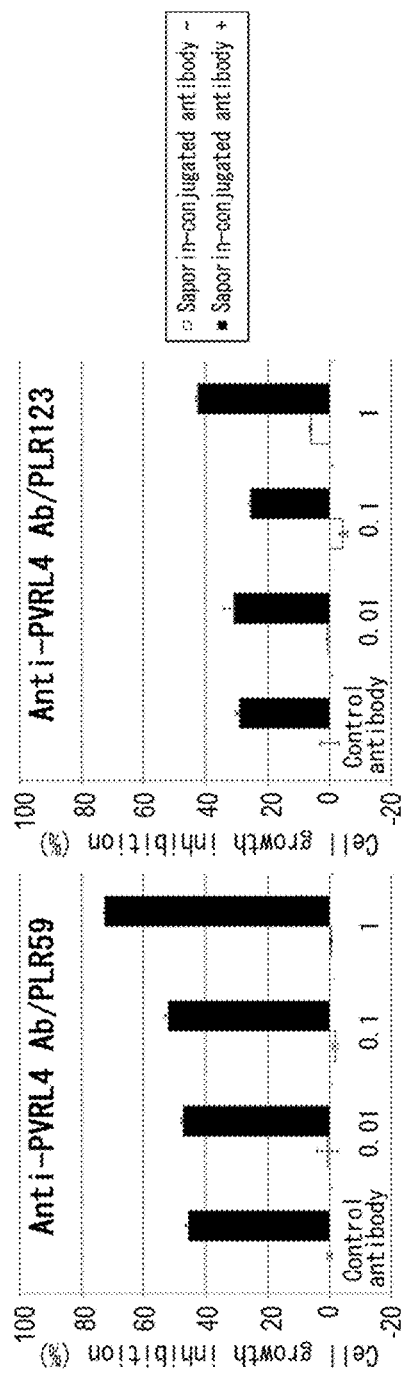
FIG. 69 is a diagram showing the anti-tumor effect of anti-PVRL4 antibody on irinotecan treated CSCs. The horizontal and vertical axes indicate the antibody concentration and % inhibition of cell growth by anti-PVRL4 antibody, respectively.
Figure 70:
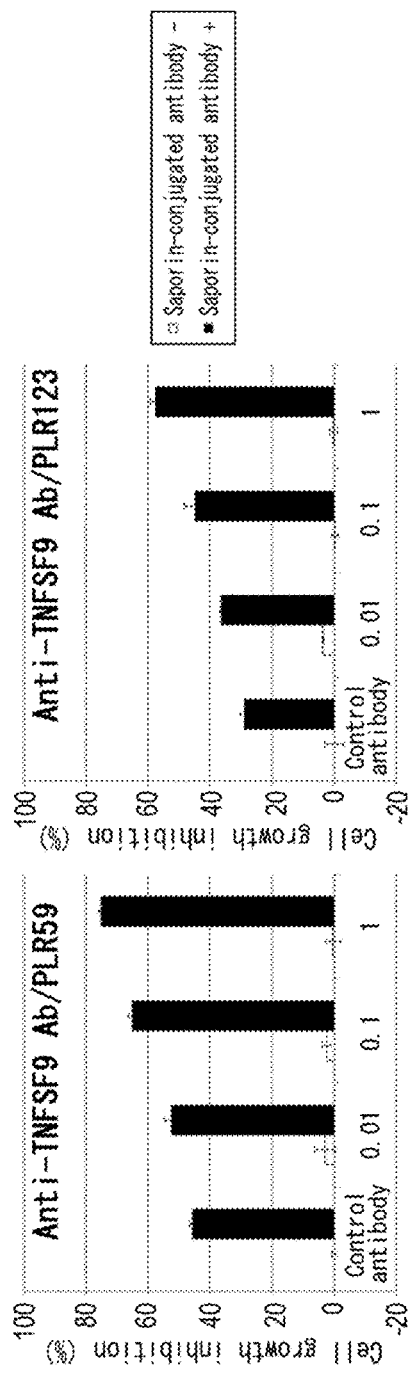
FIG. 70 is a diagram showing the anti-tumor effect of anti-TNFSF9 antibody on irinotecan treated CSCs. The horizontal and vertical axes indicate the antibody concentration and % inhibition of cell growth by anti-TNFSF9 antibody, respectively.
Figure 71:
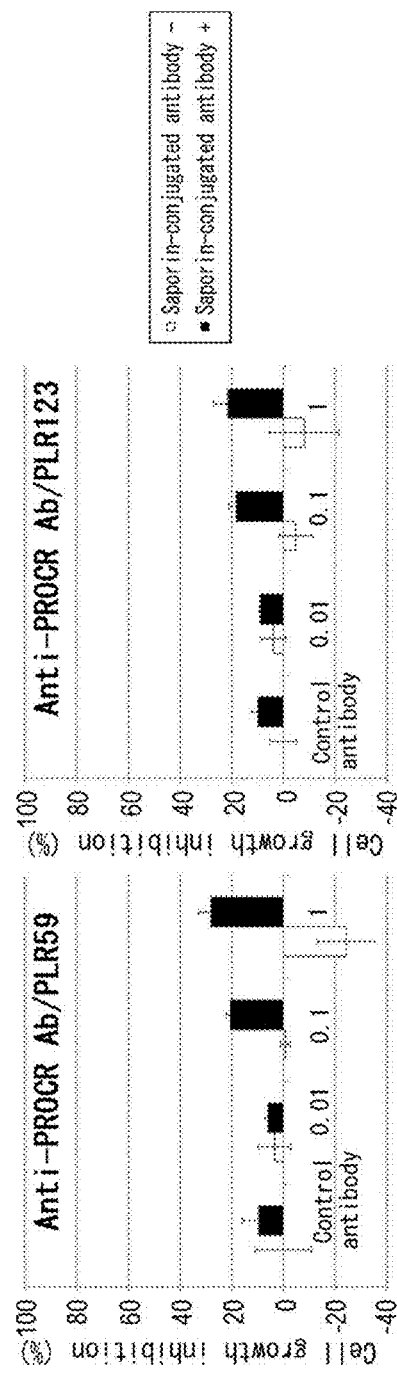
FIG. 71 is a diagram showing the anti-tumor effect of anti-PROCR antibody on irinotecan treated CSCs. The horizontal and vertical axes indicate the antibody concentration and % inhibition of cell growth by anti-PROCR antibody, respectively.
Figure 72:
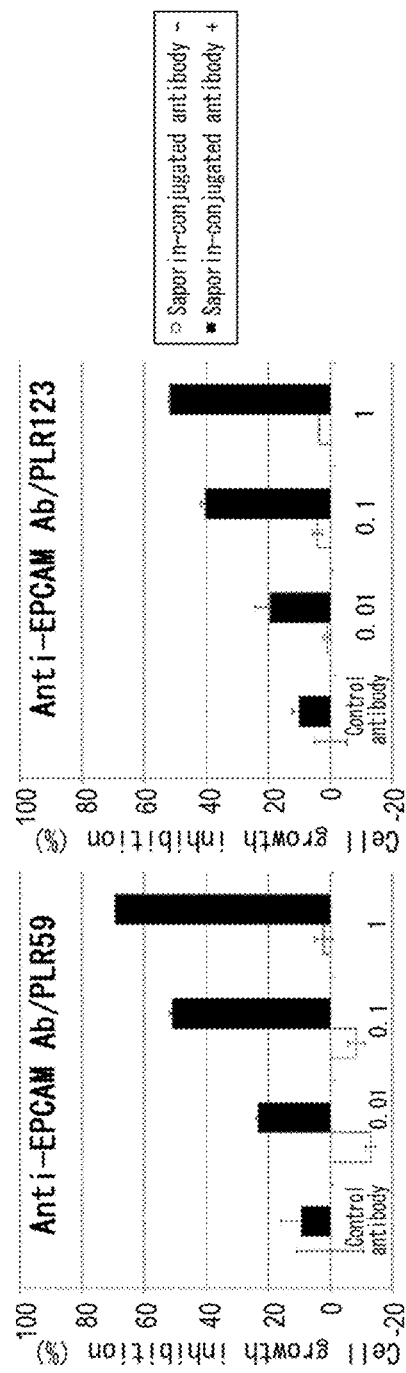
FIG. 72 is a diagram showing the anti-tumor effect of anti-EPCAM antibody on irinotecan treated CSCs. The horizontal and vertical axes indicate the antibody concentration and % inhibition of cell growth by anti-EPCAM antibody, respectively.

As shown in FIG. 66, regarding irinotecan-non-treated PLR59 and PLR123, anti-CD70 antibody and anti-FAS antibody showed the internalization activity level of 25% or more under a condition where the anti-EPCAM antibody used as a positive control had been demonstrated to exhibit a sufficient anti-tumor activity (FIGS. 60 and 62). Furthermore, regarding PLR59, anti-EDAR antibody showed the internalization activity level of 15 to 25%, and anti-PVRL4 antibody and anti-PROCR antibody exhibited the internalization activity level of 5 to 15% (FIGS. 61, 63, and 65). Meanwhile, regarding irinotecan-treated PLR59 and PLR123, anti-FAS antibody and anti-TNFRSF9 antibody showed the internalization activity level of 25% or more, and anti-PROM2 antibody exhibited the internalization activity level of 5 to 15% (FIGS. 67, 70, and 68). Both anti-PVRL4 antibody and anti-PROCR antibody showed the internalization activity for irinotecan-treated PLR59 and PLR123, and the activity for PLR59 was greater than that for PLR123 (FIGS. 69 and 71). The result described above demonstrates that all antibodies tested have an anti-tumor effect against PLR59 and PLR123.

BMP4 was assessed for the differentiation-enhancing effect on irinotecan-non-treated and irinotecan-treated PLR59 and PLR123. To assess the differentiation-enhancing effect on irinotecan-non-treated cells, PLR59 and PLR123 cells suspended in the media where BMP4 (R&D Systems; a final concentration of 20 nM) or a control buffer was added to culture media were seeded at a cell density of $5 \times 10^5$ cells/1.5 ml/well to each well of a 12-well plate. The cells were passaged while changing the culture media with the same type of medium 2, 4, and 7 days after seeding. To assess the differentiation-enhancing effect on irinotecan-treated cells, PLR59 or PLR123 was seeded at a cell density of $17 \times 10^5$ cells/5 ml/flask to a 12.5-ml culture flask. Following day, irinotecan was added at a final concentration of 15 M. The flask was incubated at 37° C. for 72 hours in a $CO_2$ incubator. Then, the medium in the flask was changed with a medium containing BMP4 or a control buffer. The medium was further changed with the same type of medium 2, 4, and 7 days after the initial medium change. From cells isolated 4 and 9 days after the initial medium change, RNAs were extracted using RNeasy Plus Mini Kit and RNase-Free DNase Set (QIAGEN). cDNAs were synthesized with ThermoScript RT-PCR System (Invitrogen) using the extracted RNAs as a template.

Figure 73A:
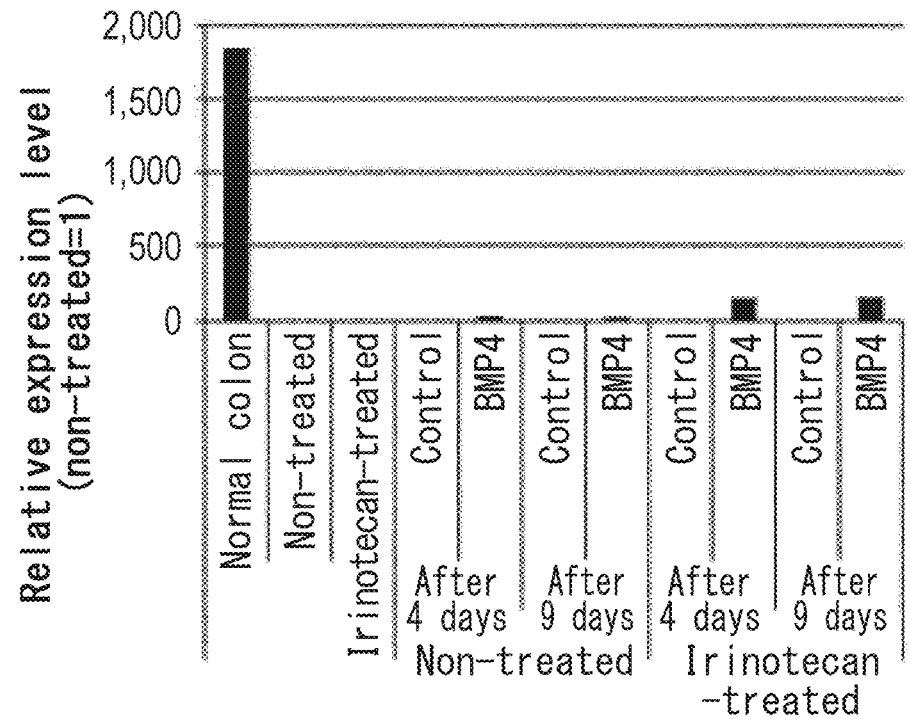
FIGS. 73A-73B are diagrams showing the expression levels of differentiation marker CK20 in CSCs cultured in the presence of BMP4.
Figure 73B:
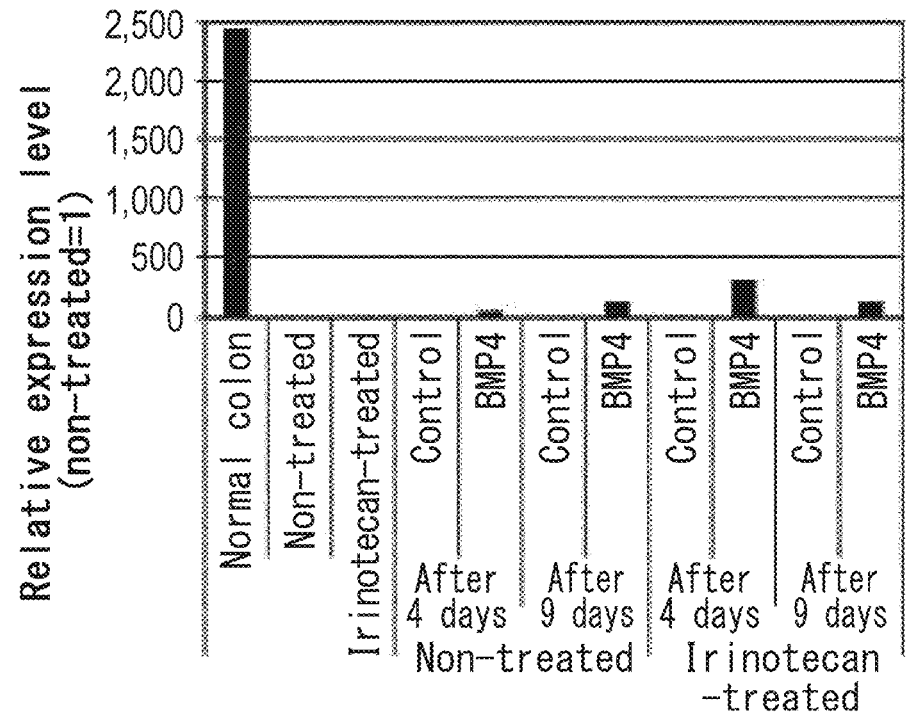

Quantitative real-time PCR was carried out using the cDNAs isolated as described above. As shown in FIG. 73, elevated CK20 levels were observed in PLR59 and PLR123 cells cultured in the presence of BMP4.

INDUSTRIAL APPLICABILITY

The present inventors identified cell surface molecules that are expressed specifically on cancer stem cells. The present invention provides novel anti-cancer drugs and reagents for detecting cancer stem cells, which use antibodies against the cell surface molecules.

The invention claimed is:

1. A method for detecting a cancer stem cell (CSC) in a sample, comprising:
    contacting the sample with at least one antibody that binds an ectodysplasin A receptor (EDAR) protein of SEQ ID NO: 1, a CD70 protein of SEQ ID NO: 2, an epiregulin (EREG) protein of SEQ ID NO: 3, a protein C receptor, endothelial (PROCR) protein of SEQ ID NO: 5, a prominin 2 (PROM2) protein of SEQ ID NO: 6, a tumor necrosis factor (ligand) superfamily, member 9 (TNFSF9) protein of SEQ ID NO: 7, a poliovirus receptor-related 4 (PVRL4) protein of SEQ ID NO: 8, or a TNF receptor superfamily, member 6 (FAS) protein of SEQ ID NO: 9; and detecting binding of the at least one antibody to the sample, thereby detecting the CSC, wherein the sample is from a patient with cancer, and the cancer is an Lgr5-negative cancer.

2. The method of claim 1, wherein the Lgr5-negative cancer is a drug-resistant cancer.

3. The method of claim 1, wherein the Lgr5-negative cancer is a solid cancer.

4. The method of claim 1, wherein the Lgr5-negative cancer is a digestive system cancer.

5. The method of claim 1, wherein the Lgr5-negative cancer is a colorectal cancer.

6. The method of claim 1, wherein the sample is an organ or tissue sample.

7. The method of claim 1, wherein the at least one antibody is a monoclonal antibody.

8. The method of claim 1, wherein the at least one antibody is a chimeric antibody, a humanized antibody, or a human antibody.

9. The method of claim 1, wherein the at least one antibody is labelled with an enzyme, a radioisotope, or a fluorescent substance.

10. The method of claim 9, wherein the enzyme is alkaline phosphatase, horseradish peroxidase, β-galactosidase, or β-glucosidase.

11. The method of claim 9, wherein the radioisotope is $^{32}P$, $^{33}P$, $^{131}I$, $^{125}I$, $^{3}H$, $^{14}C$, or $^{35}S$.

12. The method of claim 9, wherein the fluorescent substance is fluorescein isothiocyanate (FITC) or rhodamine.

13. The method of claim 1, wherein binding of the at least one antibody is detected by immunohistochemistry.

14. The method of claim 1, wherein the sample is a frozen sample.

15. The method of claim 1, wherein the sample is a fixed in paraformaldehyde.

16. The method of claim 1, wherein the at least one antibody is detected by a labeled secondary antibody.

17. The method of claim 1, wherein the wherein the labeled secondary antibody is labelled with an enzyme, a radioisotope, or a fluorescent substance.

* * * * *

SEQUENCE LISTING

<160> NUMBER OF SEQ ID NOS: 15

<210> SEQ ID NO 1
<211> LENGTH: 448
<212> TYPE: PRT
<213> ORGANISM: Homo sapiens

<400> SEQUENCE: 1

```
Met Ala His Val Gly Asp Cys Thr Gln Thr Pro Trp Leu Pro Val Leu
1               5                   10                  15

Val Val Ser Leu Met Cys Ser Ala Arg Ala Glu Tyr Ser Asn Cys Gly
            20                  25                  30

Glu Asn Glu Tyr Tyr Asn Gln Thr Gly Leu Cys Gln Glu Cys Pro
        35                  40                  45

Pro Cys Gly Pro Gly Glu Pro Tyr Leu Ser Cys Gly Tyr Gly Thr
    50                  55                      60

Lys Asp Glu Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
130                 135                 140

Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
            195                 200                 205

Tyr Ile Leu Lys Thr Lys Pro Ser Ala Pro Ala Cys Cys Thr Ser His
210                 215                 220

Pro Gly Lys Ser Val Glu Ala Gln Val Ser Lys Asp Glu Glu Lys Lys
225                 230                 235                 240

Glu Ala Pro Asp Asn Val Val Met Phe Ser Glu Lys Asp Glu Phe Glu
                245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
        355                 360                 365

Ala Val Val Lys Thr Trp Arg His Leu Ala Glu Ser Phe Gly Leu Lys
370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415
```

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
            435                 440                 445

<210> SEQ ID NO 2
<211> LENGTH: 193
<212> TYPE: PRT
<213> ORGANISM: Homo sapiens

<400> SEQUENCE: 2

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 3
<211> LENGTH: 169
<212> TYPE: PRT
<213> ORGANISM: Homo sapiens

<400> SEQUENCE: 3

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
    50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95

```
Gly Tyr Thr Gly Val Arg Cys Glu His Phe Leu Thr Val His Gln
            100                 105                 110

Pro Leu Ser Lys Glu Tyr Val Ala Leu Thr Val Ile Leu Ile Leu
            115                 120                 125

Phe Leu Ile Thr Val Val Gly Ser Thr Tyr Tyr Phe Cys Arg Trp Tyr
130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
            165
```

<210> SEQ ID NO 4
<211> LENGTH: 408
<212> TYPE: PRT
<213> ORGANISM: Homo sapiens

<400> SEQUENCE: 4

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Gly Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
290                 295                 300
```

```
Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 5
<211> LENGTH: 238
<212> TYPE: PRT
<213> ORGANISM: Homo sapiens

<400> SEQUENCE: 5

Met Leu Thr Thr Leu Leu Pro Ile Leu Leu Leu Ser Gly Trp Ala Phe
1               5                   10                  15

Cys Ser Gln Asp Ala Ser Asp Gly Leu Gln Arg Leu His Met Leu Gln
                20                  25                  30

Ile Ser Tyr Phe Arg Asp Pro Tyr His Val Trp Tyr Gln Gly Asn Ala
            35                  40                  45

Ser Leu Gly Gly His Leu Thr His Val Leu Glu Gly Pro Asp Thr Asn
        50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
                100                 105                 110

Arg Cys Phe Leu Gly Cys Glu Leu Pro Pro Glu Gly Ser Arg Ala His
            115                 120                 125

Val Phe Phe Glu Val Ala Val Asn Gly Ser Ser Phe Val Ser Phe Arg
        130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
        195                 200                 205

Thr Ser Leu Val Leu Gly Val Leu Val Gly Ser Phe Ile Ile Ala Gly
210                 215                 220

Val Ala Val Gly Ile Phe Leu Cys Thr Gly Gly Arg Arg Cys
225                 230                 235

<210> SEQ ID NO 6
<211> LENGTH: 834
<212> TYPE: PRT
```

<213> ORGANISM: Homo sapiens

<400> SEQUENCE: 6

Met Lys His Thr Leu Ala Leu Leu Ala Pro Leu Leu Gly Leu Gly Leu
1               5                   10                  15

Gly Leu Ala Leu Ser Gln Leu Ala Ala Gly Ala Thr Asp Cys Lys Phe
            20                  25                  30

Leu Gly Pro Ala Glu His Leu Thr Phe Thr Pro Ala Ala Arg Ala Arg
        35                  40                  45

Trp Leu Ala Pro Arg Val Arg Ala Pro Gly Leu Leu Asp Ser Leu Tyr
    50                  55                  60

Gly Thr Val Arg Arg Phe Leu Ser Val Val Gln Leu Asn Pro Phe Pro
65                  70                  75                  80

Ser Glu Leu Val Lys Ala Leu Leu Asn Glu Leu Ala Ser Val Lys Val
                85                  90                  95

Asn Glu Val Val Arg Tyr Glu Ala Gly Tyr Val Val Cys Ala Val Ile
            100                 105                 110

Ala Gly Leu Tyr Leu Leu Val Pro Thr Ala Gly Leu Cys Phe Cys
        115                 120                 125

Cys Cys Arg Cys His Arg Cys Gly Gly Arg Val Lys Thr Glu His
    130                 135                 140

Lys Ala Leu Ala Cys Glu Arg Ala Ala Leu Met Val Phe Leu Leu Leu
145                 150                 155                 160

Thr Thr Leu Leu Leu Leu Ile Gly Val Val Cys Ala Phe Val Thr Asn
                165                 170                 175

Gln Arg Thr His Glu Gln Met Gly Pro Ser Ile Glu Ala Met Pro Glu
            180                 185                 190

Thr Leu Leu Ser Leu Trp Gly Leu Val Ser Asp Val Pro Gln Glu Leu
        195                 200                 205

Gln Ala Val Ala Gln Gln Phe Ser Leu Pro Gln Glu Gln Val Ser Glu
    210                 215                 220

Glu Leu Asp Gly Val Gly Val Ser Ile Gly Ser Ala Ile His Thr Gln
225                 230                 235                 240

Leu Arg Ser Ser Val Tyr Pro Leu Leu Ala Ala Val Gly Ser Leu Gly
                245                 250                 255

Gln Val Leu Gln Val Ser Val His His Leu Gln Thr Leu Asn Ala Thr
            260                 265                 270

Val Val Glu Leu Gln Ala Gly Gln Gln Asp Leu Glu Pro Ala Ile Arg
        275                 280                 285

Glu His Arg Asp Arg Leu Leu Glu Leu Leu Gln Glu Ala Arg Cys Gln
    290                 295                 300

Gly Asp Cys Ala Gly Ala Leu Ser Trp Ala Arg Thr Leu Glu Leu Gly
305                 310                 315                 320

Ala Asp Phe Ser Gln Val Pro Ser Val Asp His Val Leu His Gln Leu
                325                 330                 335

Lys Gly Val Pro Glu Ala Asn Phe Ser Ser Met Val Gln Glu Glu Asn
            340                 345                 350

Ser Thr Phe Asn Ala Leu Pro Ala Leu Ala Ala Met Gln Thr Ser Ser
        355                 360                 365

Val Val Gln Glu Leu Lys Lys Ala Val Ala Gln Gln Pro Glu Gly Val
    370                 375                 380

Arg Thr Leu Ala Glu Gly Phe Pro Gly Leu Glu Ala Ala Ser Arg Trp
385                 390                 395                 400

```
Ala Gln Ala Leu Gln Glu Val Glu Ser Arg Pro Tyr Leu Gln
                405                 410                 415

Glu Val Gln Arg Tyr Glu Thr Tyr Arg Trp Ile Val Gly Cys Val Leu
                420                 425                 430

Cys Ser Val Val Leu Phe Val Val Leu Cys Asn Leu Leu Gly Leu Asn
            435                 440                 445

Leu Gly Ile Trp Gly Leu Ser Ala Arg Asp Asp Pro Ser His Pro Glu
        450                 455                 460

Ala Lys Gly Glu Ala Gly Ala Arg Phe Leu Met Ala Gly Val Gly Leu
465                 470                 475                 480

Ser Phe Leu Phe Ala Ala Pro Leu Ile Leu Leu Val Phe Ala Thr Phe
                485                 490                 495

Leu Val Gly Gly Asn Val Gln Thr Leu Val Cys Gln Ser Trp Glu Asn
            500                 505                 510

Gly Glu Leu Phe Glu Phe Ala Asp Thr Pro Gly Asn Leu Pro Pro Ser
        515                 520                 525

Met Asn Leu Ser Gln Leu Leu Gly Leu Arg Lys Asn Ile Ser Ile His
        530                 535                 540

Gln Ala Tyr Gln Gln Cys Lys Glu Gly Ala Ala Leu Trp Thr Val Leu
545                 550                 555                 560

Gln Leu Asn Asp Ser Tyr Asp Leu Glu Glu His Leu Asp Ile Asn Gln
                565                 570                 575

Tyr Thr Asn Lys Leu Arg Gln Glu Leu Gln Ser Leu Lys Val Asp Thr
            580                 585                 590

Gln Ser Leu Asp Leu Leu Ser Ser Ala Ala Arg Arg Asp Leu Glu Ala
        595                 600                 605

Leu Gln Ser Ser Gly Leu Gln Arg Ile His Tyr Pro Asp Phe Leu Val
        610                 615                 620

Gln Ile Gln Arg Pro Val Val Lys Thr Ser Met Glu Gln Leu Ala Gln
625                 630                 635                 640

Glu Leu Gln Gly Leu Ala Gln Ala Gln Asp Asn Ser Val Leu Gly Gln
                645                 650                 655

Arg Leu Gln Glu Glu Ala Gln Gly Leu Arg Asn Leu His Gln Glu Lys
            660                 665                 670

Val Val Pro Gln Gln Ser Leu Val Ala Lys Leu Asn Leu Ser Val Arg
        675                 680                 685

Ala Leu Glu Ser Ser Ala Pro Asn Leu Gln Leu Glu Thr Ser Asp Val
        690                 695                 700

Leu Ala Asn Val Thr Tyr Leu Lys Gly Glu Leu Pro Ala Trp Ala Ala
705                 710                 715                 720

Arg Ile Leu Arg Asn Val Ser Glu Cys Phe Leu Ala Arg Glu Met Gly
                725                 730                 735

Tyr Phe Ser Gln Tyr Val Ala Trp Val Arg Glu Val Thr Gln Arg
            740                 745                 750

Ile Ala Thr Cys Gln Pro Leu Ser Gly Ala Leu Asp Asn Ser Arg Val
        755                 760                 765

Ile Leu Cys Asp Met Met Ala Asp Pro Trp Asn Ala Phe Trp Phe Cys
        770                 775                 780

Leu Ala Trp Cys Thr Phe Phe Leu Ile Pro Ser Ile Phe Ala Val
785                 790                 795                 800

Lys Thr Ser Lys Tyr Phe Arg Pro Ile Arg Lys Arg Leu Ser Ser Thr
                805                 810                 815

Ser Ser Glu Glu Thr Gln Leu Phe His Ile Pro Arg Val Thr Ser Leu
```

Lys Leu
            820              825              830

<210> SEQ ID NO 7
<211> LENGTH: 254
<212> TYPE: PRT
<213> ORGANISM: Homo sapiens

<400> SEQUENCE: 7

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 8
<211> LENGTH: 510
<212> TYPE: PRT
<213> ORGANISM: Homo sapiens

<400> SEQUENCE: 8

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
50                  55                  60

-continued

```
Val Ala Trp Ala Arg Val Asp Ala Gly Glu Gly Ala Gln Glu Leu Ala
 65                  70                  75                  80

Leu Leu His Ser Lys Tyr Gly Leu His Val Ser Pro Ala Tyr Glu Gly
                 85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
        130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
        210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
        290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
        355                 360                 365

Val Leu Met Ser Arg Tyr His Arg Arg Lys Ala Gln Gln Met Thr Gln
370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
        435                 440                 445

Thr Thr Val Arg Glu Ile Glu Thr Gln Thr Glu Leu Leu Ser Pro Gly
        450                 455                 460

Ser Gly Arg Ala Glu Glu Glu Asp Gln Asp Glu Gly Ile Lys Gln
465                 470                 475                 480
```

```
Ala Met Asn His Phe Val Gln Glu Asn Gly Thr Leu Arg Ala Lys Pro
            485                 490                 495

Thr Gly Asn Gly Ile Tyr Ile Asn Gly Arg Gly His Leu Val
        500                 505                 510

<210> SEQ ID NO 9
<211> LENGTH: 335
<212> TYPE: PRT
<213> ORGANISM: Homo sapiens

<400> SEQUENCE: 9

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 10
```

```
<211> LENGTH: 24
<212> TYPE: DNA
<213> ORGANISM: Artificial Sequence
<220> FEATURE:
<223> OTHER INFORMATION: an artificially synthesized primer sequence

<400> SEQUENCE: 10
agtttatcct tctggtggta gtcc                                              24

<210> SEQ ID NO 11
<211> LENGTH: 23
<212> TYPE: DNA
<213> ORGANISM: Artificial Sequence
<220> FEATURE:
<223> OTHER INFORMATION: an artificially synthesized primer sequence

<400> SEQUENCE: 11
caagatgtag agaagggat tga                                                23

<210> SEQ ID NO 12
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 12
ctctgctcct cctgttcgac                                                   20

<210> SEQ ID NO 13
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 13
acgaccaaat ccgttgactc                                                   20

<210> SEQ ID NO 14
<211> LENGTH: 21
<212> TYPE: DNA
<213> ORGANISM: Artificial Sequence
<220> FEATURE:
<223> OTHER INFORMATION: an artificially synthesized primer sequence

<400> SEQUENCE: 14
aagtcccttg ccatcctaaa a                                                 21

<210> SEQ ID NO 15
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 15
atgctatcac ctcccctgtg                                                   20
```